US012758591B2

(12) United States Patent
Woodward et al.

(10) Patent No.: US 12,758,591 B2
(45) Date of Patent: Oct. 13, 2026

(54) ANTIBACTERIAL AGENTS AND METHODS

(71) Applicant: FOLIUM FOOD SCIENCE LIMITED, Bristol (GB)

(72) Inventors: Martin Woodward, Bristol (GB); Tristan Cogan, Bristol (GB); Edward Fuchs, Bristol (GB); Holger Kneuper, Bristol (GB); Alessandro Riccio, Bristol (GB); Christian Grøndahl, Bristol (GB); Jasper Clube, Bristol (GB)

(73) Assignee: Folium Food Science Limited, Bristol (GB)

( * ) Notice: Subject to any disclaimer, the term of this patent is extended or adjusted under 35 U.S.C. 154(b) by 1228 days.

(21) Appl. No.: 17/595,190

(22) PCT Filed: May 10, 2020

(86) PCT No.: PCT/EP2020/062957

§ 371 (c)(1),
(2) Date: Nov. 10, 2021

(87) PCT Pub. No.: WO2020/229372

PCT Pub. Date: Nov. 19, 2020

(65) Prior Publication Data

US 2022/0226396 A1 Jul. 21, 2022

(30) Foreign Application Priority Data

May 12, 2019 (GB) ..................................... 1906668

(51) Int. Cl.

| | |
|---|---|
| ***A61K 35/74*** | (2015.01) |
| ***A61K 35/00*** | (2006.01) |
| ***A61K 38/46*** | (2006.01) |
| ***A61P 31/04*** | (2006.01) |
| ***C12N 1/20*** | (2026.01) |
| ***C12N 9/22*** | (2006.01) |
| ***C12N 15/11*** | (2006.01) |
| ***C12N 15/70*** | (2006.01) |

(52) U.S. Cl.

CPC ............ *A61K 35/74* (2013.01); *A61K 38/465* (2013.01); *A61P 31/04* (2018.01); *C12N 1/20* (2013.01); *C12N 9/22* (2013.01); *C12N 15/11* (2013.01); *C12N 15/70* (2013.01); *A61K 2035/11* (2013.01); *C12N 2310/20* (2017.05); *C12N 2800/101* (2013.01); *C12N 2800/108* (2013.01); *C12N 2800/80* (2013.01)

(58) Field of Classification Search

None

See application file for complete search history.

(56) References Cited

U.S. PATENT DOCUMENTS

| | | | |
|---|---|---|---|
| 4,968,619 | A | 11/1990 | Curtiss, III |
| 5,627,275 | A | 5/1997 | Roll |
| 6,106,854 | A | 8/2000 | Belfer et al. |
| 6,153,381 | A | 11/2000 | Rothstein |
| 6,221,582 | B1 | 4/2001 | Giesendorf et al. |
| 6,261,842 | B1 | 7/2001 | Handelsman et al. |
| 6,261,843 | B1 | 7/2001 | Chang et al. |
| 6,271,359 | B1 | 8/2001 | Norris et al. |
| 9,701,964 | B2 | 7/2017 | Clube |
| 9,879,269 | B2 | 1/2018 | Barrangou |
| 10,066,233 | B2 | 9/2018 | Barrangou |
| 10,136,649 | B2 | 11/2018 | Barrangou |
| 10,195,273 | B2 | 2/2019 | Clube |
| 10,300,138 | B2 | 5/2019 | Clube |
| 10,300,139 | B2 | 5/2019 | Clube |
| 10,363,308 | B2 | 7/2019 | Clube |
| 10,463,049 | B2 | 11/2019 | Clube |
| 10,506,812 | B2 | 12/2019 | Clube |
| 10,524,477 | B2 | 1/2020 | Clube |
| 10,561,148 | B2 | 2/2020 | Clube |
| 10,582,712 | B2 | 3/2020 | Clube |
| 10,596,255 | B2 | 3/2020 | Clube |
| 10,603,379 | B2 | 3/2020 | Clube |
| 10,624,349 | B2 | 4/2020 | Clube |
| 10,660,943 | B2 | 5/2020 | Bikard et al. |
| 10,751,427 | B2 | 8/2020 | Clube |
| 10,760,065 | B2 | 9/2020 | Lu et al. |

(Continued)

FOREIGN PATENT DOCUMENTS

| | | | |
|---|---|---|---|
| CN | 114854758 | A | 8/2022 |
| CN | 116940239 | A | 10/2023 |

(Continued)

OTHER PUBLICATIONS

Robledo et al. Targeted bacterial conjugation mediated by synthetic cell-to-cell adhesions. Nucleic Acids Res. Dec. 9, 2022;50(22): 12938-12950. (Year: 2022).*

Miao et al. Antibiotics can cause weight loss by impairing gut microbiota in mice and the potent benefits of lactobacilli. Biosci Biotechnol Biochem. Feb. 2020;84(2):411-420. Epub Oct. 29, 2019. (Year: 2020).*

Minasyan. Mechanisms and pathways for the clearance of bacteria from blood circulation in health and disease. Pathophysiology. Jun. 2016;23(2):61-6. Epub Mar. 7, 2016. (Year: 2016).*

(Continued)

*Primary Examiner* — Valerie E Bertoglio
*Assistant Examiner* — Briana N Ebbinghaus
(74) *Attorney, Agent, or Firm* — Morrison & Foerster LLP

(57) ABSTRACT

The invention relates to means for carrying out conjugation between bacteria, and in particular the invention relates to carrier bacteria comprising antimicrobial agents and methods of use. The carrier bacteria are capable of conjugative transfer of DNA encoding the agent to a target cells. The invention further relates to growth or feed conversion ratio promotion in animals. The invention further relates to killing *Salmonella* or inhibiting the growth or proliferation of *Salmonella*.

12 Claims, 6 Drawing Sheets

Specification includes a Sequence Listing.

(56) References Cited

U.S. PATENT DOCUMENTS

| | | | |
|---|---|---|---|
| 10,760,075 B2 | 9/2020 | Sommer et al. | |
| 10,765,740 B2 | 9/2020 | Clube et al. | |
| 10,920,222 B2 | 2/2021 | Sommer et al. | |
| 10,953,090 B2 | 3/2021 | Clube et al. | |
| 11,141,481 B2 | 10/2021 | Clube | |
| 11,147,830 B2 | 10/2021 | Clube | |
| 11,291,723 B2 | 4/2022 | Clube | |
| 11,351,252 B2 | 6/2022 | Clube | |
| 11,400,110 B2 | 8/2022 | Clube | |
| 11,421,227 B2 | 8/2022 | Sommer et al. | |
| 11,471,530 B2 | 10/2022 | Clube | |
| 11,471,531 B2 | 10/2022 | Clube et al. | |
| 11,485,973 B2 | 11/2022 | Sommer et al. | |
| 11,517,582 B2 | 12/2022 | Clube et al. | |
| 11,547,716 B2 | 1/2023 | Clube | |
| 11,578,333 B2 | 2/2023 | Martinez et al. | |
| 2005/0163757 A1 | 7/2005 | Filutowicz | |
| 2010/0093617 A1 | 4/2010 | Barrangou | |
| 2011/0002889 A1 | 1/2011 | Barrangou | |
| 2011/0064699 A1 | 3/2011 | Appaiah et al. | |
| 2013/0011828 A1 | 1/2013 | Barrangou | |
| 2014/0199767 A1 | 7/2014 | Barrangou | |
| 2015/0004705 A1 | 1/2015 | Lu et al. | |
| 2015/0064138 A1 | 3/2015 | Lu | |
| 2015/0132263 A1 | 5/2015 | Liu et al. | |
| 2016/0024510 A1 | 1/2016 | Bikard | |
| 2016/0324938 A1 | 11/2016 | Bikard | |
| 2016/0345578 A1 | 12/2016 | Barrangou | |
| 2017/0173086 A1 | 6/2017 | Boyle et al. | |
| 2018/0084786 A1 | 3/2018 | Clube | |
| 2018/0146681 A1 | 5/2018 | Clube | |
| 2018/0200342 A1 | 7/2018 | Bikard | |
| 2018/0273940 A1 | 9/2018 | Sommer | |
| 2018/0344795 A1* | 12/2018 | Mueller ................ | A23K 50/75 |
| 2018/0371405 A1 | 12/2018 | Barrangou | |
| 2019/0021343 A1 | 1/2019 | Barrangou | |
| 2019/0230936 A1 | 8/2019 | Clube | |
| 2020/0068901 A1 | 3/2020 | Clube | |
| 2020/0077663 A1 | 3/2020 | Clube | |
| 2020/0085066 A1 | 3/2020 | Clube | |
| 2020/0102551 A1 | 4/2020 | Barrangou | |
| 2020/0115716 A1 | 4/2020 | Martinez | |
| 2020/0128832 A1 | 4/2020 | Clube | |
| 2020/0205416 A1 | 7/2020 | Clube | |
| 2020/0254035 A1 | 8/2020 | Haaber | |
| 2020/0337313 A1 | 10/2020 | Clube | |
| 2020/0354690 A1 | 11/2020 | Garofolo | |
| 2021/0060180 A1 | 3/2021 | Clube | |
| 2021/0147827 A1 | 5/2021 | Clube | |
| 2021/0163960 A1 | 6/2021 | Martinez et al. | |
| 2021/0230559 A1 | 7/2021 | Clube | |
| 2021/0283167 A1 | 9/2021 | Clube | |
| 2021/0290654 A1 | 9/2021 | Clube | |
| 2021/0386773 A1 | 12/2021 | Clube | |
| 2022/0162270 A1 | 5/2022 | Szabolcs | |
| 2022/0233575 A1 | 7/2022 | Clube et al. | |
| 2022/0241318 A1 | 8/2022 | Clube et al. | |
| 2022/0259588 A1 | 8/2022 | Sommer et al. | |
| 2022/0275380 A1 | 9/2022 | Porse | |
| 2022/0282245 A1 | 9/2022 | Sommer et al. | |
| 2022/0290133 A1 | 9/2022 | Sommer et al. | |
| 2022/0362280 A1 | 11/2022 | Clube | |
| 2022/0387559 A1 | 12/2022 | Haaber et al. | |

FOREIGN PATENT DOCUMENTS

| | | | |
|---|---|---|---|
| EP | 3630975 | A1 | 4/2020 |
| EP | 3633032 | A2 | 4/2020 |
| JP | 2017512500 | A | 9/2009 |
| JP | 2017012203 | A | 1/2017 |
| WO | 200218605 | A2 | 3/2002 |
| WO | 2009114504 | A2 | 9/2009 |
| WO | 2014124226 | A1 | 8/2014 |
| WO | 2015034872 | A2 | 3/2015 |
| WO | 2015136541 | A2 | 9/2015 |
| WO | 2015148680 | A1 | 10/2015 |
| WO | 2015155686 | A2 | 10/2015 |
| WO | 2016077453 | A1 | 5/2016 |
| WO | 2016196361 | A1 | 12/2016 |
| WO | 2016205276 | A1 | 12/2016 |
| WO | 2017058751 | A1 | 4/2017 |
| WO | 2017118598 | A1 | 7/2017 |
| WO | 2017211753 | A1 | 12/2017 |
| WO | 2018092171 | A1 | 5/2018 |
| WO | 2019002471 | A1 | 1/2019 |
| WO | 2020072248 | A1 | 4/2020 |
| WO | 2020072250 | A1 | 4/2020 |
| WO | 2020072253 | A1 | 4/2020 |
| WO | 2020072254 | A1 | 4/2020 |
| WO | 2020152369 | A1 | 7/2020 |
| WO | 2022063986 | A2 | 3/2022 |
| WO | 2022063986 | A3 | 6/2022 |

OTHER PUBLICATIONS

Percival et al. Microbiology of the skin and the role of biofilms in infection. Int Wound J. Oct. 5, 2011;9(1):14-32. (Year: 2011).*

Feighner et al. Subtherapeutic Levels of Antibiotics in Poultry Feeds and Their Effects on Weight Gain, Feed Efficiency, and Bacterial Cholyltaurine Hydrolase Activity. Appl Environ Microbiol. Feb. 1987;53(2):331-6. (Year: 1987).*

Pimentel et al. Neomycin Improves Constipation-Predominant Irritable Bowel Syndrome in a Fashion That Is Dependent on the Presence of Methane Gas: Subanalysis of a Double-Blind Randomized Controlled Study. Dig Dis Sci. Aug. 2006;51(8):1297-301. Epub Jul. 11, 2006. (Year: 2006).*

Redman et al. What is CRISPR/Cas9?. Arch Dis Child Educ Pract Ed. Apr. 8, 2016;101(4):213-215. (Year: 2016).*

May et al. *Escherichia coli* Harboring a Natural IncF Conjugative F Plasmid Develops Complex Mature Biofilms by Stimulating Synthesis of Colanic Acid and Curli. J Bacteriol. Nov. 2008;190(22):7479-90. (Year: 2008).*

*Salmonella enterica* (All Serovars). WOAH/. (accessed at: https://www.woah.org/app/uploads/2021/05/salmonella-enterica-all-serovarsinfection-with.pdf) (Year: 2021).*

Adler, H.I. et al. (1967). "Miniature *Escherichia coli* Cells Deficient in DNA," Proc. Natl. Acad. Sci. USA 57:321-326.

Bikard, D. et al. (2013, e-pub. Jun. 12, 2013). "Programmable Repression and Activation Of Bacterial Gene Expression Using an Engineered CRISPR-Cas System," Nucleic Acids Research 41(15):7429-7437.

Bikard, D. et al. (2017, e-pub. Sep. 6, 2017). "Using CRISPR-Cas Systems as Antimicrobials," Current Opinion In Microbiology 37:155-160.

Bikard, D. et al. (Aug. 16, 2012). "CRISPR Interference Can Prevent Natural Transformation and Virulence Acquisition during In Vivo Bacterial Infection," Cell Host & Microbe 12(2):177-186.

Bikard, D. et al. (Nov. 2014, e-pub. Oct. 5, 2014). "Exploiting CRISPR-Cas Nucleases to Produce Sequence-Specific Antimicrobials," Nature Biotechnology 32(11):1146-1150, 6 pages.

Carraro, N. et al. (Mar. 29, 2017). "*Salmonella* Genomic Island 1 (SGI1) Reshapes the Mating Apparatus of IncC Conjugative Plasmids to Promote Self-Propagation," PLos Gen. pp. 1-20.

Citorik, R.J. et al. (Nov. 2014, e-pub Sep. 21, 2014). "Sequence-Specific Antimicrobials Using Efficiently Delivered RNA-Guided Nucleases," Nat. Biotechnol. 32(11):1141-1145, 18 pages.

Cooper, T.F. et al. (Mar. 2000). "Transfer of Conjugative Plasmids and Bacteriophage Λ Occurs in the Presence of Antibiotics That Prevent, De Novo Gene Expression," Plasmid 43(2):171-175.

Del Solar, G. et al. (Aug. 1996). "Broad-Host-Range Plasmid Replication: An Open Question," Mol. Microbiol. 21 (4):661-666.

Deltcheva, E. et al. (Mar. 31, 2011, e-pub. Sep. 30, 2011). "CRISPR RNA Maturation by Trans-Encoded Small RNA and Host Factor RNase III," Nature 471(7340):602-607, 19 pages.

Dietrich, G. et al. (2001). "Gram-Positive and Gram-Negative Bacteria as Carrier Systems for DNA Vaccines," Vaccine 19:2506-2512.

(56) References Cited

OTHER PUBLICATIONS

Doench, J.G. et al. (Dec. 2014). "Rational Design of Highly Active sgRNAs for CRISPR-Cas9-Mediated Gene Inactivation," Nat. Biotechnol. 32(12)1262-1267, 18 pages.
EUCAST. (2013). "European Committee on Antimicrobial Susceptibility Testing. (Aug. 16, 2013). Breakpoint Tables for Interpretation of MICs and Zone Diameters," Available at: http://www.eucast.org/a, valid Feb. 2, 2013, Version 3.1, 76 pages.
Frazer, A.C. et al. (1975). "Production, Properties and Utility of Bacterial Minicells," Current Topics in Microbiology and Immunology 69:1-84.
Gagnon, J.A. et al. (May 29, 2014). "Efficient Mutagenesis by Cas9 Protein-Mediated Oligonucleotide Insertion and Large-Scale Assessment of Single-Guide RNAs," PLos One 9(5):e98186, pp. 1-8.
Gomaa, A.A. et al. (Jan. 28, 2014). "Programmable Removal Of Bacterial Strains By Use Of Genome-Targeting CRISPR-Cas Systems," mBio, 5(1):e000928-13, pp. 1-9.
Gomaa, A.A. (2016). "Sequence Specific CRISPR-Based Antimicrobials From Treating Multidrug-Resistant Infections," Dissertation to the Graduate Faculty of North Carolina State University, 188 pages.
Grillot-Courvalin, C. et al. (1999). "Bacteria as Gene Delivery Vectors for Mammalian Cells Commentary," Current Opinion in Biotech. 10:477-481.
Guiney, D.G. et al. (1989). Conjugative Transfer of IncP Plasmids, Chapter 2 in Promiscuous Plasmids in Gram- Negative Bacteria, C.M. Thomas (ed), London, Ltd. London United Kingdom, pp. 27-56.
Heineman, J.A. et al. (Feb. 1993). "Retrotransfer in *Escherichia coli* Conjugation: Bidirectional Exchange or De Novo Mating?," J. Bacteriol. 175(3):583-588.
Helinski, D.B. et al. (1996). "Replication Control and Other Stable Maintenance Mechanism of Plasmids," Chapter 122 in *Escherichia coli* and *Salmonella* Cellular and Molecular Biology, vol. 2, F. Neidhart et al. ed., ASM Press, Washington, D.C., pp. 2295-2324.
International Preliminary Report on Patentability issued on Nov. 16, 2021, for PCT Application No. PCT/EP2020/062957, filed on May 10, 2020, 6 pages.
International Search Report and Written Opinion mailed on Sep. 28, 2020, for PCT Application No. PCT/EP2020/062957, filed on May 10, 2020, 10 pages.
Jiang, W. et al. (Mar. 2013, e-pub. Jan. 29, 2013). "RNA-Guided Editing of Bacterial Genomes Using CRISPR-Cas Systems," Nature Biotechnology 31(3).233-241.
Koonin, E.V. et al. (2017, e-pub. Jun. 9, 2017). "Diversity, Classification and Evolution of CRISPR-Cas Systems," Current Opinion in Microbiology 37:67-78.
Liu, X. et al. (Jan. 27, 2016). "Sequence Features Associated With the Cleavage Efficiency of CRISPR/Cas9 System," Scientific Reports 6:19675, 1-9.
Makarova, K.S. et al. (Nov. 2015, e-pub.May 11, 2017). "An Updated Evolutionary Classification of CRISPR—Cas Systems," Nature Rev. Microbiol. 13(11):722-736, 31 pages.
Marraffini, L.A. et al. (Dec. 19, 2008). "CRISPR Interference Limits Horizontal Gene Transfer In Staphylococci By Targeting DNA," Science 322(5909):1843-1845, 12 pages.
NSAI Standards. (2007). "Microbiology of Food and Animal Feeding Stuffs- Horizontal Method for the Detection of *Salmonella* spp. In Animal Faeces and In Environmental Samples From the Primary Production Stage (ISO 6579:2002 Amd 1:2007)," NSAI Standards, Geneva, Switzerland, 62 pages.
O'Challaghan, D. et al. (Aug. 1990). "High Efficiency Transformation of *Salmonella typhimurium* and *Salmonella typhi* by Electroporation," Mol. Gen Genet. 223:156-158.
Pansegrau, W. et al. (1994). "Complete Nucleotide Sequence of Birmingham IncPα Plasmids: Compilation and Comparative Analysis," J. Mol. Biol. 239:623-663.
Phornphisutthimas, S.et al. (2007). "Laboratory Exercises. Conjugation in *Escherichia coli*," Biochem. and Mol. Bio Education 35(6):440-445.
Roberts, R. J. et al. (1996). "Rebase—Restriction Enzymes and Methylases," Nucl. Acids Res. 24(1):223-235.
Sancar A. et al. (Jan. 1979). "Simple Method for Identification of Plasmid-Coded Proteins," J. Bacteriol. 137 (1):692-693.
Sapranauskas, R. et al. (Nov. 1, 2011, e-pub. Aug. 3, 2011). "The *Streptococcus thermophilus* CRISPR/Cas System Provides Immunity In *Escherichia coli*," Nucleic Acids Research 39(21):9275-9282.
Sorek, R. et al. (2013, e-pub. Mar. 11, 2013). "CRISPR-Mediated Adaptive Immune Systems in Bacteria and Archaea," Annual Review of Biochemistry 82:237-266.
U.S. Appl. No. 16/626,035, filed Dec. 23, 2019, for Clube. (Copy not attached) (A copy of U.S. Patent Application is not submitted herewith pursuant to the waiver of 37 C.F.R. § 1.98(a)(2)(iii) issued by the Office on Sep. 21, 2004.).
U.S. Appl. No. 17/777,983, filed May 18, 2022, for Haaber et al. (Copy not attached) (A copy of U.S. Patent Application is not submitted herewith pursuant to the waiver of 37 C.F.R. § 1.98(a)(2)(iii) issued by the Office on Sep. 21, 2004.).
U.S. Appl. No. 17/931,876, filed Sep. 13, 2022, for Clube. (Copy not attached) (A copy of U.S. Patent Application is not submitted herewith pursuant to the waiver of 37 C.F.R. § 1.98(a)(2)(iii) issued by the Office on Sep. 21, 2004.).
Vercoe, R.B. et al. (Apr. 18, 2013). "Cytotoxic Chromosomal Targeting by CRISPR/Cas Systems Can Reshape Bacterial Genomes and Expel Or Remodel Pathogenicity Islands," PLOS Genetics 9(4):e1003454, 13 pages.
Westra, E.R. et al. (Jun. 8, 2012). "CRISPR Immunity Relies on the Consecutive Binding and Degradation of Negatively Supercoiled Invader DNA by Cascade and Cas3," Molecular Cell 46:595-605.
Westra, E.R. et al. (Sep. 1, 2010, e-pub. Aug. 18, 2010). "H-NS-Mediated Repression of CRISPR-Based Immunity in *Escherichia coli* K12 Can Be Relieved By The Transcription Activator LeuO," Molecular Microbiology 77 (6):1380-1393.
Westwater, C. et al. (2002). "Development of a P1 Phagemid System for the Delivery of DNA Into Gram-Negative Bacteria," Microbiology 148:943-950.
Westwater, C. et al. (Apr. 2003). "Use of Genetically Engineered Phage To Deliver Antimicrobial Agents To Bacteria: An Alternative Therapy For Treatment of Bacterial Infections," Antimicrobial Agents and Chemotherapy 47 (4):1301-1307.
Wilkins, B.M. et al. (1996). "Distribution of Restriction Enzyme Recognition Sequences on Broad Host Range Plasmid RP4: Molecular and Evolutionary Implications," J. Mol. Biol. 258:447-456.
Yosef, I. et al. (Dec. 13, 2011). "High-Temperature Protein G Is Essential For Activity Of The *Escherichia coli* Clustered Regularly Interspaced Palindromic Repeats (CRISPR)/Cas System," Proc. Natl. Acad. Sci. USA 108 (50):20136-20141.
Yosef, I. et al. (Jun. 9, 2015). "Temperate and Lytic Bacteriophages Programmed To Sensitize and Kill Antibiotic-Resistant Bacteria," Proc. Natl. Acad. Sci. USA 112(23):7267-7272.
Zatyka, M. et al. (1998). "Control of Genes for Conjugative Transfer of Plasmids and Other Mobile Elements," FEMS Microbiol. Rev. 21:291-319.
Poole, T. et al. (Aug. 1, 2009). "Conjugative Plasmid Transfer Between *Salmonella enterica* Newport and *Escherichia coli* Within the Gastrointestinal Tract of the Lesser Mealworm Beetle, *Alphitobius diaperinus* (Coleoptera: Tenebrionidae)," Poultry Science 88(8):1553-1558, 14 pages.
Chalmers, G et al. (2018, e-pub. Oct. 18, 2018). "Distribution of the pco Gene Cluster and Associated Genetic Determinants Among Swine *Escherichia coli* From a Controlled Feeding Trial," Genes 9(504):1-15.
Lee, SH. et al. (Dec. 2003). "InvB Is A Type III Secretion-Associated Chaperone for the *Salmonella enterica* Effector Protein SopE," Journal of Bacteriology 185(24):7279-7284.

* cited by examiner

ANTIBACTERIAL AGENTS AND METHODS

CROSS REFERENCE TO RELATED APPLICATIONS

This application is a national stage application under 35 U.S.C. § 371 of International Application No. PCT/EP2020/062957, filed internationally on May 10, 2020, which claims priority to European Application No. 1906668.7, filed May 12, 2019, the disclosures of each of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 238052000100SEQLIST.TXT, date recorded: Oct. 27, 2021, size: 46,448 bytes).

TECHNICAL FIELD

The invention relates to means for carrying out conjugation between bacteria, and in particular the invention relates to carrier bacteria comprising antimicrobial agents and methods of use. A carrier bacterium is capable of conjugative transfer of DNA encoding the agent to a target cell.

The invention further relates to growth or feed conversion ratio (FCR) promotion in animals. The invention further relates to killing *Salmonella* or inhibiting the growth or proliferation of *Salmonella. The invention further relates to killing Pseudomonas* or inhibiting the growth or proliferation of *Pseudomonas*, such as useful for promoting growth, dry weight, wet weight or crop production of plants.

BACKGROUND

DNA sequences controlling extra-chromosomal replication (ori) and transfer (tra) are distinct from one another; i.e., a replication sequence generally does not control plasmid transfer, or vice-versa. Replication and transfer are both complex molecular processes that make use of both plasmid- and host-encoded functions. Bacterial conjugation is the unidirectional and horizontal transmission of genetic information from one bacterium to another. The genetic material transferred may be a plasmid or it may be part of a chromosome. Bacterial cells possessing a conjugative plasmid contain a surface structure (the sex pilus) that is involved in the coupling of donor and recipient cells, and the transfer of the genetic information. Conjugation involves contact between cells, and the transfer of genetic traits can be mediated by many plasmids. Among all natural transfer mechanisms, conjugation is the most efficient. For example, F plasmid of *E. coli*, pCFlO plasmid of *Enterococcus faecalis* and pXO16 plasmid of *Bacillus thuringiensis* employ different mechanisms for the establishment of mating pairs, the sizes of mating aggregates are different, and they have different host ranges within gram-negative (F) as well as gram-positive (pCFlO and pXO16) bacteria. Their plasmid sizes are also different; 54, 100 and 200 kb, respectively. Remarkably, however, those conjugation systems have very important characteristics in common: they are able to sustain conjugative transfer in liquid medium and transfer efficiencies close to 100% are often reached in a very short time. Thus, the conjugative process permits the protection of plasmid DNA against environmental nucleases, and the very efficient delivery of plasmid DNA into a recipient cell. Conjugation functions are naturally plasmid encoded. Numerous conjugative plasmids (and transposons) are known, which can transfer associated genes within one species (narrow host range) or between many species (broad host range). Transmissible plasmids have been reported in numerous Gram-positive genera, including but not limited to pathogenic strains of *Streptococcus, Staphylococcus, Bacillus, Clostridium* and *Nocardia*. The early stages of conjugation generally differ in Gram-negative and Gram-positive bacteria. The role of some of the transfer genes in conjugative plasmids from Gram-negative bacteria are to provide pilus-mediated cell-to-cell contact, formation of a conjugation pore and related morphological functions. The pili do not appear to be involved in initiating conjugation in Gram-positive bacteria.

SUMMARY OF THE INVENTION

The invention provides:

A method (eg, a non-medical or a medical) for enhancing the growth or weight of a subject, wherein the subject comprises bacterial target cells, the method comprising administering to the subject a first episomal DNA encoding an antibacterial agent that is toxic to the target cells, wherein first DNA is transferred into target cells and the agent is expressed, thereby killing target cells in the subject or reducing the growth or proliferation of target cells and enhancing growth or weight of the subject.

In an embodiment, there is provided:

A method (eg, a non-medical or a medical) for enhancing the growth or weight of a subject, wherein the method comprises the administration of a plurality of carrier cells to the subject, wherein the subject comprises bacterial target cells and each carrier cell is a bacterial cell comprising a first episomal DNA encoding an antibacterial agent that is toxic to a target cell but is not toxic to the carrier cell, the carrier cell being capable of conjugative transfer of the DNA into a target cell for expression therein of the agent, wherein first DNA is transferred from carrier cells into target cells for expression therein to produce the antibacterial agent, thereby killing target cells in the subject or reducing the growth or proliferation of target cells and enhancing growth or weight of the subject.

Advantageously, the FCR is improved (ie, enhanced), ie, the FCR number is lowered, in the subject. When the method of the invention is carried out on a group of subjects (eg, a group of animals, such as livestock animals) the FCR is lowered in an individual in the group or the average FCR is lowered in the group. Lowering may be assessed as a comparison with FCR prior to administration of the carrier cell(s) or compared to an average for animals of the same species, age group and when fed on comparable or the same diet. The skilled addressee will be familiar with standard FCRs, such as for livestock animals, eg, piglets, pigs, sheep, cattle (dairy or meat cattle), fish, shellfish, poultry (eg, chickens (broiler or egg-layer hens), geese, ducks or turkeys).

The invention also provides:

A carrier cell, wherein the cell is a bacterial cell comprising a first episomal DNA encoding an antibacterial agent that is toxic to a bacterial target cell but is not toxic to the carrier cell, the carrier cell being capable of conjugative transfer of the DNA into a target cell for expression therein of the antibacterial agent, hereby killing the target cell, wherein the target cell is a *Salmonella* cell and the carrier cell is an Enterobacteriaceae cell.

A composition comprising a plurality of carrier cells for use in a method comprising administration of the cells to a subject to treat an infection by pathogenic bacterial target cells, wherein each carrier cell is a bacterial cell comprising a first episomal DNA encoding an antibacterial agent that is toxic to a target cell but is not toxic to the carrier cell, the carrier cell being capable of conjugative transfer of the DNA into a target cell for expression therein of the agent, wherein first DNA is transferred from carrier cells into target cells for expression therein to produce the antibacterial agent, thereby killing target cells in the subject or reducing the growth or proliferation of target cells, wherein the target cells are *Salmonella* cells and the carrier cells are Enterobacteriaceae cells.

A non-medical method of killing zoonotic bacterial target cells in an animal (optionally a livestock animal), the method comprising administering to the animal a plurality of carrier cells, wherein each carrier cell is a bacterial cell comprising a first episomal DNA encoding an antibacterial agent that is toxic to a target cell but is not toxic to the carrier cell, the carrier cell being capable of conjugative transfer of the DNA into a target cell for expression therein of the agent, wherein first DNA is transferred from carrier cells into target cells for expression therein to produce the antibacterial agent, thereby killing target cells in the subject or reducing the growth or proliferation of target cells, wherein the target cells are *Salmonella* cells and optionally the carrier cells are Enterobacteriaceae cells.

A DNA (optionally for use in the method of the invention), wherein the DNA is capable of being introduced into a target cell, wherein the DNA encodes a plurality of guide RNAs or crRNAs of a CRISPR/Cas system wherein the guide RNAs or crRNAs are operable with Cas nuclease in the target cell to recognise a plurality of protospacer sequences comprised by the target cell genome; wherein

- (a) the protospacer sequences comprise one or more pathogenic island nucleotide sequences of the target cell genome;
- (b) the protospacer sequences comprise one or more invasion gene sequences of the target cell genome;
- (c) the protospacer sequences comprise one or more secretion system gene sequences of the target cell genome; and/or
- (d) the protospacer sequences comprise one or more nucleotide sequences of genes selected from A gene selected from avrA, sptP, sicP, sipA, sipD, sipC, sipB, sicA, invB, ssaE, sseA, sseB, sscA, sseC, sseD, sseE, sscB, sseF, sseG, mgtC, cigR, pipA, pipB, pipC, sopB and pipD (optionally selected from invB, sicP, sseE, pipA, pipB, pipC, hilA, marT and sopB of *Salmonella*, and orthologues or homologues thereof.

The also invention provides the following configurations:—

In a First Configuration

A carrier bacterial cell comprising a first episomal DNA, the DNA encoding a nucleic acid sequence of interest (NSI) or encoding an antibacterial agent that is toxic to a target bacterial cell but is not toxic to the carrier cell, the carrier cell being capable of conjugative transfer of the DNA into the target cell for expression therein of the agent, optionally wherein

- (a) the carrier cell comprises a second DNA which is different from the first DNA, wherein the second DNA comprises or encodes a first factor required for replication of the first DNA;
- (b) the first DNA does not comprise or encode said first factor, wherein the first DNA is non-self-replicative in the absence of the first factor, but is able to replicate in the carrier cell in the presence of the first factor provided by the second DNA;
- (c) wherein the cell comprises genes encoding one or more conjugation factors sufficient to carry out conjugative transfer of the first DNA into a target bacterial cell.

In embodiments, the invention usefully recognizes the benefit of using antibacterial agents that act by target sequence recognition in the target cell genome but not in the carrier cell, which frees up the ability for the first DNA to be freely replicated in the carrier cell without toxicity to the carrier cell.

In a Second Configuration

A DNA encoding an NSI or encoding an antibacterial agent that is toxic to a target bacterial cell but is not toxic to a carrier cell that is capable of carrying the DNA for conjugative transfer into the target cell, wherein the first DNA does not comprise or encode a first factor required for replication of the first DNA, and wherein the first DNA is devoid of a component required for conjugative transfer of the first DNA into a target bacterial cell.

In a Third Configuration

A method for enhancing growth or weight of a human or animal subject, wherein the method comprises the administration of a plurality of carrier cells according to the invention to a microbiota of the subject, wherein the microbiota comprises target cells and first DNA is transferred from carrier cells into target cells for expression therein to produce the antibacterial agent, thereby killing target cells (eg, *Salmonella* cells) in the subject or reducing the growth or proliferation of target cells.

In a Fourth Configuration

A method for enhancing growth or weight of a plant, wherein the method comprises the administration of a plurality of carrier cells according to the invention to a microbiota of the plant, wherein the microbiota comprises target cells and first DNA is transferred from carrier cells into target cells for expression therein to produce the antibacterial agent, thereby killing target cells (eg, *Pseudomonas* cells) in the plant or reducing the growth or proliferation of target cells.

In a Fifth Configuration

A method for reducing a biofilm comprised by a subject or comprised on a surface, wherein the biofilm comprises target cells (eg, *Pseudomonas* cells), wherein the method comprises the administration of a plurality of carrier cells according to the invention to the biofilm, wherein first DNA is transferred from carrier cells into target cells for expression therein to produce the antibacterial agent, thereby killing target cells in the biofilm or reducing the growth or proliferation of target cells.

In a Sixth Configuration

A method of replicating a first DNA (eg, comprised by conjugative plasmids) to produce a plurality of copies of said DNA, the method comprising culturing a plurality of carrier bacterial cells according to the invention, wherein the first DNA is replicated in the cells; and optionally isolating a plurality of copies of the first DNA from carrier cells.

In a Seventh Configuration

A method of killing a plurality of target bacterial cells or reducing the growth or proliferation thereof, the method comprising

- (a) obtaining a sample of the carrier cells according to the invention or obtainable by the method of the sixth configuration;

(b) contacting the sample of carrier cells with the plurality of target bacterial cells to allow conjugation between carrier cells and target cells; and (c) allowing copies of first DNA to be transferred by conjugative transfer from carrier cells to target cells, wherein the antibacterial agent is provided in target cells and target cells are killed or the growth or proliferation of target cells is reduced;

(d) wherein the first DNA is not (or not substantially) replicable in the target cells.

In an Eighth Configuration

A pharmaceutical composition, livestock growth promoting composition, zoonosis control agent, biocidal agent for administration to livestock, soil improver, herbicide, plant fertilizer, food or food ingredient sterilizing composition, dental composition, personal hygiene composition or disinfectant composition (eg, for domestic or industrial use) comprising a plurality of carrier cells according to the invention.

In an Ninth Configuration

In a first aspect:—

A method of promoting the growth of an animal (eg, a livestock animal, eg, a poultry animal), the method comprising administering to the animal a guided nuclease system or a component thereof, and introducing the system or component into target bacteria comprised by the animal, wherein the guided nuclease is capable of recognising and modifying (eg, cutting) a target nucleotide sequence comprised by the target bacteria, whereby target bacteria are killed or the growth or proliferation of target bacteria are inhibited and the growth of the animal is promoted.

The method is a non-medical method and the presence of target bacteria in the animal is capable of inhibiting the growth of the animal. Thus, the method reduces the burden of such bacteria in the animal and promotes growth.

In a second aspect:—

A method of enhancing feed conversion ratio (FCR) in an animal (eg, a livestock animal, eg, a poultry animal), the method comprising administering to the animal a guided nuclease system or a component thereof, and introducing the system or component into target bacteria comprised by the animal, wherein the guided nuclease is capable of recognising and modifying (eg, cutting) a target nucleotide sequence comprised by the target bacteria, whereby target bacteria are killed or the growth or proliferation of target bacteria are inhibited and the FCR of the animal is increased.

The method is a non-medical method and the presence of target bacteria in the animal is capable of increasing the FCR of the animal. Thus, the method reduces the burden of such bacteria in the animal and enhances FCR (ie, reduces FCR number).

In a third aspect:—

A method of promoting the growth of an animal (eg, a livestock animal, eg, a poultry animal), the method comprising administering to the animal an antibacterial agent that is toxic to *Salmonella* bacteria, wherein *Salmonella* target bacteria comprised by the animal are exposed to the agent and are killed or the growth or proliferation of target bacteria are inhibited and the growth of the animal is promoted.

The method is a non-medical method and the presence of target bacteria in the animal is capable of inhibiting the growth of the animal. Thus, the method reduces the burden of such bacteria in the animal and promotes growth.

In a fourth aspect:—

A method of enhancing feed conversion ratio (FCR) in an animal (eg, a livestock animal, eg, a poultry animal), the method comprising administering to the animal an antibacterial agent that is toxic to *Salmonella* bacteria, wherein *Salmonella* target bacteria comprised by the animal are exposed to the agent and are killed or the growth or proliferation of target bacteria are inhibited and the FCR of the animal is enhanced.

The method is a non-medical method and the presence of target bacteria in the animal is capable of increasing the FCR of the animal. Thus, the method reduces the burden of such bacteria in the animal and enhances FCR (ie, reduces FCR number).

In an Tenth Configuration

In a first aspect:—

A method of promoting growth, dry weight, wet weight or crop production of a plant, the plant comprising a microbiota that comprises target bacteria, the method comprising contacting the microbiota with an antibacterial agent that is toxic to the target bacteria, wherein target bacteia are killed or the growth or proliferation of target bacteria is inhibited and the growth, dry weight, wet weight or crop production of the plant is increased.

In a second aspect:—

Use of an antibacterial agent that is toxic to target bacteria in a method wherein target bacteria comprised by a microbiota of a plant are contacted with the agent, whereby target bacteria are killed or the growth or proliferation of target bacteria is inhibited, for promoting growth, dry weight, wet weight or crop production of the plant.

In a third aspect:—

A method of increasing crop yield of a plant, the plant comprising a microbiota that comprises target bacteria, the method comprising contacting the microbiota with an antibacterial agent that is toxic to the target bacteria, wherein target bacteia are killed or the growth or proliferation of target bacteria is inhibited and the growth, dry weight, wet weight or crop production of the plant is increased.

In a fourth aspect:—

Use of an antibacterial agent that is toxic to target bacteria in a method wherein target bacteria comprised by a microbiota of a plant are contacted with the agent, whereby target bacteria are killed or the growth or proliferation of target bacteria is inhibited, for increasing crop yield of the plant.

In a fifth aspect:—

A method of increasing leaf chlorophyll of a plant, the plant comprising a microbiota that comprises target bacteria, the method comprising contacting the microbiota with an antibacterial agent that is toxic to the target bacteria, wherein target bacteia are killed or the growth or proliferation of target bacteria is inhibited and the leaf chlorophyll of the plant is increased.

In a sixth aspect:—

Use of an antibacterial agent that is toxic to target bacteria in a method wherein target bacteria comprised by a microbiota of a plant are contacted with the agent, whereby target bacteria are killed or the growth or proliferation of target bacteria is inhibited, for increasing leaf chlorophyll of the plant.

In a seventh aspect:—

A method of increasing greening of a plant, the plant comprising a microbiota that comprises target bacteria, the method comprising contacting the microbiota with an antibacterial agent that is toxic to the target bacteria, wherein target bacteia are killed or the growth or proliferation of target bacteria is inhibited and greening of the plant is increased.

In a eighth aspect:—

Use of an antibacterial agent that is toxic to target bacteria in a method wherein target bacteria comprised by a microbiota of a plant are contacted with the agent, whereby target bacteria are killed or the growth or proliferation of target bacteria is inhibited, for increasing greening of the plant.

In a ninth aspect:—

A method of decreasing a biofilm (eg, a leaf biofilm) comprised by a plant, the plant comprising a biofilm that comprises target bacteria, the method comprising contacting the microbiota with an antibacterial agent that is toxic to the target bacteria, wherein target bacteia are killed or the growth or proliferation of target bacteria is inhibited and the biofilm of the plant is decreased.

In a tenth aspect:—

Use of an antibacterial agent that is toxic to target bacteria in a method wherein target bacteria comprised by a biofilm (eg, a leaf biofilm) of a plant are contacted with the agent, whereby target bacteria are killed or the growth or proliferation of target bacteria is inhibited, for inhibiting the biofilm of the plant.

Optionally, the target bacteria are *Pseudomonas* bacteria, such as *P. syringae* or *P. aeruginosa* bacteria or any other *Pseudomonas* bacteria disclosed herein.

Optionally, the agent is a guided nuclease system or a component thereof, eg, any such system or component disclosed herein for modifying (eg, cutting) a target nucleic acid sequence comprised by target bacteria.

Optionally, the plant is any plant disclosed herein.

Optionally, the chlorophyll is a chlorophyll a and/or chlorophyll b.

Optionally, the agent is comprised by a carrier cell of the present invention and said contacting comprises contacting the cell with the carrier cell.

DETAILED DESCRIPTION

Figure 1:
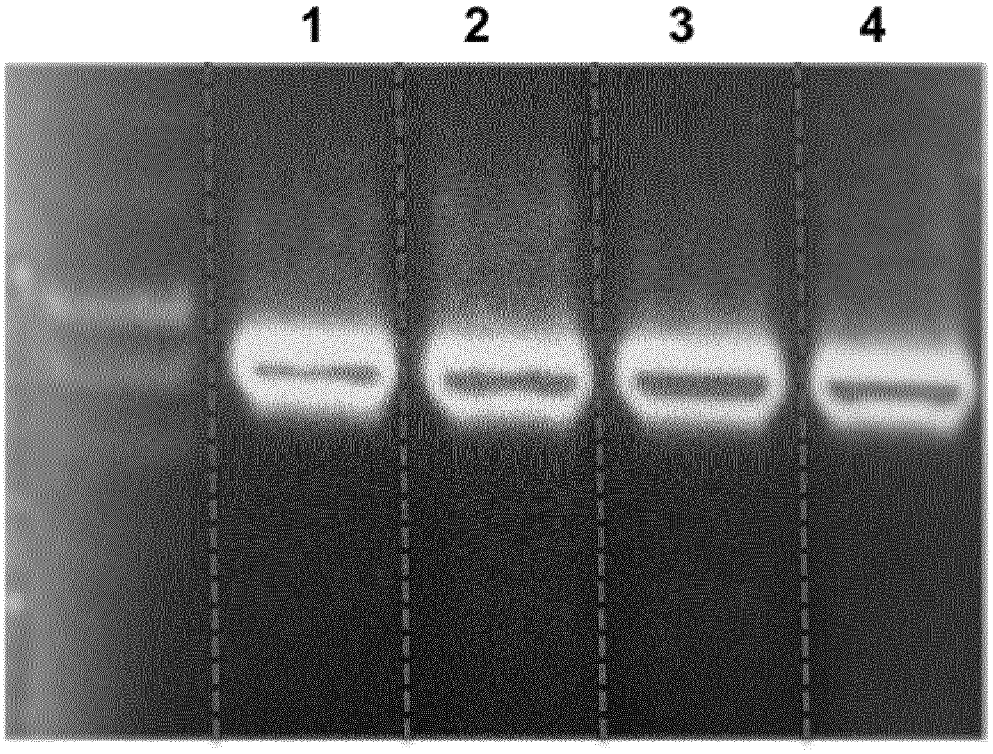
FIG. 1. PCRs performed on recipient colonies. From the left to the right: 1) Plasmid pFSMobC* (control). 2) Plasmid pFSMobC* in S17 (control). 3) Colony from transconjugants plate (Cm30+Nal25). 4) Colony n° 2 from transconjugants plate (Cm30+ Nal25)

The invention relates to means for carrying out conjugation between bacteria, and in particular the invention relates to carrier bacteria comprising antimicrobial agents and methods of use. A carrier bacterium is capable of conjugative transfer of DNA encoding the agent to a target cell.

The invention further relates to growth, weight or feed conversion ratio (FCR) promotion in animals.

The invention further relates to killing *Salmonella* or inhibiting the growth or proliferation of *Salmonella.*

Thus, there is provided:

A method (eg, a non-medical or a medical) for enhancing the growth or weight of a subject, wherein the subject comprises bacterial target cells, the method comprising administering to the subject a first episomal DNA encoding an antibacterial agent that is toxic to the target cells, wherein first DNA is transferred into target cells and the agent is expressed, thereby killing target cells in the subject or reducing the growth or proliferation of target cells and enhancing growth or weight of the subject.

Advantageously, the FCR is enhanced in the subject. Optionally, the FCR is enhanced (ie, lowered) by at least 1, 2, 3, 4, 5, 6, 7, 8, 9 or 10%, eg from 2 to 6% or from 2 to 5% (such as 2, 3, 4, 5 or 6%) compared to the FCR of the subject prior to administration of the agent or carrier cells. Optionally, the FCR is enhanced by at least 1, 2, 3, 4, 5, 6, 7, 8, 9 or 10%, eg from 2-5% (such as 2, 3, 4, or 5%) compared to the FCR of a control subject of the same species and sex that has not received administration of the agent or carrier cells. In an embodiment, the subject is a bird, poultry bird, chicken, turkey, goose or duck (preferably a chicken) and the FCR number is lowered by an amount from 0.03 to 0.07, eg, from 0.04 to 0.06, eg, 0.04, 0.05 or 0.06. Thus, for example, compared to a control bird, the FCR of the control bird is 1.7 (g feed/g bird) and after a subject bird that has been treated using the invention has a FCR of 1.64 to 1.66. The control bird (eg, chicken) of the same species, sex and age as the subject of the invention and fed on the same diet (feed), but does not receive the treatment of the invention. The birds may be from the same flock. In an embodiment, therefore, a bird (eg, chicken) has a FCR of 1.64 to 1.66, wherein the subject has been treated by the method of the invention.

In an example, the method is carried out on a group of subjects (eg, subjects of the same species, such as a group of livestock animals, eg, a poultry flock or herd of cattle or sheep). In this example, the average FCR of the group is enhanced by the method (ie, the FCR number is lowered) compared to a control group of animals of the same species, subspecies or type, or compared to the average FCR of the group prior to treatment with the method. A control group may be a group of animals of the same species, with the same average age, same proportion of males and females and fed on the same diet as the group of the invention. For example, the group of the invention and control group are both poultry (eg, chicken) flocks, eg, with common ancestry one or two or three generations back. The flock may be a flock of broiler chickens or hen-layer hens. For example, the group of the invention and control group are both beef cattle herds, or dairy herds, eg, with common ancestry one or two or three generations back.

FCR, FE & ECI

In animal husbandry, feed conversion ratio (FCR) is a ratio measuring the efficiency with which the bodies of livestock convert animal feed into the desired output. For dairy cows, for example, the output is milk, whereas in animals raised for meat (such as beef cows, pigs, chickens, and fish) the output is the flesh, that is, the body mass gained by the animal, represented either in the final mass of the animal or the mass of the dressed output. FCR is the mass of the input divided by the output (thus mass of feed per mass of milk or meat). In some sectors, Feed Efficiency (FE), which is the output divided by the input (i.e. the inverse of FCR), is used. These concepts are also closely related to efficiency of conversion of ingested foods (ECI). FCR is widely used in swine and poultry production, while FE is used more commonly with cattle. Being a ratio the FCR is dimensionless, that is, it is not affected by the units of measurement used to determine the FCR. Animals that have a low FCR are considered efficient users of feed.

Preferably, the enhancement produced by the invention is an increase in body mass of the subject. Instead of enhancement of FCR, the invention may be a method for enhancing Feed Efficiency (FE) in the subject, or enhancing the Efficiency of Conversion of Ingested Foods (ECI) in the subject.

FCR may be calculated using feed dry mass, or may be calculated on an as-fed wet mass basis.

In an embodiment, the FCR, FE or ECI number is changed by 0.2, 0.5, 1, 1.5 or 2. For example, the FCR is reduced by 1, 1.5 or 2.

Conversion Ratios for Livestock

Beef Cattle

As of 2013 in the US, an FCR calculated on live weight gain of 4.5-7.5 was in the normal range with an FCR above 6 being typical. Thus, in an example of the invention the or each animal is a beef cow and the FCR number in the animal (or average FCR of the animals) is reduced by the method to below 6 (calculated using live weight of the animal), eg, below 5.5, 5, 4.5, 4 or 3.5 (optionally, said FCR or average FCR is reduced to an FCR from 3.5 to 5.9, eg, from 4 to 5.5.

Dairy Cattle

In the US, the price of milk is based on the protein and fat content, so the FCR is often calculated to take that into account. Using an FCR calculated just on the weight of protein and fat in milk obtained from the animal(s), as of 2011 an FCR of 13 was poor, and an FCR of 8 was very good. Thus, in an example of the invention the or each animal is a dairy cow and the FCR number in the animal (or average FCR of the animals) is reduced by the method to below 11, 10, 9 or 8, (and optionally greater than 5 or 6) wherein the FCR is the FCR of milk obtained from the animal(s) that have been treated by the method of the invention, the FCR being calculated using the combined weight of protein and fat in the milk.

Another method for dealing with pricing based on protein and fat, is using energy-corrected milk (ECM), which adds a factor to normalize assuming certain amounts of fat and protein in a final milk product; that formula is (0.327×milk mass)+(12.95×fat mass)+(7.2×protein mass). In the dairy industry, Feed Efficiency (ECM/intake) is often used instead of FCR (intake/ECM); an FE less than 1.3 is considered problematic. Thus, in an example of the invention the or each animal is a dairy cow and the FE number in the animal (or average FE of the animals) is increased by the method to above 1.3, 1.5, 1.6, 1.7, 1.8, 1.9, 2, 2.5 or 3, (and optionally no greater than 4 or 5). Optionally, the FE is increased above 1.3, 1.5, 1.6 and no greater than 1.7.

FE based simply on the weight of milk is also used; an FE between 1.30 and 1.70 is normal. Thus, in an example of the invention the or each animal is a dairy cow and the FE number in the animal (or average FE of the animals) is increased by the method to above 1.3, 1.5, 1.6, 1.7, 1.8, 1.9, 2, 2.5 or 3, (and optionally no greater than 4 or 5). Optionally, the FE is increased above 1.3, 1.5, 1.6 and no greater than 1.7.

Pigs

As of 2011, pigs used commercially in the UK and Europe had an FCR, calculated using weight gain, of about 1 as piglets and ending about 3 at time of slaughter. As of 2012 in Australia and using dressed weight for the output, a FCR calculated using weight of dressed meat of 4.5 was fair, 4.0 was considered "good", and 3.8, "very good". In the US as of 2012, commercial pigs had FCR calculated using weight gain, of 3.46 for while they weighed between 240 and 250 pounds, 3.65 between 250 and 260 pounds, 3.87 between 260 and 270 lbs, and 4.09 between 280 and 270 lbs. Thus, in an example of the invention the or each animal is a piglet and the FCR number in the animal (or average FCR of the animals) is reduced by the method to 1 or less, the FCR being calculated using weight gain of the animal(s). Thus, in an example of the invention the or each animal is a pig up to 3 months old and the FCR number in the animal (or average FCR of the animals) is reduced by the method to 1 or less, the FCR being calculated using weight gain of the animal(s). Thus, in an example of the invention the or each animal is a pig greater than 3 months old, but up to 6 or 7 months' old, and the FCR number in the animal (or average FCR of the animals) is reduced by the method to 3 or less (eg, from 1 to 3), the FCR being calculated using weight gain of the animal(s). A piglet may be from 1.5 to 3 months' of age; a pig for slaughter may be greater than 3, but up to 6 months' of age. Thus, in an example of the invention the or each animal is a pig whose weight is between 240 and 250 pounds and the FCR number in the animal (or average FCR of the animals) is reduced by the method to 3.5 or less (eg, 3.4 or less, but optionally no less than 3 or 2.5), the FCR being calculated using weight gain of the animal(s). Thus, in an example of the invention the or each animal is a pig whose weight is between 250 and 260 pounds and the FCR number in the animal (or average FCR of the animals) is reduced by the method to 3.7 or less (eg, 3.65 or less, but optionally no less than 3 or 3.5), the FCR being calculated using weight gain of the animal(s). Thus, in an example of the invention the or each animal is a pig whose weight is between 260 and 270 pounds and the FCR number in the animal (or average FCR of the animals) is reduced by the method to 3.9 or less (eg, 3.8 or less, but optionally no less than 3.7 or 3.5), the FCR being calculated using weight gain of the animal(s). Thus, in an example of the invention the or each animal is a pig whose weight is between 280 and 270 pounds and the FCR number in the animal (or average FCR of the animals) is reduced by the method to 4.1 or less (eg, 4 or less, but optionally no less than 3.8 or 3.9), the FCR being calculated using weight gain of the animal(s).

Sheep

Some data for sheep illustrate variations in FCR. A FCR (kg feed dry matter intake per kg live mass gain) for lambs is often in the range of about 4 to 6. Thus, in an example of the invention the or each animal is a sheep and the FCR number in the animal (or average FCR of the animals) is reduced by the method to 6 or less (eg, from 4 to 6), the FCR being calculated using kg feed dry matter intake per kg live mass gain of the animal(s).

Poultry

As of 2011 in the US, broiler chickens typically have an FCR of 1.6 based on body weight gain, and mature in 39 days. At around the same time the FCR based on weight gain for broilers in Brazil was 1.8. Thus, in an example of the invention the or each animal is a poultry bird (eg, a broiler chicken) and the FCR number in the animal (or average FCR of the animals) is reduced by the method to 1.9, 1.8, 1.7, 1.6 or less (eg, from 1.9 to 1.5; or 1.8 to 1.6), the FCR being calculated based on body weight gain. Optionally, the FCR is calculated when each animal is 35-40, eg, 39 days old.

For hens used in egg production in the US, as of 2011 the FCR was about 2, with each hen laying about 330 eggs per year. Thus, in an example of the invention the or each animal is a poultry bird (eg, an egg-laying hen, eg, a chicken) and the FCR number in the animal (or average FCR of the animals) is reduced by the method to 2 or less (eg, from 2 to 1.5), the FCR being calculated based on body weight gain. Thus, in an example of the invention the or each animal is a poultry bird (eg, an egg-laying hen, eg, a chicken) and the number of eggs layed by the animal (or average number of eggs layed by the animals) is more than 330 eggs per year (or pro rated for a different period), eg, more than 340, 350 or 400 eggs per year (or pro rated period).

Carnivorous Fish

The FIFO ratio (or Fish In-Fish Out ratio) is a conversion ratio applied to aquaculture, where the first number is the mass of harvested fish used to feed farmed fish, and the second number is the mass of the resulting farmed fish. FIFO is a way of expressing the contribution from harvested wild fish used in aquafeed compared with the amount of edible farmed fish, as a ratio. Fishmeal and fish oil inclusion rates in aquafeeds have shown a continual decline over time as aquaculture grows and more feed is produced, but with a finite annual supply of fishmeal and fish oil. Calculations have shown that the overall fed aquaculture FIFO declined from 0.63 in 2000 to 0.33 in 2010, and 0.22 in 2015. In 2015, approximately 4.55 kg of farmed fish was produced for every 1 kg of wild fish harvested and used in feed. The fish used in fishmeal and fish oil production are not used for human consumption, but with their use as fishmeal and fish oil in aquafeed they contribute to global food production. Thus, in an example the method of the invention enhances (ie, increases) the FIFO ratio when the animal if a fish (eg, a salmon, tilapia or catfish). For example, the FIFO is increased to 0.3, 0.4, 0.5, 0.6, 0.7 or 0.8, 1, 1.5 or 2 or more. For example, the fish is a salmon or catfish and the FIFO is raised above 1, 1.5 or 2 (and optionally no more than 2 or 2.5). For example, the fish is a talapia and the FIFO is raised above 1.5 or 2 (and optionally no more than 2 or 2.5).

Enhancement of growth or weight may be an enhancement (increase) in milk production or yield, eg, an average increase for a group of the invention compared with a control group. A control group may be a group of animals of the same species, with the same average age, same proportion of males and females and fed on the same diet as the group of the invention. For example, here the subjects may be dairy cattle.

Enhancement of growth or weight may be an enhancement (increase) in egg production or yield, eg, an average increase for a group of the invention compared with a control group. A control group may be a group of animals of the same species, with the same average age, same proportion of males and females and fed on the same diet as the group of the invention. For example, here the subjects may be hen-layer chickens.

Enhancement of growth or weight may be an enhancement (increase) in meat production or yield, eg, an average increase for a group of the invention compared with a control group. A control group may be a group of animals of the same species, with the same average age, same proportion of males and females and fed on the same diet as the group of the invention. For example, here the subjects may be dairy cattle, poultry (eg, chickens), fish, shellfish, sheep or pigs.

Enhancement of growth or weight may be an enhancement (increase) in fat production or yield, eg, an average increase for a group of the invention compared with a control group. A control group may be a group of animals of the same species, with the same average age, same proportion of males and females and fed on the same diet as the group of the invention. For example, here the subjects may be dairy cattle, poultry (eg, chickens), fish (eg, salmon, talapia or catfish), shellfish, sheep or pigs.

Enhancement of growth or weight may be an enhancement (increase) in fur or hide production or yield, eg, an average increase for a group of the invention compared with a control group. A control group may be a group of animals of the same species, with the same average age, same proportion of males and females and fed on the same diet as the group of the invention. For example, here the subjects may be cows.

In an example, the subject is a shellfish. The shellfish may be selected from Shrimp, crayfish, crab, lobster, clam, scallop, oyster, prawn and mussel.

The subject may be any subject disclosed herein. The subject may be an animal, such as a livestock animal, eg, a bird (such as a poultry bird; or a chicken or a turkey) or swine. Alternatively, the subject may be a human, eg, a human suffering from an eating disorder (such as anorexia) or who is underweight, eg, wherein the human has a body mass index (BMI) less than 18.5, 18, 17, 16 or 15.

For example, the human has mild anorexia (ie, the human has a BMI<17.5), moderate anorexia (ie, the human has a BMI of from 16 to 16.99), severe anorexia (ie, the human has a BMI of from 15 to 15.99) or extreme anorexia (ie, the human has a BMI<15).

In an alternative, the subject is a plant, eg, and the target bacteria are plant pathogen bacteria. In an example, the target baceteria are *Pseudomonas*, eg, *P. syringae* or *P. aeruginosa.*

In an alternative, the target cells are archaeal cells. For example the target cells are *methanobacterium* cells.

For example the target cells are methanogen cells. For example, the target cells comprise one or more species of cell selected from:

*Methanobacterium bryantii*
*Methanobacterium formicum*
*Methanobrevibacter arboriphilicus*
*Methanobrevibacter gottschalkii*
*Methanobrevibacter ruminantium*
*Methanobrevibacter smithii*
*Methanococcus chunghsingensis*
*Methanococcus burtonii*
*Methanococcus aeolicus*
*Methanococcus deltae*
*Methanococcus jannaschii*
*Methanococcus maripaludis*
*Methanococcus vannielii*
*Methanocorpusculum labreanum*
*Methanoculleus bourgensis* (*Methanogenium olentangyi* & *Methanogenium bourgense*)
*Methanoculleus marisnigri*
*Methanoflorens stordalenmirensis*[34]
*Methanofollis liminatans*
*Methanogenium cariaci*
*Methanogenium frigidum*
*Methanogenium* organophilum
*Methanogenium wolfei*
*Methanomicrobium mobile*
*Methanopyrus kandleri*
*Methanoregula boonei*
*Methanosaeta concilii*
*Methanosaeta thermophila*
*Methanosarcina acetivorans*
*Methanosarcina barkeri*
*Methanosarcina mazei*
*Methanosphaera stadtmanae*
*Methanospirillium hungatei*
*Methanothermobacter defluvii* (*Methanobacterium defluvii*)
*Methanothermobacter thermautotrophicus* (*Methanobacterium thermoautotrophicum*)
*Methanothermobacter thermoflexus* (*Methanobacterium thermoflexum*)
*Methanothermobacter wolfei* (*Methanobacterium wolfei*)
*Methanothrix sochngenii*

Optionally, the target cells are not pathogenic to the subject, for example when the method is a non-medical method. In an example, the method is a cosmetic method.

For example the target cells are methane-producing cells, and optionally the subject is a livestock animal, preferably a ruminant, or a cow (eg, a beef or dairy cattle). By reducing methane-producing cells in such animal, the invention may in one embodiment enhance the weight of the animal (eg, enhance the yield of meat from the animal) and/or enhance the yield of milk or another product of the animal, such as fur or fat.

In an example, the target cells are selected from *E. coli, Salmonella* and *Campylobacter* cells. In an example, the target cells are *E. coli, Salmonella* or *Campylobacter* cells. In an example, each animal is a chicken (eg, a broiler or hen-layer) and the target cells are *Salmonella* or *Campylobacter* cells. In an example, each animal is a cow (eg, a beef or dairy cow) and the target cells are mehanogen cells.

In an example, the target cells are selected from *Mycoplasma* (eg, *Mycoplasma mycoides* (eg, *Mycoplasma mycoides* subsp. *Mycoides*), *Mycoplasma leachii* or *Mycoplasma bovis*), *Brucella abortus, Listeria monocytogenes, Clostridium* (eg, *Clostridium chauvoei* or *Clostridium septicum*), *Leptospira* (eg, *L. canicola, L. icterohaemorrhagiae, L. grippotyphosa, L. hardjo or L. Pomona*), *Mannheimia haemolytica, Trueperella pyogenes, Mycobacterium bovis, Campylobacter* spp. (eg, *Campylobacter jejuni* or *Campylobacter coli*), *Bacillus anthracis, E. coli* (eg, *E. coli* O157:H7) or *Pasteurella multocida* (eg, *Pasteurella multocida* B:2, E:2, A:1 or A:3). In the example, optionally the subject or animal is a livestock animal, such as a cow, sheep, goat or chicken (preferably a cow).

Optionally, eg, wherein the subject is an animal (eg, a livestock animal or a wild animal), the target cells are zoonotic bacterial cells, such as cells of a species selected from *Bacillus anthracis, Mycobacterium bovis* (eg, wherein the animal is a cow), *Campylobacter* spp (eg, wherein the animal is a poultry animal), *Mycobacterium marinum* (eg, wherein the animal is a fish), Shiga toxin-producing *E. Coli* (eg, wherein the animal is a ruminant), *Listeria* spp (eg, wherein the animal is a cow or sheep), *Chlamydia abortus* (eg, wherein the animal is a sheep), *Coxiella burnetii* (eg, wherein the animal is a cow, sheep or goat), *Salmonella* spp (eg, wherein the animal is a poultry animal), *Streptococcus suis* (eg, wherein the animal is a pig) and *Corynebacterium* (eg, *C. ulcerans*) (eg, wherein the animal is a cow).

In an example, a plurality of carrier cells as described herein (eg, carrier cells of any configuration, aspect, example or embodiment described herein) is administered to the subject, wherein the carrier cells comprise the DNA encoding the agent.

In an example, each animal is a chicken (eg, a broiler or hen-layer) and the target cells are *Salmonella* or *Campylobacter* cells. In an example, each animal is a cow (eg, a beef or dairy cow) and the target cells are mehanogen cells.

In an embodiment, therefore, there is provided:

A method (eg, a non-medical or a medical) for enhancing the growth or weight of a subject, wherein the method comprises the administration of a plurality of carrier cells to the subject, wherein the subject comprises bacterial target cells and each carrier cell is a bacterial cell comprising a first episomal DNA encoding an antibacterial agent that is toxic to a target cell but is not toxic to the carrier cell, the carrier cell being capable of conjugative transfer of the DNA into a target cell for expression therein of the agent, wherein first DNA is transferred from carrier cells into target cells for expression therein to produce the antibacterial agent, thereby killing target cells in the subject or reducing the growth or proliferation of target cells and enhancing growth or weight of the subject.

Optionally, the target cells are *Salmonella* cells. In an example, the target cells comprise *S. enterica* and/or *S. typhimurium* cells; optionally wherein the *S. enterica* is *S. enterica* subspecies *enterica. Optionally, the method kills a plurality of different S. enterica* subspecies *enterica* serovars; optionally wherein each serovar is selected from the group consisting of *Typhimurium, Enteritidis*, Virchow, Montevideo, Heidelberg, Hadar, Binza, Bredeney, *Infantis*, Kentucky, Seftenberg, Mbandaka, Anatum, Agona and Dublin. Optionally, the method kills *S. enterica* subspecies *enterica* serovars *Typhimurium, Infantis* and *Enteritidis*. Optionally, the method kills *S. enterica* subspecies *enterica* serovars *Typhimurium* and *Enteritidis*. Optionally, the method kills *S. enterica* subspecies *enterica* serovars *Typhimurium* and *Infantis*. Optionally, the method kills *S. enterica* subspecies *enterica* serovars *Enteritidis* and *Infantis*. The most prevalent serovars in chicken are *Salmonella Enteritidis, Salmonella Infantis* and *Salmonella Typhimurium*. In general, similar serovars of *Salmonella* are found in infected humans and chicken (*S. Enteritidis* and *S. Typhimurium*). By killing *Salmonella* in livestock animals, the invention is useful for reducing the pool of zoonotic bacteria that are available for transmission to humans (such as by eating the livestock or products made thereofrom, such as meat or dairy products for human consumption).

Advantageously, the carrier cells are Enterobacteriaceae cells, optionally *E. coli* cells. As exemplified by the Examples below, the inventors have surprisingly found that (i) antibacterial agents can be efficiently transferred from such cells to *Salmonella* target cells both in vivo and in vitro; and (ii) 100% killing of *Salmonella* was possible when the agent is transferred by conjugation from Enterobacteriacae cells to *Salmonella* cells. Furthermore, surprisingly DNA encoding a guided nuclease antibacterial was capable of killing 18 *Salmonella* spp. Serotypes, including the clinically- and zoonotically-important *Typhimurium, Infantis* and *Enteritidis*. Optionally, the method kills *S enterica* subspecies *enterica* serovars *Typhimurium* and *Enteritidis* serovars. Optionally, the Enterobacteriaciae cells are cells of an Enterobacteriaciae species shown in Table 5.

Importantly, reduction of target cells was observed in the GI tract of the subject. Thus, optionally the method reduces target cells in the gastrointestinal tract of the animal; optionally the method reduces target cells in the jejunum, ileum, colon, liver, spleen or caecum of the animal; optionally wherein the animal is a bird and the method reduces target cells in the caecum of the bird. This may be important to reduce spread of zoonotic or other deteremental target strains in the faeces of the subjects, such as livestock animals. Thus, in an example the method is carried out on a group of subjects (eg, a herd or flock, such as a herd of swine or a flock of birds), wherein spread of cells of the target species is reduced in the group. The inventors have also demonstrated this in a flock of poultry where *Salmonella* were killed using the invention, wherein a guided nuclease was used to cut a plurality of protospacer sequences in target cells, thereby killing the cells and reducing spread thereof in the flock.

Thus, in an example the method is carried out on a group (optionally a flock or herd) of animals, wherein some or all of the animals comprise target cells, wherein spread of cells of the target species is reduced in the group; or wherein spread is reduced from the group to a second group of animals.

Optionally, the first DNA is comprised by a plasmid, for example wherein the plasmid comprises a RP4 origin of transfer (oriT). The plasmid may be any type of plasmid disclosed herein.

The agent may be any antibacterial agent disclosed herein, preferably a guided nuclease that is programmed to cut one or more target sequences in target cells. A suitable nuclease may be a TALEN, meganuclease, zinc finger nuclease or Cas nuclease. For example, the agent comprises one or more components (eg, a Cas nuclease and/or a guide RNA or a crRNA) of a CRISPR/Cas system that is operable in a target cell to cut a protospacer sequence comprised by the target cell, optionally wherein the target cells comprise first and second strains of a bacterial species and each strain comprises the protospacer sequence, wherein cells of the strains are killed. For example, the system is operable to cut at least 3 different protospacer sequences comprised by the cell genome. Optionally, each or some of said protospacer sequences is comprised by a pathogenicity island that is comprised by the cell. As shown in the Examples, this is highly effective for target cell killing. Optionally, the agent is operable to cut a plurality of different protospacer sequences comprised by the target cell genome. Optionally, the agent comprises one or more components of a CRISPR/Cas system that is operable in a target cell to cut at least 2, 3, 4, 5, 6, 7, 8, 9, or 10 different protospacer sequences comprised by the target cell genome (eg, comprised by the target cell chromosome).

In an embodiment, the agent (a) comprises a guided nuclease that is capable of recognising and modifying a target nucleic acid sequence, wherein the target sequence is comprised by an endogenous chromosome or episome of the target cells but is not comprised by the carrier cells, wherein the nuclease modifies the chromosome or episome to kill the target cells or inhibit the growth or proliferation of the target cells; and/or (b) encodes a guide RNA or crRNA of a CRISPR/Cas system that operates with a Cas nuclease in the target cells to cut a protospacer sequence comprised by the target cells.

There is also provided:

A carrier cell (optionally for use in a method of the invention), wherein the cell is a bacterial cell comprising a first episomal DNA encoding an antibacterial agent that is toxic to a bacterial target cell but is not toxic to the carrier cell, the carrier cell being capable of conjugative transfer of the DNA into a target cell for expression therein of the antibacterial agent, hereby killing the target cell, wherein the target cell is a *Salmonella* cell and the carrier cell is an Enterobacteriaceae cell.

There is also provided:

A composition comprising a plurality of carrier cells for use in a method comprising administration of the cells to a subject to treat an infection by pathogenic bacterial target cells, wherein each carrier cell is a bacterial cell comprising a first episomal DNA encoding an antibacterial agent that is toxic to a target cell but is not toxic to the carrier cell, the carrier cell being capable of conjugative transfer of the DNA into a target cell for expression therein of the agent, wherein first DNA is transferred from carrier cells into target cells for expression therein to produce the antibacterial agent, thereby killing target cells in the subject or reducing the growth or proliferation of target cells, wherein the target cells are *Salmonella* cells and the carrier cells are Enterobacteriaceae cells. In an alternative, the method treats or reduces a symptom of an infection by pathogenic target cells.

Any administration of cells to a subject herein may be by oral administration. Any administration of cells to a subject herein may preferably be by administration to the GI tract. Any administration of cells to a subject herein may be by systemic, intranasal or inhaled administration.

There is also provided:

A non-medical method of killing zoonotic bacterial target cells in an animal, the method comprising administering to the animal a plurality of carrier cells, wherein each carrier cell is a bacterial cell comprising a first episomal DNA encoding an antibacterial agent that is toxic to a target cell but is not toxic to the carrier cell, the carrier cell being capable of conjugative transfer of the DNA into a target cell for expression therein of the agent, wherein first DNA is transferred from carrier cells into target cells for expression therein to produce the antibacterial agent, thereby killing target cells in the subject or reducing the growth or proliferation of target cells, wherein the target cells are *Salmonella* cells and optionally the carrier cells are Enterobacteriaceae cells.

The animal may be any animal disclosed herein, eg, a livestock animal, domesticated animal or wild animal (eg, a bat or bird)).

Optionally, any method herein reduces *Salmonella* in the gastrointestinal tract of the subject.

Optionally, the target cells comprise different *Salmonella* spp. types that are killed.

In any aspect, configuration, example, concept or embodiment, the carrier cell, target cell(s) or DNA is respectively a carrier cell, target cell(s) or DNA as defined in any other aspect, configuration, example, concept or embodiment.

The invention also provides:

A DNA, wherein the DNA is capable of being introduced into a target cell, wherein the DNA encodes a plurality of guide RNAs or crRNAs of a CRISPR/Cas system wherein the guide RNAs or crRNAs are operable with Cas nuclease in the target cell to recognise a plurality of protospacer sequences comprised by the target cell genome, optionally wherein the target cell is a *Salmonella* cell or a cell of a species disclosed in Table 5; and (a) the protospacer sequences comprise one or more pathogenic island nucleotide sequences of the target cell genome;

(b) the protospacer sequences comprise one or more invasion gene sequences of the target cell genome;

(c) the protospacer sequences comprise one or more secretion system gene sequences of the target cell genome; and/or (d) the protospacer sequences comprise one or more nucleotide sequences of genes selected from avrA, sptP, sicP, sipA, sipD, sipC, sipB, sicA, invB, ssaE, sseA, sseB, sscA, sseC, sseD, sseE, sscB, sseF, sseG, mgtC, cigR, pipA, pipB, pipC, sopB and pipD (optionally selected from invB, sicP, sseE, pipA, pipB, pipC, hilA, marT and sopB) of *Salmonella* (eg, *S. enterica*) or orthologues or homologues of said genes.

Homologue: A gene, nucleotide or protein sequence related to a second gene, nucleotide or protein sequence by descent from a common ancestral DNA or protein sequence. The term, homologue, may apply to the relationship between genes separated by the event of or to the relationship between genes separated by the event of genetic duplication.

Orthologue: Orthologues are genes, nucleotide or protein sequences in different species that evolved from a common ancestral gene, nucleotide or protein sequence by speciation. Normally, orthologues retain the same function in the course of evolution.

By "orthologues or homologues of said genes" it is meant that a protospacer may be a sequence comprised by a gene of the target cell genome, wherein the gene is an orthologue or homologue of a *Salmonella* gene selected from avrA, sptP, sicP, sipA, sipD, sipC, sipB, sicA, invB, ssaE, sseA, sseB, sscA, sseC, sseD, sseE, sscB, sseF, sseG, mgtC, cigR, pipA, pipB, pipC, sopB and pipD (optionally selected from invB, sicP, sseE, pipA, pipB, pipC, hilA, marT and sopB).

Optionally the DNA is the first DNA for use in the method of the invention. Preferably, the target cell is a *Salmonella* cell, eg, a *S. enterica* cell, such as a *Salmonella enterica* subsp. *enterica* serovar *Enteritidis* cell.

Optionally any *Salmonella* herein is *Salmonella enterica* subsp. *enterica* serovar *Typhimurium* str. LT2.

Optionally, the target cell is a cell of a species disclosed in Table 5 other than a *Salmonella* species and the sequences of (d) are sequences of genes selected from orthologues or homologues of avrA, sptP, sicP, sipA, sipD, sipC, sipB, sicA, invB, ssaE, sseA, sseB, sscA, sseC, sseD, sseE, sscB, sseF, sseG, mgtC, cigR, pipA, pipB, pipC, sopB and pipD (optionally selected from invB, sicP, sseE, pipA, pipB, pipC, hilA, marT and sopB).

of *Salmonella* (eg, *S. enterica*).

The DNA may comprise one or more CRISPR spacers, wherein each spacer consists of a nucleotide sequence of a secretion system gene (optionally a type III protein secretion system or a secretion system of SPI-1 or SPI-2 of *Salmonella*); or a T3SS locus gene; or with up to 10, 9, 8, 7, 6, 5, 4, 3 or 2 nucleotide differences therefrom.

Optionally, the DNA (eg, DNA of the carrier cell) encodes a plurality of guide RNAs or crRNAs of a CRISPR/Cas system wherein the guide RNAs or crRNAs are operable with Cas nuclease in the target cell to recognise a plurality of protospacer sequences comprised by the target cell genome, wherein the target cell is a *Salmonella* cell and the protospacer sequences comprise one or more nucleotide sequences of genes selected from invB, sicP and sseE. For example, the protospacer sequences comprise nucleotide sequences of genes invB, sicP and sseE. In an example, the DNA also encodes a Cas, eg, a Cas9, Cas3, Cpf1, Cas12, Cas13, CasX or CasY. In an embodiment, the Cas is a Type I, II, III, IV, V or VI Cas, preferably a Type I or II Cas. In an example, the DNA also encodes a Cas3 and cognate Cascade proteins (eg, CasA, B, C, D and E). Optionally, the Cas (and Cascade of present) are *E. coli* Cas (and Cascade).

Optionally, the gene of the target cell encodes a chaperone or secreted effector protein, eg, such a protein encoded by a pathogenicity island or type III protein secretion system (optionally a T3SS locus, such as a secretion system of SPI-1 and SPI-2 of *Salmonella*).

The DNA may comprise one or more CRISPR spacers, wherein each spacer consists of 20-40, 25-35, or 30-35 consecutive nucleotides of a gene comprised by the genome of the target cell; eg, (a) a gene selected from avrA, sptP, sicP, sipA, sipD, sipC, sipB, sicA, invB, ssaE, sseA, sseB, sscA, sseC, sseD, sseE, sscB, sseF, sseG, mgtC, cigR, pipA, pipB, pipC, sopB and pipD of *Salmonella* or a homologue or orthologue thereof;

(b) a gene comprised by a pathogenicity island that is comprised by the target cell genome;

(c) a secretion system (eg, a type III protein secretion system) gene comprised by the target cell genome Optionally, the DNA is comprised by a plasmid which comprises an origin of transfer (oriT) and an origin of replication (oriV) that is operable for replication of the DNA in a bacterial host cell.

Optionally, the first DNA is comprised by a plasmid, wherein the plasmid comprises a RP4 origin of transfer (oriT) and/or a p15A origin of replication.

Optionally, the DNA comprises SEQ ID NO: 15, optionally wherein the DNA is comprised by a plasmid in a carrier bacterial cell for conjugation to a *Salmonella* target cell. In an example, the DNA of the invention is comprised by a conjugative plasmid or phagemid.

In an example, the DNA comprises CRISPR repeat and spacer sequences, wherein (e) the repeat sequences each comprise SEQ ID NO: 16; and/or (f) the spacer sequences comprise one, two or three sequences selected from SEQ ID NOs: 17-19 and complement sequences thereof;

optionally wherein the DNA is comprised by a plasmid in a carrier bacterial cell for conjugation to a *Salmonella* target cell.

Optionally, the DNA comprises (optionally in 5' to 3' order) SEQ ID NO: 17, SEQ ID NO: 18 and SEQ ID NO: 19. Optionally, the DNA comprises one or more (eg, at least 3) spacer sequences shown in Table 6.

In an example, the DNA encodes a Cas3 and optionally one or more Cascade proteins (eg, one or more of CasA, B, C, D and E). In an embodiment, the first DNA encodes a Cas3 and CasA, B, C, D and E. In an embodiment, the first DNA encodes an *E. coli* Cas3 and CasA, B, C, D and E. Optionally, the guided nuclease (eg, Cas3) is a Type I-A, -B, -C, -D, -E, -F or -U Cas.

In an example, the agent in any configuration, example, option or embodiment herein, the agent comprises one or more components of a CRISPR/Cas system that is operable in the target cell to cut a protospacer sequence comprised by the target cell.

In an example, the system is operable to cut at least 3 different protospacer sequences comprised by the target cell genome. In an embodiment, each or some of said protospacer sequences is comprised by a pathogenicity island that is comprised by the target cell.

In an example, the agent in any configuration, example, option or embodiment herein (a) comprises a guided nuclease that is capable of recognising and modifying a target nucleic acid sequence, wherein the target sequence is comprised by an endogenous chromosome or episome of the target cells but is not comprised by the carrier cells, wherein the nuclease modifies the chromosome or episome to kill the target cells or inhibit the growth or proliferation of the target cells; and/or (b) encodes a guide RNA or crRNA of a CRISPR/Cas system that operates with a Cas nuclease in the target cell to cut a protospacer sequence comprised by the target cell.

Optionally, the DNA comprises a constitutive promoter for expression of the guide RNAs or crRNAs. Optionally, the DNA comprises a constitutive promoter for expression of a Cas nuclease that is operable in a target cell with the guide RNAs or crRNAs to modify (eg, cut) protospacer sequences of the target cell genome.

Optionally, the Cas, Cascade proteins, gRNAs and crRNAs are *E. coli* K12 (MG1655) Cas, Cascade proteins, gRNAs and crRNAs respectively. Optionally, the DNA is devoid of nucleotide sequences encoding Cas1 and Cas2 proteins.

The invention also relates to carrier bacteria encoding desired protein or RNA (eg, encoding an antimicrobial agent) and methods of use. In embodiments, the agent can be transferred into target cells by conjugation between carrier cells (to which the agent is not toxic) and the target cells, whereby the agent is toxic to the target cells and kills the target cells. In other embodiments, the growth or proliferation of target cells is reduced (eg, by at least 40, 50, 60, 70, 80, or 90% compared to growth in the absence of the agent). Each carrier cell comprises episomal DNA encoding an antibacterial agent that is toxic to a target bacterial cell but is not toxic (or is less toxic) to the carrier cell. The invention finds application, for example, in controlling or killing target bacteria that are pathogenic to humans, animals or plants. The invention finds application, for example, in controlling or killing zoonotic target bacteria comprised by an animal (eg, a livestock animal). For example, the carrier cells may be comprised by a medicament for treating or preventing a disease or condition in a human or animal; a growth promoting agent for administration to animals for promoting growth thereof; killing zoonositic bacteria in the animals; for administration to livestock as a pesticide; a pesticide to be applied to plants; or a plant fertilizer.

An advantage of the invention is that the carrier cells may be used as producer cells in which DNA encoding the antibacterial agent can be replicated. Another advantage of an example of the invention is that further replication of the DNA can be avoided in target cells that do not comprise one or more factors that are required for such replication. Thus, a scheme can be envisaged wherein the factor(s) are present in the carrier cells (and DNA encoding the agent is replicated to provide many copies for subsequent conjugative transfer into target cells) and in the target cells the DNA is not further replicated, which is useful for containing the action of the antibacterial agent, such as in environments or in a human or animal body or in (or on) a plant a Containment may be required to avoid undesired killing of non-target cells or to provide control generally over dosing and/or the administration of the killing activity regime.

The first DNA is replicable in the carrier cell (but not in the target cell), in which case it is important that the agent is not toxic to the carrier cell, whilst it is toxic to the target cell. In certain embodiments, the invention uses sequence-specific killing of the target cell to achieve this selectivity.

To this end, in an example the first DNA encodes a guided nuclease that is operable in the target cell to recognize and cut a target sequence of a target cell chromosome, thereby killing the cell or wherein the growth or proliferation of the cell is reduced. This is advantageous over the use of other types of toxic agent, which are less discriminate in their action, being able to kill several species or strain (eg, potentially also being toxic to the carrier cell to some degree). By using a guided nuclease (eg, a TALEN or Cas nuclease), these can be programmed to recognize a target sequence that is present in the target cell genome (eg, comprised by a chromosome or episome of the target cell), but is absent in the genome of the carrier cell.

Thus, in this case replication of the first DNA can freely happen in the carrier cell without risk of killing the cell or reducing its growth or proliferation due to the encoded agent and replication of sequences encoding the agent. Thus, in an example, where the first DNA encodes a guided nuclease, the guided nuclease is capable of recognizing and cutting a target nucleic acid sequence comprised by the genome (eg, chromosome) of the target cell, wherein the target cell is absent in the carrier cell.

A particularly useful example is where the first DNA encodes a Cas nuclease (eg, a Cas9 or Cas3) that is operable with a guide RNA or crRNA in the target cell, wherein the RNA is operable to guide the Cas to the target sequence, wherein the Cas modifies (eg, cuts) the target sequence and the target cell is killed or target cell growth or proliferation is inhibited. In one embodiment, the first DNA encodes the Cas and the guide RNA or crRNA. In another embodiment, the first DNA encodes the guide RNA or crRNA, but does not encode a cognate Cas. In this embodiment, the RNA is operable in the target cell with an endogenous Cas encoded by the target cell genome, wherein the RNA is operable to guide the Cas to the target sequence, wherein the Cas modifies (eg, cuts) the target sequence and the target cell is killed or target cell growth or proliferation is inhibited. In this se sense, the agent may comprise a component of a CRISPR/Cas system (eg, a Cas nuclease, Cascade Cas, crRNA, guide RNA or tracrRNA). Thus, the invention usefully recognizes the benefit of using antibacterial agents that act by target recognition in the target cell but not in the carrier cell, which opens up the ability for the first DNA to freely replicated in the carrier cell without significant toxicity to the carrier cell.

Example Plasmids

A method of delivery of any agent, such as a CRISPR-Cas system (or a component thereof) can be by bacterial conjugation, a natural process whereby a donor bacterium transfers DNA from itself to a recipient bacterium. Donor bacteria elaborate a surface structure, the pilus which can be considered to be like a syringe or drinking straw through which the DNA is delivered. The donor pilus binds to the surface of a receptive recipient and this event triggers the process of DNA transfer. Plasmids are suitable for this conjugative process, where the plasmid comprises DNA encoding the agent of the invention.

DNA transfer by conjugation may only take place with a 'susceptible recipient' but does not generally occur with a recipient carrying a similar type of plasmid. Because conjugation is via pilus bridge, it is possible for that bridge to attach itself not to a recipient but to the donor bacterium. This could result in a futile cycle of transfer of the plasmid DNA to itself. Plasmids thus naturally encode incompatibility factors. One is a surface arrayed protein that prevents the pilus binding to bacterium displaying that surface protein such as itself or any other bacterium carrying the same plasmid. Additionally, plasmids naturally encode another incompatibility system that closely regulates the copy number of the plasmid inside a bacterium. Thus, should a conjugation event manage to evade surface exclusion and start to transfer DNA by conjugation, the recipient will prevent that plasmid establishing as it already maintains the current copy number and will not accept and maintain a further unwanted additional copy.

In an example of the invention, the DNA encoding the agent is comprised by a plasmid. In an embodiment, the plasmid is a member of a plasmid incompatibility group, wherein the target cell does not comprise a plasmid of said group. Optionally, the plasmid of the invention is a member of the incompatibility group P (ie, the plasmid is an incP plasmid). *Salmonella* very rarely carry incP plasmids, so this incP plasmid is useful where the target cell is a *Salmonella* cell. For example within the Enterobacteriaceae the following is a non-exclusive list of potential plasmids that could use for delivery: IncFI, IncFII, IncFIII, IncFIV, IncFV, IncM, Inc9, IncIO, Incl, IncA, IncB, IncC, IncH, Incla, Incllc, IncI2, Incly, IncJ, IncL, IncN, Inc2e, IncO, IncP, IncS, IncT and/or IncW. Thus, optionally, the target cell is an Enterobacteriaceae cell and the DNA of the invention is comprised by a plasmid, wherein the plasmid is selected from an IncFI, IncFII, IncFIII, IncFIV, IncFV, IncM, Inc9, IncIO, Incl, IncA, IncB, IncC, IncH, Incla, Incllc, IncI2, Incly, IncJ, IncL, IncN, Inc2e, IncO, IncP, IncS, IncT and IncW plasmid.

In an example, the carrier cell of the invention comprises two or more plasmids, each plasmid comprising a DNA of the invention that encodes an antibacterial agent, wherein a first of said plasmids is a member of a first incompatibility group, wherein the target cell does not comprise a plasmid of said first group, and wherein a second of said plasmids is a member of a second incompatibility group, wherein the target cell does not comprise a plasmid of said second group. For example, a carrier cell may comprise an incP plasmid encoding an anti-target cell CRISPR-Cas system or a component thereof (eg, encoding a first crRNA or guide RNA that targets a first protospacer sequence of the target cell genome) and wherein the carrier cell further comprises an incF1 plasmid encoding an anti-target cell CRISPR-Cas system or a component thereof (eg, encoding a second crRNA or guide RNA that targets a second protospacer sequence of the target cell genome), the protospacers comprising different nucleotide sequences. For example, the protospacers are comprised by different genes of the target cell genome. For example the protospacers are comprised by one or more pathogenicity islands of the target cell genome. Optionally, the target cell is an Enterobacteriaceae cell. Optionally, the carrier cell comprises a group of plasmids comprising 2, 3, 4, 5, 6 or more different types of plasmid, wherein each plasmid is capable of being conjugatively transferred into a target cell, wherein the plasmids encode different agents or different components of an antibacterial agent. For example, the plasmids encode different cRNAs or gRNAs that target different protospacers comprised by the target cell genome. For example, the group of plasmids comprises up to n different types of plasmid, wherein the plasmids are members of up to n different incompatibility groups, eg, groups selected from IncFI, IncFII, IncFII, IncFIV, IncFV, IncM, Inc9, IncIO, Incl, IncA, IncB, IncC, IncH, IncIa, Incllc, IncI2, Incly, IncJ, IncL, IncN, Inc2e, IncO, IncP, IncS, IncT and IncW. For example, n=2, 3, 4, 5, 6, 7, 8, 9 or 10.

For example, the carrier cell comprises (i) a first plasmid that encodes a first type of CRISPR/Cas system that targets a first protospacer comprised by the target cell genome, or encodes a component of said system; and (ii) a second plasmid that encodes a second type of CRISPR/Cas system that targets a second protospacer comprised by the target cell genome, or encodes a component of said system, wherein the first and second types are different. For example, the first type is a Type I system, and the second type is a Type II system (eg, the first plasmid encodes a Cas3, Cascade and a crRNA or guide RNA that is operable with the Cas3 and Cascade in the target cell to modify the first protospacer; and the second plasmid encodes a Cas9 and a crRNA or guide RNA that is operable with the Cas9 in the target cell to modify the second protospacer). In an alternative, the Cas3 and Cascade are encoded by an endogenous target cell gene, wherein the first plasmid encodes the crRNA or guide RNA that is operable with the endogenous Cas3 and Cascade in the target cell to modify the first protospacer. In an alternative, the Cas9 is encoded by an endogenous target cell gene, wherein the second plasmid encodes the crRNA or guide RNA that is operable with the endogenous Cas9 in the target cell to modify the second protospacer. Optionally, the Cas3 and Cascade are encoded by endogenous genes of the target cell and the Cas9 is encoded by the second plasmid.

Instead of a Type I and Type II system, the invention alternatively provides in an embodiment a first plasmid encoding a Type I CRISPR/Cas system (or component thereof, eg, a Cas3 or a crRNA or a gRNA) and a second plasmid encoding a Type III CRISPR/Cas system (or a component thereof). Instead of a Type I and Type II system, the invention alternatively provides in an embodiment a first plasmid encoding a Type I CRISPR/Cas system (or component thereof) and a second plasmid encoding a Type IV CRISPR/Cas system (or a component thereof). Instead of a Type I and Type II system, the invention alternatively provides in an embodiment a first plasmid encoding a Type I CRISPR/Cas system (or component thereof) and a second plasmid encoding a Type V CRISPR/Cas system (or a component thereof). Instead of a Type I and Type II system, the invention alternatively provides in an embodiment a first plasmid encoding a Type I CRISPR/Cas system (or component thereof) and a second plasmid encoding a Type VI CRISPR/Cas system (or a component thereof).

Instead of a Type I and Type II system, the invention alternatively provides in an embodiment a first plasmid encoding a Type II CRISPR/Cas system (or component thereof, eg, a Cas9 or a crRNA or a gRNA) and a second plasmid encoding a Type III CRISPR/Cas system (or a component thereof). Instead of a Type I and Type II system, the invention alternatively provides in an embodiment a first plasmid encoding a Type II CRISPR/Cas system (or component thereof) and a second plasmid encoding a Type IV CRISPR/Cas system (or a component thereof). Instead of a Type I and Type II system, the invention alternatively provides in an embodiment a first plasmid encoding a Type II CRISPR/Cas system (or component thereof) and a second plasmid encoding a Type V CRISPR/Cas system (or a component thereof). Instead of a Type I and Type II system, the invention alternatively provides in an embodiment a first plasmid encoding a Type II CRISPR/Cas system (or component thereof) and a second plasmid encoding a Type VI CRISPR/Cas system (or a component thereof).

Instead of a Type I and Type II system, the invention alternatively provides in an embodiment a first plasmid encoding a Type V CRISPR/Cas system (or component thereof, eg, a Cas12a or a crRNA) and a second plasmid encoding a Type III CRISPR/Cas system (or a component thereof). Instead of a Type I and Type II system, the invention alternatively provides in an embodiment a first plasmid encoding a Type V CRISPR/Cas system (or component thereof) and a second plasmid encoding a Type IV CRISPR/Cas system (or a component thereof). Instead of a Type I and Type II system, the invention alternatively provides in an embodiment a first plasmid encoding a Type V CRISPR/Cas system (or component thereof) and a second plasmid encoding a Type V CRISPR/Cas system (or a component thereof). Instead of a Type I and Type II system, the invention alternatively provides in an embodiment a first plasmid encoding a Type V CRISPR/Cas system (or component thereof) and a second plasmid encoding a Type VI CRISPR/Cas system (or a component thereof).

Instead of a Type I and Type II system, the invention alternatively provides in an embodiment first and second plasmids, each encoding a Type I CRISPR/Cas system (or a component thereof). Instead of a Type I and Type II system, the invention alternatively provides in an embodiment first and second plasmids, each encoding a Type II CRISPR/Cas system (or a component thereof). Instead of a Type I and Type II system, the invention alternatively provides in an embodiment first and second plasmids, each encoding a Type III CRISPR/Cas system (or a component thereof). Instead of a Type I and Type II system, the invention alternatively provides in an embodiment first and second plasmids, each encoding a Type IV CRISPR/Cas system (or a component thereof). Instead of a Type I and Type II system, the invention alternatively provides in an embodiment first and second plasmids, each encoding a Type V CRISPR/Cas system (or a component thereof). Instead of a Type I and Type II system, the invention alternatively provides in an embodiment first and second plasmids, each encoding a Type VI CRISPR/Cas system (or a component thereof).

Optionally, the plasmids are members of different incompatibility groups, eg, groups selected from IncFI, IncFII, IncFIII, IncFIV, IncFV, IncM, Inc9, IncIO, Incl, IncA, IncB, IncC, IncH, IncIa, IncIIc, IncI2, Incly, IncJ, IncL, IncN, Inc2e, IncO, IncP, IncS, IncT and IncW. In an example here, the target cell is an Enterobacteriaceae cell.

EMBODIMENTS

Thus, by way of example the invention provides the following Embodiments.

1. A carrier bacterial cell comprising a first episomal DNA, the DNA comprising a nucleic acid of interest (NSI) that encodes a protein of interest (POI) or RNA of interest (ROI) for expressing the POI or ROI in a target bacterial cell, the carrier cell being capable of conjugative transfer of the DNA into the target cell for expression therein of the POI, ROI or agent, wherein
   (a) the carrier cell comprises a second DNA which is different from the first DNA, wherein the second DNA comprises or encodes a first factor required for replication of the first DNA;
   (b) the first DNA does not comprise or encode said first factor, wherein the first DNA is non-self-replicative in the absence of the first factor, but is able to replicate in the carrier cell in the presence of the first factor provided by the second DNA;
   (c) wherein the carrier cell comprises genes encoding one or more conjugation factors sufficient to carry out conjugative transfer of the first DNA into a target bacterial cell.

In a first alternative, Embodiment 1 provides:—

A carrier bacterial cell comprising a first episomal DNA, the DNA comprising a nucleic acid of interest (NSI) that encodes a protein of interest (POI) or RNA of interest (ROI) for expressing the POI or ROI in a target bacterial cell, the carrier cell being capable of conjugative transfer of the DNA into the target cell for expression therein of the POI or ROI.

In a second alternative, Embodiment 1 provides:—

A carrier bacterial cell comprising a first episomal DNA, the DNA encoding an antibacterial agent that is toxic to a target bacterial cell but is not toxic to the carrier cell, the carrier cell being capable of conjugative transfer of the DNA into the target cell for expression therein of the agent.

In an example, the agent comprises a guided nuclease that is capable of recognizing and cutting a target nucleic acid sequence comprised by the target cell genome, wherein the target sequence is not comprised by the carrier cell. In this sense, therefore, the antibacterial agent is toxic to a target bacterial cell but is not toxic to the carrier cell.

For example, there is provided:—

A carrier bacterial cell comprising a first episomal DNA, the DNA encoding an antibacterial agent that is toxic to a target bacterial cell but is not toxic to the carrier cell, the carrier cell being capable of conjugative transfer of the DNA into the target cell for expression therein of the agent, wherein the agent is a component of a CRISPR/Cas system that is operable in the target cell to modify a target nucleic acid sequence comprised by the target cell genome (eg, comprised by the target cell chromosome).

Another example provides:—

A carrier bacterial cell comprising a first episomal DNA, the DNA encoding an antibacterial agent that is toxic to a target bacterial cell but is not toxic to the carrier cell, the carrier cell being capable of conjugative transfer of the DNA into the target cell for expression therein of the agent, wherein
   (a) the carrier cell comprises a second DNA which is different from the first DNA, wherein the second DNA comprises or encodes a first factor required for replication of the first DNA;
   (b) the first DNA does not comprise or encode said first factor, wherein the first DNA is non-self-replicative in the absence of the first factor, but is able to replicate in the carrier cell in the presence of the first factor provided by the second DNA;
   (c) wherein the carrier cell comprises genes encoding one or more conjugation factors sufficient to carry out conjugative transfer of the first DNA into a target bacterial cell.

An example also provides:—

A carrier bacterial cell comprising a plasmid comprising a first DNA, the DNA encoding a guided nuclease that is capable of recognising and modifying a target nucleic acid sequence, the carrier cell being capable of conjugative transfer of the plasmid into the target cell for expression therein of the nuclease, wherein the target sequence is comprised by an endogenous chromosome or episome of the target cell but is not comprised by the carrier cell, wherein the nuclease is capable of modifying (eg, cutting) the chromosome or episome to kill the target cell or inhibit the growth or proliferation of the target cell.

Optionally, the nuclease is a Cas nuclease, meganuclease, zinc finger nuclease or TALEN.

Optionally, the nuclease is a Cas nuclease of a Type I, II, III, IV or V CRISPR system.

An example also provides:—

A carrier bacterial cell comprising a plasmid comprising a first DNA, the DNA encoding a component of a CRISPR/Cas system that is capable of recognising and modifying a target nucleic acid sequence, the carrier cell being capable of conjugative transfer of the plasmid into the target cell for expression therein of the component, whereby the expressed component forms part of a said system in the target cell, wherein the target sequence is comprised by an endogenous chromosome or episome of the target cell but is not comprised by the carrier cell, wherein the system is capable of modifying (eg, cutting) the chromosome or episome to kill the target cell or inhibit the growth or proliferation of the target cell.

In an aspect, the component is a guide RNA or crRNA that is capable of hybridising to the target sequence of the target cell. They system may be a Type I, II, III, IV or V CRISPR system.

Optionally, (a) the carrier cell comprises a second DNA which is different from the first DNA, wherein the second DNA comprises or encodes a first factor required for replication of the first DNA;

(b) the first DNA does not comprise or encode said first factor, wherein the first DNA is non-self-replicative in the absence of the first factor, but is able to replicate in the carrier cell in the presence of the first factor provided by the second DNA;

(c) wherein the carrier cell comprises genes encoding one or more conjugation factors sufficient to carry out conjugative transfer of the first DNA into a target bacterial cell.

The second DNA may be comprised by a chromosome or episome (eg, plasmid) of the carrier cell. Any method of the invention may use carrier cell(s) of any of these examples. Advantageously, the cell is for treating or preventing a target cell infection in a human or an animal subject (eg, a chicken, cow, pig, fish or shellfish). Advantageously, the carrier cell is a cell of a species that is probiotic to said subject or is probioitic to humans or animals (eg, chickens). For example, the carrier cell is a probiotic *E. coli* cell. For example, the carrier cell is a probiotic *Bacillus* cell. In an example, the target cell is a cell of a species that is pathogenic to said subject, or is pathogenic to humans or aniumals (eg, chickens). Advantageously, the first DNA encodes one or more guide RNAs or one or more crRNAs that are capable of hybridizing in the target cell to respective target nucleic acid sequence(s), wherein the target sequence(s) are comprised by an endogenous chromosome and/or endogenous episome of the target cell. For example, the first DNA encodes 2, 3, 4, 5, 6, 7, 7, 9, or 10 (or more than 10) different gRNAs or different crRNAs that hybridise to a respective target sequence, wherein the target sequences are different from each other. For example, 3 different gRNAs or crRNAs are encoded by the first DNA. For example, 2 different gRNAs or crRNAs are encoded by the first DNA. For example, 3 different gRNAs or crRNAs are encoded by the first DNA. For example, 4 different gRNAs or crRNAs are encoded by the first DNA. For example, 3 different gRNAs or crRNAs are encoded by the first DNA. For example, 5 different gRNAs or crRNAs are encoded by the first DNA. For example, 6 different gRNAs or crRNAs are encoded by the first DNA. For example, 7 different gRNAs or crRNAs are encoded by the first DNA. For example, 8 different gRNAs or crRNAs are encoded by the first DNA. For example, 9 different gRNAs or crRNAs are encoded by the first DNA. For example, 10 different gRNAs or crRNAs are encoded by the first DNA. For example, 11 different gRNAs or crRNAs are encoded by the first DNA. For example, 12 different gRNAs or crRNAs are encoded by the first DNA. For example, 13 different gRNAs or crRNAs are encoded by the first DNA. In an example, the target cells are *Salmonella* cells (eg, wherein the subject is a chicken). In an example, the target cells are *E. coli* cells. In an example, the target cells are *Campylobacter* cells (eg, wherein the subject is a chicken). In an example, the target cells are Edwardsiella cells (eg, wherein the subject is a fish or shellfish, eg, a catfish or a shrimp or prawn). In an example, the target cells are *E. coli* cells.

In an alternative herein, the carrier and target cells are archaeal cells. In an alternative herein, the carrier and target cells are yeast cells and "conjugation" is to be read instead as referring to yeast "mating" and, eg, the second DNA is comprised by a chromosome of the carrier yeast cell.

In a preferred example, the NOI encodes an antibacterial agent that is toxic to a target bacterial cell but is not toxic to the carrier cell. In an example, the POI is an antibiotic agent, an antibody, an antibody chain or an antibody variable domain. In an example, the ROI is a guide RNA or a crRNA that is operable in the target cell with a cognate Cas (eg, a Cas nuclease to target and cut a protospacer sequence comprised by a chromosome or episome of the target cell). In an example the RNA is a siRNA that is capable of hybridizing to an endogenous target nucleic acid sequence of the target cell to silence transcription and/or translation thereof.

The the carrier cell comprises a chromosome or second episomal DNA which is different from the first DNA. Thus, for example the second DNA is comprised by a chromosome of the carrier cell. In an other example, the second DNA is comprised by a plasmid of the carrier cell.

2. The carrier cell of Embodiment 1, wherein (d) the first DNA is devoid of a component required for conjugative transfer of the first DNA into a target bacterial cell; and (e) the carrier cell comprises said component, wherein the component is comprised by or encoded by the second DNA or a third DNA comprised by the carrier cell.

The third DNA may be comprised by a chromosome or episome (eg, plasmid). Where explicitly recited in Embodiments 2 onwards, the component is referring to the component required for conjugative transfer, as the context makes clear.

3. The carrier cell of Embodiment 2, wherein the component is comprised by a Mpf or Dtr module. For example, the module is a RK2, RP4 or R6K tra module. Optionally, the component is comprised by a Mpf (mating pair formation) module, eg, a RK2 or RP4 tra1 module or a homologue thereof. Optionally, the component is comprised by a Dtr (DNA-transfer replication) module, eg, a RK2 or RP4 tra2 module or a homologue thereof.

4. The carrier cell of Embodiment 2, wherein the component is encoded by an operon of a Mpf (eg, tra1) or Dtr (eg, tra2) module.

For example, the module is a RK2, RP4 or R6K tra module. Optionally, the module is a Mpf (mating pair formation) module, eg, a RK2 or RP4 tra1 module or a homologue thereof. Optionally, the module is a Dtr (DNA-transfer replication) module, eg, a RK2 or RP4 tra2 module or a homologue thereof.

The Mpf operon of RP4 or RK2 is the tra2 operon (comprising the trb genes trbBCDEFGHIJKL) together with gene traF. The gene traF is comprised in RK2 or RP4 in a tra1 operon (along with traJXIHG). Thus, in an embodiment, the component is a gene selected from trbB, trbC, trbD, trbE, trbF, trbG, trbH, trbI, trbJ, trbK, trbL and traF. In an embodiment the first DNA is devoid of two or more genes selected from RP4 trbB, trbC, trbD, trbE, trbF, trbG, trbH, trbI, trbJ, trbK, trbL and traF or homologues thereof. In an embodiment the first DNA is devoid of two or more genes selected from RK2 trbB, trbC, trbD, trbE, trbF, trbG, trbH, trbI, trbJ, trbK, trbL and traF or homologues thereof. In an example, the component is a traK, traL or traM gene. In an embodiment the first DNA is devoid of two or more genes selected from RP4 traK, traL and traM or homologues thereof. In an embodiment the first DNA is devoid of two or more genes selected from RK2 traK, traL and traM or homologues thereof. Optionally, in these embodiments the first DNA is comprised by a RP4 or RK2-type plasmid.

R6K Mpf is encoded by the sltX1tivB1B2B3-4B5B6B7B8B9B10B11 operon that also includes clpX1 of the Dtr module. Thus, in an embodiment, the component is a gene comprises by the RK6 sltX1tivB1B2B3-4B5B6B7B8B9B10B11 operon. In an embodiment, the the component is clpX1 of the RK6 Dtr module. In an embodiment, the component is a gene selected from clpX1 and dtrX1rlxX1. In an embodiment, the component is a gene selected from a RK6 clpX1 and dtrX1rlxX1 or homologues thereof. Optionally, in these embodiments the first DNA is comprised by a RK6-type plasmid.

The carrier cell of any preceding Embodiment, wherein the carrier cell chromosome and/or an episome of the carrier cell (other than an episome comprising the first DNA) comprises an expressible tra1 and/or tra2 module or a homologue thereof.

Any episome herein may be a plasmid.

5. The carrier cell of any preceding Embodiment, wherein the carrier cell chromosome and/or an episome of the carrier cell (other than an episome comprising the first DNA) comprises an expressible operon of a tra1 and/or tra2 module or a homologue thereof.
6. The carrier cell of any one of Embodiments 3 to 6, wherein the component is tra1 component.
7. The carrier cell of any one of Embodiments 3 to 6, wherein the component is tra2 component.
8. The carrier cell of any one of Embodiments 2 to 7, wherein the carrier cell chromosome encodes the first factor and comprises said component.
9. The carrier cell of any preceding Embodiment, wherein the first factor is a rep protein, optionally wherein the protein is encoded by pir or trfA or a homologue thereof.
10. The carrier cell of any preceding Embodiment, wherein the first DNA is comprised by a RK2 or R6K plasmid.
11. The carrier cell of any preceding Embodiment, wherein the first DNA comprises an oriV of a RK2 or R6K plasmid, or a homologue thereof.
12. The carrier cell of any preceding Embodiment, wherein the first DNA comprises an oriT of a RK2 or R6K plasmid, or a homologue thereof.
13. The carrier cell of any preceding Embodiment, wherein the first DNA is comprised by a plasmid.
14. The carrier cell of any preceding Embodiment, wherein the second DNA is comprised by a plasmid or is comprised by a chromosome of the carrier cell.
15. The carrier cell of any preceding Embodiment, wherein the agent comprises one or more components of a CRISPR/Cas system that is operable in the target cell to cut a protospacer sequence comprised by the target cell, eg, wherein the protospacer sequence is comprised by the cell chromosome.

In an embodiment, the cutting herein kills the target cell. In another embodiment, the cutting inhibits the growth or proliferation of the target cell.

16. The carrier cell of any preceding Embodiment, wherein the agent encodes a guide RNA or crRNA of a CRISPR/Cas system that is operable with a Cas nuclease in the target cell to cut a protospacer sequence comprised by the target cell, eg, wherein the protospacer sequence is comprised by the cell chromosome.

In an example, the target cell is a *Salmonella* cell and the protospacer is comprised by a pipA, pipB, pipC, hilA, sicP, mart or sopB gene. In an example, the protospacer is comprised by a gene that is a homologue or orthologue of a *Salmonella* sicP, sseF, pipA, pipB, pipC, hilA, sicP, mart or sopB gene.

17. The carrier cell of any preceding Embodiment, wherein the first DNA comprises a gene that encodes a product, wherein the product is essential for survival or proliferation of the carrier cell when in an environment that is devoid of the product, wherein the carrier cell chromosome does not comprise an expressible gene encoding the product and optionally the first DNA is the only episomal DNA comprised by the carrier cell that encodes the product.
18. The carrier cell of Embodiment 17, wherein the gene is selected from an aroA, argH, hisD, leuB, lysA, metB, proC, thrC, pheA, tyrA, trpC and pflA gene; or wherein the gene is an anti-toxin gene and optionally the first DNA encodes a cognate toxin.
19. The carrier cell of any preceding Embodiment, wherein the carrier cell is an *E. coli* (eg, Nissle, F18 or S17 *E. coli* strain), *Bacillus* (eg, *B subtilis*), *Enterococcus* or *Lactobacillus* cell. Optionally, the carrier cell is a cell of a human, chicken pig, sheep, cow, fish (eg, catfish or salmon) or shellfish (eg, shrimp or lobster) commensal bacterial strain (eg, a commensal *E. coli* strain).
20. The carrier cell of any preceding Embodiment, wherein the carrier cell is for administration to a microbiota of a human or animal subject for medical use.

For example, the medical use is for treating or preventing a disease disclosed herein. For example, the medical use is for treating or preventing a condition disclosed herein.

21. The carrier of Embodiment 20, wherein the medical use is for the treatment or prevention of a disease or condition mediated by said target cells.
22. The carrier of any one of Embodiments 1 to 20 for administration to an animal for enhancing growth or weight of the animal.

In alternative, the administration is to a human for enhancing the growth or weight of the human. Optionally, the enhancing is not a medical therapy. Optionally, the enhancing is a medical therapy.

23. The carrier of any one of Embodiments 20 to 22, wherein the use comprises the administration of a plurality of carrier cells to a microbiota (eg, a gut microbiota) of the subject, wherein the microbiota comprises target cells and first DNA is transferred into target cells for expression therein to produce the antibacterial agent, thereby killing target cells in the subject or reducing the growth or proliferation of target cells.
24. A DNA encoding an antibacterial agent that is toxic to a target bacterial cell but is not toxic to a carrier cell, wherein the first DNA comprises an origin of replication but does not comprise or encode a first factor required for replication of the first DNA, and wherein the first DNA comprises an origin of transfer but is devoid of a component required for conjugative transfer of the first DNA into a target bacterial cell, wherein when in the presence of the component the DNA is capable of conjugative transfer into the target cell.

Thus, when the DNA is in a carrier cell, the DNA is capable of conjugative transfer into a target cell.

25. The DNA of Embodiment 24, wherein the DNA is according to the DNA recited in any one of Embodiments 1 to 23.

26. The DNA of Embodiment 24 or 25, wherein the cells are according to the cells recited in any one of Embodiments 1 to 23.
27. A method for enhancing growth or weight of an animal subject (eg, a chicken), wherein the method comprises the administration of a plurality of carrier cells according to any one of Embodiments 1 to 23 to a microbiota of the subject, wherein the microbiota comprises target cells and first DNA is transferred from carrier cells into target cells for expression therein to produce the antibacterial agent, thereby killing target cells (eg, *Salmonella* cells) in the subject or reducing the growth or proliferation of target cells.

In alternative, the administration is to a human for enhancing the growth or weight of the human. Optionally, the enhancing is not a medical therapy. Optionally, the enhancing is a medical therapy.

28. A method for enhancing growth or weight of a plant (eg, a tomato plant), wherein the method comprises the administration of a plurality of carrier cells according to any one of Embodiments 1 to 23 to a microbiota of the plant, wherein the microbiota comprises target cells and first DNA is transferred from carrier cells into target cells for expression therein to produce the antibacterial agent, thereby killing target cells (eg, *Pseudomonas* cells) in the plant or reducing the growth or proliferation of target cells.

The plant may be any plant disclosed herein. For example a plant herein in any configuration or embodiment of the invention is selected from a tomato plant, a potato plant, a wheat plant, a corn plant, a maize plant, an apple tree, a bean-producing plant, a pea plant, a beetroot plant, a stone fruit plant, a barley plant, a hop plant and a grass. For example, the plant is a tree, eg, palm, a horse chestnut tree, a pine tree, an oak tree or a hardwood tree. For example the plant is a plant that produces fruit selected from strawberries, raspberries, blackberries, reducrrants, kiwi fruit, bananas, apples, apricots, avoocados, cherries, oranges, clementines, satsumas, grapefruits, plus, dates, figs, limes, lemons, melons, mangos, pears, olives or grapes. Optionally, the plant is a dicotyledon. Optionally, the plant is a flowering plant. Optionally, the plant is a monocotyledon.

In any configuration, embodiment or example herein, the target bacteria are *P. syringae* bacteria (eg, comprised by a plant). *Pseudomonas syringae* pv. *syringae* is a common plant-associated bacterium that causes diseases of both monocot and dicot plants worldwide. In an example the targt bacteria are *P. syringae* bacteria of a pathovar selected from *P. s.* pv. *aceris, P. s.* pv. *aptata, P. s.* pv. *atrofaciens,*

- *P. s.* pv. *dysoxylis, P. s.* pv. *japonica, P. s.* pv. *lapsa, P. s.* pv. *panici, P. s.* pv. *papulans, P. s.* pv. *pisi,*
- *P. s.* pv. *syringae* and *P. s.* pv. *morsprunorum.*
- *P. s.* pv. *aceris* attacks maple Acer species.
- *P. s.* pv. *actinidiae* attacks kiwifruit *Actinidia deliciosa.*
- *P. s.* pv. *aesculi* attacks horse chestnut *Aesculus hippocastanum*, causing bleeding canker.
- *P. s.* pv. *aptata* attacks beets *Beta vulgaris.*
- *P. s.* pv. *atrofaciens* attacks wheat *Triticum aestivum.*
- *P. s.* pv. *dysoxylis* attacks the kohekohe tree *Dysoxylum spectabile.*
- *P. s.* pv. *japonica* attacks barley *Hordeum vulgare.*
- *P. s.* pv. *lapsa* attacks wheat *Triticum aestivum.*
- *P. s.* pv. *panici* attacks *Panicum* grass species.
- *P. s.* pv. *papulans* attacks crabapple *Malus sylvestris* species.
- *P. s.* pv. *phaseolicola* causes halo blight of beans.
- *P. s.* pv. *pisi* attacks peas *Pisum sativum.*
- *P. s.* pv. *syringae* attacks *Syringa, Prunus*, and *Phaseolus* species.
- *P. s.* pv. *glycinea* attacks soybean, causing bacterial blight of soybean.

In an example, the target bacteria are *P. syringae* selected from a serovar recited in a bullet point in the immediately preceding paragraph and the bacteria are comprised by a plant also mentioned in that bullet point.

In an example, the weight is dry weight. For example, the method is for increasing dry weight (eg, within 1 or 2 weeks of said administration). Optionally, the increase is an increase of at least 5, 10, 11, 12, 13, 14, 15, 16, 17, 18, 19 or 20% compared to a control plant of the same species or strain to which the administration if carrier cells has not taken place, wherein all plants are kept under the same environmental conditions. For example, such an increase is within 1, 2, 3, 4, 5, 6, or 8 weeks following the first administration of the carrier cells. In an example, the method is for increasing the dry weight of a leaf and/or fruit of the plant, such as a tomato plant.

In an example, the weight is wet weight. For example, the method is for increasing wet weight (eg, within 1 or 2 weeks of said administration). Optionally, the increase is an increase of at least 5, 10, 11, 12, 13, 14, 15, 16, 17, 18, 19 or 20% compared to a control plant of the same species or strain to which the administration if carrier cells has not taken place, wherein all plants are kept under the same environmental conditions. For example, such an increase is within 1, 2, 3, 4, 5, 6, or 8 weeks following the first administration of the carrier cells. In an example, the method is for increasing the dry weight of a leaf and/or fruit of the plant, such as a tomato plant.

29. The method of Embodiment 28, wherein the microbiota is comprised by a leaf, trunk, root or stem of the plant.

In an example, in any configuration or embodiment herein the target bacteria (or taraget cell) is comprised by a microbiota of a plant. In an example, the microbiota is comprised by a leaf. In an example, the microbiota is comprised by a xylem. In an example, the microbiota is comprised by a phloem. In an example, the microbiota is comprised by a root. In an example, the microbiota is comprised by a tuber. In an example, the microbiota is comprised by a bulb. In an example, the microbiota is comprised by a seed. In an example, the microbiota is comprised by an exocarp, epicarp, mesocarp or endocarp. In an example, the microbiota is comprised by a fruit, eg, a simple fruits; aggregate fruits; or multiple fruits. In an example, the microbiota is comprised by a seed or embryo, eg, by a seed coat; a seed leaf; cotyledons; or a radicle. In an example, the microbiota is comprised by a flower, eg, comprised by a peduncle; sepal: petals; stamen; filament; anther or pistil. In an example, the microbiota is comprised by a root; eg, a tap root system, or a fibrous root system. In an example, the microbiota is comprised by a leaf or leaves, eg, comprised by a leaf blade, petiole or stipule. In an example, the microbiota is comprised by a stem, eg, comprised by bark, epidermis, phloem, cambium, xylem or pith.

30. A method for reducing a biofilm comprised by a subject or comprised on a surface, wherein the biofilm comprises target cells (eg, *Pseudomonas* cells), wherein the method comprises the administration of a plurality of carrier cells according to any one of Embodiments 1 to 23 to the biofilm, wherein first DNA is transferred from carrier cells into target cells for expression therein to produce the antibacterial agent, thereby killing target cells in the biofilm or reducing the growth or proliferation of target cells.

In an example "reducing a biofilm" comprises reducing the coverage area of the biofilm. In an example "reducing a biofilm" comprises reducing the proliferation of the biofilm. In an example "reducing a biofilm" comprises reducing the durability of the biofilm. In an example "reducing a biofilm" comprises reducing the spread of the biofilm (eg, in or on the subject, eg, spread to the environment containing the subject).

31. The method of Embodiment 30, wherein the subject is a human or animal.

For example, the biofilm is comprised by a lung of the subject, eg, wherein the target cells are *Pseudomonas* (eg, *P. aeruginosa*) cells. This may be useful wherein the subject is a human suffering from a lung disease or condition, such as pneumonia or cystic fibrosis. For example, the biofilm is comprised by an animal or human organ disclosed herein. For example, the biofilm is comprised by a microbiota of a human or animal disclosed herein.

32. The method of Embodiment 30, wherein the subject is a plant (eg, any plant disclosed herein).

Optionally, in this Embodiment the target cells are *Pseudomonas syringae* cells.

33. The method of Embodiment 31 or 32, wherein the biofilm is comprised by a leaf, trunk, root or stem of the plant.

In an example, in any configuration or embodiment herein the target bacteria (or taraget cell) is comprised by a biofilm of a plant. In an example, the biofilm is comprised by a leaf. In an example, the biofilm is comprised by a xylem. In an example, the biofilm is comprised by a phloem. In an example, the biofilm is comprised by a root. In an example, the biofilm is comprised by a tuber. In an example, the biofilm is comprised by a bulb. In an example, the biofilm is comprised by a seed. In an example, the biofilm is comprised by an exocarp, epicarp, mesocarp or endocarp. In an example, the biofilm is comprised by a fruit, eg, a simple fruits; aggregate fruits; or multiple fruits. In an example, the biofilm is comprised by a seed or embryo, eg, by a seed coat; a seed leaf; cotyledons; or a radicle. In an example, the biofilm is comprised by a flower, eg, comprised by a peduncle; sepal: petals; stamen; filament; anther or pistil. In an example, the biofilm is comprised by a root; eg, a tap root system, or a fibrous root system. In an example, the biofilm is comprised by a leaf or leaves, eg, comprised by a leaf blade, petiole or stipule. In an example, the biofilm is comprised by a stem, eg, comprised by bark, epidermis, phloem, cambium, xylem or pith.

34. The method of any one of Embodiments 30 to 33 (eg, 30), wherein the surface is a surface ex vivo, such as a surface comprised by a domestic or industrial apparatus or container.

35. A method of replicating a first DNA to produce a plurality of copies of said DNA, the method comprising culturing a plurality of carrier bacterial cells according to any one of Embodiments 1 to 23, wherein the first DNA is replicated in the cells.

Optionally, the method further comprises isolating first DNA after said culturing. The skilled addresse is familiar with techniques and conditions for culturing cells that can be used.

36. The method of Embodiment 35, comprising
(a) obtaining a sample of the carrier cells after culturing;
(b) contacting the sample of carrier cells with a plurality of target bacterial cells to allow conjugation between carrier cells and target cells; and
(c) allowing copies of first DNA to be transferred by conjugative transfer from carrier cells to target cells, wherein the antibacterial agent is provided in target cells and target cells are killed or the growth or proliferation of target cells is reduced;
(d) wherein the first DNA is not replicable in the target cells.

For example, the first DNA is not substantially replicable in the target cells, eg, less than 10, 5, 4, 3, 2 or 1% replication).

The first DNA is not (or not substantially) replicable in the target cells due to the absence of the first factor or sequence encoding it in the target cells.

37. A method of killing a plurality of target bacterial cells or reducing the growth or proliferation thereof, the method comprising
(a) obtaining a sample of the carrier cells according to any one of Embodiments 1 to 23 or obtainable by the method of Embodiment 35;
(b) contacting the sample of carrier cells with the plurality of target bacterial cells to allow conjugation between carrier cells and target cells; and
(c) allowing copies of first DNA to be transferred by conjugative transfer from carrier cells to target cells, wherein the antibacterial agent is provided in target cells and target cells are killed or the growth or proliferation of target cells is reduced;
(d) wherein the first DNA is not (or not substantially) replicable in the target cells.

38. The method of Embodiment 36 or 37, wherein the target cells are comprised by a biofilm, eg, a biofilm as disclosed herein.

39. A method for containing the action of an antibacterial agent in an environment, wherein the agent is toxic to target bacterial cells, the method comprising carrying out the method of Embodiment 37 or 38 and the agent is said agent recited of the Embodiment.

40. The method of Embodiment 39, wherein the environment is comprised by a human or animal subject and the target cells are comprised by a biofilm of the subject, wherein the method comprises administering the sample of carrier cells to the biofilm of the subject, wherein the carrier cells are contacted with the target cells in step (b), wherein the method is a contained method for treating or preventing a disease or condition mediated by target cells in the subject.

41. The carrier cell, DNA or method of any preceding Embodiment, wherein the target bacteria are *Salmonella, Pseudomonas, Escherichia, Klebsiella, Campylobacter, Helicobacter, Acinetobacter, Enterobacteriacea, Clostridium, Staphylococcus* or *Streptococcus* bacteria.

42. The carrier cell, DNA or method of any preceding Embodiment, wherein the target bacteria are *Salmonella enterica* bacteria.

For example, the target bacteria are selected from the group consisting of *Salmonella enterica* subsp. *enterica*, serovars *Typhimurium, Enteritidis*, Virchow, Montevideo, Hadar and Binza.

43. The carrier cell, DNA or method of any one of Embodiments 1 to 41, wherein the target bacteria are *Pseudomonas* (eg, *P. syringae* or *P. aeruginosa*) bacteria.

44. The carrier cell or method of any one of Embodiments 1 to 41, wherein the target bacteria are *E coli* bacteria.

Optionally, the target bacteria are enterohemorrhagic *E. coli* (EHEC), *E. coli* Serotype O157:H7 or Shiga-toxin producing *E. coli* (STEC)). In an example, the taraget bacteria are selected from Shiga toxin-producing *E. coli* (STEC) (STEC may also be referred to as Verocytotoxin-producing *E. coli* (VTEC);
Enterohemorrhagic *E. coli* (EHEC) (this pathotype is the one most commonly heard about in the news in association with foodborne outbreaks);
Enterotoxigenic *E. coli* (ETEC);
Enteropathogenic *E. coli* (EPEC);
Enteroaggregative *E. coli* (EAEC);
Enteroinvasive *E. coli* (EIEC); and
Diffusely adherent *E. coli* (DAEC).

Enterohemorrhagic *Escherichia coli* (EHEC) serotype O157:H7 is a human pathogen responsible for outbreaks of bloody diarrhoea and haemolytic uremic syndrome (HUS) worldwide. Conventional antimicrobials trigger an SOS response in EHEC that promotes the release of the potent Shiga toxin that is responsible for much of the morbidity and mortality associated with EHEC infection. Cattle are a natural reservoir of EHEC, and approximately 75% of EHEC outbreaks are linked to the consumption of contaminated bovine-derived products. EHEC causes disease in humans but is asymptomatic in adult ruminants. Characteristics of *E. coli* serotype O157:H7 (EHEC) infection includes abdominal cramps and bloody diarrhoea, as well as the life-threatening complication haemolytic uremic syndrome (HUS). Currently there is a need for a treatment for EHEC infections (Goldwater and Bettelheim, 2012). The use of conventional antibiotics exacerbates Shiga toxin-mediated cytotoxicity. In an epidemiology study conducted by the Centers for Disease Control and Prevention, patients treated with antibiotics for EHEC enteritis had a higher risk of developing HUS (Slutsker et al., 1998). Additional studies support the contraindication of antibiotics in EHEC infection; children on antibiotic therapy for hemorrhagic colitis associated with EHEC had an increased chance of developing HUS (Wong et al., 2000; Zimmerhackl, 2000; Safdar et al., 2002; Tarr et al., 2005). Conventional antibiotics promote Shiga toxin production by enhancing the replication and expression of stx genes that are encoded within a chromosomally integrated lambdoid prophage genome. The approach of some configurations of present invention rely on nuclease cutting. Stx induction also promotes phage-mediated lysis of the EHEC cell envelope, allowing for the release and dissemination of Shiga toxin into the environment (Karch et al., 1999; Matsushiro et al., 1999; Wagner et al., 2002). Thus, advantageously, these configurations of the invention provide alternative means for treating EHEC in human and animal subjects. This is exemplified below with surprising results on the speed and duration of anti-EHEC action produced by nuclease action (as opposed to conventional antibiotic action).

In an example, the subject (eg, a human or animal) is suffering from or at risk of haemolytic uremic syndrome (HUS), eg, the subject is suffering from an *E. coli* infection, such as an EHEC *E. coli* infection.

45. A pharmaceutical composition, livestock growth promoting composition, soil improver, herbicide, plant fertilizer, food or food ingredient sterilizing composition, dental composition, personal hygiene composition or disinfectant composition (eg, for domestic or industrial use) comprising a plurality of carrier cells according to any one of Embodiments 1 to 23.

Herein, a carrier cell is, eg, a probiotic cell for administration to a human or animal subject. For example, the carrier cell is commensal in a microbiome (eg, gut or blood microbiome) of a human or animal subject, wherein the carrier is for administration to the subject. In an example, a carrier cell is a bacterial cell (and optionally the target cell is a bacterial cell). In an example, a carrier cell is an archaeal cell (and optionally the target cell is an archaeal cell) Optionally, the carrier cell is a gram-positive bacterial cell and the target cell is a gram-positive bacterial cell.

Optionally, the carrier cell is a gram-positive bacterial cell and the target cell is a gram-negative bacterial cell.

Optionally, the carrier cell is a gram-negative bacterial cell and the target cell is a gram-positive bacterial cell.

Optionally, the carrier cell is a gram-negative bacterial cell and the target cell is a gram-negative bacterial cell.

Optionally, the carrier cell is a *Bacillus* bacterial cell and the target cell is a gram-positive bacterial cell.

Optionally, the carrier cell is a *Bacillus* bacterial cell and the target cell is a gram-netative bacterial cell.

Optionally, the carrier cell is a *Bacillus* bacterial cell and the target cell is a *Salmonella* bacterial cell.

Optionally, the carrier cell is a *Bacillus* bacterial cell and the target cell is an *E. coli* bacterial cell.

Optionally, the carrier cell is an *E. coli* bacterial cell and the target cell is a *Pseudomonas* bacterial cell.

Optionally, the carrier cell is an *E. coli* bacterial cell and the target cell is a gram-positive bacterial cell.

Optionally, the carrier cell is an *E. coli* bacterial cell and the target cell is a gram-netative bacterial cell.

Optionally, the carrier cell is an *E. coli* bacterial cell and the target cell is a *Salmonella* bacterial cell.

Optionally, the carrier cell is an *E. coli* bacterial cell and the target cell is an *E. coli* bacterial cell.

Optionally, the carrier cell is an *E. coli* bacterial cell and the target cell is a *Pseudomonas* bacterial cell.

A *Bacillus* cell herein is optionally a *B subtilis* cell.

Optionally, the carrier cell is a probiotic or commensal *E. coli* bacterial cell for administration to a human or animal subject. Optionally, the carrier cell is a probiotic or commensal *Bacillus* bacterial cell for administration to a human or animal subject.

Herein, optionally the first DNA is comprised by a plasmid, eg, a closed circular DNA.

In an embodiment, in an example the first DNA is dsDNA. In an embodiment, in an example the first DNA is ssDNA.

In an alternative configuration, the first DNA is instead a first RNA.

Optionally, the target cell is a *Salmonella* cell (eg, wherein the carrier cell is an *E. coli* cell), eg, a *Salmonella enterica* subsp. *enterica*, eg, a *Salmonella enterica* subsp. *enterica* serovar *Typhimurium, Enteritidis*, Virchow, Montevideo, Hadar or Binza.

For example, the target bacteria are selected from the group consisting of *S. enterica; S. typhimurium; P. aeruginosa; E. coli; K. pneumoniae; C. jujeni; H. pylori; A. baumanii; C. difficile; S. aureus; S. pyogenes* or *S. thermophilus.*

In an example, the target cell is a cell of a species that causes nosocomial infection in humans.

Optionally, the target cell is comprised by an animal (eg, poultry animal (such as chicken), swine, cow, fish (eg, catfish or salmon) or shellfish (eg, prawn or lobster)) microbiome. Optionally, the microbiome is a gut microbiome. For example, the target cell is a *Salmonella* cell comprised by a chicken gut biofilm. For example, the target cell is a *Salmonella* cell comprised by a chicken gut biofilm sample ex vivo.

In an embodiment, the first DNA comprises a bacterial oriV and/or an oriT. In an embodiment, the first DNA is comprised by a plasmid, wherein the plasmid comprises and oriV and/or an oriT.

The first factor may be a protein or RNA. For example, the first factor is pir or trfA. In an example the first factor is operable with an oriV comprised by the first DNA for replication thereof.

In an embodiment, the first DNA is comprised by a plasmid, wherein the plasmid comprises an oriV and does not encode any replication protein (eg, pir or trfA) that is operable with the oriV to initiate replication of the plasmid.

In an embodiment, the first DNA is devoid of a component required for conjugative transfer of the first DNA into a target bacterial cell. Optionally, the component is a protein. Optionally, the component is a RNA. Optionally, the component is a tra1 component. Optionally, the component is a tra2 component. In an example, the carrier cell comprises said component, wherein the component is comprised by or encoded by the carrier cell chromosome, the second DNA or a third DNA in the carrier cell. Preferably, the component is comprised by or encoded by the carrier cell chromosome.

Optionally, the component required for conjugative transfer is a RP4 plasmid component, eg, a component of a RP4 tra module (eg, tra1 or tra2 module).

Optionally, the component required for conjugative transfer is a RK2 plasmid component, eg, a component of a RK2 tra module (eg, tra1 or tra2 module).

Optionally, the component required for conjugative transfer is a R6K plasmid component, eg, a component of a R6K tra module (eg, tra1 or tra2 module).

Optionally, the first DNA is comprised by a plasmid that does not comprise an antibiotic resistance marker gene and/or a plasmid addiction system gene. As explained in the Examples section, this may be advantageous in the rare case of an identical IncP plasmid being present in the target cell that will provide trfA (or other component required for conjugation where that component is not encoded by the plasmid comprising the first DNA), both plasmids will compete for the available TrfA (or other component), resulting in loss of one plasmid, and thus will be quickly lost from any offspring target cells.

Optionally, the plasmid comprising the first DNA further comprises an anti-restriction gene encoding a product for inhibiting a restriction enzyme of the target cell (eg, an Type I restriction enzyme). as anti-restriction genes that inhibit Type I restriction enzymes (eg, the anti-restriction gene product is an ocr of T7, klcA of RK2, ard or ardB).

Additionally or alternatively, the plasmid comprises a gene encoding an essential component of a type IV secretion system, wherein the chromosome of the carrier cell comprises genes encoding the remainder of the secretion system, wherein the essential component is required for conjugative transfer of the plasmid from the carrier cell to the target cell. For example, with the exception of a tra1 or tra2 gene encoding the essential component, the chromosome comprises all of the remainder of traKLM, traJXIHGF genes of RK2 tra1 and all of the remainder of trbBCEFGHJL genes of RK2 tra2 (preferably when the plasmid is a RK2-type plasmid). In an alternative example, with the exception of a gene encoding the essential component, the chromosome comprises all of the reaminder of RK6 homologues of traKLM, traJXIHGF genes of RK2 tra1 and all of the remainder of RK6 homologues of trbBCEFGHJL genes of RK2 tra2 (preferably when the plasmid is a RK6-type plasmid). In an alternative example, with the exception of a gene encoding the essential component, the chromosome comprises all of the reaminder of RP4 homologues of traKLM, traJXIHGF genes of RK2 tra1 and all of the remainder of RP4 homologues of trbBCEFGHJL genes of RK2 tra2 (preferably when the plasmid is a RP4-type plasmid).

For example, with the exception of a tra1 or tra2 gene encoding the essential component, the chromosome comprises all of the remainder of a DNA fragment of the RK2 plasmid from traF to traM and all of the remainder of a DNA fragment of the RK2 plasmid from trbB to trK (preferably when the plasmid is a RK2-type plasmid). For example, with the exception of a tra1 or tra2 gene encoding the essential component, the chromosome comprises all of the remainder of the RK2 plasmid genes from traF to traM and all of the remainder of the RK2 plasmid genes from trbB to trK (preferably when the plasmid is a RK2-type plasmid). For example, the chromosome comprises (in the following order 5' to 3', or 3' to 5') the following RK2 tra1 genes: traFGHIXJKLM, or traKLM, or traJXIHGF. For example, the chromosome comprises (in the following order 5' to 3', or 3' to 5') the following RK2 tra2 genes: trbBCDEFGHIJKL or trbBCEFGHJL.

For example, with the exception of a gene encoding the essential component, the chromosome comprises all of the remainder of a DNA fragment of the RK6 plasmid from a homologue of RK2 traF to a homologue of RK2 traM and all of the remainder of a DNA fragment of the RK6 plasmid from a homologue of RK2 trbB to a homologue of a RK2 trK (preferably when the plasmid is a RK6-type plasmid). For example, with the exception of a gene encoding the essential component, the chromosome comprises all of the remainder of the RK6 plasmid genes from a homologue of RK2 traF to a homologue of RK2 traM and all of the remainder of the RK6 plasmid genes from a homologue of RK2 trbB to a homologue of RK2 trK (preferably when the plasmid is a RK6-type plasmid). For example, the chromosome comprises (in the following order 5' to 3', or 3' to 5') RK6 homologues of the following RK2 tra1 genes: traFGHIXJKLM, or traKLM, or traJXIHGF. For example, the chromosome comprises (in the following order 5' to 3', or 3' to 5') RK6 homologues of the following RK2 tra2 genes: trbBCDEFGHIJKL or trbBCEFGHJL.

For example, with the exception of a gene encoding the essential component, the chromosome comprises all of the remainder of a DNA fragment of the RP4 plasmid from a homologue of RK2 traF to a homologue of RK2 traM and all of the remainder of a DNA fragment of the RP4 plasmid from a homologue of RK2 trbB to a homologue of a RK2 trK (preferably when the plasmid is a RP4-type plasmid). For example, with the exception of a gene encoding the essential component, the chromosome comprises all of the remainder of the RP4 plasmid genes from a homologue of RK2 traF to a homologue of RK2 traM and all of the remainder of the RP4 plasmid genes from a homologue of RK2 trbB to a homologue of RK2 trK (preferably when the plasmid is a RP4-type plasmid). For example, the chromosome comprises (in the following order 5' to 3', or 3' to 5') RP4 homologues of the following RK2 tra1 genes: traFGHIXJKLM, or traKLM, or traJXIHGF. For example, the chromosome comprises (in the following order 5' to 3', or 3' to 5') RP4 homologues of the following RK2 tra2 genes: trbBCDEFGHIJKL or trbBCEFGHJL.

Preferably, the second DNA or a chromosome comprising the second DNA is devoid of a oriT. Preferably, the third DNA or a chromosome comprising the third DNA is devoid of a oriT. For example, the oriT is only comprised by the first DNA (or plasmid comprising this) and is not comprised by any other DNA in the carrier cell. Thus, transfer is confined just to the first DNA or its plasmid.

The first DNA in all embodiments and configurations may preferably not be comprised by a runaway replication plasmid. Naturally occurring plasmids are present within host cells at a characteristic concentration (referred to herein as a particular plasmid "copy number"). Mutations that destroy the elements of the control cause an over-replication phenotype that manifests itself by an increase in the plasmid copy number ("copy-up" phenotype). In extreme cases of copy-up mutations, plasmid replication is completely unchecked due to the loss of copy control mechanisms. This is referred to as "runaway plasmid replication" or simply "runaway replication" and the plasmid engaging in such runaway replication is a "runaway replication plasmid".

In an example, the invention relates to a composition comprising a plurality of carrier cells of the invention (eg, wherein copies of the first DNA are comprised by respective plasmids). Optionally, all of the carrier cells comprise identical said first and second DNAs. Optionally, the plurality comprises a first sub-population of carrier cells (first cells) and a second sub-population of carrier cells (second cells) wherein the first cells comprise identical first DNAs and the second cells comprise identical first DNAs (which are different from the first DNAs of the first cells). For example, the former DNAs comprise a NSI that is different from the NSI comprised by the other DNAs. For example, the first DNAs encode a first guide RNA or crRNA and the second DNAs encode a second guide RNA or crRNA, wherein the first guide RNA/crRNA is capable of hybridizing to a first protospacer sequence in first target cells; and the second guide RNA/crRNA is capable of hybridizing to a second protospacer sequence in second target cells, wherein the protospacers are different. Optionally, the first target cells are different from the second target cells. Optionally, the first target cells are of the same species or strain as the second target cells. Alternatively, the first target cells are of species or strain that is different from the species or strain of the second target cells (in this way a cocktail of carrier cells is provided, eg, for administration to a human or animal or plant, to target and kill a plurality of target cells of different species or strains).

In an example, the or each first DNA comprises a plurality (eg, a first and a second) NSIs wherein a first NSI is different from a second NSI (eg, they encode different proteins or RNAs, such as different guide RNAs or crRNAs). In an example, the or each first DNA comprises 2, 3, 4, 5, 6, 7, 8, 9, 10, 11, 12, 13, 14, 15, 16, 17, 18, 19 or 20 different types of NSIs. In an example, the or each first DNA comprises NSIs encoding 2, 3, 4, 5, 6, 7, 8, 9, 10, 11, 12, 13, 14, 15, 16, 17, 18, 19 or 20 different guide RNAs. In an example, the or each first DNA comprises NSIs encoding 2, 3, 4, 5, 6, 7, 8, 9, 10, 11, 12, 13, 14, 15, 16, 17, 18, 19 or 20 different crRNAs. In an example, the or each first DNA comprises NSIs encoding at least 2, 3, 4, 5, 6, 7, 8, 9, 10, 11, 12, 13, 14, 15, 16, 17, 18, 19 or 20 different guide RNAs. In an example, the or each first DNA comprises NSIs encoding at least 2, 3, 4, 5, 6, 7, 8, 9, 10, 11, 12, 13, 14, 15, 16, 17, 18, 19 or 20 different crRNAs.

Optionally, the composition is comprised by a liquid (eg, an aqueous liquid or in water), the composition comprising the carrier cells at an amount of from $1\times10^3$ to $1\times10^{10}$ (eg, from $1\times10^4$ to $1\times10^{10}$; from $1\times10^4$ to $1\times10^9$; from $1\times10^4$ to $1\times10^8$; from $1\times10^4$ to $1\times10^7$; from $1\times10^3$ to $1\times10^{10}$; from $1\times10^3$ to $1\times10^9$; from $1\times10^3$ to $1\times10^8$; from $1\times10^3$ to $1\times10^7$; from $1\times10^6$ to $1\times10^{10}$; from $1\times10^5$ to $1\times10^9$; from $1\times10^5$ to $1\times10^8$; from $1\times10^5$ to $1\times10^7$; from $1\times10^6$ to $1\times10^{10}$; from $1\times10^6$ to $1\times10^9$; from $1\times10^6$ to $1\times10^8$; or from $1\times10^6$ to $1\times10^7$) cfu/ml. For example, the liquid is a beverage, such for human or animal consumption. For example, the beverage is a livestock beverage, eg, a poultry beverage (ie, a beverage for consumption by poultry, such as chicken).

In an example, the composition is a dietary (eg, dietary supplement) composition for consumption by humans or animals. In an example, the composition is a slimming composition for consumption by humans or animals. In an example, the composition is a growth promotion composition for consumption by humans or animals. In an example, the composition is a body building composition for consumption by humans. In an example, the composition is a probiotic composition for consumption by humans or animals. In an example, the composition is a biocidal composition for consumption by humans or animals. In an example, the composition is a pesticidal composition for consumption by humans or animals. In an example, the composition is a zoonosis control composition for consumption by animals.

In an example, the composition comprises vitamins in addition to the carrier cells. In an example, the composition comprises vitamin A, B (eg, B12), C, D, E and/or K in addition to the carrier cells. In an example, the composition comprises lipids in addition to the carrier cells. In an example, the composition comprises carbohydrates in addition to the carrier cells. In an example, the composition comprises proteins and/or amino acids in addition to the carrier cells. In an example, the composition comprises minerals in addition to the carrier cells. In an example, the composition comprises metal ions (eg, $Mg^{2+}$, $Cu^{2+}$ and/or $Zn^{2+}$) in addition to the carrier cells. In an example, the composition comprises sodium ions, potassium ions, magnesium ions, calcium ions, manganese ions, iron ions, cobalt ions, copper ions, zinc ions and/or molybdenum ions.

In an example, the composition is a plant fertilizer composition. In an example, the composition is a herbicide. In an example, the composition is a pesticide composition for application to plants.

In any embodiment or example, where appropriate: The plants are, for example, crop plants. The plants are, for example, wheat. The plants are, for example, corn. The plants are, for example, maize. The plants are, for example, fruiting plants. The plants are, for example, vegetable plants. The plants are, for example, tomato plants. The plants are, for example, potato plants. The plants are, for example, grass plants. The plants are, for example, flowering plants. The plants are, for example, trees. The plants are, for example, shrubs.

In an example, the composition is for environmental application, wherein the environment is an outdoors environment (eg, application to a field or waterway or reservoir).

In an example, the composition is comprised by a food or food ingredient (eg, for human or animal consumption). In an example, the composition is comprised by a beverage or beverage ingredient (eg, for human or animal consumption).

In an example the target cell(s) are human biofilm cells, eg, wherein the biofilm is a gut, skin, lung, eye, nose, ear, gastrointestinal tract (GI tract), stomach, hair, kidney, urethra, bronchiole, oral cavity, mouth, liver, heart, anus, rectum, bladder, bowel, intestine, penis, vagina or scrotum biofilm. In an example the target cell(s) are animal biofilm cells, eg, wherein the biofilm is a gut, skin, lung, eye, nose, ear, gastrointestinal tract (GI tract), caecum, jejunum, ileum, colon, stomach, hair, feather, scales, kidney, urethra, bronchiole, oral cavity, mouth, liver, spleen, heart, anus, rectum, bladder, bowel, intestine, penis, vagina or scrotum biofilm. For example, the biofilm is a bird (eg, chicken) caecum biofilm. For example, the biofilm is a bird (eg, chicken) gastrointestinal tract (GI tract), caecum, jejunum, ileum, colon or stomach biofilm.

In an example, any method herein is ex vivo. In an example, a method herein is in vivo. In an example, a method herein is in vitro. In an example, a method herein is carried out in an environment, eg, in a domestic (such as in a house), industrial (such as in a factory) or agricultural environment (such as in a field). In an example, a method herein is carried out in or on a container; or on a surface.

In an example, the NSI (or a RNA product thereof) is capable of recombination with the target cell chromosome or an episome comprised by the target cell to modify the chromosome or episome. Optionally, this is carried out in a method wherein the chromosome or episome is cut (eg, at a predetermined site using a guided nuclease, such as a Cas, TALEN, zinc finger nuclease or meganuclease) and simultaneously or sequentially the first DNA is introduced into the target cell by conjugation with the carrier cell and the NSI or a sequence thereof is inserted into the chromosome or episome at or adjacent the cut site.

In an example the first DNA comprises one or more components of a CRISPR/Cas system operable to perform protospacer cutting in the target cell (eg, wherein the protospacer comprises 10-20, 10-30, 10-40, 10-100, 12-15 or 12-20 consecutive nucleotides that are capable of hybridizing in the target cell with a crRNA or gRNA encoded by the NSI).

For example, the system is a Type I, II, III, IV or V CRISPR/Cas system.

In an example, the NSI encodes a Cas9 (and optionally a second, different, Cas, such as a Cas3, Cas9, Cpf1, Cas13a, Cas13b or Cas10). In an example, the NSI encodes a Cas3 (and optionally a second, different, Cas, such as a Cas3, Cas9, Cpf1, Cas13a, Cas13b or Cas10). In an example, the NSI encodes a Cas selected from a Cas3, Cas9, Cpf1, Cas13a, Cas13b and Cas10. Additionally or alternatively, the first DNA (eg, the NSI) encodes a guide RNA or crRNA or tracrRNA. For example, the guide RNA or crRNA or tracrRNA is cognate to (ie, operable with in the target cell) the first Cas.

In an example, a Cas herein is a Cas9. In an example, a Cas herein is a Cas3. The Cas may be identical to a Cas encoded by the target bacteria.

In an embodiment, the presence in the target bacterium of the NSI or its encoded protein or RNA mediates target cell killing, or downregulation of growth or propagation of target cells. In an embodiment, the presence in the target bacterium of the NSI or its encoded protein or RNA mediates switching off of expression of one or more RNA or proteins encoded by the target cell genome, or downregulation thereof.

In an embodiment, the presence in the target bacterium of the NSI or its encoded protein or RNA mediates upregulation of growth or propagation of the target cell. In an embodiment, the presence in the target bacterium of the NSI or its encoded protein or RNA mediates switching on of expression of one or more RNA or proteins encoded by the target cell genome, or upregulation thereof.

In an embodiment, the NSI encodes a component of a CRISPR/Cas system that is toxic to the target bacterium.

In an embodiment, the first DNA is comprised by a plasmid or shuttle vector. In an embodiment, the second DNA is comprised by a vector (eg, a plasmid or shuttle vector), helper phage (eg, a helper phagemid) or is integrated in the genome of a host bacterial cell.

Optionally, the target cell is devoid of a functional endogenous CRISPR/Cas system before transfer therein of the first DNA, eg, a first DNA comprising component of an exogenous CRISPR/Cas system that is functional in the target cell and toxic to the target cell. An embodiment provides an antibacterial composition comprising a plurality of carrier cells of the invention, wherein each target cell is optionally according to this paragraph, for administration to a human or animal subject for medical use.

In an example, the composition of the invention is a herbicide, pesticide, insecticide, plant fertilizer or cleaning agent.

Optionally, target bacteria herein are comprised by a microbiome of the subject, eg, a gut microbiome. Alternatively, the microbiome is a skin, scalp, hair, eye, ear, oral, throat, lung, blood, rectal, anal, vaginal, scrotal, penile, nasal or tongue microbiome.

In an example the subject (eg, human or animal) is further administered a medicament simultaneously or sequentially with the carrier cell administration. In an example, the medicament is an antibiotic, antibody, immune checkpoint inhibitor (eg, an anti-PD-1, anti-PD-L1 or anti-CTLA4 antibody), adoptive cell therapy (eg, CAR-T therapy) or a vaccine.

In an embodiment, the NSI encodes a guided nuclease, such as a Cas nuclease, TALEN, zinc finger nuclease or meganuclease. Thus, the toxic agent may comprise a guided nuclease, such as a Cas nuclease, TALEN, zinc finger nuclease or meganuclease. Optionally, the NSI encodes a restriction nuclease that is capable of cutting the chromosome of the target cell.

Optionally, the composition is a pharmaceutical composition for use in medicine practised on a human or animal subject.

In an example, the animal is a livestock or companion pet animal (eg, a cow, pig, goat, sheep, horse, dog, cat or rabbit). In an example, the animal is an insect (an insect at any stage of its lifecycle, eg, egg, larva or pupa). In an example, the animal is a protozoan. In an example, the animal is a cephalopod.

Optionally, the composition is a herbicide, pesticide, food or beverage processing agent, food or beverage additive, petrochemical or fuel processing agent, water purifying agent, cosmetic additive, detergent additive or environmental (eg, soil) additive or cleaning agent.

The invention also provides: A target bacterial cell or a plurality of target bacterial cells each comprising a said first DNA.

For example the carrier bacteria are *Lactobacillus* (eg, *L. reuteri* or *L. lactis*), *E. coli, Bacillus* or *Streptococcus* (eg, *S. thermophilus*) bacteria. Usefully, the carrier can provide protection for the first DNA from the surrounding environment. The use of a carrier may be useful for oral administration or other routes where the carrier can provide protection for the first DNA from the acid stomach or other harsh environments in the subject. Furthermore, the carrier can be formulated into a beverage, for example, a probiotic drink, eg, an adapted Yakult (trademark), Actimel (trademark), Kevita (trademark), Activia (trademark), Jarrow (trademark) or similar drink for human consumption.

Optionally, the carrier cell(s) or composition are for administration to a human or animal subject for medical use, comprising killing target bacteria using the agent or expression product of the NSI, wherein the target bacteria mediate as disease or condition in the subject. In an example, when the subject is a human, the subject is not an embryo. In an example, the carrier cells are probiotic in the subject.

The invention also provides: A method of killing target bacterial cells in an environment, optionally wherein the method is not practised on a human or animal body, wherein the method comprises exposing the environment to the carrier cell(s) or composition of the invention and allowing the product of the NSI to be expressed in the target cells, wherein the target bacteria are killed in the presence of said product. For example, the product encodes a CRISPR/Cas system or component thereof, such as a system or component disclosed herein. Thus, the system may be capable of recognisisng and cutting a chromosomal protopspacer sequence of the target cell, whereby the target cell is killed. Optionally, in a further step killed target cells are isolated.

The invention also provides: Use of the composition or cell(s) of the invention, in the manufacture of an antibacterial agent that kills target bacteria, for the treatment of a disease or condition in a human or animal subject comprising the target bacteria.

Optionally, the environment is a microbiome of soil; a plant, part of a part (e.g., a leaf, fruit, vegetable or flower) or plant product (e.g., pulp); water; a waterway; a fluid; a foodstuff or ingredient thereof; a beverage or ingredient thereof; a medical device; a cosmetic; a detergent; blood; a bodily fluid; a medical apparatus; an industrial apparatus; an oil rig; a petrochemical processing, storage or transport apparatus; a vehicle or a container.

Optionally, the environment is an ex vivo bodily fluid (e.g., urine, blood, blood product, sweat, tears, sputum or spit), bodily solid (e.g., faeces) or tissue of a human or animal subject that has been administered the composition.

Optionally, the environment is an in vivo bodily fluid (e.g., urine, blood, blood product, sweat, tears, sputum or spit), bodily solid (e.g., faeces) or tissue of a human or animal subject that has been administered the composition.

In an embodiment, the first DNA is comprised by a phagemid or cloning vector (eg, a shuttle vector, eg, a pUC vector).

In an embodiment, the second DNA is comprised by the bacterial carrier cell chromosome.

Optionally, the toxic agent comprises one or more components of a CRISPR/Cas system, eg, a DNA sequence encoding one or more components of Type I Cascade (eg, CasA).

Optionally, the toxic agent comprises a DNA sequence encoding guided nuclease, such as a Cas nuclease, TALEN, zinc finger nuclease or meganuclease.

In an example, the carrier cell(s) or composition are comprised by a medical container, eg, a syringe, vial, IV bag, inhaler, eye dropper or nebulizer. In an example, the carrier cell(s) or composition are comprised by a sterile container. In an example, the carrier cell(s) or composition are comprised by a medically-compatible container. In an example, the carrier cell(s) or composition are comprised by a fermentation vessel, eg, a metal, glass or plastic vessel. In an example, the carrier cell(s) or composition are comprised by an agricultural apparatus. In an example, the carrier cell(s) or composition are comprised by food production or processing apparatus. In an example, the carrier cell(s) or composition are comprised by a horticultural apparatus. In an example, the carrier cell(s) or composition are comprised by a farming apparatus. In an example, the carrier cell(s) or composition are comprised by petrochemicals recovery or processing apparatus. In an example, the carrier cell(s) or composition are comprised by a distillation apparatus. In an example, the carrier cell(s) or composition are comprised by cell culture vessel (eg, having a capacity of at least 50, 100, 1000, 10000 or 100000 litres). Additionally or alternatively, the target cell(s) are comprised by any of these apparatus etc.

In an example, the carrier cell(s) or composition are comprised by a medicament, e.g in combination with instructions or a packaging label with directions to administer the medicament by oral, IV, subcutaneous, intranasal, intraocular, vaginal, topical, rectal or inhaled administration to a human or animal subject. In an example, the carrier cell(s) or composition are comprised by an oral medicament formulation. In an example, the carrier cell(s) or composition are comprised by an intranasal or ocular medicament formulation. In an example, the carrier cell(s) or composition are comprised by a personal hygiene composition (eg, shampoo, soap or deodorant) or cosmetic formulation. In an example, th the carrier cell(s) or composition are comprised by a detergent formulation. In an example, the carrier cell(s) or composition are comprised by a cleaning formulation, eg, for cleaning a medical or industrial device or apparatus. In an example, the carrier cell(s) or composition are comprised by foodstuff, foodstuff ingredient or foodstuff processing agent.

In an example, the carrier cell(s) or composition are comprised by beverage, beverage ingredient or beverage processing agent. In an example, the carrier cell(s) or composition are comprised by a medical bandage, fabric, plaster or swab. In an example, the carrier cell(s) or composition are comprised by a herbicide or pesticide. In an example, the carrier cell(s) or composition are comprised by an insecticide.

In an example, the CRISPR/Cas component(s) are component(s) of a Type I CRISPR/Cas system. In an example, the CRISPR/Cas component(s) are component(s) of a Type II CRISPR/Cas system. In an example, the CRISPR/Cas component(s) are component(s) of a Type III CRISPR/Cas system. In an example, the CRISPR/Cas component(s) are component(s) of a Type IV CRISPR/Cas system. In an example, the CRISPR/Cas component(s) are component(s) of a Type V CRISPR/Cas system. In an example, the CRISPR/Cas component(s) comprise a Cas9-encoding nucleotide sequence (eg, *S pyogenes* Cas9, *S. aureus* Cas9 or *S. thermophilus* Cas9). In an example, the CRISPR/Cas component(s) comprise a Cas3-encoding nucleotide sequence (eg, *E. coli* Cas3, *C. dificile* Cas3 or *Salmonella* Cas3). In an example, the CRISPR/Cas component(s) comprise a Cpf-encoding nucleotide sequence. In an example, the CRISPR/Cas component(s) comprise a CasX-encoding nucleotide sequence. In an example, the CRISPR/Cas component(s) comprise a CasY-encoding nucleotide sequence.

In an example, each carrier cell encodes a CRISPR/Cas component or protein of interest from a nucleotide sequence (NSI) comprising a promoter that is operable in the target bacteria.

Optionally, target bacteria are gram negative bacteria (eg, a *spirilla* or *vibrio*). Optionally, target bacteria are gram positive bacteria. Optionally, target bacteria are *mycoplasma*, chlamydiae, spirochete or *mycobacterium* bacteria. Optionally, target bacteria are *Streptococcus* (eg, *pyogenes* or *thermophilus*). Optionally, target bacteria are *Staphylococcus* (eg, *aureus*, eg, MRSA). Optionally, target bacteria are *E. coli* (eg, O157: H7), eg, wherein the Cas is encoded by the vecor or an endogenous target cell Cas nuclease (eg, Cas3) activity is de-repressed. Optionally, target bacteria are *Pseudomonas* (eg, *syringae* or *aeruginosa*). Optionally, target bacteria are Vibro (eg, *cholerae* (eg, O139) or *vulnificus*). Optionally, target bacteria are *Neisseria* (eg, *gonnorrhoeae* or *meningitidis*). Optionally, target bacteria are *Bordetella* (eg, pertussis). Optionally, target bacteria are *Haemophilus* (eg, *influenzae*). Optionally, target bacteria are *Shigella* (eg, *dysenteriae*). Optionally, target bacteria are *Brucella* (eg, *abortus*). Optionally, target bacteria are *Francisella* host. Optionally, target bacteria are *Xanthomonas*. Optionally, target bacteria are *Agrobacterium*. Optionally, target bacteria are *Erwinia*. Optionally, target bacteria are *Legionella* (eg, *pneumophila*). Optionally, target bacteria are *Listeria* (eg, *monocytogenes*). Optionally, target bacteria are *Campylobacter* (eg, *jejuni*). Optionally, target bacteria are *Yersinia* (eg, *pestis*). Optionally, target bacteria are *Borelia* (eg, *burgdorferi*). Optionally, target bacteria are *Helicobacter* (eg, *pylori*). Optionally, target bacteria are *Clostridium* (eg, *dificile* or *botulinum*). Optionally, target bacteria are *Erlichia* (eg, *chaffeensis*). Optionally, target bacteria are *Salmonella* (eg, *typhi* or *enterica*, eg, serotype *typhimurium*, eg, DT 104). Optionally, target bacteria are *Chlamydia* (eg, *pneumoniae*). Optionally, target bacteria are Parachlamydia host. Optionally, target bacteria are *Corynebacterium* (eg, *amycolatum*). Optionally, target bacteria are *Klebsiella* (eg, *pneumoniae*). Optionally, target bacteria are *Enterococcus* (eg, *faecalis* or *faecim*, eg, linezolid-resistant). Optionally, target bacteria are *Acinetobacter* (eg, *baumannii*, eg, multiple drug resistant).

Further examples of target cells are as follows:—

1. Optionally the target bacteria are *Staphylococcus aureus* cells, eg, resistant to an antibiotic selected from methicillin, vancomycin, linezolid, daptomycin, quinupristin, dalfopristin and teicoplanin.
2. Optionally the target bacteria are *Pseudomonas aeruginosa* cells, eg, resistant to an antibiotic selected from cephalosporins (eg, ceftazidime), carbapenems (eg, imipenem or meropenem), fluoroquinolones, aminoglycosides (eg, gentamicin or tobramycin) and colistin.
3. Optionally the target bacteria are *Klebsiella* (eg, *pneumoniae*) cells, eg, resistant to carbapenem.
4. Optionally the target bacteria are *Streptococcus* (eg, *thermophilus, pneumoniae* or *pyogenes*) cells, eg, resistant to an antibiotic selected from erythromycin, clindamycin, beta-lactam, macrolide, amoxicillin, azithromycin and penicillin.
5. Optionally the target bacteria are *Salmonella* (eg, serotype *Typhi*) cells, eg, resistant to an antibiotic selected from ceftriaxone, azithromycin and ciprofloxacin.
6. Optionally the target bacteria are *Shigella* cells, eg, resistant to an antibiotic selected from ciprofloxacin and azithromycin.
7. Optionally the target bacteria are *Mycobacterium tuberculosis* cells, eg, resistant to an antibiotic selected from Resistance to isoniazid (INH), rifampicin (RMP), fluoroquinolone, amikacin, kanamycin and capreomycin and azithromycin.
8. Optionally the target bacteria are *Enterococcus* cells, eg, resistant to vancomycin.
9. Optionally the target bacteria are Enterobacteriaceae cells, eg, resistant to an antibiotic selected from a cephalosporin and carbapenem.
10. Optionally the target bacteria are *E. coli* cells, eg, resistant to an antibiotic selected from trimethoprim, itrofurantoin, cefalexin and amoxicillin.
11. Optionally the target bacteria are *Clostridium* (eg, *dificile*) cells, eg, resistant to an antibiotic selected from fluoroquinolone antibiotic and carbapenem.
12. Optionally the target bacteria are *Neisseria gonnorrhoea* cells, eg, resistant to an antibiotic selected from cefixime (eg, an oral cephalosporin), ceftriaxone (an injectable cephalosporin), azithromycin and tetracycline.
13. Optionally the target bacteria are *Acinetoebacter baumannii* cells, eg, resistant to an antibiotic selected from beta-lactam, meropenem and a carbapenem.
14. Optionally the target bacteria are *Campylobacter* (eg, *jejuni*) cells, eg, resistant to an antibiotic selected from ciprofloxacin and azithromycin.
15. Optionally, the target cell(s) produce Beta (β)-lactamase (eg, ESBL-producing *E. coli* or ESBL-producing *Klebsiella*).
16. Optionally, the target cell(s) are bacterial cells that are resistant to an antibiotic recited in any one of examples 1 to 14.

In an example, the target cell(s) is a cell of a species selected from *Shigella, E. coli, Salmonella, Serratia, Klebsiella, Yersinia, Pseudomonas* and *Enterobacter.*

Optionally, the composition comprises carrier cells that are each or in combination capable of conjugative transfer of first DNAs into target cells of species selected from two or more of *Shigella, E coli, Salmonella, Serratia, Klebsiella, Yersinia, Pseudomonas* and *Enterobacter.*

In an example, the reduction in growth or proliferation of carrier cells is at least 50, 60, 70, 80, 90 or 95%. Optionally, the composition or carrier cell(s) are administered simultaneously or sequentially with an an antibiotic that is toxic to the target cells. For example, the antibiotic can be any antibiotic disclosed herein.

Optionally, the expression of the NSI is under the control of an inducible promoter that is operable in the target cell. Optionally, the expression of the NSI is under the control of a constitutive promoter that is operable in the target cell.

In embodiments, the first DNA (eg, comprised by a plasmid) contains a screenable or selectable marker gene. For example, the selectable marker gene is an antibiotic resistance gene.

The carrier bacteria can be bacteria of a species or genus selected from those appearing in Table 5. For example, the species is found in warm-blooded animals (eg, livestock vertebrates). For example, the species is found in humans. For example, the species is found in plants. Preferably, non-pathogenic bacteria that colonize the non-sterile parts of the human or animal body (e.g., skin, digestive tract, urogenital region, mouth, nasal passages, throat and upper airway, ears and eyes) are utilized as carrier cells, and in an example the methodology of the invention is used to combat a target cell bacterial infection of such a part of the body of a human or animal. In another embodiment, the infection is systemic infection. Examples of particularly preferred carrier bacterial species include, but are not limited to: non-pathogenic strains of *Escherichia coli* (*E. coli* F18, S17 and *E. coli* strain Nissle), various species of *Lactobacillus* (such as *L. casei, L. plantarum, L. paracasei, L. acidophilus, L. fermentum, L. zeae* and *L. gasseri*), or other nonpathogenic or probiotic skin- or GI colonizing bacteria such as *Lactococcus*, Bifidobacteria, Eubacteria, and bacterial mini-cells, which are anucleoid cells destined to die but still capable of transferring plasmids (see; e.g., Adler et al., Proc. Natl. Acad. Sci. USA 57; 321-326, 1970; Frazer and Curtiss III, Current Topics in Microbiology and Immunology 69: 1-84, 1975; U.S. Pat. No. 4,968,619 to Curtiss III). In some embodiments, the target recipient cells are pathogenic bacteria comprised by a human, animal or plant, eg, on the skin or in the digestive tract, urogenital region, mouth, nasal passage, throat and upper airway, eye(s) and ear(s). Of particular interest for targeting and eradication are pathogenic strains of *Pseudomonas aeruginosa, Escherichia coli, Staphylococcus pneumoniae* and other species, *Enterobacter* spp., *Enterococcus* spp. and *Mycobacterium tuberculosis*. In an example, the target cell genus or species is any genus or species listed in Table 5.

The present invention finds use with a wide array of settings or environments, eg, in therapeutic, agricultural, or other settings, including, but not limited to, those described in U.S. Pat. Nos. 6,271,359, 6,261,842, 6,221,582, 6,153, 381, 6,106,854, and 5,627,275. Others are also discussed herein, and still others will be readily apparent to those of skill in the art.

Numerous types of plasmids comprising the first DNA are suitable for use in the present invention. In view of this, one of skill in the art will appreciate that a single carrier bacterial strain might harbor more than one type of such plasmid (eg, differing in the antibacterial agent that they encode). Further, in another example two or more different carrier bacterial strains, each containing one or more such plasmids, may be combined for a multi-target effect, ie, for killing two or more different target species or strains, or for killing the cells of the same species or strain of target cell.

The present invention finds utility for treatment of humans and in a variety of veterinary, agronomic, horticultural and food processing applications. For human and veterinary use, and depending on the cell population or tissue targeted for protection, the following modes of administration of the carrier bacteria of the invention are contemplated: topical, oral, nasal, ocular, aural, pulmonary (e.g., via an inhaler), ophthalmic, rectal, urogenital, subcutaneous, intraperitoneal and intravenous. The bacteria may be supplied as a pharmaceutical composition, in a delivery vehicle suitable for the mode of administration selected for the patient being treated. The term "patient" or "subject" as used here refers to humans or animals (animals being particularly useful as models for clinical efficacy of a particular donor strain, for example, or being farmed or livestock animals). Commercially-relevant animals are chicken, turkey, duck, catfish, salmon, cod, herring, lobster, shrimp, prawns, cows, sheep, goats, pigs, goats, geese or rabbits.

For example, to deliver the carrier bacteria to the gastrointestinal tract or to the nasal passages, the preferred mode of administration may be by oral ingestion or nasal aerosol, or by feeding (alone or incorporated into the subject's feed or food and/or beverage, such as drinking water). In this regard, the carrier cells may be comprised by a food of livestock (or farmed or companion animal), eg, the carrier bacteria are comprised by a feed additive for livestock. Alternatively, the additive is a beverage (eg, water) additive for livestock. It should be noted that probiotic bacteria, such as *Lactobacillus acidophilus*, are sold as gel capsules containing a lyophilized mixture of bacterial cells and a solid support such as mannitol. When the gel capsule is ingested with liquid, the lyophilized cells are re-hydrated and become viable, colonogenic bacteria. Thus, in a similar fashion, carrier bacterial cells of the present invention can be supplied as a powdered, lyophilized preparation in a gel capsule, or in bulk, eg, for sprinkling onto food or beverages. The re-hydrated, viable bacterial cells will then populate and/or colonze sites throughout the upper and/or lower gastrointestinal system, and thereafter come into contact with the target bacteria.

For topical applications, the carrier bacteria may be formulated as an ointment or cream to be spread on the affected skin surface. Ointment or cream formulations are also suitable for rectal or vaginal delivery, along with other standard formulations, such as suppositories. The appropriate formulations for topical, vaginal or rectal administration are well known to medicinal chemists. The present invention will be of particular utility for topical or mucosal administrations to treat a variety of bacterial infections or bacterially related undesirable conditions. Some representative examples of these uses include treatment of (1) conjunctivitis, caused by *Haemophilus* sp., and corneal ulcers, caused by *Pseudomonas aeruginosa*; (2) otitis externa, caused by *Pseudomonas aeruginosa*; (3) chronic sinusitis, caused by many Gram-positive cocci and Gram-negative rods, or for general decontamination of bronchii; (4) cystic fibrosis, associated with *Pseudomonas aeruginosa*; (5) enteritis, caused by *Helicobacter pylori* (eg, to treat or prevent gastric ulcers), *Escherichia coli, Salmonella typhimurium, Campylobacter* or *Shigella* sp.; (6) open wounds, such as surgical or non-surgical, eg, as a prophylactic measure; (7) burns to eliminate *Pseudomonas aeruginosa* or other Gram-negative pathogens; (8) acne, eg, caused by *Propionobacter acnes*; (9) nose or skin infection, eg, caused by metlncillin resistant *Staphylococcus aureus* (MSRA); (10) body odor, eg, caused by Gram-positive anaerobic bacteria (i.e., use of carrier cells in deodorants); (11) bacterial vaginosis, eg, associated with *Gardnerella vaginalis* or other anaerobes; and (12) gingivitis and/or tooth decay caused by various organisms.

In one example, the target cells are *E. coli* cells and the disease or condition to be treated in a human is a uterine tract infection or a ventilator associated infection, eg, pneumonia.

In other embodiments, the carrier cells of the present invention find application in the treatment of surfaces for the removal or attenuation of unwanted target bacteria, for example use in a method of treating such a surface or an environment comprising target bacteria, wherein the method comprises contacting the surface or environment with carrier bacteria of the invention, allowing conjugative transfer of the first DNA of the invention from the carrier to the target bacteria, and allowing the antibacterial agent to kill target cells. For example, surfaces that may be used in invasive treatments such as surgery, catheterization and the like may be treated to prevent infection of a subject by bacterial contaminants on the surface. It is contemplated that the methods and compositions of the present invention may be used to treat numerous surfaces, objects, materials and the like (e.g., medical or first aid equipment, nursery and kitchen equipment and surfaces) to control bacterial contamination thereon.

Pharmaceutical preparations or other compositions comprising the carrier bacteria may be formulated in dosage unit form for ease of administration and uniformity of dosage. Dosage unit form, as used herein, refers to a physically discrete unit of the pharmaceutical preparation appropriate for the patient or plant or environment or surface undergoing treatment. Each dosage should contain a quantity of the carrier bacteria calculated to produce the desired antibacterial effect in association with the selected carrier. Procedures for determining the appropriate dosage unit are well known to those skilled in the art. Dosage units may be proportionately increased or decreased based on the weight of a patient, plant, surface or environment. Appropriate concentrations for achieving eradication of pathogenic target cells (eg, comprised by a tissue of the patient) may be determined by dosage concentration curve calculations, as known in the art.

Other uses for the carrier bacteria of the invention are also contemplated. These include a variety agricultural, horticultural, environmental and food processing applications. For example, in agriculture and horticulture, various plant pathogenic bacteria may be targeted in order to minimize plant disease. One example of a plant pathogen suitable for targeting is *Erwinia* (eg, *E. amylovora*, the causal agent of fire blight). Similar strategies may be utilized to reduce or prevent wilting of cut flowers. For veterinary or animal farming, the carrier cells of the invention may be incorporated into animal feed (chicken, swine, poultry, goat, sheep, fish, shellfish or cattle feed) to reduce bio-burden or to eliminate certain pathogenic organisms (e.g., *Salmonella*, such as in chicken, turkey or other poultry). In other embodiments, the invention may be applied on meat or other foods to eliminate unwanted or pathogenic bacteria (e.g., *E. coli O*157:1H7 on meat, or *Proteus* spp., one cause of “fishy odour” on seafood).

Environmental utilities comprise, for example, engineering carrier bacteria, eg, *Bacillus thurengiensis* and one of its conjugative plasmids, to deliver and conditionally express an insecticidal agent in addition to or instead of an antibacterial agent (e.g., for the control of mosquitos that disseminate malaria or West Nile virus). In such applications, as well as in the agricultural and horticultural or other applications described above, formulation of the carrier bacteria as solutions, aerosols, or gel capsules are contemplated.

In preferred embodiments of the present invention, certain features are employed in the DNA, plasmids and carrier cells of the invention to minimize potential risks associated with the use of engineered DNA or genetically modified organisms in the environment. For instance, eg, in environmentally sensitive circumstances, it may be advantageous to utilise non-self-transmissible DNA or plasmids. Instead, the DNA or plasmids will be mobilisable by conjugative machinery but will not be self-transmissible. This may be accomplished in some embodiments by integrating into the carrier cell chromosome all or some of the tra genes whose products are necessary for the assembly of conjugative machinery. In such embodiments, DNA or plasmids of the invention are configured to possess an origin of transfer (oriT) but not the tra genes that are provided on the cell's chromosome. This feature prevents the recipient killer cell, before or even after it dies, from transferring the killer DNA or plasmid further. Another biosafety feature comprises utilizing conjugation systems with predetermined host-ranges. Certain elements are known to function only in few related bacteria (narrow-host-range) and others are known to function in many unrelated bacteria (broad-host-range or promiscuous) (del Solar et al., Mol. Microbiol. 32: 661-666, 1996; Zatyka and Thomas, FEMS Microbiol. Rev. 21: 291-319, 1998). Also, many of those conjugation systems can function in either gram-positive or gram-negative bacteria but generally not in both (del Solar, 1996, supra; Zatyka and Thomas, 1998).

Inadvertant proliferation of antibiotic resistance may be minimized in embodiments by avoiding the use of antibiotic resistance markers on the DNA or plasmids of the invention which are conjugatively transferred into target cells. In an alternative approach, the gene responsible for the synthesis of an amino acid (i.e. serine) can be mutated, generating the requirement for this amino acid in the donor. Such mutant bacteria will prosper on media lacking serine provided that they contain a plasmid with the ser gene whose product is needed for growth. Thus, the invention contemplates the advantageous use of plasmids containing the ser gene or another nutritional genetic marker. These markers will permit selection and maintenance of the DNA or plasmids in carrier cells. Another biosafety approach comprises the use of restriction-modification systems to modulate the host range of the DNA or plasmids. Conjugation and plasmid establishment are expected to occur more frequently between taxonomically related species in which plasmid can evade restriction systems and replicate. Type II restriction endonucleases make a double-strand break within or near a specific recognition sequence of duplex DNA. Cognate modification enzymes can methylate the same sequence and protect it from cleavage. Restriction-modification systems (RM) are ubiquitous in bacteria and archaebacteria but are absent in eukaryotes. Some of RM systems are plasmid-encoded, while others are on the bacterial chromosome (Roberts and Macelis, Nucl. Acids Res. 24: 223-235, 1998). Restriction enzymes cleave foreign DNA such as viral or plasmid DNA when this DNA has not been modified by the appropriate modification enzyme. In this way, cells are protected from invasion of foreign DNA. Thus, by using a carrier strain producing one or more methylases, cleavage by one or more restriction enzymes could be evaded. Site-directed mutagenesis is used to produce plasmid DNA that is either devoid of specific restriction sites or that comprises new sites, protecting or making plasmid DNA vulnerable, respectively against endonucleases. Broad-host range plasmids (eg. RP4) may evade restriction systems simply by not having many of the restriction cleavage sites that are typically present on narrow-host plasmids (Willkins et al., 1996, J. Mol. Biol 258, 447-456). Preferred embodiments of the present invention also utilize environmentally safe bacteria as carriers. For example, delivery of DNA vaccines by attenuated intracellular gram-positive and gram-negative bacteria has been reported (Dietrich et al., 2001 Vaccine 19, 2506-2512; Grillot-Courvalin et al, 1999 Current Opinion in Biotech. 10, 477-481). In addition, the donor strain can be one of thousands of harmless bacteria that colonize the non-sterile parts of the body (e.g., skin, gastrointestinal, urogenital, mouth, nasal passages, throat and upper airway systems). Examples of preferred donor (ie, carrier) bacterial species are set forth hereinabove.

In another strategy, non-dividing, non-growing carrier cells are utilized instead of living cells. Minicells and maxicells are well studied model systems of metabolically active but nonviable bacterial cells. Minicells lack chromosomal DNA and are generated by special mutant cells that undergo cell division without DNA replication. If the cell contains a multicopy plasmid, many of the minicells will contain plasmids. Minicells neither divide nor grow. However, minicells that possess conjugative plasmids are capable of conjugal replication and transfer of plasmid DNA to living recipient cells. (Adler et al., 1970, supra; Frazer and Curtiss, 1975, supra; U.S. Pat. No. 4,968,619, supra). Maxicells can be obtained from a strain of *E. coli* that carries mutations in the key DNA repair pathways (recA, uvrA and phr). Because maxicells lack so many DNA repair functions, they die upon exposure to low doses of UV. Importantly, plasmid molecules (e.g., pBR322) that do not receive an UV hit continue to replicate. Transcription and translation (plasmid-directed) can occur efficiently under such conditions (Sancar et al., J. Bacteriol. 137: 692-693, 1979), and the proteins made prior to irradiation should be sufficient to sustain conjugation. This is supported by the following two observations: i) that streptomycin-killed cells remain active donors, and ii) that transfer of conjugative plasmids can occur in the presence of antibiotics that prevent de novo gene expression (Heineman and Ankenbauer, 1993, J. Bacteriol. 175, 583-588; Cooper and Heineman, 2000. Plasmid 43, 171-175). Accordingly, UV-treated maxicells will be able to transfer plasmid DNA to live recipients. It should also be noted that the conservation of recA and uvrA genes among bacteria should allow maxicells of donor strains other than *E. coli* to be obtained.

Also contemplated for use in the invention are any of the modified bacteria that cannot function because they contain temperature-sensitive mutation(s) in genes that encode for essential cellular functions (e.g., cell wall, protein synthesis, RNA synthesis, as described, for example, in U.S. Pat. No. 4,968,619, supra).

In an alternative, archaea are used instead of bacteria for the carrier cells. Additionally or alternatively, the target cells are archaeal cells.

As used herein, the term "carrier cell" includes dividing and/or non-dividing bacterial cells (minicells and maxicells), or conditionally non-functional cells.

In an example the first DNA is comprised by an engineered RK2 plasmid (ie, a RK2 plasmid that has been modified by recombinant DNA technology or a progeny of such a modified plasmid). Plasmid RK2 is a promiscuous plasmid that can replicate in 29 (and probably many more) gram-negative species (Guiney and Lanka, 1989, p 27-54. In C. M. Thomas (ed) Promiscous plasmids in gram-negative bacteria. London, Ltd London United Kingdom). Plasmid RK2 is a 60-kb self-transmissible plasmid with a complete nucleotide sequence known (Pansegrau et al., 1994, J. Mol. Biol. 239, 623-663). A minimal replicon derived from this large plasmid has been obtained that is devoid of all its genes except for a trfA gene, that encodes plasmid's Rep protein called TrfA, and an origin of vegetative replication oriV For a review of RK2 replication and its control by TrfA protein, see Helinski et al., 1996 (In *Escherichia coli* and *Salmonella* Cellular and Molecular Biology, Vol. 2 (ed. F. Neidhardt, et al., 2295-2324, ASM Press, Washington D.C.).

In an example the first DNA is comprised by an engineered R6K plasmid (ie, a R6K plasmid that has been modified by recombinant DNA technology or a progeny of such a modified plasmid).

The present invention is optionally for an industrial or domestic use, or is used in a method for such use. For example, it is for or used in agriculture, oil or petroleum industry, food or drink industry, clothing industry, packaging industry, electronics industry, computer industry, environmental industry, chemical industry, aerospace industry, automotive industry, biotechnology industry, medical industry, healthcare industry, dentistry industry, energy industry, consumer products industry, pharmaceutical industry, mining industry, cleaning industry, forestry industry, fishing industry, leisure industry, recycling industry, cosmetics industry, plastics industry, pulp or paper industry, textile industry, clothing industry, leather or suede or animal hide industry, tobacco industry or steel industry.

The present invention is optionally for use in an industry or the environment is an industrial environment, wherein the industry is an industry of a field selected from the group consisting of the medical and healthcare; pharmaceutical; human food; animal food; plant fertilizers; beverage; dairy; meat processing; agriculture; livestock farming; poultry farming; fish and shellfish farming; veterinary; oil; gas; petrochemical; water treatment; sewage treatment; packaging; electronics and computer; personal healthcare and toiletries; cosmetics; dental; non-medical dental; ophthalmic; non-medical ophthalmic; mineral mining and processing; metals mining and processing; quarrying; aviation; automotive; rail; shipping; space; environmental; soil treatment; pulp and paper; clothing manufacture; dyes; printing; adhesives; air treatment; solvents; biodefence; vitamin supplements; cold storage; fibre retting and production; biotechnology; chemical; industrial cleaning products; domestic cleaning products; soaps and detergents; consumer products; forestry; fishing; leisure; recycling; plastics; hide, leather and suede; waste management; funeral and undertaking; fuel; building; energy; steel; and tobacco industry fields.

In an example, the first DNA comprises a CRISPR array that targets target bacteria, wherein the array comprises one, or two or more different spacers (eg, 2, 3, 4, 5, 6, 7, 8, 9, 10, 20, 30, 40, 50 or more spacers) for targeting the genome of target bacteria.

In an example, the target bacteria are comprised by an environment as follows. In an example, the environment is a microbiome of a human, eg, the oral cavity microbiome or gut microbiome or the bloodstream. In an example, the environment is not an environment in or on a human. In an example, the environment is not an environment in or on a non-human animal. In an embodiment, the environment is an air environment. In an embodiment, the environment is an agricultural environment. In an embodiment, the environment is an oil or petroleum recovery environment, eg, an oil or petroleum field or well. In an example, the environment is an environment in or on a foodstuff or beverage for human or non-human animal consumption. In an example, the environment is a maritime environment, eg, in seawater or on a boat (eg, in ship or boat ballast water).

In an example, the environment is a a human or animal microbiome (eg, gut, vaginal, scalp, armpit, skin or oral cavity microbiome). In an example, the target bacteria are comprised by a human or animal microbiome (eg, gut, vaginal, scalp, armpit, skin or oral cavity microbiome).

In an example, the carrier bacteria or composition of the invention are administered intranasally, topically or orally to a human or non-human animal, or is for such administration. The skilled person aiming to treat a microbiome of the human or animal will be able to determine the best route of administration, depending upon the microbiome of interest. For example, when the microbiome is a gut microbiome, administration can be intranasally or orally. When the microbiome is a scalp or armpit microbiome, administration can be topically. When the microbiome is in the mouth or throat, the administration can be orally.

In an example, the environment is harboured by a beverage or water (eg, a waterway or drinking water for human consumption) or soil. The water is optionally in a heating, cooling or industrial system, or in a drinking water storage container.

In an example, the carrier and/or target bacteraia are Firmicutes selected from *Anaerotruncus, Acetanaerobacterium, Acetitomaculum, Acetivibrio, Anaerococcus, Anaerofilum, Anaerosinus, Anaerostipes, Anaerovorax, Butyrivibrio, Clostridium, Capracoccus, Dehalobacter, Dialister, Dorea, Enterococcus, Ethanoligenens, Faecalibacterium, Fusobacterium, Gracilibacter, Guggenheimella, Hespellia, Lachnobacterium, Lachnospira, Lactobacillus, Leuconostoc, Megamonas, Moryella, Mitsuokella, Oribacterium, Oxobacter, Papillibacter, Proprionispira, Pseudobutyrivibrio, Pseudoramibacter, Roseburia, Ruminococcus, Sarcina, Seinonella, Shuttleworthia, Sporobacter, Sporobacterium, Streptococcus, Subdoligranulum, Syntrophococcus, Thermobacillus, Turibacter* and Weisella.

In an example, the carrier bacteria, composition, use or method is for reducing pathogenic infections or for rebalancing gut or oral biofilm eg, for treating or preventing obesity or disease in a human or animal; or for treating or preventing a GI condition (such as Crohn's disease, IBD or colitis). For example, the DNA, carrier bacteria, composition, use or method is for knocking-down *Salmomnella, Campylobacter, Erwinia, Xanthomonous, Edwardsiella, Pseudomonas, Klebsiella, Pectobacterium, Clostridium*

*dificile* or *E. coli* bacteria in a gut biofilm of a human or animal or a plant, preferably in a human or animal.

In an example, the animal is a chicken, eg, and the target bacteria are *Salmonella* or *Campylobacter*. In an example, the animal is a fish (eg, catfish or salmon) or shellfish (eg, prawn or lobster), eg, and the target bacteria are Edwardsiella. In an example, the plant is a potato plant and, eg, the target bacteria are *Pectobacterium*. In an example, the plant is a cabbage plant and, eg, the target bacteria are *Xanthomonous* (eg, *X. campestris*). In an example, the plant is a marijuana plant and, eg, the targt bacteria are *Pseudomonas* (eg, *P. cannabina* or *P. amygdali*), *Agrobacterium* (eg, *A. tumefaciens*) or *Xanthomonas* (eg, *X. campestris*). In an example, the plant is a hemp plant and, eg, the targt bacteria are are *Pseudomonas* (eg, *P. cannabina* or *P. amygdali*), *Agrobacterium* (eg, *A. tumefaciens*) or *Xanthomonas* (eg, *X. campestris*).

In an example, the disease or condition is a cancer, inflammatory or autoimmune disease or condition, eg, obesity, diabetes IBD, a GI tract condition or an oral cavity condition.

Optionally, the environment is comprised by, or the target bacteria are comprised by, a gut biofilm, skin biofilm, oral cavity biofilm, throat biofilm, hair biofilm, armpit biofilm, vaginal biofilm, rectal biofilm, anal biofilm, ocular biofilm, nasal biofilm, tongue biofilm, lung biofilm, liver biofilm, kidney biofilm, genital biofilm, penile biofilm, scrotal biofilm, mammary gland biofilm, ear biofilm, urethra biofilm, labial biofilm, organ biofilm or dental biofilm. Optionally, the environment is comprised by, or the target bacteria are comprised by, a plant (eg, a tobacco, crop plant, fruit plant, vegetable plant or tobacco, eg on the surface of a plant or contained in a plant) or by an environment (eg, soil or water or a waterway or aqueous liquid).

In an example, the carrier cell(s) or composition is for treating a disease or condition in an animal or human, wherein the disease or condition. In an example, the disease or condition is caused by or mediated by an infection of target cells comprised by the subject or patient. In an example, the disease or condition is associated with an infection of target cells comprised by the subject or patient.

In an example, a symptom of the disease or condition is an infection of target cells comprised by the subject or patient.

Optionally, the disease or condition of a human or animal subject is selected from (a) A neurodegenerative disease or condition;
(b) A brain disease or condition;
(c) A CNS disease or condition;
(d) Memory loss or impairment;
(e) A heart or cardiovascular disease or condition, eg, heart attack, stroke or atrial fibrillation;
(f) A liver disease or condition;
(g) A kidney disease or condition, eg, chronic kidney disease (CKD);
(h) A pancreas disease or condition;
(i) A lung disease or condition, eg, cystic fibrosis or COPD;
(j) A gastrointestinal disease or condition;
(k) A throat or oral cavity disease or condition;
(l) An ocular disease or condition;
(m) A genital disease or condition, eg, a vaginal, labial, penile or scrotal disease or condition;
(n) A sexually-transmissible disease or condition, eg, gonorrhea, HIV infection, syphilis or *Chlamydia* infection;

(o) An ear disease or condition;
(p) A skin disease or condition;
(q) A heart disease or condition;
(r) A nasal disease or condition
(s) A haematological disease or condition, eg, anaemia, eg, anaemia of chronic disease or cancer;
(t) A viral infection;
(u) A pathogenic bacterial infection;
(v) A cancer;
(w) An autoimmune disease or condition, eg, SLE;
(x) An inflammatory disease or condition, eg, rheumatoid arthritis, psoriasis, eczema, asthma, ulcerative colitis, colitis, Crohn's disease or IBD;
(y) Autism;
(z) ADHD;
(aa) Bipolar disorder;
(bb) ALS [Amyotrophic Lateral Sclerosis];
(cc) Osteoarthritis;
(dd) A congenital or development defect or condition;
(ee) Miscarriage;
(ff) A blood clotting condition;
(gg) Bronchitis;
(hh) Dry or wet AMD;
(ii) Neovascularisation (eg, of a tumour or in the eye);
(jj) Common cold;
(kk) Epilepsy;
(ll) Fibrosis, eg, liver or lung fibrosis;
(mm) A fungal disease or condition, eg, thrush;
(nn) A metabolic disease or condition, eg, obesity, anorexia, diabetes, Type I or Type II diabetes.
(oo) Ulcer(s), eg, gastric ulceration or skin ulceration;
(pp) Dry skin;
(qq) Sjogren's syndrome;
(rr) Cytokine storm;
(ss) Deafness, hearing loss or impairment;
(tt) Slow or fast metabolism (ie, slower or faster than average for the weight, sex and age of the subject);
(uu) Conception disorder, eg, infertility or low fertility;
(vv) Jaundice;
(ww) Skin rash;
(xx) Kawasaki Disease;
(yy) Lyme Disease;
(zz) An allergy, eg, a nut, grass, pollen, dust mite, cat or dog fur or dander allergy;
(aaa) Malaria, typhoid fever, tuberculosis or cholera;
(bbb) Depression;
(ccc) Mental retardation;
(ddd) Microcephaly;
(eee) Malnutrition;
(fff) Conjunctivitis;
(ggg) Pneumonia;
(hhh) Pulmonary embolism;
(iii) Pulmonary hypertension;
(jjj) A bone disorder;
(kkk) Sepsis or septic shock;
(lll) Sinusitus;
(mmm) Stress (eg, occupational stress);
(nnn) Thalassaemia, anaemia, von Willebrand Disease, or haemophilia;
(ooo) Shingles or cold sore;
(ppp) Menstruation;
(qqq) Low sperm count.

Neurodegenerative or CNS Diseases or Conditions for Treatment or Prevention by the Invention In an example, the neurodegenerative or CNS disease or condition is selected from the group consisting of Alzheimer disease, geriopsychosis, Down syndrome, Parkinson's disease, Creutzfeldt-jakob disease, diabetic neuropathy, Parkinson syndrome, Huntington's disease, Machado-Joseph disease, amyotrophic lateral sclerosis, diabetic neuropathy, and Creutzfeldt Creutzfeldt-Jakob disease. For example, the disease is Alzheimer disease. For example, the disease is Parkinson syndrome.

In an example, wherein the method of the invention is practised on a human or animal subject for treating a CNS or neurodegenerative disease or condition, the method causes downregulation of Treg cells in the subject, thereby promoting entry of systemic monocyte-derived macrophages and/or Treg cells across the choroid plexus into the brain of the subject, whereby the disease or condition (eg, Alzheimer's disease) is treated, prevented or progression thereof is reduced. In an embodiment the method causes an increase of IFN-gamma in the CNS system (eg, in the brain and/or CSF) of the subject. In an example, the method restores nerve fibre and/or reduces the progression of nerve fibre damage. In an example, the method restores nerve myelin and/or reduces the progression of nerve myelin damage. In an example, the method of the invention treats or prevents a disease or condition disclosed in WO2015136541 and/or the method can be used with any method disclosed in WO2015136541 (the disclosure of this document is incorporated by reference herein in its entirety, eg, for providing disclosure of such methods, diseases, conditions and potential therapeutic agents that can be administered to the subject for effecting treatment and/or prevention of CNS and neurodegenerative diseases and conditions, eg, agents such as immune checkpoint inhibitors, eg, anti-PD-1, anti-PD-L1, anti-TIM3 or other antibodies disclosed therein).

Cancers for Treatment or Prevention by the Method

Cancers that may be treated include tumours that are not vascularized, or not substantially vascularized, as well as vascularized tumours. The cancers may comprise non-solid tumours (such as haematological tumours, for example, leukaemias and lymphomas) or may comprise solid tumours. Types of cancers to be treated with the invention include, but are not limited to, carcinoma, blastoma, and sarcoma, and certain leukaemia or lymphoid malignancies, benign and malignant tumours, and malignancies e.g., sarcomas, carcinomas, and melanomas. Adult tumours/cancers and paediatric tumours/cancers are also included.

Haematologic cancers are cancers of the blood or bone marrow. Examples of haematological (or haematogenous) cancers include leukaemias, including acute leukaemias (such as acute lymphocytic leukaemia, acute myelocytic leukaemia, acute myelogenous leukaemia and myeloblasts, promyeiocytic, myelomonocytic, monocytic and erythroleukaemia), chronic leukaemias (such as chronic myelocytic (granulocytic) leukaemia, chronic myelogenous leukaemia, and chronic lymphocytic leukaemia), polycythemia vera, lymphoma, Hodgkin's disease, non-Hodgkin's lymphoma (indolent and high grade forms), multiple myeloma, Waldenstrom's macroglobulinemia, heavy chain disease, myeiodysplastic syndrome, hairy cell leukaemia and myelodysplasia.

Solid tumours are abnormal masses of tissue that usually do not contain cysts or liquid areas. Solid tumours can be benign or malignant. Different types of solid tumours are named for the type of cells that form them (such as sarcomas, carcinomas, and lymphomas). Examples of solid tumours, such as sarcomas and carcinomas, include fibrosarcoma, myxosarcoma, liposarcoma, chondrosarcoma, osteosarcoma, and other sarcomas, synovioma, mesothelioma, Ewing's tumour, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous eel! carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumour, cervical cancer, testicular tumour, seminoma, bladder carcinoma, melanoma, and CNS tumours (such as a glioma (such as brainstem glioma and mixed gliomas), glioblastoma (also known as glioblastoma multiforme) astrocytoma, CNS lymphoma, germinoma, medu!loblastoma, Schwannoma craniopharyogioma, ependymoma, pineaioma, hemangioblastoma, acoustic neuroma, oligodendroglioma, menangioma, neuroblastoma, retinoblastoma and brain metastases).

Autoimmune Diseases for Treatment or Prevention by the Method

1. Acute Disseminated Encephalomyelitis (ADEM)
2. Acute necrotizing hemorrhagic leukoencephalitis
3. Addison's disease
4. Agammaglobulinemia
5. Alopecia areata
6. Amyloidosis
7. Ankylosing spondylitis
8. Anti-GBM/Anti-TBM nephritis
9. Antiphospholipid syndrome (APS)
10. Autoimmune angioedema
11. Autoimmune aplastic anemia
12. Autoimmune dysautonomia
13. Autoimmune hepatitis
14. Autoimmune hyperlipidemia
15. Autoimmune immunodeficiency
16. Autoimmune inner ear disease (AIED)
17. Autoimmune myocarditis
18. Autoimmune oophoritis
19. Autoimmune pancreatitis
20. Autoimmune retinopathy
21. Autoimmune thrombocytopenic purpura (ATP)
22. Autoimmune thyroid disease
23. Autoimmune urticaria
24. Axonal & neuronal neuropathies
25. Balo disease
26. Behcet's disease
27. Bullous pemphigoid
28. Cardiomyopathy
29. Castleman disease
30. Celiac disease
31. Chagas disease
32. Chronic fatigue syndrome
33. Chronic inflammatory demyelinating polyneuropathy (CIDP)
34. Chronic recurrent multifocal osteomyelitis (CRMO)
35. Churg-Strauss syndrome
36. Cicatricial pemphigoid/benign mucosal pemphigoid
37. Crohn's disease
38. Cogans syndrome
39. Cold agglutinin disease
40. Congenital heart block
41. Coxsackie myocarditis
42. CREST disease
43. Essential mixed cryoglobulinemia
44. Demyelinating neuropathies
45. Dermatitis herpetiformis
46. Dermatomyositis
47. Devic's disease (neuromyelitis optica)
48. Discoid lupus 49. Dressler's syndrome
50. Endometriosis
51. Eosinophilic esophagitis
52. Eosinophilic fasciitis
53. Erythema nodosum
54. Experimental allergic encephalomyelitis
55. Evans syndrome
56. Fibromyalgia
57. Fibrosing alveolitis
58. Giant cell arteritis (temporal arteritis)
59. Giant cell myocarditis
60. Glomerulonephritis
61. Goodpasture's syndrome
62. Granulomatosis with Polyangiitis (GPA) (formerly called Wegener's Granulomatosis)
63. Graves' disease
64. Guillain-Barre syndrome
65. Hashimoto's encephalitis
66. Hashimoto's thyroiditis
67. Hemolytic anemia
68. Henoch-Schonlein purpura
69. Herpes gestationis
70. Hypogammaglobulinemia
71. Idiopathic thrombocytopenic purpura (ITP)
72. IgA nephropathy
73. IgG4-related sclerosing disease
74. Immunoregulatory lipoproteins
75. Inclusion body myositis
76. Interstitial cystitis
77. Juvenile arthritis
78. Juvenile diabetes (Type 1 diabetes)
79. Juvenile myositis
80. Kawasaki syndrome
81. Lambert-Eaton syndrome
82. Leukocytoclastic vasculitis
83. Lichen planus
84. Lichen sclerosus
85. Ligneous conjunctivitis
86. Linear IgA disease (LAD)
87. Lupus (SLE)
88. Lyme disease, chronic
89. Meniere's disease
90. Microscopic polyangiitis
91. Mixed connective tissue disease (MCTD)
92. Mooren's ulcer
93. Mucha-Habermann disease
94. Multiple sclerosis
95. Myasthenia gravis
96. Myositis
97. Narcolepsy
98. Neuromyelitis optica (Devic's)
99. Neutropenia
100. Ocular cicatricial pemphigoid
101. Optic neuritis
102. Palindromic rheumatism
103. PANDAS (Pediatric Autoimmune Neuropsychiatric Disorders Associated with *Streptococcus*)
104. Paraneoplastic cerebellar degeneration
105. Paroxysmal nocturnal hemoglobinuria (PNH)
106. Parry Romberg syndrome
107. Parsonnage-Turner syndrome
108. Pars planitis (peripheral uveitis)
109. Pemphigus
110. Peripheral neuropathy
111. Perivenous encephalomyelitis
112. Pernicious anemia
113. POEMS syndrome
114. Polyarteritis nodosa
115. Type I, II, & III autoimmune polyglandular syndromes
116. Polymyalgia rheumatica
117. Polymyositis
118. Postmyocardial infarction syndrome
119. Postpericardiotomy syndrome
120. Progesterone dermatitis
121. Primary biliary cirrhosis
122. Primary sclerosing cholangitis
123. Psoriasis
124. Psoriatic arthritis
125. Idiopathic pulmonary fibrosis
126. Pyoderma gangrenosum
127. Pure red cell aplasia
128. Raynauds phenomenon
129. Reactive Arthritis
130. Reflex sympathetic dystrophy
131. Reiter's syndrome
132. Relapsing polychondritis
133. Restless legs syndrome
134. Retroperitoneal fibrosis
135. Rheumatic fever
136. Rheumatoid arthritis
137. Sarcoidosis
138. Schmidt syndrome
139. Scleritis
140. Scleroderma
141. Sjogren's syndrome
142. Sperm & testicular autoimmunity
143. Stiff person syndrome
144. Subacute bacterial endocarditis (SBE)
145. Susac's syndrome
146. Sympathetic ophthalmia
147. Takayasu's arteritis
148. Temporal arteritis/Giant cell arteritis
149. Thrombocytopenic purpura (TTP)
150. Tolosa-Hunt syndrome
151. Transverse myelitis
152. Type 1 diabetes
153. Ulcerative colitis
154. Undifferentiated connective tissue disease (UCTD)
155. Uveitis
156. Vasculitis
157. Vesiculobullous dermatosis
158. Vitiligo
159. Wegener's granulomatosis (now termed Granulomatosis with Polyangiitis (GPA).

Inflammatory Diseases for Treatment or Prevention by the Method

1. Alzheimer
2. ankylosing spondylitis
3. arthritis (osteoarthritis, rheumatoid arthritis (RA), psoriatic arthritis)
4. asthma
5. atherosclerosis
6. Crohn's disease
7. colitis
8. dermatitis
9. diverticulitis
10. fibromyalgia
11. hepatitis
12. irritable bowel syndrome (IBS)
13. systemic lupus erythematous (SLE)
14. nephritis
15. Parkinson's disease
16. ulcerative colitis.

Growth Promoters & Lowering Food Conversion Ratios

The Examples demonstrate that target bacteria can be targeted using an antibacterial agent to promote growth and enhance FCR in poultry. In the Example, a guided nuclease system was used to specifically target *Salmonella* in the poultry.

In a first aspect, there is provided:—

A method of promoting the growth of an animal (eg, a livestock animal, eg, a poultry animal), the method comprising administering to the animal a guided nuclease system or a component thereof, and introducing the system or component into target bacteria comprised by the animal, wherein the guided nuclease is capable of recognising and modifying (eg, cutting) a target nucleotide sequence comprised by the target bacteria, whereby target bacteria are killed or the growth or proliferation of target bacteria are inhibited and the growth of the animal is promoted.

The method is a non-medical method and the presence of target bacteria in the animal is capable of inhibiting the growth of the animal. Thus, the method reduces the burden of such bacteria in the animal and promotes growth.

In a second aspect there is provided:—

A method of enhancing feed conversion ratio (FCR) in an animal (eg, a livestock animal, eg, a poultry animal), the method comprising administering to the animal a guided nuclease system or a component thereof, and introducing the system or component into target bacteria comprised by the animal, wherein the guided nuclease is capable of recognising and modifying (eg, cutting) a target nucleotide sequence comprised by the target bacteria, whereby target bacteria are killed or the growth or proliferation of target bacteria are inhibited and the FCR of the animal is enhanced.

The method is a non-medical method and the presence of target bacteria in the animal is capable of increasing the FCR of the animal. Thus, the method reduces the burden of such bacteria in the animal and enhances FCR (ie, reduces FCR number).

In a third aspect there is provided:—

A method of promoting the growth of an animal (eg, a livestock animal, eg, a poultry animal), the method comprising administering to the animal an antibacterial agent that is toxic to *Salmonella* bacteria, wherein *Salmonella* target bacteria comprised by the animal are exposed to the agent and are killed or the growth or proliferation of target bacteria are inhibited and the growth of the animal is promoted.

The method is a non-medical method and the presence of target bacteria in the animal is capable of inhibiting the growth of the animal. Thus, the method reduces the burden of such bacteria in the animal and promotes growth.

In a fourth aspect there is provided:—

A method of enhancing feed conversion ratio (FCR) in an animal (eg, a livestock animal, eg, a poultry animal), the method comprising administering to the animal an antibacterial agent that is toxic to *Salmonella* bacteria, wherein *Salmonella* target bacteria comprised by the animal are exposed to the agent and are killed or the growth or proliferation of target bacteria are inhibited and the FCR of the animal is enhanced.

The method is a non-medical method and the presence of target bacteria in the animal is capable of increasing the FCR of the animal. Thus, the method reduces the burden of such bacteria in the animal and enhances FCR (ie, reduces FCR number).

In any of these aspects, optionally the animal is a livestock animal. Optionally, the animal is a bird, eg, a poultry bird, eg, a chicken, turkey, goose or duck. Preferably, the animal is a chicken.

In any of these aspects, optionally the bacteria are Enterobacteriaciae bacteria, eg, *Salmonella*. For example, the bacteria are *Salmonella enterica, typhimurium* or *enteritidis*. For example, the *Salmonella* is any *Salmonella* species or strain disclosed herein.

For example, the system, component or agent is supplied to the animal in an animal feed and/or beverage (eg, mixed in drinking water). When supplied in a beverage, the system, component or agent may be comprised by carrier bacteria, wherein the carrier bacteria are comprised in the beverage at an amount of from $1\times10^3$ to $1\times10^{10}$ (eg, from $1\times10^4$ to $1\times10^{10}$; from $1\times10^4$ to $1\times10^9$; from $1\times10^4$ to $1\times10^8$; from $1\times10^4$ to $1\times10^7$; from $1\times10^3$ to $1\times10^{10}$; from $1\times10^3$ to $1\times10^9$; from $1\times10^3$ to $1\times10^8$; from $1\times10^3$ to $1\times10^7$; from $1\times10^5$ to $1\times10^{10}$; from $1\times10^5$ to $1\times10^9$; from $1\times10^5$ to $1\times10^8$; from $1\times10^5$ to $1\times10^7$; from $1\times10^6$ to $1\times10^{10}$; from $1\times10^6$ to $1\times10^9$; from $1\times10^6$ to $1\times10^8$; or from $1\times10^6$ to $1\times10^7$) cfu/ml. When supplied in a beverage, the system, component or agent may be comprised by carrier bacteria, wherein the carrier bacteria are comprised in the beverage at an amount of at least $1\times10^8$ cfu/ml, eg, wherein the animal is a poultry bird, such as a chicken.

Optionally, the guided nuclease is any guided nuclease disclosed herein, eg, a Cas, TALEN, meganuclease or a zinc finger nuclease. In an example, the component is a crRNA or guide RNA that is operable in target cells with a cognate Cas nuclease. The Cas nuclease can be any Cas nuclease disclosed herein. The Cas nuclease may be an endogenous Cas of the target cells or may be encoded by an exogenous nucleic acid that is administered to the animal.

Systems, components and agents of the invention may be introduced into target bacteria by bacterial conjugation (eg, conjugative transfer from a carrier cell to the target cell) or by phage wherein the phage transduce into the target cells nucleic acid encoding the system, component or agent.

Optionally, the target bacteria are comprised by any microbiota disclosed herein that is found in animals. Preferably, the microbiota is a gut microbiota (eg, a gut microbiota of a chicken).

The livestock animal can be any livestock animal disclosed herein, eg, a chicken, pig, cow, sheep, farmed fish (such as salmon or catfish) or farmed shellfish (eg, lobster, prawn or shrimp).

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications and all US equivalent patent applications and patents are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps The term "or combinations thereof" or similar as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

EXAMPLES

Example 1: Target Gene Sequence Assessment & crRNA Array Design

List of Putative Target Genes in *Salmonella*

Through careful analysis and decision making, we compiled the following target genes for assessment by cutting using CRISPR/Cas components delivered by conjugative plasmids from carrier cells as per the invention.

1) pipA Pathogenicity island encoded protein: SPI5
2) mViM putative virulence factor
3) mViN putative virulence factor
4) phoP Transcribes genes expressed under low Mg+ concentration (OmpR family); virulence transcriptional regulatory protein PHOP
5) hilA Invasion genes transcription activator
6) BigA putative surface-exposed virulence protein
7) sugR ATP binding protein; Pathogenicity island encoded protein: SPI3
8) rhuM Pathogenicity island encoded protein: SPI3
9) pipC invasion gene E protein/Pathogenicity island encoded protein: SPI5
10) pipB Pathogenicity island encoded protein: SPI5
11) sicP chaperone related to virulence
12) sopB invasion gene D protein/Pathogenicity island encoded protein: SPI5
13) marT putative transcriptional regulatory protein/ Pathogenicity island encoded protein: SPI3

Target Selection

Initial target selection of *Salmonella*-specific genes identified 13 putative candidates located almost exclusively in *Salmonella* pathogenicity islands (listed at the start of this example). After close inspection, the list of targets was reduced to seven genes, namely pipA, pipB, pipC, hilA, marT, sicP and sopB, that we found importantly showed no significant sequence homology to other genes from Enterobacteria, thus enabling high specificity of targeting *Salmonella* cells in vivo and in microbiomes containing non-target Enterobacteria of different (non-*Salmonella*) species. Target sites for *S. pyogenes* Cas9 defined by presence of the PAM motif (NGG) were extracted using the respective function available in molecular biology software. A number of 6 to 14 putative target sites were identified in each of the seven selected genes.

crRNA Design and Synthesis

To select target sites most likely to result in efficient restriction of dsDNA, all potential sequences were screened for the presence of nucleotides at key position that have been described to have positive or negative effects on the efficiency of double strand cuts introduced by Cas9 in the available literature. Three publications reported such data, although on sgRNA:

(1) Doench et al. 2014, Nature Biotechnology
(2) Gagnon et al. 2014, PLoS One
(3) Liu et al. 2016, Scientific Reports One target sequence for each gene that adhered to most of the parameters described influencing restriction efficiency in each of the three publications was selected to be incorporated into a crRNA array, resulting in three arrays to be tested. crRNA arrays were designed based on the sequence data from *S. pyogenes* (published in Deltcheva et al. 2011, Nature). The following sequences were constructed: SEQ ID NOs: 1-3.

Two of these sequences encoding crRNAs were assembled with sequences encoding cognate tracrRNA and Cas9.

Cas9 Constructs (tracrRNA-Cas9-crRNA)

The selected sequences encoding crRNAs were combined with different versions of the tracrRNA-Cas9 modules, resulting in a varied set of plasmids.

For constitutive expression of all components (tracrRNA, Cas9 and crRNA), a tracr-Cas fragment based on plasmid pCas9 (Jiang et al. 2013, Nature Biotechnology; sequence presented as SEQ ID NO: 4) was amplified from *S. pyogenes* gDNA. We will join this fragment with the available crRNA-encoding fragments and clone into high copy number general cloning plasmid pJet1.2. This series of construct is named pFS1.

To determine whether expression of this constitutive CRISPR/Cas construct in a low copy number background will work as efficiently, we will move the system described above into a low copy number plasmid. pFS2 constructs are therefore based on the low copy number pSC101 origin from pZS21MCS (Expressys).

To control expression of at least one of the CRISPR/Cas components by means of an inducible promoter, we will replace the constitutive Cas9 promoter with the TetR regulated promoter PLtetO-1. The resulting plasmids of pFS3 are based on the low copy number pSC101 origin of pZS21MCS as well. The introduced changes will be as follows:

Spacing between RBS and Start ATG has been shortened to 7 bp (TAAATAC)

Stop codon has been changed from a less effective TGAC to a tandem TAATAAT sequence Lastly, we will produce a mobilisable version of the constitutively expressed plasmids like pFS1 and pFS2 mentioned above. To this end, we will clone the origin of transfer (oriT) of plasmid RP4 into an intermediate copy number plasmid (p15A origin) carrying a chloramphenicol resistance. This construct should be able to be mobilised and transferred by a chromosomally integrated conjugation machinery as present in RP4 and other mobilisable plasmids.

Further Constructs

To determine the efficiency of dsDNA restriction by the selected crRNAs prior to a final selection and transformation into *Salmonella*, we will aim to clone the target genes (or substantial parts thereof) into a compatible plasmid. The plasmid selected is pZA31MCS (Expressys) with a p15A origin compatible to the pFS1/pFS2/pFS3 constructs described above. Efficiency can then be tested in *E. coli* by loss of chloramphenicol resistance (or loss of fluorescence if a yfp derivative is present as a reporter). The best performing target sequences can then be used in future, more targeted plasmids.

We made the following plasmids:— pFSmob-C tracrRNA/Cas9—mob—pZA31MCS pFSmobSal7 tracrRNA/Cas9—Salcr7-3—mob—pZA31MCS pFSmobSal3 tracrRNA/Cas9—Salcr3.2—mob—pZA31MCS pFSmob-C* control based on Salcr7-3—mob—pZA31MCS Plasmid Details Plasmid Name: pFSmob-C Description: p15A origin plasmid based on pZA31MCS (Expressys) carrying 4768 bp insert (tracrRNA-Cas9-oriT/mob)

Plasmid Length: 6685 bp

Sequence verified: Yes; Insert sequence verified by primer walking sequencing

Additional Notes: No crRNA array present; Control plasmid

Plasmid Details

Plasmid Name: pFSmobSal7

Description: p15A origin plasmid based on pZA31MCS (Expressys) carrying 5598 bp insert (tracrRNA-Cas9-crRNA-oriT/mob)

Plasmid Length: 7515 bp

Sequence verified: Yes; Insert sequence verified by primer walking sequencing

Plasmid Details

Plasmid Name: pFSmobSal3

Description: p15A origin plasmid based on pZA31MCS (Expressys) carrying 5341 bp insert (tracrRNA-Cas9-crRNA-oriT/mob)

Plasmid Length: 7258 bp

Sequence verified: Yes; Insert sequence verified by primer walking sequencing

Plasmid Details

Plasmid Name: pFSmob-C*

Description: p15A origin plasmid based on pZA31MCS (Expressys)

Plasmid Length: 7348 bp

Sequence verified: Yes; Insert sequence verified by primer walking sequencing

Example 2: Selectively Removal of Unwanted *Salmonella* Strains by Conjugation Using a Guided Nuclease Purpose of the Study The objective of this study was to selectively remove unwanted *Salmonella* strains by conjugation experiment. We mobilised the pFSMobSal7 plasmid from *E. coli* S17 to *Salmonella* spp. This plasmid contains tracr-Cas9 the crRNA-encoding array (Sal7-3) and the origin of transfert (oriT).

SUMMARY

As a proof of concept the conjugation experiment was first done from *E. coli* to *E. coli* before mobilising to *Salmonella* spp. The plasmid pFSMobSal7 (chloramphenicol resistant, CmR) was first transformed into a carrier strain that allows the mobilisation. In this experiment, the strain that produced the pilus was *E. coli* S17 (ATCC® 47055™). The conjugative functions are provided by an RP4 plasmid integrated into the chromosome. The recipient cell should be Nalidixic acid resistant (25 μg/ml), here we used *E. coli* JM109 (ATCC® 53323™). The *Salmonella* targeted was FS26 from our *Salmonella* spp collection. The results showed a good efficiency of conjugation from *E. coli* S17 to *E. coli* JM109 and from *E. coli* S17 to *Salmonella enteritidis* (FS26). After conjugation to *Salmonella* as a recipient the killing with pFSMob-3 was efficient.

Introduction

The pFSmobSal7 plasmid was originated from the intermediated copy number pZA31MCS (Expressys). An origin of transfer (OriT) sequence was synthesised (called mob2) and cloned into pZA31MCS by assembly method in addition to the tracr-Cas9 and the crRNA array fragments.

Before starting the conjugation experiment, *E. coli* S17 strains were made electro-competent by a standard protocol (O'Challahan and Charbit, 1990). Plasmids pFSMobsal7 and pFSMobC* were then transformed into *E. coli* S17 by electroporation and selected in chloramphenicol (Cm30, 30 μg/mL).

pFSMobSal7 and pFSMobC* were mobilised from the donor *E. coli* S17 to the recipient *E. coli* JM109 and to *Salmonella* spp that are Nalidixic resistant (NalR) and chloramphenicol sensitive (CmS) by mating on a filter followed by an incubation at 37° C. The mixtures were then plated in Cm30, Nal25 and Cm30+Nal25. The transconjugants were selected in double antibiotics Cm30+Nal25 (Phornphisutthimas et al, 2007).

Note that before starting the conjugation experiment, the efficiency of killing of pFSMob plasmids were first tested by transformation in *Salmonella.*

Methodology

Material:

Donor strain: *E. coli* S17 transformed with pFSMobSal7/pFSMobC*

Recipient strains: JM109/*Salmonella enteritidis* FS26

Luria Bertani Broth (LB) (Product number L3522, Sigma-Aldrich), LB Cm30 g/ml

Plates of LB agar 1%

Plates of LB agar 1% Cm30 g/ml

Plates of LB agar 1% NaL25 g/ml

Plates of LB agar 1% Cm30+NaL25

Whatman® membrane filters nylon, pore size 0.45 m to 1 m, diameter 25 mm. Reference number 28420770 supplied by Sigma-Aldrich Experiment 1: Mobilisation of pFSMobC* from *E. coli* S17 to *E. coli* JM109

As a proof of concept, the conjugation experiment was done first from *E. coli* S17 containing a control plasmid (pFSMobC*) to *E. coli* JM109. This experiment followed the protocol from of Phornphisutthimas (Phornphisutthimas et al, 2007):

1. Grow overnight cultures of donors pFSMobC*(S17) from our collection in LB+Cm30 and recipient strain JM109 in LB broth.
2. In the morning pre-warm the plates of LB agar (1%) for at least 30 minutes before starting the experiment
3. Mix the donor strains with the recipient at the ratio of 1:1 as following:
4. 50 µl of pFSMobC*(S17)+50 µl of JM109
5. 50 µl of pFSMobC*(S17)+50 µl of LB
6. 50 µl of LB+50 µl of JM109
7. For each reaction, put a filter membrane (0.45 µM to 1 µM) on the top of the pre-warmed LB agar plate (1%)
8. Load each sample of mating on a filter
9. Leave the plates 3 hours at 37° C. without shaking, the LB will be absorbed and the bacteria should stay on the filter
10. After incubation, put each filter into a universal tube with lml LB broth and vortex well
11. Plate 100 µl (And serial dilution) on Cm30, Nal25 and Cm30+Nal25, leave O.N at 37° C.

The plates of Cm30 give the number of donors. Plates of Nal25 give the number of recipient and plates of Nal25+Cm30 give the number of transconjugants (i.e plasmid mobilised from donor to recipient). Plates with donors and recipient alone (no mating) are negative controls Results 1) After 18 hours at 37° C. colonies were individually counted at different dilutions, when countable, and the number of colonies was expressed as cfu/mL. No colonies were recovered on negative control plates, as expected (Data not shown). The results (Table 1) show a good efficiency of conjugation from *E. coli* S17 to *E. coli* JM109.

TABLE 1

Conjugation of pFSMobC* from *E. coli* S17 to *E. coli* JM109. Results obtained from mating on filter after 3 hours of incubation at 37° C.

| Conjugative plasmid | Number of donors per ml S17 (Cm30) [a] | Number of recipient per ml JM109 (Nal25) [a] | Number of transconjugants per ml (Cm30 + Nal25) [a] | Efficiency [b] |
|---|---|---|---|---|
| pFSMobC* | $9.46*10^4$ | $1.004*10^5$ | $2.35*10^4$ | $2.4*10^{-1}$ |

[a] All the controls have been checked.
[b] The efficiency of conjugation is the number of transconjugants per donor cell 2) The mobilisation of pFSmobC* plasmid in the recipient strain was confirmed by PCR. Primers spCas9-6 forward (5'-ATTGTTTGTGGAGCAGCATAAGC)(SEQ ID NO: 8) and mob2 reverse (5'-GCCTCTAGCACGCGTACCATGG-GAT) (SEQ ID NO: 9) were used with an annealing temperature of 50° C. Two colonies from plates with transconjugants have been tested by PCR. Positive controls were also included (FIG. 1).

Conclusion 1

The conjugation experiment from *E. coli* to *E. coli* has shown a good efficiency of mobilisation. Further optimisation tests on *E. coli* conjugation showed a higher efficiency of conjugation when the mating was incubated for 6 hours at 37° C. with a ratio of 1:4.

Experiment 2: Conjugation of pFSMobSal7 from *E. coli* S17 to *Salmonella* Spp

This experiment is following the protocol from of Phornphisutthimas (Phornphisutthimas et al, 2007) and Carraro et al, 2017 with some modifications:

1. Grow overnight cultures of pFSMobSal7 (S17) and the control pFSMobC*(S17) from our collection in LB+Cm30 and recipient strain *Salmonella enteritidis* FS26 in LB broth.
2. In the morning, pre-warm the plates of LB agar (1%) for at least 30 minutes before starting the experiment
3. Mix the donor strains with the recipient at the ratio of 1:4 as following:
4. 100 µl of pFSMobC*(S17)+400 µl of *Salmonella* FS26
5. 100 µl of pFSMobSal7(S17)+400 µl of *Salmonella* FS26
6. 100 µl of pFSMobC*(S17)+400 µl of LB
7. 100 µl of pFSMobSal7 (S17)+400 µl of LB
8. 100 µl of LB+400 µl of *Salmonella*
9. Spin at 2000×g for 3 minutes
10. Resuspend in 200 µl of LB
11. Spin at 2000×g for 3 minutes
12. Resuspend in 25 µl of LB
13. For each reaction, put a filter membrane (0.45 µM to 1 µM) on the top of the pre-warmed LB agar plate (1%)
14. Load each sample of mating on a filter
15. Leave the plates 6 hours at 37° C. without shaking, the LB will be absorbed and the bacteria should stay on the filter
16. After incubation, put each filter into a universal tube with 1 ml LB broth and vortex well
17. Plate 100 µl (And serial dilution) on Cm30, Nal25 and Cm30+Nal25, leave O.N at 37° C.

The plates of Cm30 plates give the number of donors. Plates of Nal25 give the number of recipient and plates of Nal25+Cm30 give the number of transconjugants (i.e plasmid mobilised from donor to recipient).

Results

After 18 hours at 37° C. colonies were individually counted at dilution −3, and the number of colonies was expressed as cfu/mL (Table 2). No colonies were recovered on negative control plates, as expected (Data not shown).

TABLE 2

Conjugation experiment results of pFSMob plasmids from *E. coli* S17 to *Salmonella enteritidis* FS26. Results obtained from mating of a filter for 6 hours at 37° C.

| Conjugative plasmid | Donor S17/ml (Cm30) | Recipient FS26/ml (Nal25) | Number of transconjugants | Number of transconjugants/ ml (Cm30 + Nal25) | Conjugation efficiency[a] |
|---|---|---|---|---|---|
| pFSMobC* | 6.6*10$^6$ | Full | 72 | 7.2*10$^5$ | 1.09*10$^{-1}$ |
| pFSMobSal7 | 4.7*10$^6$ | Full | 0 | 0 | 0 |

Figure 2:
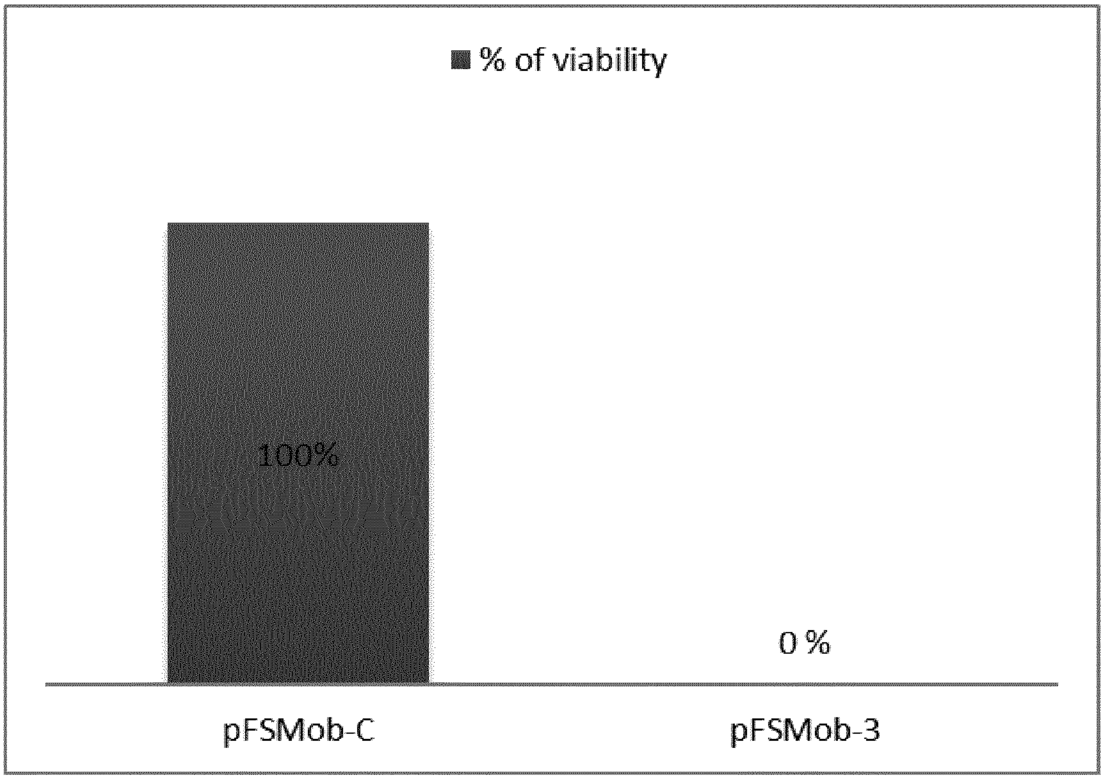
FIG. 2: Effect of viability of pFSMobSal7 delivered by conjugation on *Salmonella enteritidis* FS26.

In comparison with the plasmid control pFSMobC*, these data show that the plasmid pFSMobSal7 delivered to the target strain by conjugation is able to remove by 100% the strain *Salmonella enteritidis* (FS26) (FIG. 2).

Conclusion

The study showed that the conjugation is a good method of delivery from *E. coli* S17 to *Salmonella enteritidis* (FS26) and that pFSMobSal7 is still efficiently killing when delivered to the recipient by conjugation. Conjugation was able to remove (kill) 100% of the *Salmonella.*

REFERENCES

Carraro N, Durand R, Rivard N, Anquetil C, Barrette C, Humbert M, Burrus V. (2017). *Salmonella* genomic island 1 (SGI1) reshapes the mating apparatus of IncC conjugative plasmids to promote self-propagation. PLOS Gen.

O'Challahan D, Charbit A. (1990). High efficiency transformation of *Salmonella typhimurium* and *Salmonella typhi* by electroporation. Mol. Gen. Genet., 223; 156-8.

Phornphisutthimas S, Thamchaipenet A, and Panijpan B. (2007). Conjugation in *Escherichia coli. Biochem and Mol Bio Education Vol.* 35, No. 6, 440-445

Example 3: Pan-Serotype Conjugative Transfer and Killing of *Salmonella*

Purpose of the Study

The purpose of this study was to test the in vitro ability of pFSmobSal7 and pFSmobSal3 plasmids to selectively remove *Salmonella enterica* subsp. *enterica* serotypes by conjugation.

Summary

Eighteen strains of *Salmonella enterica* subsp. *enterica*, serovars *Typhimurium* (4), *Enteritidis* (1), Virchow (1), Montevideo (1), Heidelberg (1), Hadar (1), Binza (1), Bredeney (1), *Infantis* (1), Kentucky (1), Seftenberg (1), Mbandaka (1), Anatum (1), Agona (1) and Dublin (1), were selected from our *Salmonella* spp. collection (Table 3). Bacteria were made competent and transformed with two versions of pFSmob plasmid, i.e. pFSmobSal7 and pFSmobSal3, two versions of pFSmob control plasmid, i.e. pFSmob-C* and pFSmob-C, and pZA31MCS (Expressys) as further control. After electroporation and 2 hrs of incubation in SOC Outgrowth Medium (NEB, B90205, LOT-10019857) at 37° C., different dilutions of the original solution were plated out on 1% LB agar supplemented by chloramphenicol ($Cm_{30}$, 30 g/mL). Plates were incubated at 37° C. for 18 hrs. Results were interpreted as colony forming unit/mL (CFU/mL).

Introduction

The pFSmobSal7 and pFSmobSal3 plasmids carry on their crRNA arrays 7 target genes (pipA, pipB, pipC, hilA, sicP, mart, sopB), and 3 target genes (pipC, hilA, mart), respectively. Positive control pFSmob-C originated from pFSmobSal7 plasmid was used, in particular pFSmob-C does not contain the crRNA array. Control pFSmob-C originated from the intermediated copy number pZA31MCS (Expressys) used as a further control. Selection of positive colonies was performed on chloramphenicol ($Cm_{30}$, 30 g/mL). It was previously showed the in vitro ability of pFSmobSal7 to selectively remove by transformation *Salmonella enterica* serovar *Typhimurium, Enteritidis*, Virchow, Montevideo, Hadar and Binza. The purpose of this study was to assess all the *Salmonella* spp. serotypes present in our collection, in order to evaluate the in vitro ability of both pFSmobSal7 and pFSmobSal3 plasmids to selectively unwanted bacteria; in order to collect significant results, 18 different serotypes were selected from our collection and tested by electroporation (Table 3). Plasmids pFSmob-C, pFSmob-C* and pZA31MCS (Expressys) were used as controls.

Methodology

Bacterial strains were recovered from frozen stock kept at −80° C., and cultured at 37° C. for 24 hrs (Edwards and Ewing, 1986). Susceptibility to $Cm_{30}$ (30 g/mL) was tested using an agar dilution method in accordance with EUCAST clinical breakpoint tables. Bacteria were made competent using O'Challahan and Charbit protocol (O'Challahan and Charbit, 1990). All the selected strains were transformed with 100 ng of pFSmobSal7, pFSmobSal3, pFSmob-C, pFSmob-C*, and pZA31MCS (Expressys); a negative control was also included (competent cells without the addition of DNA) (Table 4). After 18 hrs of incubation, countable colonies (number of colonies between 30 and 300) were expressed as number of colonies per mL (CFU/mL) (Table 4).

TABLE 3

*Salmonella* spp. collection. Eighteen strains of *Salmonella enterica* subsp. *enterica*, serovars Typhimurium (4), Enteritidis (1), Virchow (1), Montevideo (1), Heidelberg (1), Hadar (1), Binza (1), Bredeney (1), Infantis (1), Kentucky (1), Seftenberg (1), Mbandaka (1), Anatum (1), Agona (1) and Dublin (1), were selected from our *Salmonella* spp. collection.

| Collection no | *Salmonella* sertypes |
|---|---|
| FS2 | Typhimurium |
| FS3 | Typhimurium |
| FS10 | Typhimurium |
| FS11 | Typhimurium |
| FS11 | Typhimurium |
| FS26 | Enteritidis |
| FS35 | Virchow |
| FS38 | Montevideo |
| FS41 | Heidelberg |
| FS42 | Hadar |

TABLE 3-continued

*Salmonella* spp. collection. Eighteen strains of *Salmonella enterica* subsp. *enterica*, serovars Typhimurium (4), Enteritidis (1), Virchow (1), Montevideo (1), Heidelberg (1), Hadar (1), Binza (1), Bredeney (1), Infantis (1), Kentucky (1), Seftenberg (1), Mbandaka (1), Anatum (1), Agona (1) and Dublin (1), were selected from our *Salmonella* spp. collection.

| Collection no | *Salmonella* sertypes |
|---|---|
| FS43 | Binza |
| FS44 | Bredeney |
| FS50 | Infantis |

TABLE 3-continued

*Salmonella* spp. collection. Eighteen strains of *Salmonella enterica* subsp. *enterica*, serovars Typhimurium (4), Enteritidis (1), Virchow (1), Montevideo (1), Heidelberg (1), Hadar (1), Binza (1), Bredeney (1), Infantis (1), Kentucky (1), Seftenberg (1), Mbandaka (1), Anatum (1), Agona (1) and Dublin (1), were selected from our *Salmonella* spp. collection.

| Collection no | *Salmonella* sertypes |
|---|---|
| FS58 | Kentucky |
| FS60 | Seftenberg |
| FS61 | Mbandaka |
| FS62 | Anatum |
| FS64 | Agona |
| FS67 | Dublin |

Results

All the bacteria selected were found to be susceptible to $Cm_{30}$ according to EUCAST breakpoints (EUCAST, 2013). After electroporation and plating of different dilutions (undiluted, $10^{-1}$, $10^{-2}$) on LB agar plates (Fisher Bioreagents, BP1425-500, LOT-171784) supplemented with $Cm_{30}$ (30 g/mL) (Sigma), plates were incubated for 18 hrs at 37° C. Bacteria were considered transformed when they grew on $Cm_{30}$ (30 g/mL) agar plates. Countable colonies (between 30 and 300) were expressed as CFU/ml (Table 4). No colonies were recovered on negative control plates, as expected. All the serotypes but one (FS67, S. Dublin) were efficiently transformed with pZA31MCS (Expressys). Almost all the serotypes were efficiently transformed with the two control plasmids (pFSmob-C* and pFSmob-C) with a number of colonies between $10^2$ and $10^6$ CFU/mL.

With regard to pFSmobSal7 and pFSmobSal3, the killing effect occurred in all the serotypes and it was found to be similar. In the majority of the serotypes, a decreasing in the number of colonies was relatively evident in comparison to the ones transformed with the control plasmids. No significant differences were found between pFSmobSal7 and pFSmobSal3 in their killing effect, except in one strain (FS38, S. Montevideo).

TABLE 4

Transformation of 18 *Salmonella* spp. serotypes. Eighteen *Salmonella* spp. Serotypes were transformed with pZA31MCS (Expressys), pFSmob-C*, pFSmob-C, pFSmobSal7, and pFSmobSal3. Almost all the serotypes were efficiently transformed with pZA31MCS (Expressys), pFSmob-C*, and pFSmob-C, with some exceptions. No significant differences were observed in the transformation with pFSmobSal7 and pFSmobSal3. Strain FS67, S. Dublin, was found to be not transformable (NT*) with all the plasmids used in this study.

| Collection | Serotype | pZA31MCS | pFSmob-C* | pFSmob-C | pFSmobSal7 | pFSmobSal3 |
|---|---|---|---|---|---|---|
| FS2 | Typhimurium | 4.8*10^4 | 1*10^5 | 4*10^4 | 0 | 6*10^1 |
| FS3 | Typhimurium | 5*10^5 | 1*10^5 | 3*10^3 | 1*10^1 | 6*10^1 |
| FS10 | Typhimurium | 5*10^5 | 0 | 1.1*10^2 | 0 | 0 |
| FS11 | Typhimurium | 4.7*10^4 | 7*10^2 | 4.1*10^2 | 0 | 0 |
| FS26 | Enteritidis | >1*10^6 | 9*10^5 | >1*10^6 | 3*10^1 | 4*10^1 |
| FS35 | Virchow | >1*10^6 | 2.8*10^3 | 1.3^10^4 | 0 | 0 |
| FS38 | Montevideo | >1*10^6 | 2.1*10^4 | 4.2*10^4 | 1.4*10^2 | 0 |
| FS41 | Heidelberg | 1.1*10^4 | 4.1*10^2 | 6*10^2 | 0 | 0 |
| FS42 | Hadar | >1*10^6 | 7*10^2 | 0 | 0 | 0 |
| FS43 | Binza | 1.7*10^4 | 7*10^1 | 1*10^1 | 0 | 0 |
| FS44 | Bredeney | >1*10^6 | 1*10^5 | 9*10^4 | 1.7*10^3 | 3*10^3 |
| FS50 | Infantis | 1*10^4 | 1.8*10^2 | 2*10^3 | 0 | 4*10^1 |
| FS58 | Kentucky | 1.7*10^4 | 7.5*10^3 | 3.6*10^3 | 0 | 0 |
| FS60 | Seftenberg | >1*10^6 | 1.2*10^5 | >1*10^5 | 2*10^1 | 2.4*10^2 |
| FS61 | Mbandaka | 2*10^2 | 2*10^1 | 0 | 0 | 0 |
| FS62 | Anatum | 1.4*10^3 | 4*10^1 | 0 | 0 | 0 |
| FS64 | Agona | >1*10^6 | >1*10^6 | 3*10^4 | 7.8*10^2 | 3*10^3 |
| FS67 | Dublin | NT* | NT | NT | NT | NT |

Conclusion

All the *Salmonella* spp. serotypes used in this experiment were efficiently made competent and transformed with pZA31MCS (Expressys), pFSmob-C and pFSmob-C* used as controls. *Salmonella Typhimurium* serotype seems not to be always transformable by pFSmob-C*, as observed previously. More in general, no particular differences occurred between the two pFSmob-derived control plasmids used in this study (between $10^2$ and $10^6$ CFU/mL). On the other hand, the killing effect of pFSmobSal7 and pFSmobSal3 was found to be similar (between $10^1$ and $10^3$). In conclusion, in this study it was demonstrated that pFSmobSal7 and pFSmobSal3 can selectively remove different *Salmonella* spp. serotypes in comparison with the control plasmids.

REFERENCE

Edwards P R, Ewing W H. (1986). Identification of Enterobateriaceae ($4^{th}$ ed.). Elsevier, New York.

EUCAST, European Committee on Antimicrobial Susceptibility Testing. (2013). Breakpoint tables for interpretation of MICs and zone diameters (last accessed 10 Aug. 16, 2013., Version 3.1).

O'ChallahanD, Charbit A. (1990). High efficiency transformation of *Salmonella typhimurium* and *Salmonella typhi* by electroporation. Mol. Gen. Genet., 223; 156-8.

Example 4: Feed Conversion Ratio Improvement in Chickens. Combined Second 2 Week Efficacy, 2 Week Safety and 6 Week Productivity Trial Purpose of study To determine the effect antibacterial conjugative plasmids (pFSmobSal7) on the health, welfare and productivity of chickens over 6 weeks.

Methodology

Ross 308 birds were housed under controlled biosecure conditions and given water and standard commercial rations ad libitum.

Birds were dosed continually with either:

1. No addition to water (60 birds)
2. Strain S17 @ $10^8$ cfu/ml drinking water (30 birds)
3. Strain S17 containing pFSmob-C* @ $10^8$ cfu/ml drinking water (30 birds)
4. Strain S17 containing pFSmobSal7 @ $10^8$ cfu/ml drinking water (60 birds)
5. Strain S17 containing pFSmobSal7 @ $10^9$ cfu/ml drinking water (30 birds)
6. Strain S17 containing pFSmobSal7 @ $10^{10}$ cfu/ml drinking water (30 birds)

Bacterial strains were recovered from frozen stocks kept at −78 C and cultured on LB agar for 24 h at 37 C. Cultures were prepared daily in LB broth containing antibiotic to prevent loss of plasmid with shaking at 180 rpm for 16 h at 37 C then centrifuged for 10 min at 4000×g. Medium was removed and the pellet resuspended in PBS then diluted in PBS to give solution for dosage to chickens.

In parallel, a group of 30 birds was dosed orally with 0.5 ml $10^5$ CFU/mL *Salmonella Enteritidis* strain FS26 (Folium) on day 1. Birds were checked for *Salmonella* colonisation at day 3 of the experiment by cloacal swab using ISO 6759 methods (1). On day 5 of the experiment 3 of these verified *Salmonella*-colonised birds (seeder birds) were marked and added to each of groups 1-6. Birds were weighed weekly and feed consumption and mortality recorded.

Fifteen birds from each group were euthanised on days 12 and 19 (7 and 14 days post mixing with seeder birds). Caeca were removed for examination for *Salmonella* by ISO 6759. Hock and pad marks were recorded. Samples of 1 g liver and caecal contents were snap frozen.

Thirty birds from each of group 1 and 4 were then monitored for behaviour and weight weekly until day 42, when they were euthanised and examined as for birds above.

Results were recorded on paper or dictated via telephone or radio in biosecure accommodation and transcribed to Microsoft Excel™. For the purposes of data transformation birds with no bacteria detected were allocated a count of 1 bacterium per g. Counts and weight were log transformed and statistical analysis conducted using GraphPad Prism™. Data was assessed for normality of distribution using a D'Agostino and Pearson omnibus normality test and as non-normal was analysed using a Kruskall-Wallis test with Dunn's multiple comparison test post hoc. Differences in proportions of birds was analysed using Fisher's exact test.

Results

All seeder birds were colonised with *Salmonella* by day 3. Those used to seed infections in the test groups had counts of >$10^5$ cfu/g faeces.

Figure 3:
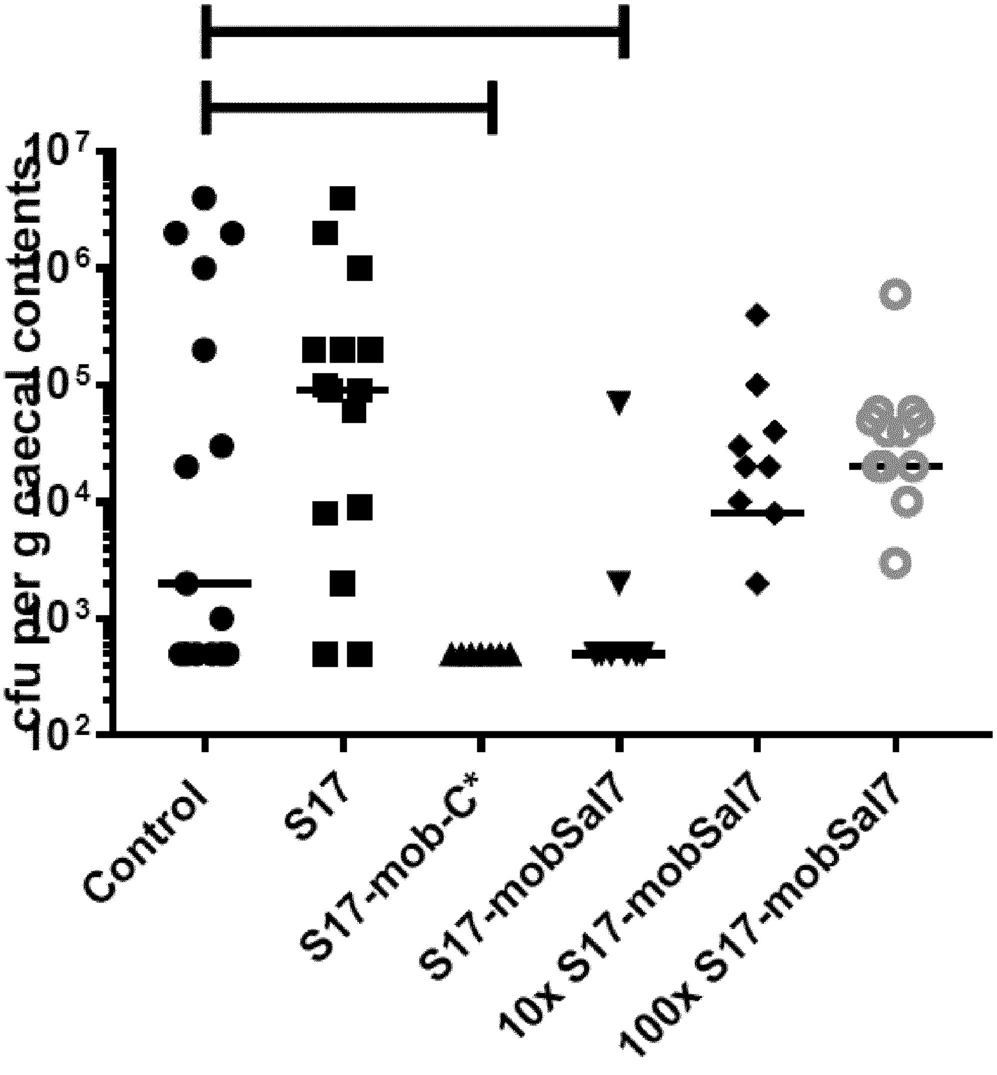
FIG. 3. Numbers of *Salmonella* in the caecum at 7 days post infection. N=15 birds per group.
Figure 4:
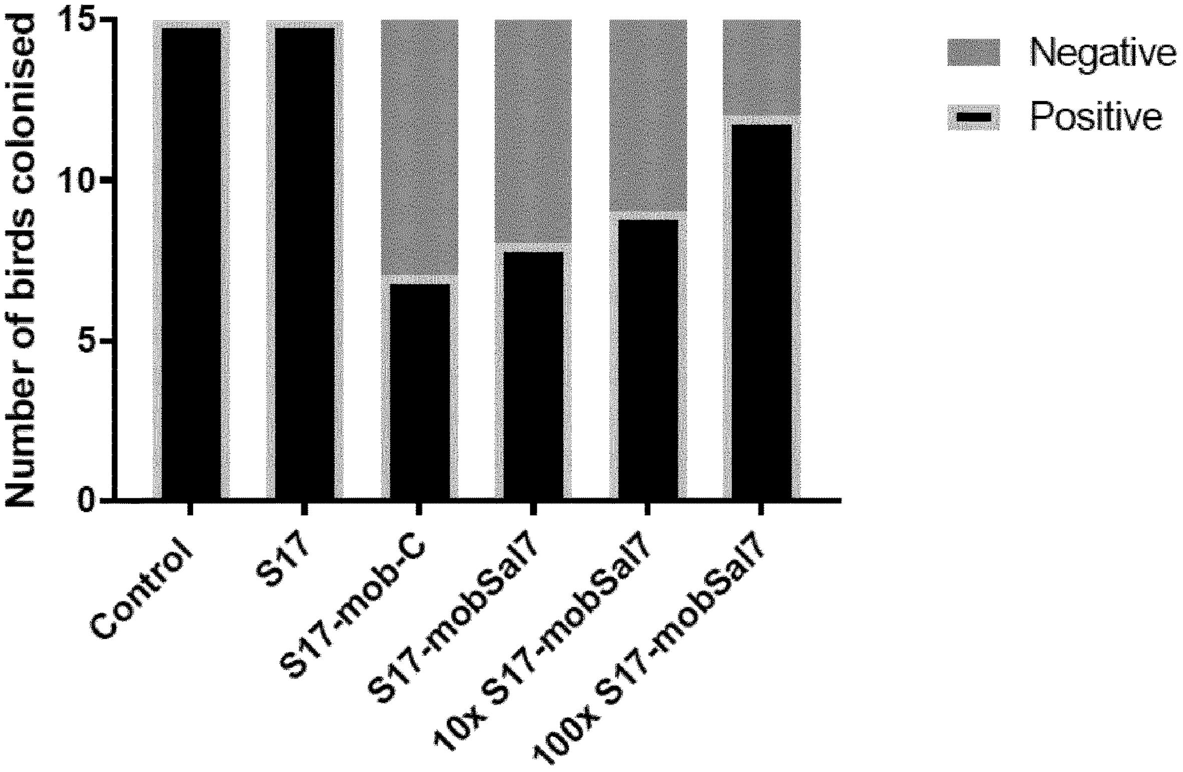
FIG. 4. Frequency of detection of *Salmonella* in the caecum at 7 days post infection. N=15 birds per group.

At day seven 15 birds per group were euthanised and *Salmonella* in the caecum enumerated (FIG. 3). FIG. 4 shows data presented a birds positive/negative for *Salmonella.*

Birds dosed with S17-pFSmobSal7 (lowest dose) and pFSmob-C* had significantly lower numbers of *Salmonella* in the caecum than controls (FIG. 3) and were significantly less likely to have detectable *Salmonella* in the caecum at day 7 post mixing with seeder birds.

No mortality was seen in any group; no morbidity was observed and high dosage of S17-mobSal7 was tolerated well. Birds were scored for positive and negative behaviours, but no difference was seen between groups.

Figure 5:
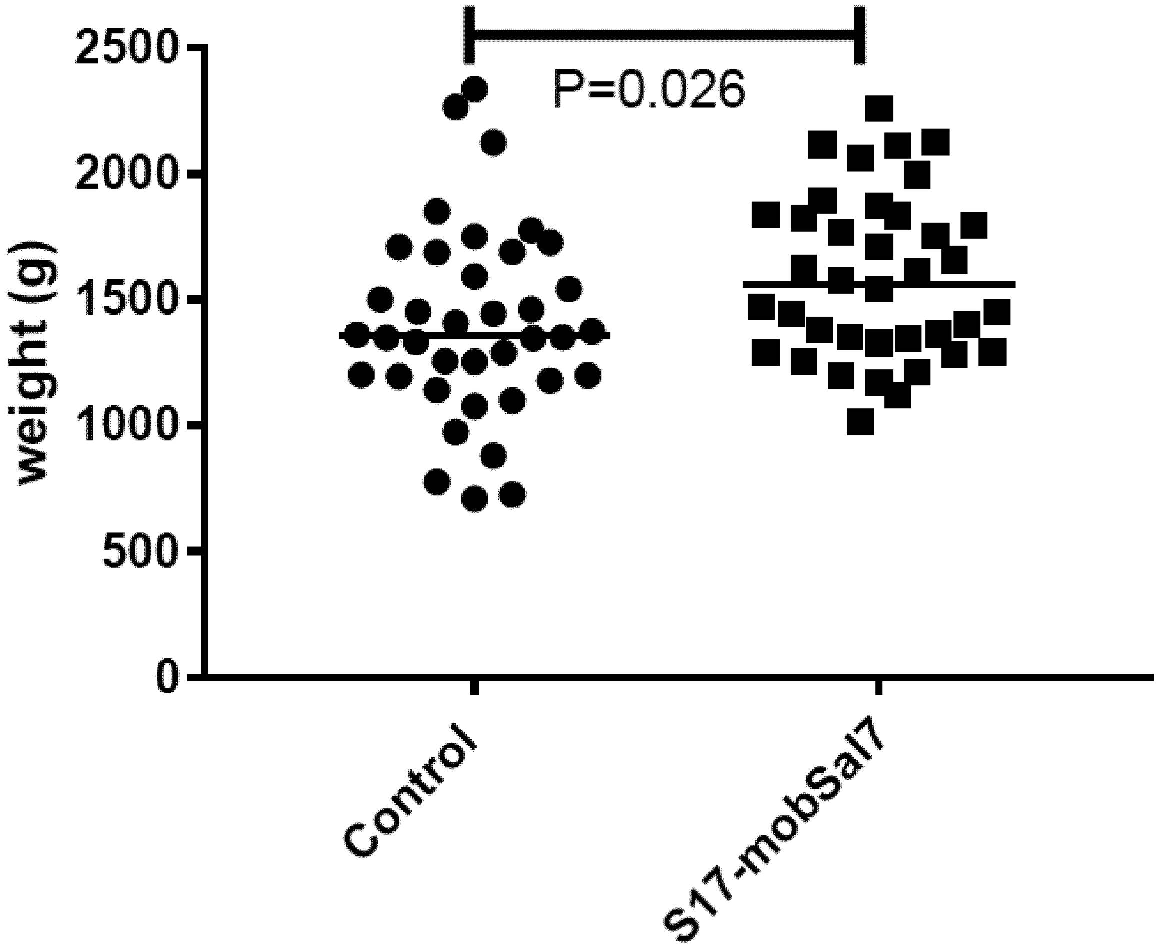
FIG. 5. Post mortem carcass weight of birds at 6 weeks of age.

Thirty birds from each of groups 1 and 4 were monitored further until 42 days of age. During this period again, no significant differences in behaviour were observed. Feed consumption between groups was not significantly different and weights did not differ significantly between groups measured in life. At post mortem *Salmonella* was not detectable in the caecum by direct count; no hock or pad marks were observed. Median carcass weight of birds in the S17-pFSmobSal7 group was 205 g greater than in the control group, a significant increase (FIG. 5). As this was associated with equivalent feed consumption between groups, the S17-pFSmobSal7 group had a significantly improved feed conversion ratio (FCR).

REFERENCES

ISO. 2007. ISO 6579:2007: Microbiology of food and animal feeding stuffs—Horizontal method for the detection of *Salmonella* spp. (ISO 6579:2002+Amd 1:2007). Geneva, Switzerland Example 5: Non-Replicative Conjugative Plasmid with Conditionally Essential Gene Marker To meet regulatory requirements, any plasmid used will preferably be devoid of an antibiotic selection marker and will be non-replicative in the vast majority, if not all, cells except for the host cell (ie, carrier cell). To render the plasmid non-replicative, the replication system of broad host range plasmid RK2, a fairly low copy number plasmid, will be utilised. RK2 replication is dependent on the presence of a replication protein, TrfA encoded by trfA on RK2, and binding of TrfA to the vegetative origin (oriV) of the plasmid and does not utilize the host machinery for replication initiation. Physical separation of trfA from the plasmid and incorporation of this gene into the chromosome will make the resulting plasmid carrying RK2 oriV dependent on a host encoded function. This will prevent the plasmid from actively replicating in a target strain after delivery via conjugation. In the rare case of an identical IncP plasmid being present in the target cell that will provide trfA, both plasmids will compete for the available TrfA, resulting in loss of one plasmid. As our plasmid in this example further does not carry an advantageous antibiotic resistance marker or similar and lacks plasmid addiction systems, it will be quickly lost from the offspring.

As a selection marker in the absence of an antibiotic resistance, the aroA gene encoding for an enzyme in the biosynthesis pathway of aromatic amino acids will be used. This is a conditionally essential gene that is essential when the host cell is grown in the absence of available aromatic amino acids or an intermediate from the reaction catalysed by aroA. Moving the aroA gene from the host genome to the plasmid backbone will provide this selection marker. The aroA gene of the chromosome will be replaced in the host (carrier cell) strain by a copy of trfA.

An aroA knock-out and replacement of the chromosomal copy by a trfA expression cassette in a *E. coli* lab strain DH10B will be made to generate a test strain of bacteria for testing the plasmid. The trfA expression cassette to be used has the sequence of SEQ ID NO: 10.

The final host (carrier) strain, a commensal *E. coli* isolate from chicken, will undergo the same strain construction procedure.

The aroA coding sequence (SEQ ID NO: 11) will be amplified with a similar promoter and terminator region and assembled into the plasmid along with modules for the Cas9, tracrRNA, crRNA and the oriV of RK2.

Additionally, alternative modules can be tested in this plasmid configuration such as anti-restriction genes that inhibit Type I restriction enzymes (ocr of T7, klcA of RK2, ardA from conjugative plasmids/transposons, ardB from conjugative plasmids) to improve DNA stability after transfer into target cells.

Further or alternatively, a module encoding an essential part of the type IV secretion system present for conjugation will located on the plasmid as this will lead to a non-functional transfer system present in the cell if the plasmid is not present. To facilitate conjugation by the host cell, the type IV secretion system present on plasmid RK2 will have to be integrated into the host genome. The essential components of this system are encoded within three operons on two locations of the plasmid, tra1 and tra2. Tral encodes the the traKLM and traJXIHGF operons, tra2 the trbBCEFGHJL genes. During the integration process, the regulatory region present in tra1 located between the traKLM and traJXIHGF operons will be modified. This sequence contains the origin of transfer (oriT), harbouring the binding site for the TraJ protein responsible for initiating transfer of the DNA. If this binding site is not altered by mutagenesis to prevent TraJ binding, transfer of chromosomal DNA fragments during the conjugation process will be initiated, leading to transfer of unwanted genetic information.

Sequences of the RK2 tra1 and tra2 modules to be used are in SEQ ID NOs 13 and 14.

Example 6: Anti-*Salmonella* Plasmid Construction & Testing

Summary

The type I-E Cas system from *E. coli* K12 (MG1655) is a RNA guide-directed DNase machinery, known as Clustered Regularly Interspaced Short Palindromic Repeat (CRISPR) and CRISPR-associated proteins system (CRISPR-Cas), which represents an adaptive immune system for prokaryotes that targets invading foreign genetic material for degradation. The *Escherichia coli* type I-E Cascade system is made up of different Cas proteins (casABCDE12 and cas3) and recognizes a wide variety of PAM sequences with varying degrees of efficacy. The main PAM sequences are: 5'-AAG, AGG, ATG, GAG-3'. Type I-E Cas system from *E. coli* K12 was used to selectively remove *Salmonella* species. The system was modified as in *E. coli* MG1655 the main components of the cas protein complex are expressed from two transcription units, cas3 and casABCDE12, respectively. The modifications introduced during the plasmid construction process included the exchange of the native, regulated promoter element of the casABCDE operon with the constitutive J23114 promoter and replacing the cas1 and cas2 genes with the cas3 gene including its native ribosomal binding site. These changes, in effect, created a constitutively expressed CRISPR-Cas module that was subsequently tested for functionality by addition of a crRNA array for specific targeting of *Salmonella* species.

Two versions of Guided Biotic® plasmids were constructed differing in origin of replication (oriV) and antibiotic selection marker. The resulting plasmids were named pFS-Sal-08-rm and pFS-Sal-09-rm and were tested in vitro to selectively inhibit growth of *Salmonella enterica* subsp. *enterica* serovar *Enteritidis* by conjugative DNA transfer. In the conjugation experiments, pFS-EcoCas3-01-rm and pFS-EcoCas3-03-rm were used as control plasmids for *Salmonella*-specific growth inhibition Plasmids were constructed, each comprising nucleotide sequences encoding Type I-E *E. coli* Cas3 and cognate casA, B, C, D and E; a CRISPR array that is operable with the Cas3 and comprises a first spacer that is complementary to a sequence of an invB gene of *S. enterica*, a second spacer that is complementary to a sequence of a sicP gene of *S. enterica* and a third spacer that is complementary to a sequence of a sseE gene of *S. enterica*; an RP4 oriT; a p15A ori; an *E. coli* proA gene; and an *E. coli* proB gene. See Table 7 for more details.

Methodology crRNA Array Design

Target gene selection, to design the CRISPR spacers, was focused on the *Salmonella*-specific pathogenicity islands (SPIs), which are major virulence factors for *Salmonella*. Criteria for selection were conservation within *Salmonella enterica* and a low to very low occurrence and conservation of the respective gene in other bacteria. These analyses were performed using the Basic Local Alignment Search Tool (BLAST). Cut-off for number of hits in non-*Salmonella* species was set at 1000. Level of conservation was considered as high if a search produced >1000 hits. Between 100 and 1000 was medium, between 20 and 100 low, very low if <20 hits. Specifically, genes associated with the type III protein secretion systems, T3SS, of SPI-1 and SPI-2 were explored as targets, taking care to include gene candidates that are conserved across *Salmonella* species but exclude those that are conserved across other bacteria species. Initially, the search focused on secreted effectors and chaperones, avoiding regulators and functional components of the T3SS.

The three selected highly conserved gene targets sicP, invB and sseE are all part of the T3SS loci encoded by *Salmonella* pathogenicity islands (SPIs), SPI-1 in the case of sicP and invB (both chaperones), and SPI-2 in the case of sseE (secreted effector). They all occur in only one copy in *Salmonella enterica* subsp. *enterica* serovar *Typhimurium* str. LT2 and this is the case for all *Salmonella enterica* although their duplication in some strains cannot be ruled out.

Candidate target genes (a) and, subsequently, spacers (b) were searched on Blast to make sure they are specific for *Salmonella* and to minimize off-targets. Search was performed using RefSeq Database, which contains around 10600 *Salmonella enterica* genomes:

a) Blast search parameters for gene selection:
   - *Salmonella* conservation: RefSeq DB restricted to *Salmonella enterica* (taxid:28901), megablast, max hits: 20000, standard parameters
   - Occurrence outside *Salmonella*: RefSeq DB restricted to bacteria (taxid:2) excluding *Salmonella* (taxid: 590), Blastn, max hits 1000, standard parameters b) Blast search parameters for spacer sequences (including PAMs):
   - *Salmonella* conservation: RefSeq DB restricted to *Salmonella enterica* (taxid:28901), blastn, max hits: 20000, standard parameters
   - Occurrence outside *Salmonella*: RefSeq DB restricted to bacteria (taxid:2) excluding *Salmonella enterica*

(taxid:28901), Blastn, max hits 1000, standard parameters but expect value set to 100 to catch sequences with low but still significant homology A number of spacers targeting different *Salmonella enterica* genes were initially screened in silico, selected, cloned and individually tested in vitro for their efficacy of targeting *Salmonella enterica* subsp. *enterica* serovar *Enteritidis* FS26 (see Summary on target gene and spacer selection and Rep-21: Construction and in vitro testing of spacer reporter systems). The three best performing spacer sequences active against *Salmonella* species were selected and combined into a short crRNA array. The spacer sequences were derived from three highly conserved genes present in *Salmonella* pathogenicity islands (SPIs), invB, sicP and sseE. In brief, a limited potential spacer sequences characterized by the presence of a strong consensus 5'-PAM sequence capable of initiating DNA restriction were selected and ranked according to sequence features associated with efficient target DNA restriction, conservation within *Salmonella* isolates and lack of DNA homology outside of *Salmonella enterica*. Three spacer sequences meeting these criteria were finally selected and incorporated into a functional crRNA array. The finalised crRNA array was ordered as a synthetic gene sequence inserted into a standard cloning plasmid (GeneArt, Thermo Fisher Scientific).

Sequences of selected genes are shown in SEQ ID NOs: 20-22. In each gene, spacers are highlighted in bold and respective PAMs in italics (in the case of invB, the spacer was selected on the negative DNA strand (anti-sense) so the PAM appears 3' to the spacer. PAM sequences used for spacer selection were AAG, ATG, AGG and GAG. Blast searches for the spacers with their respective PAMs was conducted (Table 10).

The non-*Salmonella* hits were further analysed for their conservation level (spacers accepted when level of conservation in off-targets was <75%). Sequence selection also depended on where the mismatches were located in the off-target hit, ruling out the ones showing conserved PAM and seed (first 8pb of the spacer). One additional criterion for our selection also included the type of bacteria where the hit was present, if present in a pathogen, the spacer was still considered as a possible candidate.

Each spacer was individually tested in vitro for their efficacy of targeting *Salmonella enterica* subsp. *enterica* serovar *Enteritidis* FS26, before combining them together in the array present in the plasmid pFS-Sal-09-rm.

Plasmid Assembly

For the homology-based DNA assembly, individual DNA modules were carrying 5' and/or 3' extensions with exact homology to the adjacent module. The extensions were either introduced during a PCR amplification step of the module or were incorporated during the design of synthetic DNA modules. The constitutive J23114 promoter was introduced.

CasA-E: The 4464 bp casA-casB-casC-casD-casE module was amplified from *E. coli* K12 (MG1655) genomic DNA.

Cas3: The 2709 bp Cas3 module was amplified.

crRNA: The crRNA array module Sal-crRNA 1 (546 bp), carries a 25 bp homology extension to the 3'-end of the Cas3 module. The sequence of the Sal-crRNA Array1 is shown in SEQ ID NO: 15, with the −10 region of the promoter in italic, direct repeats underlined and the spacer regions corresponding to the selected *Salmonella* target sequences of invB, sicP and seeE, in bold.

pFS-Sal-08-Rm and pFS-Sal-09-Rm Validation and In Vitro Testing by Conjugation

Having confirmed the sequences of both constructs, the plasmids were transformed into a carrier strain that allowed plasmid mobilization via conjugation to assess the efficacy of the Cas3 system to selectively kill *Salmonella* in presence of the Sal-crRNA array 1. In this study, *E. coli* strain S17-1 ΔTn7 was used. 100 ng of pFS-Sal-08-rm and pFS-Sal-09-rm were used for transformation of 50 l electrocompetent cells of *E. coli* S17-1 ΔTn7 by electroporation and selected on Kanamycin and Chloramphenicol, respectively. Transformation with both plasmids resulted in a good transformation efficiency of *E. coli* S17-1 ΔTN7 ($10\text{-}10^6$ transformed CFU/mL). Control plasmids, pFS-EcoCas3-01-rm and pFS-EcoCas3-03, lacking the crRNA array, were also transformed in the S17-1 ΔTn7 carrier strain to be used as controls in FS26 transformation for pFS-Sal-09-rm and pFS-Sal-08-rm. In order to confirm the mobilization capability of the new plasmids, S17-1 carrier cells, were first used to conjugate *E. coli* JM109 cells (nalidixic acid, Nal, resistant). Results, reported in Table 8, show a similar conjugation efficiency between pFS-EcoCas3-01 and pFS-Sal-09-rm and between pFS-EcoCas3-03 and pFS-Sal-08-rm, in *E. coli* JM109. Conjugation efficiency is calculated dividing the number (CFU/mL) of transconjugants (selected on plates with double antibiotics) by the number of recipients (selected on plate with Nal).

Subsequently, *E. coli* carrier strain S17-1 ΔTn7, previously transformed with the plasmids, were used to assess whether there is a significant growth inhibition of *Salmonella Enteritidis* FS26 by conjugation of pFS-Sal-08-rm compared to the control plasmid pFS-EcoCas3-03-rm and of pFS-Sal-09-rm compared to pFS-EcoCas3-01-rm. Conjugation was performed from *E. coli* S17-1 ΔTn7 into nalidixic acid (Nal) resistant *Salmonella Enteritidis* FS26. Results showed a significant reduction (CFU/mL) in *S. enteritidis* strain FS26 conjugated with both pFS-Sal-08-rm and pFS-Sal-09-rm compared to the respective control plasmids (Table 9).

In conclusion, inhibition of *Salmonella* growth by both plasmids carrying the Sal-crRNA array 1 generated in this study indicated that the modified Cas module is functional and was able to express all the individual components of the Type I-E Cascade complex, the Cas3 nuclease and the crRNA array without negatively affecting growth of non-target *E. coli* host strains 517-1 and JM109. We demonstrated the ability of the *E. coli* type I-E Cas system-based plasmids to be transferred by conjugation from the *E. coli* S17-1 carrier strain to *S. enteritidis* strain FS26. We observed a significant inhibition of growth in the *Salmonella* transconjugants (>99.9%) of the selected strain through conjugation of both pFS-Sal-08-rm and pFS-Sal-09-rm in comparison to the control used. These data therefore highlighted the potential of these *E. coli* type I-E Cascade based constructs for the removal of unwanted bacteria, such as for zoonotic control.

Example 7: Test of Stability and Efficacy of a Folium *E. coli*-Based Product in Chickens Fed a Diet Containing *Salmonella*

In Example 4, we tested a Guided Biotic® plasmid contained in *E. coli* carrier cells of S17 strain. In this present Example 7, we instead tested a Guided Biotic® plasmid (GB plasmid pFS-Sal-09-proAB-rm, Example 6 & Table 7) contained in a different strain (Strain X) of *E. coli* carrier. A helper plasmid pCon_aroA carried a functional copy of the conjugation machinery of plasmid RP4 (traJXIHGFtraKLM-trbBCDEFGHIJKL) that was found to facilitate mobilization of oriT-containing plasmids from the host cell to a recipient cell in vitro.

Purpose of Study

- To determine the stability of *E. coli* Strain X with the Guided Biotic® in drinking water over 24 hours.
- To enumerate intestinal and organ contamination with *Salmonella* given in-feed.
- To determine the efficacy of *E. coli* Strain X containing an active GB plasmid in chickens challenged with *Salmonella* in-feed.

Summary

- *E. coli* Strain X was found at the expected level of 5×log-8 CFU/mL immediately after dosing into deionised water containing stabilizers, and 24 hrs had dropped to 8×log-7 CFU/mL.
- Following challenge in-feed ($10^4$ CFU/g feed) for 24 hrs, low levels (~log-2-5 CFU/g) of *Salmonella* were found in the crop and caeca on days 1, 3 and 7 after challenge. Lower levels (~log-1 CFU/g) were also found in ileal contents, liver and spleen 7 days post-challenge.
- The active Guided Biotic®, *E. coli* Strain X containing an active GB plasmid, reduced ($P<0.03$) *Salmonella* counts in the crop 7 days post-challenge by ~log-1 CFU/g.

Methodology

Ross 308 birds (30) were housed under controlled biosecurity conditions and given water and a standard commercial ration ad libitum. Each experimental group was held in a separate pen with wood shaving bedding. Birds had a 18 h light/6 h dark lighting regime. Temperature and humidity were kept between the standard levels shown in Table 11.

Treatment Groups:

- Low Control—no addition to water, $10^4$ CFU *Salmonella* per gram feed for 24 hrs on day 7 (15 birds)
- GB-Sal—*E. coli* Strain X Guided Biotic® containing active GB plasmid (pFS-Sal-09-proAB-rm) at $10^8$ CFU/mL in drinking water from days 1-14, $10^4$ CFU *Salmonella* per gram feed for 24 hrs on day 7 (15 birds)

Guided Biotic® strains were recovered daily from frozen stocks kept at −78° C. and cultured on LB agar plus Chloramphenicol (30 g/mL) for 24 h at 37° C. Strain X with active GB plasmid strains were prepared in Terrific broth, grown with shaking at 180 rpm for 16 h at 37° C. After measuring $OD_{600}$ to estimate cell numbers, cells were centrifuged and resuspended in deionised water containing stabilizers to give solutions for dosage to chickens ($10^8$ CFU/mL in drinking water). Vac Pac containing blue dye was included 3 hrs before collection on sampling days, to confirm water and GB intake. Supplemented water samples were collected on GB addition and 24 hrs later on days 4-14 of the trial, for enumeration for GB. Water samples were decimally diluted in PBS and then plated on to MacConkey agar number 3 (Oxoid CM0115), then incubated at 24 h at 37° C.

*Salmonella* strain (FS26, with Nalidixic acid marker) was recovered from frozen stocks kept at −78° C. and cultured on LB agar for 24 h at 37° C. Test cultures were prepared daily in LB broth grown with shaking at 180 rpm for 16 h at 37° C. After measuring $OD_{600}$ to estimate cell numbers, cells were centrifuged and resuspended and diluted in phosphate-buffered saline to give solutions of $1\times10^7$ CFU/ml which was dripped on to the feed at a rate of 1 ml bacterial suspension to 100 g feed while the feed was mixed thoroughly. Four feed samples were collected for enumeration of *Salmonella* content.

Animal Sample Collection and Plating

No bird mortality was recorded. Lighting level, additions of bedding, temperature, humidity and stocking density were logged and did not differ between treatments. Three birds from each group on days 1 & 3 and nine birds on day 7 after challenge were euthanised and samples taken from the crop, ileal, caecal, liver and spleen. Euthanasia, post-mortem and dissection times were recorded. Feathers were spray wetted with water. Birds were opened with a disposable scalpel that was discarded after opening and gloves were changed. Samples of 1 g liver and crop, ileal and caecal contents were taken and snap frozen in liquid nitrogen. Scalpels were disposed of as each organ was taken. Samples were homogenised in 9 volumes of phosphate-buffered saline, decimally diluted in phosphate-buffered saline and examined, with agars incubated for 16-18 h at 37° C. Samples that were negative in direct plating were examined for *Salmonella* by enrichment in 9 volumes of selenite cystine broth (Oxoid CM0699) for 16-18 h at 37° C. The enriched broth was subsequently streaked on to XLD agar (CM0469) containing antibiotics as Table 12 and incubated at 37° C. for 16-18 h.

Birds with no bacteria detected in direct counts were allocated a count of 0 bacterium per g, while those negative in direct counts but positive in the enhanced method were allocated 50 CFU/g. Results were recorded on paper or dictated via telephone or radio in biosecure accommodation and transcribed to Microsoft Excel. Data were analysed in GraphPad Prism. Data were assessed for normality of distribution using a D'Agostino and Pearson omnibus normality test and as non-normal was analysed using a Mann-Whitney U test. Paired data were analysed using a paired T-test.

Results

1. *Salmonella* In-Feed

The presence of *Salmonella* in-feed (average 9×log-4 CFU/g) was as expected.

2. Guided Biotic® Levels in Drinking Water

The analysed GB level in drinking water immediately on mixing (average 5×log-8 CFU/mL) was as planned. Samples taken 24 hrs later confirmed an average drop to 8×log-7 CFU/mL.

3. Effects of *Salmonella* Dose

Overall, low levels of *Salmonella* were found in the crop (~log 1-3 CFU/g) and caeca (~log 4-5 CFU/g) on days 1 and 3 after challenge. No *Salmonella* was found in ileal, liver or spleen samples at these times.

At day 7 post challenge similar levels of *Salmonella* were again found in the crop and caeca, as well as lower levels (~log 1) in the ileum, liver and spleen.

4. Effects of Active Guided Biotic (Control vs GB)

Figure 6:
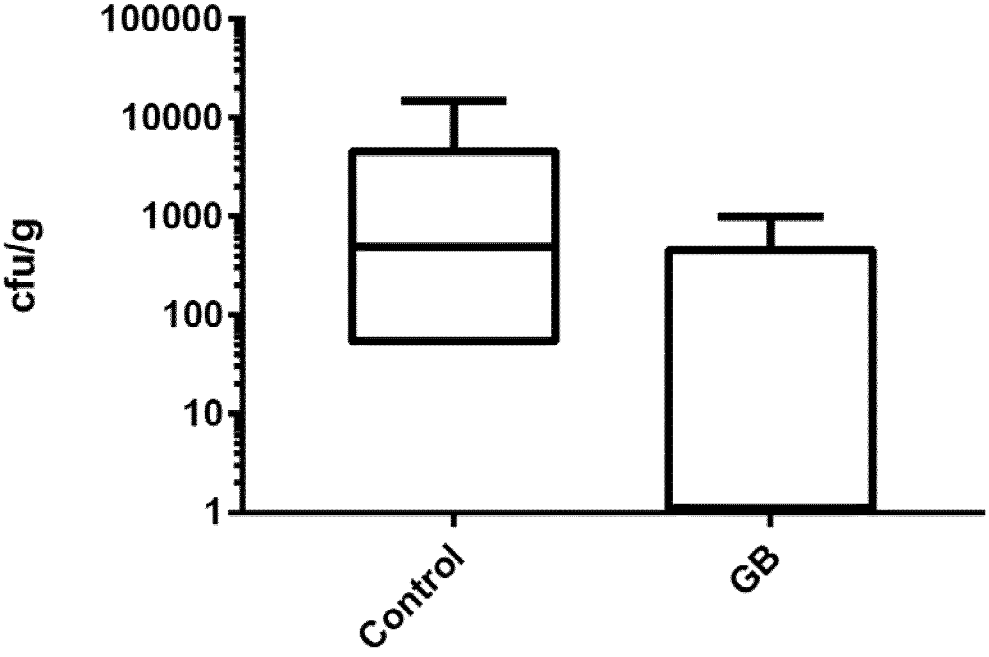
FIG. 6. Numbers (CFU/g) of *Salmonella* in crop digesta 7 days post-challenge; N=9 birds; P=0.03.

GB reduced ($P<0.03$) *Salmonella* counts in the crop 7 days post-challenge (FIG. 6).

There was a weak trend for GB to reduce *Salmonella* in the crop ($P=0.40$) and caeca ($P=0.50$) on day 3, and the ileum ($P=0.58$) and caeca ($P=0.60$) on day 7.

TABLE 5

Example Bacteria

Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *Abiotrophia* | *Acidocella* | *Actinomyces* | *Alkalilimnicola* | *Aquaspirillum* |
| *Abiotrophia defectiva* | *Acidocella aminolytica* | *Actinomyces bovis* | *Alkalilimnicola ehrlichii* | *Aquaspirillum polymorphum* |
| *Acaricomes* | *Acidocella facilis* | *Actinomyces denticolens* | *Alkaliphilus* | *Aquaspirillum* |
| *Acaricomes phytoseiuli* | *Acidomonas* | *Actinomyces europaeus* | *Alkaliphilus oremlandii* | *putridiconchylium* |
| *Acetitomaculum* | *Acidomonas methanolica* | *Actinomyces georgiae* | *Alkaliphilus transvaalensis* | *Aquaspirillum serpens* |
| *Acetitomaculum ruminis* | *Acidothermus* | *Actinomyces gerencseriae* | *Allochromatium* | *Aquimarina* |
| *Acetivibrio* | *Acidothermus cellulolyticus* | *Actinomyces* | *Allochromatium vinosum* | *Aquimarina latercula* |
| *Acetivibrio cellulolyticus* | *Acidovorax* | *hordeovulneris* | *Alloiococcus* | *Arcanobacterium* |
| *Acetivibrio ethanolgignens* | *Acidovorax anthurii* | *Actinomyces howellii* | *Alloiococcus otitis* | *Arcanobacterium* |
| *Acetivibrio multivorans* | *Acidovorax caeni* | *Actinomyces hyovaginalis* | *Allokutzneria* | *haemolyticum* |
| *Acetoanaerobium* | *Acidovorax cattleyae* | *Actinomyces israelii* | *Allokutzneria albata* | *Arcanobacterium pyogenes* |
| *Acetoanaerobium noterae* | *Acidovorax citrulli* | *Actinomyces johnsonii* | *Altererythrobacter* | *Archangium* |
| *Acetobacter* | *Acidovorax defluvii* | *Actinomyces meyeri* | *Altererythrobacter ishigakiensis* | *Archangium gephyra* |
| *Acetobacter aceti* | *Acidovorax delafieldii* | *Actinomyces naeslundii* | *Altermonas* | *Arcobacter* |
| *Acetobacter cerevisiae* | *Acidovorax facilis* | *Actinomyces neuii* | *Altermonas haloplanktis* | *Arcobacter butzleri* |
| *Acetobacter cibinongensis* | *Acidovorax konjaci* | *Actinomyces odontolyticus* | *Altermonas macleodii* | *Arcobacter cryaerophilus* |
| *Acetobacter estunensis* | *Acidovorax temperans* | *Actinomyces oris* | *Alysiella* | *Arcobacter halophilus* |
| *Acetobacter fabarum* | *Acidovorax valerianellae* | *Actinomyces radingae* | *Alysiella crassa* | *Arcobacter nitrofigilis* |
| *Acetobacter ghanensis* | *Acinetobacter* | *Actinomyces slackii* | *Alysiella filiformis* | *Arcobacter skirrowii* |
| *Acetobacter indonesiensis* | *Acinetobacter baumannii* | *Actinomyces turicensis* | *Aminobacter* | *Arhodomonas* |
| *Acetobacter lovaniensis* | *Acinetobacter baylyi* | *Actinomyces viscosus* | *Aminobacter aganoensis* | *Arhodomonas aquaeolei* |
| *Acetobacter malorum* | *Acinetobacter bouvetii* | *Actinoplanes* | *Aminobacter aminovorans* | *Arsenophonus* |
| *Acetobacter nitrogenifigens* | *Acinetobacter calcoaceticus* | *Actinoplanes auranticolor* | *Aminobacter niigataensis* | *Arsenophonus* |
| *Acetobacter oeni* | *Acinetobacter gerneri* | *Actinoplanes brasiliensis* | *Aminobacterium* | *nasoniae* |
| *Acetobacter orientalis* | *Acinetobacter haemolyticus* | *Actinoplanes consettensis* | *Aminobacterium mobile* | *Arthrobacter* |
| *Acetobacter orleanensis* | *Acinetobacter johnsonii* | *Actinoplanes deccanensis* | *Aminomonas* | *Arthrobacter agilis* |
| *Acetobacter pasteurianus* | *Acinetobacter junii* | *Actinoplanes derwentensis* | *Aminomonas paucivorans* | *Arthrobacter albus* |
| *Acetobacter pornorurn* | *Acinetobacter lwoffi* | *Actinoplanes digitatis* | *Ammoniphilus* | *Arthrobacter aurescens* |
| *Acetobacter senegalensis* | *Acinetobacter parvus* | *Actinoplanes durhamensis* | *Ammoniphilus oxalaticus* | *Arthrobacter chlorophenolicus* |
| *Acetobacter xylinus* | *Acinetobacter radioresistens* | *Actinoplanes ferrugineus* | *Ammoniphilus oxalivorans* | *Arthrobacter citreus* |
| *Acetobacterium* | *Acinetobacter schindleri* | *Actinoplanes globisporus* | *Amphibacillus* | *Arthrobacter crystallopoietes* |
| *Acetobacterium bakii* | *Acinetobacter soli* | *Actinoplanes humidus* | *Amphibacillus xylanus* | *Arthrobacter cumminsii* |
| *Acetobacterium carbinolicum* | *Acinetobacter tandoii* | *Actinoplanes italicus* | *Amphritea* | *Arthrobacter globiformis* |
| *Acetobacterium dehalogenans* | *Acinetobacter tjernbergiae* | *Actinoplanes liguriensis* | *Amphritea balenae* | *Arthrobacter* |
| *Acetobacterium fimetarium* | *Acinetobacter towneri* | *Actinoplanes lobatus* | *Amphritea japonica* | *histidinolovorans* |
| *Acetobacterium malicum* | *Acinetobacter ursingii* | *Actinoplanes missouriensis* | *Amycolatopsis* | *Arthrobacter ilicis* |
| *Acetobacterium paludosum* | *Acinetobacter venetianus* | *Actinoplanes palleronii* | *Amycolatopsis alba* | *Arthrobacter luteus* |
| *Acetobacterium tundrae* | *Acrocarpospora* | *Actinoplanes philippinensis* | *Amycolatopsis albidoflavus* | *Arthrobacter methylotrophus* |
| *Acetobacterium wieringae* | *Acrocarpospora corrugata* | *Actinoplanes rectilineatus* | *Amycolatopsis azurea* | *Arthrobacter mysorens* |
| *Acetobacterium woodii* | *Acrocarpospora* | *Actinoplanes regularis* | *Amycolatopsis coloradensis* | *Arthrobacter nicotianae* |
| *Acetofilamentum* | *macrocephala* | *Actinoplanes* | *Amycolatopsis lurida* | *Arthrobacter nicotinovorans* |
| *Acetofilamentum rigidum* | *Acrocarpospora pleiomorpha* | *teichomyceticus* | *Amycolatopsis mediterranei* | *Arthrobacter oxydans* |
| *Acetohalobium* | *Actibacter* | *Actinoplanes utahensis* | *Amycolatopsis rifamycinica* | *Arthrobacter pascens* |
| *Acetohalobium arabaticum* | *Actibacter sediminis* | *Actinopolyspora* | *Amycolatopsis rubida* | *Arthrobacter* |
| *Acetomicrobium* | *Actinoalloteichus* | *Actinopolyspora halophila* | *Amycolatopsis sulphurea* | *phenanthrenivorans* |

TABLE 5-continued

Example Bacteria

Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *Acetomicrobium faecale* | *Actinoalloteichus* | *Actinopolyspora mortivallis* | *Amycolatopsis tolypomycina* | *Arthrobacter* |
| *Acetomicrobium flavidum* | *cyanogriseus* | *Actinosynnema* | *Anabaena* | *polychromogenes* |
| *Acetonema* | *Actinoalloteichus* | *Actinosynnema mirum* | *Anabaena cylindrica* | *Atrhrobacter protophormiae* |
| *Acetonema longum* | *hymeniacidonis* | *Actinotalea* | *Anabaena flos-aquae* | *Arthrobacter* |
| *Acetothermus* | *Actinoalloteichus spitiensis* | *Actinotalea fermentans* | *Anabaena variabilis* | *psychrolactophilus* |
| *Acetothermus paucivorans* | *Actinobaccillus* | *Aerococcus* | *Anaeroarcus* | *Arthrobacter ramosus* |
| *Acholeplasma* | *Actinobacillus capsulatus* | *Aerococcus sanguinicola* | *Anaeroarcus burkinensis* | *Arthrobacter sulfonivorans* |
| *Acholeplasma axanthum* | *Actinobacillus delphinicola* | *Aerococcus urinae* | *Anaerobaculum* | *Arthrobacter sulfureus* |
| *Acholeplasma brassicae* | *Actinobacillus hominis* | *Aerococcus urinaeequi* | *Anaerobaculum mobile* | *Arthrobacter uratoxydans* |
| *Acholeplasma cavigenitalium* | *Actinobacillus indolicus* | *Aerococcus urinaehominis* | *Anaerobiospirillum* | *Arthrobacter ureafaciens* |
| *Acholeplasma equifetale* | *Actinobacillus lignieresii* | *Aerococcus viridans* | *Anaerobiospirillum* | *Arthrobacter viscosus* |
| *Acholeplasma granularum* | *Actinobacillus minor* | *Aeromicrobium* | *succiniciproducens* | *Arthrobacter woluwensis* |
| *Acholeplasma hippikon* | *Actinobacillus muris* | *Aeromicrobium erythreum* | *Anaerobiospirillum thomasii* | *Asaia* |
| *Acholeplasma laidlawii* | *Actinobacillus* | *Aeromonas* | *Anaerococcus* | *Asaia bogorensis* |
| *Acholeplasma modicum* | *pleuropneumoniae* | *Aeromonas* | *Anaerococcus hydrogenalis* | *Asanoa* |
| *Acholeplasma morum* | *Actinobacillus porcinus* | *allosaccharophila* | *Anaerococcus lactolyticus* | *Asanoa ferruginea* |
| *Acholeplasma multilocale* | *Actinobacillus rossii* | *Aeromonas bestiarum* | *Anaerococcus prevotii* | *Asticcacaulis* |
| *Acholeplasma oculi* | *Actinobacillus scotiae* | *Aeromonas caviae* | *Anaerococcus tetradius* | *Asticcacaulis biprosthecium* |
| *Acholeplasma palmae* | *Actinobacillus seminis* | *Aeromonas encheleia* | *Anaerococcus vaginalis* | *Asticcacaulis excentricus* |
| *Acholeplasma parvum* | *Actinobacillus succinogenes* | *Aeromonas* | *Anaerofustis* | *Atopobacter* |
| *Acholeplasma pleciae* | *Actinobaccillus suis* | *enteropelogenes* | *Anaerofustis stercorihominis* | *Atopobacter phocae* |
| *Acholeplasma vituli* | *Actinobacillus ureae* | *Aeromonas eucrenophila* | *Anaeromusa* | *Atopobium* |
| *Achromobacter* | *Actinobaculum* | *Aeromonas ichthiosmia* | *Anaeromusa acidaminophila* | *Atopobium fossor* |
| *Achromobacter denitrificans* | *Actinobaculum massiliense* | *Aeromonas jandaei* | *Anaeromyxobacter* | *Atopobium minutum* |
| *Achromobacter insolitus* | *Actinobaculum schaalii* | *Aeromonas media* | *Anaeromyxobacter* | *Atopobium parvulum* |
| *Achromobacter piechaudii* | *Actinobaculum suis* | *Aeromonas popoffii* | *dehalogenans* | *Atopobium rimae* |
| *Achromobacter ruhlandii* | *Actinomyces urinale* | *Aeromonas sobria* | *Anaerorhabdus* | *Atopobium vaginae* |
| *Achromobacter spanius* | *Actinocatenispora* | *Aeromonas veronii* | *Anaerorhabdus furcosa* | *Aureobacterium* |
| *Acidaminobacter* | *Actinocatenispora rupis* | *Agrobacterium* | *Anaerosinus* | *Aureobacterium barkeri* |
| *Acidaminobacter* | *Actinocatenispora* | *Agrobacterium* | *Anaerosinus glycerini* | *Aurobacterium* |
| *hydrogenoformans* | *thailandica* | *gelatinovorum* | *Anaerovirgula* | *Aurobacterium liquefaciens* |
| *Acidaminococcus* | *Actinocatenispora sera* | *Agrococcus* | *Anaerovirgula multivorans* | *Avibacterium* |
| *Acidaminococcus fermentans* | *Actinocorallia* | *Agrococcus citreus* | *Ancalomicrobium* | *Avibacterium avium* |
| *Acidaminococcus intestini* | *Actinocorallia aurantiaca* | *Agrococcus jenensis* | *Ancalomicrobium adetum* | *Avibacterium gallinarum* |
| *Acidicaldus* | *Actinocorallia aurea* | *Agromonas* | *Ancylobacter* | *Avibacterium paragallinarum* |
| *Acidicaldus organivorans* | *Actinocorallia cavernae* | *Agromonas oligotrophica* | *Ancylobacter aquaticus* | *Avibacterium volantium* |
| *Acidimicrobium* | *Actinocorallia glomerata* | *Agromyces* | *Aneurinibacillus* | *Azoarcus* |
| *Acidimicrobium ferrooxidans* | *Actinocorallia herbida* | *Agromyces fucosus* | *Aneurinibacillus aneurinilyticus* | *Azoarcus indigens* |
| *Acidiphilium* | *Actinocorallia libanotica* | *Agromyces hippuratus* | *Aneurinibacillus migulanus* | *Azoarcus tolulyticus* |
| *Acidiphilium acidophilum* | *Actinocorallia longicatena* | *Agromyces luteolus* | *Aneurinibacillus* | *Azoarcus toluvorans* |
| *Acidiphilium angustum* | *Actinomadura* | *Agromyces mediolanus* | *thermoaerophilus* | *Azohydromonas* |
| *Acidiphilium cryptum* | *Actinomadura alba* | *Agromyces ramosus* | *Angiococcus* | *Azohydromonas australica* |
| *Acidiphilium multivorum* | *Actinomadura atramentaria* | *Agromyces rhizospherae* | *Angiococcus disciformis* | *Azohydromonas lata* |
| *Acidiphilium organovorum* | *Actinomadura* | *Akkermansia* | *Angulomicrobium* | *Azomonas* |
| *Acidiphilium rubrum* | *bangladeshensis* | *Akkermansia muciniphila* | *Angulomicrobium tetraedrale* | *Azomonas agilis* |
| *Acidisoma* | *Actinomadura catellatispora* | *Albidiferax* | *Anoxybacillus* | *Azomonas insignis* |
| *Acidisoma sibiricum* | *Actinomadura chibensis* | *Albidiferax ferrireducens* | *Anoxybacillus pushchinoensis* | *Azomonas macrocytogenes* |

TABLE 5-continued

Example Bacteria

Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *Acidisoma tundrae* | *Actinomadura chokoriensis* | *Albidovulum* | *Aquabacterium* | *Azorhizobium* |
| *Acidisphaera* | *Actinomadura citrea* | *Albidovulum inexpectatum* | *Aquabacterium commune* | *Azorhizobium caulinodans* |
| *Acidisphaera rubrifaciens* | *Actinomadura coerulea* | *Alcaligenes* | *Aquabacterium parvum* | *Azorhizophilus* |
| *Acidithiobacillus* | *Actinomadura echinospora* | *Alcaligenes denitrificans* | | *Azorhizophilus paspali* |
| *Acidithiobacillus albertensis* | *Actinomadura fibrosa* | *Alcaligenes faecalis* | | *Azospirillum* |
| *Acidithiobacillus caldus* | *Actinomadura formosensis* | *Alcanivorax* | | *Azospirillum brasilense* |
| *Acidithiobacillus ferrooxidans* | *Actinomadura hibisca* | *Alcanivorax borkumensis* | | *Azospirillum halopraeferens* |
| *Acidithiobacillus thiooxidans* | *Actinomadura kijaniata* | *Alcanivorax jadensis* | | *Azospirillum irakense* |
| *Acidobacterium* | *Actinomadura latina* | *Algicola* | | *Azotobacter* |
| *Acidobacterium capsulatum* | *Actinomadura livida* | *Algicola bacteriolytica* | | *Azotobacter beijerinckii* |
| | *Actinomadura* | *Alicyclobacillus* | | *Azotobacter chroococcum* |
| | *luteofluorescens* | *Alicyclobacillus* | | *Azotobacter nigricans* |
| | *Actinomadura macra* | *disulfidooxidans* | | *Azotobacter salinestris* |
| | *Actinomadura madurae* | *Alicyclobacillus* | | *Azotobacter vinelandii* |
| | *Actinomadura oligospora* | *sendaiensis* | | |
| | *Actinomadura pelletieri* | *Alicyclobacillus vulcanalis* | | |
| | *Actinomadura rubrobrunea* | *Alishewanella* | | |
| | *Actinomadura rugatobispora* | *Alishewanella fetalis* | | |
| | *Actinomadura umbrina* | *Alkalibacillus* | | |
| | *Actinomadura* | *Alkalibacillus* | | |
| | *verrucosospora* | *haloalkaliphilus* | | |
| | *Actinomadura vinacea* | | | |
| | *Actinomadura viridilutea* | | | |
| | *Actinomadura viridis* | | | |
| | *Actinomadura yumaensis* | | | |
| *Bacillus* | *Bacteroides* | *Bibersteinia* | *Borrelia* | *Brevinema* |
| [see below] | *Bacteroides caccae* | *Bibersteinia trehalosi* | *Borrelia afzelii* | *Brevinema andersonii* |
| *Bacteriovorax* | *Bacteroides coagulans* | *Bifidobacterium* | *Borrelia americana* | *Brevundimonas* |
| *Bacteriovorax stolpii* | *Bacteroides eggerthii* | *Bifidobacterium adolescentis* | *Borrelia burgdorferi* | *Brevundimonas alba* |
| | *Bacteroides fragilis* | *Bifidobacterium angulatum* | *Borrelia carolinensis* | *Brevundimonas aurantiaca* |
| | *Bacteroides galacturonicus* | *Bifidobacterium animalis* | *Borrelia coriaceae* | *Brevundimonas diminuta* |
| | *Bacteroides helcogenes* | *Bifidobacterium asteroides* | *Borrelia garinii* | *Brevundimonas intermedia* |
| | *Bacteroides ovatus* | *Bifidobacterium bifidum* | *Borrelia japonica* | *Brevundimonas subvibrioides* |
| | *Bacteroides pectinophilus* | *Bifidobacterium boum* | *Bosea* | *Brevundimonas vancanneytii* |
| | *Bacteroides pyogenes* | *Bifidobacterium breve* | *Bosea minatitlanensis* | *Brevundimonas variabilis* |
| | *Bacteroides salyersiae* | *Bifidobacterium catenulatum* | *Bosea thiooxidans* | *Brevundimonas vesicularis* |
| | *Bacteroides stercoris* | *Bifidobacterium choerinum* | *Brachybacterium* | *Brochothrix* |
| | *Bacteroides suis* | *Bifidobacterium coryneforme* | *Brachybacterium* | *Brochothrix campestris* |
| | *Bacteroides tectus* | *Bifidobacterium cuniculi* | *alimentarium* | *Brochothrix thermosphacta* |
| | *Bacteroides thetaiotaomicron* | *Bifidobacterium dentium* | *Brachybacterium faecium* | *Brucella* |
| | *Bacteroides uniformis* | *Bifidobacterium gallicum* | *Brachybacterium* | *Brucella canis* |
| | *Bacteroides ureolyticus* | *Bifidobacterium gallinarum* | *paraconglomeratum* | *Brucella neotomae* |
| | *Bacteroides vulgatus* | *Bifidobacterium indicum* | *Brachybacterium rhamnosum* | *Bryobacter* |
| | *Balnearium* | *Bifidobacterium longum* | *Brachybacterium* | *Bryobacter aggregatus* |
| | *Balnearium lithotrophicum* | *Bifidobacterium* | *tyrofermentans* | *Burkholderia* |
| | *Balneatrix* | *magnumBifidobacterium* | *Brachyspira* | *Burkholderia ambifaria* |
| | *Balneatrix alpica* | *merycicum* | *Brachyspira alvinipulli* | *Burkholderia andropogonis* |

TABLE 5-continued

Example Bacteria

Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| | *Balneola* | *Bifidobacterium minimum* | *Brachyspira hyodysenteriae* | *Burkholderia anthina* |
| | *Balneola vulgaris* | *Bifidobacterium* | *Brachyspira innocens* | *Burkholderia caledonica* |
| | *Barnesiella* | *pseudocatenulatum* | *Brachyspira murdochii* | *Burkholderia caryophylli* |
| | *Barnesiella viscericola* | *Bifidobacterium* | *Brachyspira* | *Burkholderia cenocepacia* |
| | *Bartonella* | *pseudolongum* | *pilosicoli* | *Burkholderia cepacia* |
| | *Bartonella alsatica* | *Bifidobacterium pullorum* | *Bradyrhizobium* | *Burkholderia cocovenenans* |
| | *Bartonella bacilliformis* | *Bifidobacterium ruminantium* | *Bradyrhizobium canariense* | *Burkholderia dolosa* |
| | *Bartonella clarridgeiae* | *Bifidobacterium saeculare* | *Bradyrhizobium elkanii* | *Burkholderia fungorum* |
| | *Bartonella doshiae* | *Bifidobacterium subtile* | *Bradyrhizobium japonicum* | *Burkholderia glathei* |
| | *Bartonella elizabethae* | *Bifidobacterium* | *Bradyrhizobium liaoningense* | *Burkholderia glumae* |
| | *Bartonella grahamii* | *thermophilum* | *Brenneria* | *Burkholderia graminis* |
| | *Bartonella henselae* | *Bilophila* | *Brenneria alni* | *Burkholderia kururiensis* |
| | *Bartonella rochalimae* | *Bilophila wadsworthia* | *Brenneria nigrifluens* | *Burkholderia multivorans* |
| | *Bartonella vinsonii* | *Biostraticola* | *Brenneria quercina* | *Burkholderia phenazinium* |
| | *Bavariicoccus* | *Biostraticola tofi* | *Brenneria quercina* | *Burkholderia plantarii* |
| | *Bavariicoccus seileri* | *Bizionia* | *Brenneria salicis* | *Burkholderia pyrrocinia* |
| | *Bdellovibrio* | *Bizionia argentinensis* | *Brevibacillus* | *Burkholderia silvatlantica* |
| | *Bdellovibrio bacteriovorus* | *Blastobacter* | *Brevibacillus agri* | *Burkholderia stabilis* |
| | *Bdellovibrio exovorus* | *Blastobacter capsulatus* | *Brevibacillus borstelensis* | *Burkholderia thailandensis* |
| | *Beggiatoa* | *Blastobacter denitrificans* | *Brevibacillus brevis* | *Burkholderia tropica* |
| | *Beggiatoa alba* | *Blastococcus* | *Brevibacillus centrosporus* | *Burkholderia unamae* |
| | *Beijerinckia* | *Blastococcus aggregatus* | *Brevibacillus choshinensis* | *Burkholderia vietnamiensis* |
| | *Beijerinckia derxii* | *Blastococcus saxobsidens* | *Brevibacillus invocatus* | *Buttiauxella* |
| | *Beijerinckia fluminensis* | *Blastochloris* | *Brevibacillus laterosporus* | *Buttiauxella agrestis* |
| | *Beijerinckia indica* | *Blastochloris viridis* | *Brevibacillus parabrevis* | *Buttiauxella brennerae* |
| | *Beijerinckia mobilis* | *Blastomonas* | *Brevibacillus reuszeri* | *Buttiauxella ferragutiae* |
| | *Belliella* | *Blastomonas natatoria* | *Brevibacterium* | *Buttiauxella gaviniae* |
| | *Belliella baltica* | *Blastopirellula* | *Brevibacterium abidum* | *Buttiauxella izardii* |
| | *Bellilinea* | *Blastopirellula marina* | *Brevibacterium album* | *Buttiauxella noackiae* |
| | *Bellilinea caldifistulae* | *Blautia* | *Brevibacterium aurantiacum* | *Buttiauxella warmboldiae* |
| | *Belnapia* | *Blautia coccoides* | *Brevibacterium celere* | *Butyrivibrio* |
| | *Belnapia moabensis* | *Blautia hansenii* | *Brevibacterium epidermidis* | *Butyrivibrio fibrisolvens* |
| | *Bergeriella* | *Blautia producta* | *Brevibacterium* | *Butyrivibrio hungatei* |
| | *Bergeriella denitrificans* | *Blautia wexlerae* | *frigoritolerans* | *Butyrivibrio proteoclasticus* |
| | *Beutenbergia* | *Bogoriella* | *Brevibacterium halotolerans* | |
| | *Beutenbergia cavernae* | *Bogoriella caseilytica* | *Brevibacterium iodinum* | |
| | | *Bordetella* | *Brevibacterium linens* | |
| | | *Bordetella avium* | *Brevibacterium lyticum* | |
| | | *Bordetella bronchiseptica* | *Brevibacterium mcbrellneri* | |
| | | *Bordetella hinzii* | *Brevibacterium otitidis* | |
| | | *Bordetella holmesii* | *Brevibacterium oxydans* | |
| | | *Bordetella parapertussis* | *Brevibacterium paucivorans* | |
| | | *Bordetella pertussis* | *Brevibacterium stationis* | |
| | | *Bordetella petrii* | | |
| | | *Bordetella trematum* | | |
| *Bacillus* | | | | |
| *B. acidiceler* | *B. aminovorans* | *B. glucanolyticus* | *B. taeanensis* | *B. lautus* |

TABLE 5-continued

Example Bacteria

Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *B. acidicola* | *B. amylolyticus* | *B. gordonae* | *B. tequilensis* | *B. lehensis* |
| *B. acidiproducens* | *B. andreesenii* | *B. gottheilii* | *B. thermantarcticus* | *B. lentimorbus* |
| *B. acidocaldarius* | *B. aneurinilyticus* | *B. graminis* | *B. thermoaerophilus* | *B. lentus* |
| *B. acidoterrestris* | *B. anthracis* | *B. halmapalus* | *B. thermoamylovorans* | *B. licheniformis* |
| *B. aeolius* | *B. aquimaris* | *B. haloalkaliphilus* | *B. thermocatenulatus* | *B. ligniniphilus* |
| *B. aerius* | *B. arenosi* | *B. halochares* | *B. thermocloacae* | *B. litoralis* |
| *B. aerophilus* | *B. arseniciselenatis* | *B. halodenitrificans* | *B. thermocopriae* | *B. locisalis* |
| *B. agaradhaerens* | *B. arsenicus* | *B. halodurans* | *B. thermodenitrificans* | *B. luciferensis* |
| *B. agri* | *B. aurantiacus* | *B. halophilus* | *B. thermoglucosidasius* | *B. luteolus* |
| *B. aidingensis* | *B. arvi* | *B. halosaccharovorans* | *B. thermolactis* | *B. luteus* |
| *B. akibai* | *B. aryabhattai* | *B. hemicellulosilyticus* | *B. thermoleovorans* | *B. macauensis* |
| *B. alcalophilus* | *B. asahii* | *B. hemicentroti* | *B. thermophilus* | *B. macerans* |
| *B. algicola* | *B. atrophaeus* | *B. herbersteinensis* | *B. thermoruber* | *B. macquariensis* |
| *B. alginolyticus* | *B. axarquiensis* | *B. horikoshii* | *B. thermosphaericus* | *B. macyae* |
| *B. alkalidiazotrophicus* | *B. azotofixans* | *B. horneckiae* | *B. thiaminolyticus* | *B. malacitensis* |
| *B. alkalinitrilicus* | *B. azotoformans* | *B. horti* | *B. thioparans* | *B. mannanilyticus* |
| *B. alkalisediminis* | *B. badius* | *B. huizhouensis* | *B. thuringiensis* | *B. marisflavi* |
| *B. alkalitelluris* | *B. barbaricus* | *B. humi* | *B. tianshenii* | *B. marismortui* |
| *B. altitudinis* | *B. bataviensis* | *B. hwajinpoensis* | *B. trypoxylicola* | *B. marmarensis* |
| *B. alveayuensis* | *B. beijingensis* | *B. idriensis* | *B. tusciae* | *B. massiliensis* |
| *B. alvei* | *B. benzoevorans* | *B. indicus* | *B. validus* | *B. megaterium* |
| *B. amyloliquefaciens* | *B. beringensis* | *B. infantis* | *B. vallismortis* | *B. mesonae* |
| B. | *B. berkeleyi* | *B. infernus* | *B. vedderi* | *B. methanolicus* |
| a. subsp. *amyloliquefaciens* | *B. beveridgei* | *B. insolitus* | *B. velezensis* | *B. methylotrophicus* |
| B. a. subsp. *plantarum* | *B. bogoriensis* | *B. invictae* | *B. vietnamensis* | *B. migulanus* |
| | *B. boroniphilus* | *B. iranensis* | *B. vireti* | *B. mojavensis* |
| *B. dipsosauri* | *B. borstelensis* | *B. isabeliae* | *B. vulcani* | *B. mucilaginosus* |
| *B. drentensis* | *B. brevis Migula* | *B. isronensis* | *B. wakoensis* | *B. muralis* |
| *B. edaphicus* | *B. butanolivorans* | *B. jeotgali* | *B. weihenstephanensis* | *B. murimartini* |
| *B. ehimensis* | *B. canaveralius* | *B. kaustophilus* | *B. xiamenensis* | *B. mycoides* |
| *B. eiseniae* | *B. carboniphilus* | *B. kobensis* | *B. xiaoxiensis* | *B. naganoensis* |
| *B. enclensis* | *B. cecembensis* | *B. kochii* | *B. zhanjiangensis* | *B. nanhaiensis* |
| *B. endophyticus* | *B. cellulosilyticus* | *B. kokeshiiformis* | *B. peoriae* | *B. nanhaiisediminis* |
| *B. endoradicis* | *B. centrosporus* | *B. koreensis* | *B. persepolensis* | *B. nealsonii* |
| *B. farraginis* | *B. cereus* | *B. korlensis* | *B. persicus* | *B. neidei* |
| *B. fastidiosus* | *B. chagannorensis* | *B. kribbensis* | *B. pervagus* | *B. neizhouensis* |
| *B. fengqiuensis* | *B. chitinolyticus* | *B. krulwichiae* | *B. plakortidis* | *B. niabensis* |
| *B. firmus* | *B. chondroitinus* | *B. laevolacticus* | *B. pocheonensis* | *B. niacini* |
| *B. flexus* | *B. choshinensis* | *B. larvae* | *B. polygoni* | *B. novalis* |
| *B. foraminis* | *B. chungangensis* | *B. laterosporus* | *B. polymyxa* | *B. oceanisediminis* |
| *B. fordii* | *B. cibi* | *B. salexigens* | *B. popilliae* | *B. odysseyi* |
| *B. formosus* | *B. circulans* | *B. saliphilus* | *B. pseudalcalophilus* | *B. okhensis* |
| *B. fortis* | *B. clarkii* | *B. schlegelii* | *B. pseudofirmus* | *B. okuhidensis* |
| *B. fumarioli* | *B. clausii* | *B. sediminis* | *B. pseudomycoides* | *B. oleronius* |
| *B. funiculus* | *B. coagulans* | *B. selenatarsenatis* | *B. psychrodurans* | *B. oryzaecorticis* |
| *B. fusiformis* | *B. coahuilensis* | *B. selenitireducens* | *B. psychrophilus* | *B. oshimensis* |
| *B. galactophilus* | *B. cohnii* | *B. seohaeanensis* | *B. psychrosaccharolyticus* | *B. pabuli* |

TABLE 5-continued

Example Bacteria
Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *B. galactosidilyticus* | *B. composti* | *B. shacheensis* | *B. psychrotolerans* | *B. pakistanensis* |
| *B. galliciensis* | *B. curdlanolyticus* | *B. shackletonii* | *B. pulvifaciens* | *B. pallidus* |
| *B. gelatini* | *B. cycloheptanicus* | *B. siamensis* | *B. pumilus* | *B. pallidus* |
| *B. gibsonii* | *B. cytotoxicus* | *B. silvestris* | *B. purgationiresistens* | *B. panacisoli* |
| *B. ginsengi* | *B. daliensis* | *B. simplex* | *B. pycnus* | *B. panaciterrae* |
| *B. ginsengihumi* | *B. decisifrondis* | *B. siralis* | *B. qingdaonensis* | *B. pantothenticus* |
| *B. ginsengisoli* | *B. decolorationis* | *B. smithii* | *B. qingshengii* | *B. parabrevis* |
| *B. globisporus* (eg, B. | *B. deserti* | *B. soli* | *B. reuszeri* | *B. paraflexus* |
| g. subsp. *Globisporus*; or B. | | *B. solimangrovi* | *B. rhizosphaerae* | *B. pasteurii* |
| g. subsp. *Marinus*) | | *B. solisalsi* | *B. rigui* | *B. patagoniensis* |
| | | *B. songklensis* | *B. ruris* | |
| | | *B. sonorensis* | *B. safensis* | |
| | | *B. sphaericus* | *B. salarius* | |
| | | *B. sporothermodurans* | | |
| | | *B. stearothermophilus* | | |
| | | *B. stratosphericus* | | |
| | | *B. subterraneus* | | |
| | | *B. subtilis* (eg, B. | | |
| | | s. subsp. *Inaquosorum*, or B. | | |
| | | s. subsp. *Spizizenr*, or B. | | |
| | | s. subsp. *Subtilis*) | | |
| *Caenimonas* | *Campylobacter* | *Cardiobacterium* | *Catenuloplanes* | *Curtobacterium* |
| *Caenimonas koreensis* | *Campylobacter coli* | *Cardiobacterium hominis* | *Catenuloplanes atrovinosus* | *Curtobacterium albidum* |
| *Caldalkalibacillus* | *Campylobacter concisus* | *Carnimonas* | *Catenuloplanes castaneus* | *Curtobacterium citreus* |
| *Caldalkalibacillus uzonensis* | *Campylobacter curvus* | *Carnimonas nigrificans* | *Catenuloplanes crispus* | |
| *Caldanaerobacter* | *Campylobacter fetus* | *Carnobacterium* | *Catenuloplanes indicus* | |
| *Caldanaerobacter subterraneus* | *Campylobacter gracilis* | *Carnobacterium alterfunditum* | *Catenuloplanes japonicus* | |
| *Caldanaerobius* | *Campylobacter helveticus* | *Carnobacterium divergens* | *Catenuloplanes nepalensis* | |
| *Caldanaerobius fijiensis* | *Campylobacter hominis* | *Carnobacterium funditum* | *Catenuloplanes niger* | |
| *Caldanaerobius* | *Campylobacter hyointestinalis* | *Carnobacterium gallinarum* | *Chryseobacterium* | |
| *polysaccharolyticus* | *Campylobacter jejuni* | *Carnobacterium* | *Chryseobacterium* | |
| *Caldanaerobius zeae* | *Campylobacter lari* | *maltaromaticum* | *balustinum* | |
| *Caldanaerovirga* | *Campylobacter mucosalis* | *Carnobacterium mobile* | *Citrobacter* | |
| *Caldanaerovirga acetigignens* | *Campylobacter rectus* | *Carnobacterium viridans* | *C. amalonaticus* | |
| *Caldicellulosiruptor* | *Campylobacter showae* | *Caryophanon* | *C. braakii* | |
| *Caldicellulosiruptor bescii* | *Campylobacter sputorum* | *Caryophanon latum* | *C. diversus* | |
| *Caldicellulosiruptor kristjanssonii* | *Campylobacter upsaliensis* | *Caryophanon tenue* | *C. farmeri* | |
| *Caldicellulosiruptor owensensis* | *Capnocytophaga* | *Catellatospora* | *C. freundii* | |
| | *Capnocytophaga canimorsus* | *Catellatospora citrea* | *C. gillenii* | |
| | *Capnocytophaga cynodegmi* | *Catellatospora* | *C. koseri* | |
| | *Capnocytophaga gingivalis* | *methionotrophica* | *C. murliniae* | |
| | *Capnocytophaga granulosa* | *Catenococcus* | *C. pasteurii*[1] | |
| | *Capnocytophaga haemolytica* | *Catenococcus thiocycli* | *C. rodentium* | |
| | *Capnocytophaga ochracea* | | *C. sedlakii* | |
| | *Capnocytophaga sputigena* | | *C. werkmanii* | |
| | | | *C. youngae* | |
| | | | *Clostridium* | |

TABLE 5-continued

| Example Bacteria<br>Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells. | | | |
|---|---|---|---|
| | | | (see below)<br>*Coccochloris*<br>*Coccochloris elabens*<br>*Corynebacterium*<br>*Corynebacterium flavescens*<br>*Corynebacterium variabile* |
| *Clostridium*<br>*Clostridium absonum*, *Clostridium aceticum*, *Clostridium acetireducens*, *Clostridium acetobutylicum*, *Clostridium acidisoli*, *Clostridium aciditolerans, Clostridium acidurici*, *Clostridium aerotolerans*, *Clostridium aestuarii*, *Clostridium akagii*, *Clostridium aldenense*, *Clostridium aldrichii*, *Clostridium algidicarni*, *Clostridium algidixylanolyticum*, *Clostridium algifaecis*, *Clostridium algoriphilum*, *Clostridium alkalicellulosi*, *Clostridium aminophilum*, *Clostridium aminovalericum*, *Clostridium amygdalinum*, *Clostridium amylolyticum*, *Clostridium arbusti*, *Clostridium arcticum*, *Clostridium argentinense*, *Clostridium asparagiforme*, *Clostridium aurantibutyricum*, *Clostridium autoethanogenum*, *Clostridium baratii*, *Clostridium barkeri*, *Clostridium bartlettii*, *Clostridium beijerinckii*, *Clostridium bifermentans*, *Clostridium bolteae*, *Clostridium bornimense*, *Clostridium botulinum*, *Clostridium bowmanii*, *Clostridium bryantii*, *Clostridium butyricum*, *Clostridium cadaveris*, *Clostridium caenicola*, *Clostridium caminithermale*, *Clostridium carboxidivorans*, *Clostridium carnis*, *Clostridium cavendishii*, *Clostridium celatum*, *Clostridium celerecrescens*, *Clostridium cellobioparum*, *Clostridium cellulofermentans*, *Clostridium cellulolyticum*, *Clostridium cellulosi*, *Clostridium cellulovorans*, *Clostridium chartatabidum*, *Clostridium chauvoei*, *Clostridium chromiireducens*, *Clostridium citroniae*, *Clostridium clariflavum*, *Clostridium clostridioforme*, *Clostridium coccoides*, *Clostridium cochlearium*, *Clostridium colletant*, *Clostridium colicanis*, *Clostridium colinum*, *Clostridium collagenovorans*, *Clostridium cylindrosporum*, *Clostridium difficile*, *Clostridium diolis*, *Clostridium disporicum*, *Clostridium drakei*, *Clostridium durum*, *Clostridium estertheticum*, *Clostridium estertheticum estertheticum*, *Clostridium estertheticum laramiense*, *Clostridium fallax*, *Clostridium felsineum*, *Clostridium fervidum*, *Clostridium fimetarium*, *Clostridium formicaceticum*, *Clostridium frigidicarnis*, *Clostridium frigoris*, *Clostridium ganghwense*, *Clostridium gasigenes*, *Clostridium ghonii*, *Clostridium glycolicum*, *Clostridium glycyrrhizinilyticum*, *Clostridium grantii*, *Clostridium haemolyticum*, *Clostridium halophilum*, *Clostridium hastiforme*, *Clostridium hathewayi*, *Clostridium herbivorans*, *Clostridium hiranonis*, *Clostridium histolyticum*, *Clostridium homopropionicum*, *Clostridium huakuii*, *Clostridium hungatei*, *Clostridium hydrogeniformans*, *Clostridium hydroxybenzoicum*, *Clostridium hylemonae*, *Clostridium jejuense*, *Clostridium indolis*, *Clostridium innocuum*, *Clostridium intestinale*, *Clostridium irregulare*, *Clostridium isatidis*, *Clostridium josui*, *Clostridium kluyveri*, *Clostridium lactatifermentans*, *Clostridium lacusfryxellense*, *Clostridium laramiense*, *Clostridium lavalense*, *Clostridium lentocellum*, *Clostridium lentoputrescens*, *Clostridium leptum*, *Clostridium limosum*, *Clostridium litorale*, *Clostridium lituseburense*, *Clostridium ljungdahlii*, *Clostridium lortetii*, *Clostridium lundense*, *Clostridium magnum*, *Clostridium malenominatum*, *Clostridium mangenotii*, *Clostridium mayombei*, *Clostridium methoxybenzovorans*, *Clostridium methylpentosum*, *Clostridium neopropionicum*, *Clostridium nexile*, *Clostridium nitrophenolicum*, *Clostridium novyi*, *Clostridium oceanicum*, *Clostridium orbiscindens*, *Clostridium oroticum*, *Clostridium oxalicum*, *Clostridium papyrosolvens*, *Clostridium paradoxum*, *Clostridium paraperfringens* (Alias: *C. welchii*), *Clostridium paraputrificum*, *Clostridium pascui*, *Clostridium pasteurianum*, *Clostridium peptidivorans*, *Clostridium perenne*, *Clostridium perfringens*, *Clostridium pfennigii*, *Clostridium phytofermentans*, *Clostridium piliforme*, *Clostridium polysaccharolyticum*, *Clostridium populeti*, *Clostridium propionicum*, *Clostridium proteoclasticum*, *Clostridium proteolyticum*, *Clostridium psychrophilum*, *Clostridium puniceum*, *Clostridium purinilyticum*, *Clostridium putrefaciens*, *Clostridium putrificum*, *Clostridium quercicolum*, *Clostridium quinii*, *Clostridium ramosum*, *Clostridium rectum*, *Clostridium roseum*, *Clostridium saccharobutylicum*, *Clostridium saccharogumia*, *Clostridium saccharolyticum*, *Clostridium saccharoperbutylacetonicum*, *Clostridium sardiniense*, *Clostridium sartagoforme*, *Clostridium scatologenes*, *Clostridium schirmacherense*, *Clostridium scindens*, *Clostridium septicum*, *Clostridium sordellii*, *Clostridium sphenoides*, *Clostridium spiroforme*, *Clostridium sporogenes*, *Clostridium sporosphaeroides*, *Clostridium stercorarium*, *Clostridium stercorarium leptospartum*, *Clostridium stercorarium stercorarium*, *Clostridium stercorarium thermolacticum*, *Clostridium sticklandii*, *Clostridium straminisolvens*, *Clostridium subterminale*, *Clostridium sufflavum*, *Clostridium sulfidigenes*, *Clostridium symbiosum*, *Clostridium tagluense*, *Clostridium tepidiprofundi*, *Clostridium termitidis*, *Clostridium tertium*, *Clostridium tetani*, *Clostridium tetanomorphum*, *Clostridium thermaceticum*, *Clostridium thermautotrophicum*, *Clostridium thermoalcaliphilum*, *Clostridium thermobutyricum*, *Clostridium thermocellum*, *Clostridium thermocopriae*, *Clostridium thermohydrosulfuricum*, *Clostridium thermolacticum*, *Clostridium thermopalmarium*, *Clostridium thermopapyrolyticum*, *Clostridium thermosaccharolyticum*, *Clostridium thermosuccinogenes*, *Clostridium thermosulfurigenes*, *Clostridium thiosulfatireducens*, *Clostridium tyrobutyricum*, *Clostridium uliginosum*, *Clostridium ultunense*, *Clostridium villosum*, *Clostridium vincentii*, *Clostridium viride*, *Clostridium xylanolyticum*, *Clostridium xylanovorans* | | | |
| *Dactylosporangium*<br>*Dactylosporangium aurantiacum*<br>*Dactylosporangium fulvum*<br>*Dactylosporangium matsuzakiense*<br>*Dactylosporangium roseum*<br>*Dactylosporangium thailandense*<br>*Dactylosporangium vinaceum* | *Deinococcus*<br>*Deinococcus aerius*<br>*Deinococcus apachensis*<br>*Deinococcus aquaticus*<br>*Deinococcus aquatilis*<br>*Deinococcus caeni*<br>*Deinococcus radiodurans*<br>*Deinococcus radiophilus* | *Delftia*<br>*Delftia acidovorans*<br>*Desulfovibrio*<br>*Desulfovibrio desulfuricans*<br>*Diplococcus*<br>*Diplococcus pneumoniae* | *Echinicola*<br>*Echinicola pacifica*<br>*Echinicola vietnamensis* |
| *Enterobacter*<br>*E. aerogenes*<br>*E. amnigemis*<br>*E. agglomerans*<br>*E. arachidis* | *Enterobacter kobei*<br>*E. ludwigii*<br>*E. mori*<br>*E. nimipressuralis*<br>*E. oryzae* | *Faecalibacterium*<br>*Faecalibacterium prausnitzii*<br>*Fangia*<br>*Fangia hongkongensis*<br>*Fastidiosipila* | *Flavobacterium*<br>*Flavobacterium antarcticum*<br>*Flavobacterium aquatile*<br>*Flavobacterium aquidurense*<br>*Flavobacterium balustinum* |

TABLE 5-continued

Example Bacteria

Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *E. asburiae* | *E. pulveris* | *Fastidiosipila sanguinis* | *Flavobacterium croceum* | |
| *E. cancerogenous* | *E. pyrinus* | *Fusobacterium* | *Flavobacterium cucumis* | |
| *E. cloacae* | *E. radicincitans* | *Fusobacterium nucleatum* | *Flavobacterium daejeonense* | |
| *E. cowanii* | *E. taylorae* | | *Flavobacterium defluvii* | |
| *E. dissolvens* | *E. turicensis* | | *Flavobacterium degerlachei* | |
| *E. gergoviae* | *E. sakazakii Enterobacter soli* | | *Flavobacterium* | |
| *E. helveticus* | *Enterococcus* | | *denitrificans* | |
| *E. hormaechei* | *Enterococcus durans* | | *Flavobacterium filum* | |
| *E. intermedins* | *Enterococcus faecalis* | | *Flavobacterium flevense* | |
| | *Enterococcus faecium* | | *Flavobacterium frigidarium* | |
| | *Erwinia* | | *Flavobacterium mizutaii* | |
| | *Erwinia hapontici* | | *Flavobacterium* | |
| | *Escherichia* | | *okeanokoites* | |
| | *Escherichia coli* | | | |
| *Gaetbulibacter* | *Haemophilus* | *Ideonella* | *Janibacter* | |
| *Gaetbulibacter saemankumensis* | *Haemophilus aegyptius* | *Ideonella azotifigens* | *Janibacter anophelis* | |
| *Gallibacterium* | *Haemophilus aphrophilus* | *Idiomarina* | *Janibacter corallicola* | |
| *Gallibacterium anatis* | *Haemophilus felis* | *Idiomarina abyssalis* | *Janibacter limosus* | |
| *Gallicola* | *Haemophilus gallinarum* | *Idiomarina baltica* | *Janibacter melonis* | |
| *Gallicola barnesae* | *Haemophilus haemolyticus* | *Idiomarina fontislapidosi* | *Janibacter terrae* | |
| *Garciella* | *Haemophilus influenzae* | *Idiomarina loihiensis* | *Jannaschia* | |
| *Garciella nitratireducens* | *Haemophilus paracuniculus* | *Idiomarina ramblicola* | *Jannaschia cystaugens* | |
| *Geobacillus* | *Haemophilus parahaemolyticus* | *Idiomarina seosinensis* | *Jannaschia helgolandensis* | |
| *Geobacillus thermoglucosidasius* | *Haemophilus parainfluenzae* | *Idiomarina zobellii* | *Jannaschia* | |
| *Geobacillus stearothermophilus* | *Haemophilus* | *Ignatzschineria* | *pohangensis* | |
| *Geobacter* | *paraphrohaemolyticus* | *Ignatzschineria* | *Jannaschia rubra* | |
| *Geobacter bemidjiensis* | *Haemophilus parasuis* | *larvae* | *Janthinobacterium* | |
| *Geobacter bremensis* | *Haemophilus pittmaniae* | *Ignavigranum* | *Janthinobacterium* | |
| *Geobacter chapellei* | *Hafnia* | *Ignavigranum ruoffiae* | *agaricidamnosum* | |
| *Geobacter grbiciae* | *Hafnia alvei* | *Ilumatobacter* | *Janthinobacterium lividum* | |
| *Geobacter hydrogenophilus* | *Hahella* | *Ilumatobacter fluminis* | *Jejuia* | |
| *Geobacter lovleyi* | *Hahella ganghwensis* | *Ilyobacter* | *Jejuia pallidilutea* | |
| *Geobacter metallireducens* | *Halalkalibacillus* | *Ilyobacter delafieldii* | *Jeotgalibacillus* | |
| *Geobacter pelophilus* | *Halalkalibacillus halophilus* | *Ilyobacter insuetus* | *Jeotgalibacillus* | |
| *Geobacter pickeringii* | *Helicobacter* | *Ilyobacter polytropus* | *alimentarius* | |
| *Geobacter sulfurreducens* | *Helicobacter pylori* | *Ilyobacter tartaricus* | *Jeotgalicoccus* | |
| *Geodermatophilus* | | | *Jeotgalicoccus halotolerans* | |
| *Geodermatophilus obscurus* | | | | |
| *Gluconacetobacter* | | | | |
| *Gluconacetobacter xylinus* | | | | |
| *Gordonia* | | | | |
| *Gordonia rubripertincta* | | | | |
| *Kaistia* | *Labedella* | *Listeria ivanovii* | *Micrococcus* | *Nesterenkonia* |
| *Kaistia adipata* | *Labedella gwakjiensis* | *L. marthii* | *Micrococcus luteus* | *Nesterenkonia holobia* |
| *Kaistia soli* | *Labrenzia* | *L. monocytogenes* | *Micrococcus lylae* | *Nocardia* |
| *Kangiella* | *Labrenzia aggregata* | *L. newyorkensis* | *Moraxella* | *Nocardia argentinensis* |
| *Kangiella aquimarina* | *Labrenzia alba* | *L. riparia* | *Moraxella bovis* | *Nocardia corallina* |

TABLE 5-continued

Example Bacteria
Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *Kangiella* | *Labrenzia alexandrii* | *L. rocourtiae* | *Moraxella nonliquefaciens* | *Nocardia* |
| *koreensis* | *Labrenzia marina* | *L. seeligeri* | *Moraxella osloensis* | *otitidiscaviarum* |
| *Kerstersia* | *Labrys* | *L. weihenstephanensis* | *Nakamurella* | |
| *Kerstersia gyiorum* | *Labrys methylaminiphilus* | *L. welshimeri* | *Nakamurella multipartita* | |
| *Kiloniella* | *Labrys miyagiensis* | *Listonella* | *Nannocystis* | |
| *Kiloniella laminariae* | *Labrys monachus* | *Listonella anguillarum* | *Nannocystis pusilia* | |
| *Klebsiella* | *Labrys okinawensis* | *Macrococcus* | *Natranaerobius* | |
| *K. gramilomatis* | *Labrys* | *Macrococcus bovicus* | *Natranaerobius* | |
| *K. oxytoca* | *portucalensis* | *Marinobacter* | *thermophilus* | |
| *K. pneumoniae* | *Lactobacillus* | *Marinobacter algicola* | *Natranaerobius trueperi* | |
| *K. terrigena* | [see below] | *Marinobacter bryozoorum* | *Naxibacter* | |
| *K. variicola* | *Laceyella* | *Marinobacter flavimaris* | *Naxibacter alkalitolerans* | |
| *Kluyvera* | *Laceyella putida* | *Meiothermus* | *Neisseria* | |
| *Kluyvera ascorbata* | *Lechevalieria* | *Meiothermus ruber* | *Neisseria cinerea* | |
| *Kocuria* | *Lechevalieria aerocolonigenes* | *Methylophilus* | *Neisseria denitrificans* | |
| *Kocuria roasea* | *Legionella* | *Methylophilus methylotrophus* | *Neisseria gonorrhoeae* | |
| *Kocuria varians* | [see below] | *Microbacterium* | *Neisseria lactamica* | |
| *Kurthia* | *Listeria* | *Microbacterium* | *Neisseria mucosa* | |
| *Kurthia zopfii* | *L. aquatica* | *ammoniaphilum* | *Neisseria sicca* | |
| | *L. booriae* | *Microbacterium arborescens* | *Neisseria subflava* | |
| | *L. cornellensis* | *Microbacterium liquefaciens* | *Neptunomonas* | |
| | *L. fleischmannii* | *Microbacterium oxydans* | *Neptunomonas japonica* | |
| | *L. floridensis* | | | |
| | *L. grandensis* | | | |
| | *L. grayi* | | | |
| | *L. innocua* | | | |
| *Lactobacillus* | | | | |
| *L. acetotolerans* | *L. catenaformis* | *L. mali* | *L. parakefiri* | *L. sakei* |
| *L. acidifarinae* | *L. ceti* | *L. manihotivorans* | *L. paralimentarius* | *L. salivarius* |
| *L. acidipiscis* | *L. coleohominis* | *L. mindensis* | *L. paraplantarum* | *L. sanfranciscensis* |
| *L. acidophilus* | *L. collinoides* | *L. mucosae* | *L. pentosus* | *L. satsumensis* |
| *Lactobacillus agilis* | *L. composti* | *L. murinus* | *L. perolens* | *L. secaliphilus* |
| *L. algidus* | *L. concavus* | *L. nagelii* | *L. plantarum* | *L. sharpeae* |
| *L. alimentarius* | *L. coryniformis* | *L. namurensis* | *L. pontis* | *L. siliginis* |
| *L. amylolyticus* | *L. crispatus* | *L. nantensis* | *L. protectus* | *L. spicheri* |
| *L. amylophilus* | *L. crustorum* | *L. oligofermentans* | *L. psittaci* | *L. suebicus* |
| *L. amylotrophicus* | *L. curvatus* | *L. oris* | *L. rennini* | *L. thailandensis* |
| *L. amylovorus* | *L. delbrueckii* subsp. *bulgaricus* | *L. panis* | *L. reuteri* | *L. ultunensis* |
| *L. animalis* | *L. delbrueckii* subsp. | *L. pantheris* | *L. rhamnosus* | *L. vaccinostercus* |
| *L. antri* | *delbrueckii* | *L. parabrevis* | *L. rimae* | *L. vaginalis* |
| *L. apodemi* | *L. delbrueckii* subsp. *lactis* | *L. parabuchneri* | *L. rogosae* | *L. versmoldensis* |
| *L. aviarius* | *L. dextrinicus* | *L. paracasei* | *L. rossiae* | *L. vini* |
| *L. bifermentans* | *L. diolivorans* | *L. paracollinoides* | *L. ruminis* | *L. vitulinus* |
| *L. brevis* | *L. equi* | *L. parafarraginis* | *L. saerimneri* | *L. zeae* |
| *L. buchneri* | *L. equigenerosi* | *L. homohiochii* | *L. jensenii* | *L. zymae* |
| *L. camelliae* | *L. farraginis* | *L. iners* | *L. johnsonii* | *L. gastricus* |
| *L. casei* | *L. farciminis* | *L. ingluviei* | *L. kalixensis* | *L. ghanensis* |

TABLE 5-continued

Example Bacteria
Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *L. kitasatonis* | *L. fermentum* | *L. intestinalis* | *L. kefiranofaciens* | *L. graminis* |
| *L. kunkeei* | *L. fornicalis* | *L. fuchuensis* | *L. kefiri* | *L. hammesii* |
| *L. leichmannii* | *L. fructivorans* | *L. gallinarum* | *L. kimchii* | *L. hamsteri* |
| *L. lindneri* | *L. frumenti* | *L. gasseri* | *L. helveticus* | *L. harbinensis* |
| *L. malefermentans* | | | *L. hilgardii* | *L. hayakitensis* |
| *Legionella* | | | | |
| *Legionella adelaidensis* | *Legionella drancourtii* | *Candidatus Legionella jeonii* | *Legionella quinlivanii* | |
| *Legionella anisa* | *Legionella dresdenensis* | *Legionella jordanis* | *Legionella rowbothamii* | |
| *Legionella beliardensis* | *Legionella drozanskii* | *Legionella lansingensis* | *Legionella rubrilucens* | |
| *Legionella birminghamensis* | *Legionella dumoffii* | *Legionella londiniensis* | *Legionella sainthelensi* | |
| *Legionella bozemanae* | *Legionella erythra* | *Legionella longbeachae* | *Legionella santicrucis* | |
| *Legionella brunensis* | *Legionella fairfieldensis* | *Legionella lytica* | *Legionella shakespearei* | |
| *Legionella busanensis* | *Legionella fallonii* | *Legionella maceachernii* | *Legionella spiritensis* | |
| *Legionella cardiaca* | *Legionella feeleii* | *Legionella massiliensis* | *Legionella steelei* | |
| *Legionella cherrii* | *Legionella geestiana* | *Legionella micdadei* | *Legionella steigerwaltii* | |
| *Legionella cincinnatiensis* | *Legionella genomospecies* | *Legionella monrovica* | *Legionella taurinensis* | |
| *Legionella clemsonensis* | *Legionella gormanii* | *Legionella moravica* | *Legionella tucsonensis* | |
| *Legionella donaldsonii* | *Legionella gratiana* | *Legionella nagasakiensis* | *Legionella tunisiensis* | |
| | *Legionella gresilensis* | *Legionella nautarum* | *Legionella wadsworthii* | |
| | *Legionella hackeliae* | *Legionella norrlandica* | *Legionella waltersii* | |
| | *Legionella impletisoli* | *Legionella oakridgensis* | *Legionella worsleiensis* | |
| | *Legionella israelensis* | *Legionella parisiensis* | *Legionella yabuuchiae* | |
| | *Legionella jamestowniensis* | *Legionella pittsburghensis* | | |
| | | *Legionella pneumophila* | | |
| | | *Legionella quateirensis* | | |
| *Oceanibulbus* | *Paenibacillus* | *Prevotella* | *Quadrisphaera* | |
| *Oceanibulbus indolifex* | *Paenibacillus thiaminolyticus* | *Prevotella albensis* | *Quadrisphaera* | |
| *Oceanicaulis* | *Pantoea* | *Prevotella amnii* | *granulorum* | |
| *Oceanicaulis alexandrii* | *Pantoea* | *Prevotella bergensis* | *Quatrionicoccus* | |
| *Oceanicola* | *agglomerans* | *Prevotella bivia* | *Quatrionicoccus* | |
| *Oceanicola batsensis* | *Paracoccus* | *Prevotella brevis* | *australiensis* | |
| *Oceanicola granulosus* | *Paracoccus alcaliphilus* | *Prevotella bryantii* | *Quinella* | |
| *Oceanicola nanhaiensis* | *Paucimonas* | *Prevotella buccae* | *Quinella* | |
| *Oceanimonas* | *Paucimonas lemoignei* | *Prevotella buccalis* | *ovalis* | |
| *Oceanimonas baumannii* | *Pectobacterium* | *Prevotella copri* | *Ralstonia* | |
| *Oceaniserpentilla* | *Pectobacterium aroidearum* | *Prevotella dentalis* | *Ralstonia eutropha* | |
| *Oceaniserpentilla haliotis* | *Pectobacterium atrosepticum* | *Prevotella denticola* | *Ralstonia insidiosa* | |
| *Oceanisphaera* | *Pectobacterium betavasculorum* | *Prevotella disiens* | *Ralstonia mannitolilytica* | |
| *Oceanisphaera donghaensis* | *Pectobacterium cacticida* | *Prevotella histicola* | *Ralstonia pickettii* | |
| *Oceanisphaera litoralis* | *Pectobacterium carnegieana* | *Prevotella intermedia* | *Ralstonia* | |
| *Oceanithermus* | *Pectobacterium carotovorum* | *Prevotella maculosa* | *pseudosolanacearum* | |
| *Oceanithermus desulfurans* | *Pectobacterium chrysanthemi* | *Prevotella marshii* | *Ralstonia syzygii* | |
| *Oceanithermus profundus* | *Pectobacterium cypripedii* | *Prevotella melaninogenica* | *Ralstonia solanacearum* | |
| *Oceanobacillus* | *Pectobacterium rhapontici* | *Prevotella micans* | *Ramlibacter* | |
| *Oceanobacillus caeni* | *Pectobacterium wasabiae* | *Prevotella multiformis* | *Ramlibacter henchirensis* | |
| *Oceanospirillum* | *Planococcus* | *Prevotella nigrescens* | *Ramlibacter* | |
| *Oceanospirillum linum* | *Planococcus citreus* | *Prevotella oralis* | *tataouinensis* | |

TABLE 5-continued

Example Bacteria
Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| | *Planomicrobium* | *Prevotella oris* | *Raoultella* | |
| | *Planomicrobium okeanokoites* | *Prevotella oulorum* | *Raoultella ornithinolytica* | |
| | *Plesiomonas* | *Prevotella pallens* | *Raoultella planticola* | |
| | *Plesiomonas shigelloides* | *Prevotella salivae* | *Raoultella terrigena* | |
| | *Proteus* | *Prevotella stercorea* | *Rathayibacter* | |
| | *Proteus vulgaris* | *Prevotella tannerae* | *Rathayibacter caricis* | |
| | | *Prevotella timonensis* | *Rathayibacter festucae* | |
| | | *Prevotella veroralis* | *Rathayibacter iranicus* | |
| | | *Providencia* | *Rathayibacter rathayi* | |
| | | *Providencia stuartii* | *Rathayibacter toxicus* | |
| | | *Pseudomonas* | *Rathayibacter tritici* | |
| | | *Pseudomonas aeruginosa* | *Rhodobacter* | |
| | | *Pseudomonas alcaligenes* | *Rhodobacter sphaeroides* | |
| | | *Pseudomonas anguillispetica* | *Ruegeria* | |
| | | *Pseudomonas fluorescens* | *Ruegeria gelatinovorans* | |
| | | *Pseudoalteromonas* | | |
| | | *haloplanktis* | | |
| | | *Pseudomonas mendocina* | | |
| | | *Pseudomonas* | | |
| | | *pseudoalcaligenes* | | |
| | | *Pseudomonas putida* | | |
| | | *Pseudomonas tutzeri* | | |
| | | *Pseudomonas syringae* | | |
| | | *Psychrobacter* | | |
| | | *Psychrobacter faecalis* | | |
| | | *Psychrobacter* | | |
| | | *phenylpyruvicus* | | |
| *Saccharococcus* | *Sagittula* | *Sanguibacter* | *Stenotrophomonas* | *Tatlockia* |
| *Saccharococcus thermophilus* | *Sagittula stellata* | *Sanguibacter keddieii* | *Stenotrophomonas* | *Tatlockia maceachernii* |
| *Saccharomonospora* | *Salegentibacter* | *Sanguibacter suarezii* | *maltophilia* | *Tatlockia micdadei* |
| *Saccharomonospora azurea* | *Salegentibacter salegens* | *Saprospira* | *Streptococcus* | *Tenacibaculum* |
| *Saccharomonospora cyanea* | *Salimicrobium* | *Saprospira grandis* | [also see below] | *Tenacibaculum* |
| *Saccharomonospora viridis* | *Salimicrobium album* | *Sarcina* | *Streptomyces* | *amylolyticum* |
| *Saccharophagus* | *Salinibacter* | *Sarcina maxima* | *Streptomyces* | *Tenacibaculum discolor* |
| *Saccharophagus degradans* | *Salinibacter ruber* | *Sarcina ventriculi* | *achromogenes* | *Tenacibaculum* |
| *Saccharopolyspora* | *Salinicoccus* | *Sebaldella* | *Streptomyces* | *gallaicum* |
| *Saccharopolyspora erythraea* | *Salinicoccus alkaliphilus* | *Sebaldella* | *cesalbus* | *Tenacibaculum* |
| *Saccharopolyspora gregorii* | *Salinicoccus hispanicus* | *termitidis* | *Streptomyces cescaepitosus* | *lutimaris* |
| *Saccharopolyspora hirsuta* | *Salinicoccus roseus* | *Serratia* | *Streptomyces cesdiastaticus* | *Tenacibaculum* |
| *Saccharopolyspora hordei* | *Salinispora* | *Serratia fonticola* | *Streptomyces cesexfoliatus* | *mesophilum* |
| *Saccharopolyspora rectivirgula* | *Salinispora arenicola* | *Serratia marcescens* | *Streptomyces fimbriatus* | *Tenacibaculum* |
| *Saccharopolyspora spinosa* | *Salinispora tropica* | *Sphaerotilus* | *Streptomyces fradiae* | *skagerrakense* |
| *Saccharopolyspora taberi* | *Salinivibrio* | *Sphaerotilus natans* | *Streptomyces fulvissimus* | *Tepidanaerobacter* |
| *Saccharothrix* | *Salinivibrio costicola* | *Sphingobacterium* | *Streptomyces griseoruber* | *Tepidanaerobacter* |
| *Saccharothrix australiensis* | *Salmonella* | *Sphingobacterium multivorum* | *Streptomyces griseus* | *syntrophicus* |
| *Saccharothrix coeruleofusca* | *Salmonella bongori* | *Staphylococcus* | *Streptomyces lavendulae* | *Tepidibacter* |
| *Saccharothrix espanaensis* | *Salmonella enterica* | [see below] | *Streptomyces* | *Tepidibacter* |

TABLE 5-continued

Example Bacteria
Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *Saccharothrix longispora* | *Salmonella subterranea* | | *phaeochromogenes* | *formicigenes* |
| *Saccharothrix mutabilis* | *Salmonella typhi* | | *Streptomyces* | *Tepidibacter thalassicus* |
| *Saccharothrix syringae* | | | *thermodiastaticus* | *Thermus* |
| *Saccharothrix tangerinus* | | | *Streptomyces tubercidicus* | *Thermus aquaticus* |
| *Saccharothrix texasensis* | | | | *Thermus filiformis* |
| | | | | *Thermus thermophilus* |
| *Staphylococcus* | | | | |
| *S. arlettae* | *S. equorum* | *S. microti* | *S. schleiferi* | |
| *S. agnetis* | *S. felis* | *S. muscae* | *S. sciuri* | |
| *S. aureus* | *S. fleurettii* | *S. nepalensis* | *S. simiae* | |
| *S. auricularis* | *S. gallinarum* | *S. pasteuri* | *S. simulans* | |
| *S. capitis* | *S. haemolyticus* | *S. petrasii* | *S. stepanovicii* | |
| *S. caprae* | *S. hominis* | *S. pettenkoferi* | *S. succinus* | |
| *S. carnosus* | *S. hyicus* | *S. piscifermentans* | *S. vitulinus* | |
| *S. caseolyticus* | *S. intermedius* | *S. pseudintermedius* | *S. warneri* | |
| *S. chromogenes* | *S. kloosii* | *S. pseudolugdunensis* | *S. xylosus* | |
| *S. cohnii* | *S. leei* | *S. pulvereri* | | |
| *S. condimenti* | *S. lentus* | *S. rostri* | | |
| *S. delphini* | *S. lugdunensis* | *S. saccharolyticus* | | |
| *S. devriesei* | *S. lutrae* | *S. saprophyticus* | | |
| *S. epidermidis* | *S. lyticans* | | | |
| | *S. massiliensis* | | | |
| *Streptococcus* | | | | |
| *Streptococcus agalactiae* | *Streptococcus infantarius* | *Streptococcus orisratti* | *Streptococcus thermophilus* | |
| *Streptococcus anginosus* | *Streptococcus iniae* | *Streptococcus parasanguinis* | *Streptococcus sanguinis* | |
| *Streptococcus bovis* | *Streptococcus intermedius* | *Streptococcus peroris* | *Streptococcus sobrinus* | |
| *Streptococcus canis* | *Streptococcus lactarius* | *Streptococcus pneumoniae* | *Streptococcus suis* | |
| *Streptococcus constellatus* | *Streptococcus milleri* | *Streptococcus* | *Streptococcus uberis* | |
| *Streptococcus downei* | *Streptococcus mitis* | *pseudopneumoniae* | *Streptococcus vestibularis* | |
| *Streptococcus dysgalactiae* | *Streptococcus mutans* | *Streptococcus pyogenes* | *Streptococcus viridans* | |
| *Streptococcus equines* | *Streptococcus oralis* | *Streptococcus ratti* | *Streptococcus* | |
| *Streptococcus faecalis* | *Streptococcus tigurinus* | *Streptococcus salivariu* | *zooepidemicus* | |
| *Streptococcus ferus* | | | | |
| *Uliginosibacterium* | *Vagococcus* | *Vibrio* | *Virgibacillus* | *Xanthobacter* |
| *Uliginosibacterium* | *Vagococcus carniphilus* | *Vibrio aerogenes* | *Virgibacillus* | *Xanthobacter agilis* |
| *gangwonense* | *Vagococcus elongatus* | *Vibrio aestuarianus* | *halodenitrificans* | *Xanthobacter* |
| *Ulvibacter* | *Vagococcus fessus* | *Vibrio albensis* | *Virgibacillus* | *aminoxidans* |
| *Ulvibacter litoralis* | *Vagococcus fluvialis* | *Vibrio alginolyticus* | *pantothenticus* | *Xanthobacter* |
| *Umezawaea* | *Vagococcus lutrae* | *Vibrio campbellii* | *Weissella* | *autotrophicus* |
| *Umezawaea tangerina* | *Vagococcus salmoninarum* | *Vibrio cholerae* | *Weissella cibaria* | *Xanthobacter flavus* |
| *Undibacterium* | *Variovorax* | *Vibrio cincinnatiensis* | *Weissella confusa* | *Xanthobacter tagetidis* |
| *Undibacterium pigrum* | *Variovorax boronicumulans* | *Vibrio coralliilyticus* | *Weissella halotolerans* | *Xanthobacter viscosus* |
| *Ureaplasma* | *Variovorax dokdonensis* | *Vibrio cyclitrophicus* | *Weissella hellenica* | *Xanthomonas* |
| *Ureaplasma* | *Variovorax paradoxus* | *Vibrio diazotrophicus* | *Weissella kandleri* | *Xanthomonas* |
| *urealyticum* | *Variovorax soli* | *Vibrio fluvialis* | *Weissella koreensis* | *albilineans* |
| *Ureibacillus* | *Veillonella* | *Vibrio furnissii* | *Weissella minor* | *Xanthomonas alfalfae* |
| *Ureibacillus composti* | *Veillonella atypica* | *Vibrio gazogenes* | *Weissella* | *Xanthomonas* |

TABLE 5-continued

Example Bacteria

Optionally, the carrier cells are selected from this Table and/or the target cells are selected from this Table (eg, wherein the carrier and target cells are of a different species; or of the same species but are a different strain or the carrier cells are engineered but the target cells are wild-type or vice versa). For example the carrier cells are *E coli* cells and the target cells are *C dificile*, *E coli*, *Akkermansia*, *Enterobacteriacea*, *Ruminococcus*,*Faecalibacterium*, *Firmicutes*, *Bacteroidetes*, *Salmonella*, *Klebsiella*, *Pseudomonas*, *Acintenobacter* or *Streptococcus* cells.

| | | | | |
|---|---|---|---|---|
| *Ureibacillus suwonensis* | *Veillonella caviae* | *Vibrio halioticoli* | *paramesenteroides* | *arboricola* |
| *Ureibacillus terrenus* | *Veillonella criceti* | *Vibrio harveyi* | *Weissella soli* | *Xanthomonas* |
| *Ureibacillus thermophilus* | *Veillonella dispar* | *Vibrio ichthyoenteri* | *Weissella thailandensis* | *axonopodis* |
| *Ureibacillus thermosphaericus* | *Veillonella montpellierensis* | *Vibrio mediterranei* | *Weissella viridescens* | *Xanthomonas* |
| | *Veillonella parvula* | *Vibrio metschnikovii* | *Williamsia* | *campestris* |
| | *Veillonella ratti* | *Vibrio mytili* | *Williamsia marianensis* | *Xanthomonas citri* |
| | *Veillonella rodentium* | *Vibrio natriegens* | *Williamsia maris* | *Xanthomonas codiaei* |
| | *Venenivibrio* | *Vibrio navarrensis* | *Williamsia serinedens* | *Xanthomonas* |
| | *Venenivibrio stagnispumantis* | *Vibrio nereis* | *Winogradskyella* | *cucurbitae* |
| | *Verminephrobacter* | *Vibrio nigripulchritudo* | *Winogradskyella* | *Xanthomonas* |
| | *Verminephrobacter eiseniae* | *Vibrio ordalii* | *thalassocola* | *euvesicatoria* |
| | *Verrucomicrobium* | *Vibrio orientalis* | *Wolbachia* | *Xanthomonas fragariae* |
| | *Verrucomicrobium spinosum* | *Vibrio parahaemolyticus* | *Wolbachia persica* | *Xanthomonas fuscans* |
| | | *Vibrio pectenicida* | *Wolinella* | *Xanthomonas gardneri* |
| | | *Vibrio penaeicida* | *Wolinella succinogenes* | *Xanthomonas hortorum* |
| | | *Vibrio proteolyticus* | *Zobellia* | *Xanthomonas hyacinthi* |
| | | *Vibrio shilonii* | *Zobellia galactanivorans* | *Xanthomonas perforans* |
| | | *Vibrio splendidus* | *Zobellia uliginosa* | *Xanthomonas phaseoli* |
| | | *Vibrio tubiashii* | *Zoogloea* | *Xanthomonas pisi* |
| | | *Vibrio vulnificus* | *Zoogloea ramigera* | *Xanthomonas populi* |
| | | | *Zoogloea resiniphila* | *Xanthomonas theicola* |
| | | | | *Xanthomonas* |
| | | | | *translucens* |
| | | | | *Xanthomonas* |
| | | | | *vesicatoria* |
| | | | | *Xylella* |
| | | | | *Xylella fastidiosa* |
| | | | | *Xylophilus* |
| | | | | *Xylophilus ampelinus* |
| *Xenophilus* | *Yangia* | *Yersinia mollaretii* | *Zooshikella* | *Zobellella* |
| *Xenophilus azovorans* | *Yangia pacifica* | *Yersinia philomiragia* | *Zooshikella ganghwensis* | *Zobellella denitrificans* |
| *Xenorhabdus* | *Yaniella* | *Yersinia pestis* | *Zunongwangia* | *Zobellella taiwanensis* |
| *Xenorhabdus beddingii* | *Yaniella flava* | *Yersinia pseudotuberculosis* | *Zunongwangia profunda* | *Zeaxanthinibacter* |
| *Xenorhabdus bovienii* | *Yaniella halotolerans* | *Yersinia rohdei* | *Zymobacter* | *Zeaxanthinibacter* |
| *Xenorhabdus cabanillasii* | *Yeosuana* | *Yersinia ruckeri* | *Zymobacter palmae* | *enoshimensis* |
| *Xenorhabdus doucetiae* | *Yeosuana aromativorans* | *Yokenella* | *Zymomonas* | *Zhihengliuella* |
| *Xenorhabdus griffiniae* | *Yersinia* | *Yokenella regensburgei* | *Zymomonas mobilis* | *Zhihengliuella* |
| *Xenorhabdus hominickii* | *Yersinia aldovae* | *Yonghaparkia* | *Zymophilus* | *halotolerans* |
| *Xenorhabdus koppenhoeferi* | *Yersinia bercovieri* | *Yonghaparkia alkaliphila* | *Zymophilus paucivorans* | *Xylanibacterium* |
| *Xenorhabdus nematophila* | *Yersinia enterocolitica* | *Zavarzinia* | *Zymophilus raffinosivorans* | *Xylanibacterium ulmi* |
| *Xenorhabdus poinarii* | *Yersinia entomophaga* | *Zavarzinia compransoris* | | |
| *Xylanibacter* | *Yersinia frederiksenii* | | | |
| *Xylanibacter oryzae* | *Yersinia intermedia* | | | |
| | *Yersinia kristensenii* | | | |

TABLE 6

| SEQ ID NO: | Sequences: |
| --- | --- |
| 1 | Salcr7-1<br>Sequence written 5' to 3'.<br>Underlined: direct repeat<br>Between direct repeats: spacer region corresponding (in 5' to 3' direction) to selected target sequences<br>TGAAACACGCATTGATTTGAGTCAGCTAGGAGGTGACTGAAGTATATTTTAGATGAAGATTATTTCTTAATAACTAAAAATATGGTATAATACTCTTAATAAATGCAGTAATACAGGGGCTTTTCAAGACTGAAGT<br>CTAGCTGAGACAAATAGTGCGATTACGAAATTTTTTAGACAAAAATAGTCTACGAGGTTTTAGAGCTATGCTGTTTTGAATGGTCCCAAAACCGCTTTGGGTATACGCATTTTGAAGTACGGGTTTTAGAGCTATG<br>CTGTTTTGAATGGTCCCAAAACTGTCAACGGGTGTACTATATGTCTGTCATGGTTTTAGAGCTATGCTGTTTTGAATGGTCCCAAAACGCAAACCAGTACCGAAGAAGAGGCGCTCACGTTTTAGAGCTATGCTGT<br>TTTGAATGGTCCCAAAACTGCCGTTCTGGTCATCCTGCTCGAAGCCGCGTTTTAGAGCTATGCTGTTTTGAATGGTCCCAAAACCCAGAAATGAATCGCCTGGCTTCATTATCGGTTTTAGAGCTATGCTGTTTTG<br>AATGGTCCCAAAACATCAGCAGGAAGCGCTCAAAAACATACTGCGTTTTAGAGCTATGCTGTTTTGAATGGTCCCAAAACAAGTGCGCCTGGTAGTCTTCCGGATAGCGGGTTTTAGAGCTATGCTGTTTTGAATG<br>GACTCCATTCTTCAGCACACTGAGACTTGTTGAGTTCCATGTTTTAGAGCTATGCTGTTTTGAATGGACTCCATTCAACATTGCCGATGATAACTTGAGAAAGAGGGTTAATACCAGCAGTCGGATACCTTCCTAT<br>TCTTTCTGTTAAAGCGTTTTCATGTTATAATAGGCAAAAGAAGAGTAGTGTGAT |
| 2 | Salcr7-2<br>Sequence written 5' to 3'.<br>Underlined: direct repeat<br>Between direct repeats: spacer region corresponding (in 5' to 3' direction) to selected target sequences of pipA, pipB, pipC, hilA, marT, sicP and sopB.<br>TGAAACACGCATTGATTTGAGTCAGCTAGGAGGTGACTGAAGTATATTTTAGATGAAGATTATTTCTTAATAACTAAAAATATGGTATAATACTCTTAATAAATGCAGTAATACAGGGGCTTTTCAAGACTGAAGT<br>CTAGCTGAGACAAATAGTGCGATTACGAAATTTTTTAGACAAAAATAGTCTACGAGGTTTTAGAGCTATGCTGTTTTGAATGGTCCCAAAACTCTTTTTCATATGCGTAATTCATCAGTCTGGTTTTAGAGCTATG<br>CTGTTTTGAATGGTCCCAAAACTATAACCGAGGATGGTTTTCTGAACCTGCGGTTTTAGAGCTATGCTGTTTTGAATGGTCCCAAAACTATTAAATCGTTTATATGACGCGTTAGGCCGTTTTAGAGCTATGCTGT<br>TTTGAATGGTCCCAAAACCACAATAATCCACAAGCTTTAGGATTACTGGTTTTAGAGCTATGCTGTTTTGAATGGTCCCAAAACTCTATTTCCCTTCCAGCAGTCGCACCCCAGGTTTTAGAGCTATGCTGTTTTG<br>AATGGTCCCAAAACTTATCGCCTGTTTGTGGCGATTCTATCTGGGTTTTAGAGCTATGCTGTTTTGAATGGTCCCAAAACTACTCACCGCGTCGAATATTTTCGGCAAAGGTTTTAGAGCTATGCTGTTTTGAATG<br>GACTCCATTCTTCAGCACACTGAGACTTGTTGAGTTCCATGTTTTAGAGCTATGCTGTTTTGAATGGACTCCATTCAACATTGCCGATGATAACTTGAGAAAGAGGGTTAATACCAGCAGTCGGATACCTTCCTAT<br>TCTTTCTGTTAAAGCGTTTTCATGTTATAATAGGCAAAAGAAGAGTAGTGTGAT |
| 3 | Salcr7-3<br>Sequence written 5' to 3'.<br>Underlined: direct repeat<br>Between direct repeats: spacer region corresponding (in 5' to 3' direction) to selected target sequences of pipA, pipB, pipC, hilA, marT, sicP and sopB.<br>TGAAACACGCATTGATTTGAGTCAGCTAGGAGGTGACTGAAGTATATTTTAGATGAAGATTATTTCTTAATAACTAAAAATATGGTATAATACTCTTAATAAATGCAGTAATACAGGGGCTTTTCAAGACTGAAGT<br>CTAGCTGAGACAAATAGTGCGATTACGAAATTTTTTAGACAAAAATAGTCTACGAGGTTTTAGAGCTATGCTGTTTTGAATGGTCCCAAAACCTATTTATTGAAGATGTAGACCATTCTGGGGTTTTAGAGCTATG<br>CTGTTTTGAATGGTCCCAAAACAGAAGCAATGAAAAGTGCAACTTCACCACGGTTTTAGAGCTATGCTGTTTTGAATGGTCCCAAAACATCGCTTGCCGCAAACCAGTACCGAAGAAGGTTTTAGAGCTATGCTGT<br>TTTGAATGGTCCCAAAACTTCGATTGACAGTACTATGGTTTACTTACGGTTTTAGAGCTATGCTGTTTTGAATGGTCCCAAAACATTGATTTGTCAGCAACCTTATAAAACGCGGTTTTAGAGCTATGCTGTTTTG<br>AATGGTCCCAAAACGAAGCAATCTTATAAAAGATATAATTCAAGGTTTTAGAGCTATGCTGTTTTGAATGGTCCCAAAACTAACCTGGAGATTCAGAAACAAAATACGGGGTTTTAGAGCTATGCTGTTTTGAATG<br>GACTCCATTCTTCAGCACACTGAGACTTGTTGAGTTCCATGTTTTAGAGCTATGCTGTTTTGAATGGACTCCATTCAACATTGCCGATGATAACTTGAGAAAGAGGGTTAATACCAGCAGTCGGATACCTTCCTAT<br>TCTTTCTGTTAAAGCGTTTTCATGTTATAATAGGCAAAAGAAGAGTAGTGTGAT |
| 4 | tracrRNA-Cas9 fragment sequence based on pCas9<br>Bold: tracrRNA<br>Underlined: Cas9 coding sequence<br>CGAAATCATCCTGTGGAGCTTAGTAGGTTTAGCAAGATGGCAGCGCCTAAATGTAGAATGATAAAAGGATTAAGAGATTAATTTCCCTAAAAATGATAAAACAAGCGTTTTGAAAGCGCTTTTTTTGGTTTGCAGT<br>CAGAGTAGAATAGAAGTATC**AAAAAAAGCACCGACTCGGTGCCACTTTTTCAAGTTGATAACGGACTAGCCTTATTTTAACTTGCTATGCTGTTTTGAATGGTTCCAACAAGATTATTTTATAACTTTTATAACAAA**<br>**TAATCAAGGAGAAATTCAAAGAAATTTATCAGCCATAAAACAATACTTAATAC**TATAGAATGATAACAAAATAAACTACTTTTTAAAAGAATTTTGTGTTATAATCTATTTATTATTAAGTATTGGGTAATATTTTT |

TABLE 6-continued

| SEQ ID NO: | Sequences: |
|---|---|
| | TGAAGAGATATTTTGAAAAAGAAAAATTAAAGCATATTAAACTAATTTCGGAGGTCATTAAAACTATTATTGAAATCATCAAACTCATTATGGATTTAATTTAAACTTTTTATTTTAGGAGGCAAAAATGGATAAG<br>AAATACTCAATAGGCTTAGATATCGGCACAAATAGCGTCGGATGGGCGGTGATCACTGATGAATATAAGGTTCCGTCTAAAAAGTTCAAGGTTCTGGGAAATACAGACCGCCACAGTATCAAAAAAAATCTTATAG<br>GGGCTCTTTTATTTGACAGTGGAGAGACAGCGGAAGCGACTCGTCTCAAACGGACAGCTCGTAGAAGGTATACACGTCGGAAGAATCGTATTTGTTATCTACAGGAGATTTTTTCAAATGAGATGGCGAAAGTAGA<br>TGATAGTTTCTTTCATCGACTTGAAGAGTCTTTTTTGGTGGAAGAAGACAAGAAGCATGAACGTCATCCTATTTTTGGAAATATAGTAGATGAAGTTGCTTATCATGAGAAATATCCAACTATCTATCATCTGCGA<br>AAAAAATTGGTAGATTCTACTGATAAAGCGGATTTGCGCTTAATCTATTTGGCCTTAGCGCATATGATTAAGTTTCGTGGTCATTTTTTGATTGAGGGAGATTTAAATCCTGATAATAGTGATGTGGACAAACTAT<br>TTATCCAGTTGGTACAAACCTACAATCAATTATTTGAAGAAAACCCTATTAACGCAAGTGGAGTAGATGCTAAAGCGATTCTTTCTGCACGATTGAGTAAATCAAGACGATTAGAAAATCTCATTGCTCAGCTCCC<br>CGGTGAGAAGAAAAATGGCTTATTTGGGAATCTCATTGCTTTGTCATTGGGTTTGACCCCTAATTTTAAATCAAATTTTGATTTGGCAGAAGATGCTAAATTACAGCTTTCAAAAGATACTTACGATGATGATTTA<br>GATAATTTATTGGCGCAAATTGGAGATCAATATGCTGATTTGTTTTTGGCAGCTAAGAATTTATCAGATGCTATTTTACTTTCAGATATCCTAAGAGTAAATACTGAAATAACTAAGGCTCCCCTATCAGCTTCAA<br>TGATTAAACGCTACGATGAACATCATCAAGACTTGACTCTTTTAAAAGCTTTAGTTCGACAACAACTTCCAGAAAAGTATAAAGAAATCTTTTTTGATCAATCAAAAAACGGATATGCAGGTTATATTGATGGGGG<br>AGCTAGCCAAGAAGAATTTTATAAATTTATCAAACCAATTTTAGAAAAAATGGATGGTACTGAGGAATTATTGGTGAAACTAAATCGTGAAGATTTGCTGCGCAAGCAACGGACCTTTGACAACGGCTCTATTCCC<br>CATCAAATTCACTTGGGTGAGCTGCATGCTATTTTGAGAAGACAAGAAGACTTTTATCCATTTTTAAAAGACAATCGTGAGAAGATTGAAAAAATCTTGACTTTTCGAATTCCTTATTATGTTGGTCCATTGGCGC<br>GTGGCAATAGTCGTTTTGCATGGATGACTCGGAAGTCTGAAGAAACAATTACCCCATGGAATTTTGAAGAAGTTGTCGATAAAGGTGCTTCAGCTCAATCATTTATTGAACGCATGACAAACTTTGATAAAAATCT<br>TCCAAATGAAAAAGTACTACCAAAACATAGTTTGCTTTATGAGTATTTTACGGTTTATAACGAATTGACAAAGGTCAAATATGTTACTGAAGGAATGCGAAAACCAGCATTTCTTTCAGGTGAACAGAAGAAAGCC<br>ATTGTTGATTTACTCTTCAAAACAAATCGAAAAGTAACCGTTAAGCAATTAAAAGAAGATTATTTCAAAAAAATAGAATGTTTTGATAGTGTTGAAATTTCAGGAGTTGAAGATAGATTTAATGCTTCATTAGGTA<br>CCTACCATGATTTGCTAAAAATTATTAAAGATAAAGATTTTTTGGATAATGAAGAAAATGAAGATATCTTAGAGGATATTGTTTTAACATTGACCTTATTTGAAGATAGGGAGATGATTGAGGAAAGACTTAAAAC<br>ATATGCTCACCTCTTTGATGATAAGGTGATGAAACAGCTTAAACGTCGCCGTTATACTGGTTGGGGACGTTTGTCTCGAAAATTGATTAATGGTATTAGGGATAAGCAATCTGGCAAAACAATATTAGATTTTTTG<br>AAATCAGATGGTTTTGCCAATCGCAATTTTATGCAGCTGATCCATGATGATAGTTTGACATTTAAAGAAGACATTCAAAAAGCACAAGTGTCTGGACAAGGCGATAGTTTACATGAACATATTGCAAATTTAGCTG<br>GTAGCCCTGCTATTAAAAAAGGTATTTTACAGACTGTAAAAGTTGTTGATGAATTGGTCAAAGTAATGGGGCGGCATAAGCCAGAAAATATCGTTATTGAAATGGCACGTGAAAATCAGACAACTCAAAAGGGCCA<br>GAAAAATTCGCGAGAGCGTATGAAACGAATCGAAGAAGGTATCAAAGAATTAGGAAGTCAGATTCTTAAAGAGCATCCTGTTGAAAATACTCAATTGCAAAATGAAAAGCTCTATCTCTATTATCTCCAAAATGGA<br>AGAGACATGTATGTGGACCAAGAATTAGATATTAATCGTTTAAGTGATTATGATGTCGATCACATTGTTCCACAAAGTTTCCTTAAAGACGATTCAATAGACAATAAGGTCTTAACGCGTTCTGATAAAAATCGTG<br>GTAAATCGGATAACGTTCCAAGTGAAGAAGTAGTCAAAAAGATGAAAAACTATTGGAGACAACTTCTAAACGCCAAGTTAATCACTCAACGTAAGTTTGATAATTTAACGAAAGCTGAACGTGGAGGTTTGAGTGA<br>ACTTGATAAAGCTGGTTTTATCAAACGCCAATTGGTTGAAACTCGCCAAATCACTAAGCATGTGGCACAAATTTTGGATAGTCGCATGAATACTAAATACGATGAAAATGATAAACTTATTCGAGAGGTTAAAGTG<br>ATTACCTTAAAATCTAAATTAGTTTCTGACTTCCGAAAAGATTTCCAATTCTATAAAGTACGTGAGATTAACAATTACCATCATGCCCATGATGCGTATCTAAATGCCGTCGTTGGAACTGCTTTGATTAAGAAAT<br>ATCCAAAACTTGAATCGGAGTTTGTCTATGGTGATTATAAAGTTTATGATGTTCGTAAAATGATTGCTAAGTCTGAGCAAGAAATAGGCAAAGCAACCGCAAAATATTTCTTTTACTCTAATATCATGAACTTCTT<br>CAAAACAGAAATTACACTTGCAAATGGAGAGATTCGCAAACGCCCTCTAATCGAAACTAATGGGGAAACTGGAGAAATTGTCTGGGATAAAGGGCGAGATTTTGCCACAGTGCGCAAAGTATTGTCCATGCCCCAA<br>GTCAATATTGTCAAGAAAACAGAAGTACAGACAGGCGGATTCTCCAAGGAGTCAATTTTACCAAAAAGAAATTCGGACAAGCTTATTGCTCGTAAAAAAGACTGGGATCCAAAAAAATATGGTGGTTTTGATAGTC<br>CAACGGTAGCTTATTCAGTCCTAGTGGTTGCTAAGGTGGAAAAAGGGAAATCGAAGAAGTTAAAATCCGTTAAAGAGTTACTAGGGATCACAATTATGGAAAGAAGTTCCTTTGAAAAAAATCCGATTGACTTTTT<br>AGAAGCTAAAGGATATAAGGAAGTTAAAAAAGACTTAATCATTAAACTACCTAAATATAGTCTTTTTGAGTTAGAAAACGGTCGTAAACGGATGCTGGCTAGTGCCGGAGAATTACAAAAAGGAAATGAGCTGGCT<br>CTGCCAAGCAAATATGTGAATTTTTTATATTTAGCTAGTCATTATGAAAAGTTGAAGGGTAGTCCAGAAGATAACGAACAAAAACAATTGTTTGTGGAGCAGCATAAGCATTATTTAGATGAGATTATTGAGCAAA<br>TCAGTGAATTTTCTAAGCGTGTTATTTTAGCAGATGCCAATTTAGATAAAGTTCTTAGTGCATATAACAAACATAGAGACAAACCAATACGTGAACAAGCAGAAAATATTATTCATTTATTTACGTTGACGAATCT<br>TGGAGCTCCCGCTGCTTTTAAATATTTTGATACAACAATTGATCGTAAACGATATACGTCTACAAAAGAAGTTTTAGATGCCACTCTTATCCATCAATCCATCACTGGTCTTTATGAAACACGCATTGATTTGAGT<br>CAGCTAGGAGGTGACTGA |
| 5 | Salcr3.2 (crRNA-pipC-hilA-marT)<br>Sequence written 5' to 3'.<br>Underlined: direct repeat<br>Between direct repeats: spacer region corresponding (in 5' to 3' direction) to selected target sequences of pipC-hilA-marT<br>TGTCGACGGTATATTTAGATGAAGATTATTTCTTAATAACTAAAAATATGGTATAATACTCTTAATAAATGCAGTAATACAGGGGCTTTTCAAGACTGAAGTCTAGCTGAGACAAATAGTGCGATTACGAAATTT<br>TTTAGACAAAAATAGTCTACGAGGTTTTAGAGCTATGCTGTTTTGAATGGTCCCAAAACATCGCTTGCCGCAAACCAGTACCGAAGAAGGTTTTAGAGCTATGCTGTTTTGAATGGTCCCAAAACTTCGATTGACA<br>GTACTATGGTTTACTTACGGTTTTAGAGCTATGCTGTTTTGAATGGTCCCAAAACATTGATTTGTCAGCAACCTTATAAAACGCGGTTTTAGAGCTATGCTGTTTTGAATGGTCCCAAAACTTCAGCACACTGAGA<br>CTTGTTGAGTTCCATGTTTTAGAGCTATGCTGTTTTGAATGGTCTCCATTCAACATTGCCGATGATAACTTGAGAAAGAGGGTTAATACCAGCAGTCGGATACCTTCCTATTCTTTCTGTTAAAGCGTTTTCATGT<br>TATAATAGGCAAAAGAAGAGTAGTGTGAT |
| 6 | mob (oriT)<br>TTGAGCACCGCCAGGTGCGAATAAGGGACAGTGAAGAAGGAACACCCGCTCGCGGGTGGGCCTACTTCACCTATCCTGCCCGGCTGACGCCGTTGGATACACCAAGGAAAGTCTACACGAA |

TABLE 6-continued

| SEQ ID NO: | Sequences: |
|---|---|
| 7 | pZA31MCS<br>ATCCCATGGTACGCGTGCTAGAGGCATCAAATAAAACGAAAGGCTCAGTCGAAAGACTGGGCCTTTCGTTTTATCTGTTGTTTGTCGGTGAACGCTCTCCTGAGTAGGACAAATCCGCCGCCCTAGACCTAGGGAT<br>ATATTCCGCTTCCTCGCTCACTGACTCGCTACGCTCGGTCGTTCGACTGCGGCGAGCGGAAATGGCTTACGAACGGGGCGGAGATTTCCTGGAAGATGCCAGGAAGATACTTAACAGGGAAGTGAGAGGGCCGCGG<br>CAAAGCCGTTTTTCCATAGGCTCCGCCCCCCTGACAAGCATCACGAAATCTGACGCTCAAATCAGTGGTGGCGAAACCCGACAGGACTATAAAGATACCAGGCGTTTCCCCCTGGCGGCTCCCTCGTGCGCTCTCC<br>TGTTCCTGCCTTTCGGTTTACCGGTGTCATTCCGCTGTTATGGCCGCGTTTGTCTCATTCCACGCCTGACACTCAGTTCCGGGTAGGCAGTTCGCTCCAAGCTGGACTGTATGCACGAACCCCCCGTTCAGTCCGA<br>CCGCTGCGCCTTATCCGGTAACTATCGTCTTGAGTCCAACCCGGAAAGACATGCAAAAGCACCACTGGCAGCAGCCACTGGTAATTGATTTAGAGGAGTTAGTCTTGAAGTCATGCGCCGGTTAAGGCTAAACTGA<br>AAGGACAAGTTTTGGTGACTGCGCTCCTCCAAGCCAGTTACCTCGGTTCAAAGAGTTGGTAGCTCAGAGAACCTTCGAAAAACCGCCCTGCAAGGCGGTTTTTTCGTTTTCAGAGCAAGAGATTACGCGCAGACCA<br>AAACGATCTCAAGAAGATCATCTTATTAATCAGATAAAATATTACTAGATTTCAGTGCAATTTATCTCTTCAAATGTAGCACCTGAAGTCAGCCCCATACGATATAAGTTGTTACTAGTGCTTGGATTCTCACCAA<br>TAAAAAACGCCCGGCGGCAACCGAGCGTTCTGAACAAATCCAGATGGAGTTCTGAGGTCATTACTGGATCTATCAACAGGAGTCCAAGCGAGCTCGATATCAAATTACGCCCCGCCCTGCCACTCATCGCAGTACT<br>GTTGTAATTCATTAAGCATTCTGCCGACATGGAAGCCATCACAGACGGCATGATGAACCTGAATCGCCAGCGGCATCAGCACCTTGTCGCCTTGCGTATAATATTTGCCCATGGTGAAAACGGGGGCGAAGAAGTT<br>GTCCATATTGGCCACGTTTAAATCAAAACTGGTGAAACTCACCCAGGGATTGGCTGAGACGAAAAACATATTCTCAATAAACCCTTTAGGGAAATAGGCCAGGTTTTCACCGTAACACGCCACATCTTGCGAATAT<br>ATGTGTAGAAACTGCCGGAAATCGTCGTGGTATTCACTCCAGAGCGATGAAAACGTTTCAGTTTGCTCATGGAAAACGGTGTAACAAGGGTGAACACTATCCCATATCACCAGCTCACCGTCTTTCATTGCCATAC<br>GAAATTCCGGATGAGCATTCATCAGGCGGGCAAGAATGTGAATAAAGGCCGGATAAAACTTGTGCTTATTTTTCTTTACGGTCTTTAAAAAGGCCGTAATATCCAGCTGAACGGTCTGGTTATAGGTACATTGAGC<br>AACTGACTGAAATGCCTCAAAATGTTCTTTACGATGCCATTGGGATATATCAACGGTGGTATATCCAGTGATTTTTTTCTCCATTTTAGCTTCCTTAGCTCCTGAAAATCTCGATAACTCAAAAAATACGCCCGGT<br>AGTGATCTTATTTCATTATGGTGAAAGTTGGAACCTCTTACGTGCCGATCAACGTCTCATTTTCGCCAGATATCGACGTCTAAGAAACCATTATTATCATGACATTAACCTATAAAAATAGGCGTATCACGAGGCC<br>CTTTCGTCTTCAC |
| 8 | spCas9-6 forward primer<br>ATTGTTTGTGGAGCAGCATAAGC |
| 9 | mob2 reverse primer<br>GCCTCTAGCACGCGTACCATGGGAT |
| 10 | trfA module for genomic insertion DH10B (written 5' to 3')<br>Bracketed sequence: encodes trfA mRNA (complement strand)<br>Capital letters at 5': bi-directional synthetic rho-independent terminator to prevent read-through from the trfA gene as well as upstream gene on the chromosome<br>Lower case letters at 3': J23105 promoter, a weak to intermediate strength promoter (capital T indicates transcription start site)<br>CTTAATAAAAACCCGCTTGGGCAAGCGGGTTTTATTGTGCAATTAGGCC[CTAGCGTTTGCAATGCACCAGGTCATCATTGACCCAGGCGTGTTCCACCAGGCCGCTGCCTCGCAACTCTTCGCAGGCTTCGCCGA<br>CCTGCTCGCGCCACTTCTTCACGCGGGTGGAATCCGATCCGCACATGAGGCGGAAGGTTTCCAGCTTGAGCGGGTACGGCTCCCGGTGCGAGCTGAAATAGTCGAACATCCGTCGGGCCGTCGGCGACAGCTTGCG<br>GTACTTCTCCCATATGAATTTCGTGTAGTGGTCGCCAGCAAACAGCACGACGATTTCCTCGTCGATCAGGACCTGGCAACGGGACGTTTTCTTGCCACGGTCCAGGACGCGGAAGCGGTGCAGCAGCGACACCGAT<br>TCCAGGTGCCCAACGCGGTCGGACGTGAAGTCCATCGCCGTCGCCTGTAGGCGCGACAGGCATTCCTCGGCCTTCGTGTAATACCGGCCATTGATCGACCAGCCCAGGTCCTGGCAAAGCTCGTAGAACGTGAAGG<br>TGATCGGCTCGCCGATAGGGGTGCGCTTCGCGTACTCCAACACCTGCTGCCACACCAGTTCGTCATCGTCGGCCCGCAGCTCGACGCCGGTGTAGGTGATCTTCACGTCCTTGTTGACGTGGAAAATGACCTTGTT<br>TTGCAGCGCCTCGCGCGGGATTTTCTTGTTGCGCGTGGTGAACAGGGCAGAGCGGGCCGTGTCGTTTGGCATCGCTCGCATCGTGTCCGGCCACGGCGCAATATCGAACAAGGAAAGCTGCATTTCCTTGATCTGC<br>TGCTTCGTGTGTTTCAGCAACGCGGCCTGCTTGGCCTCGCTGACCTGTTTTGCCAGGTCCTCGCCGGCGGTTTTTCGCTTCTTGGTCGTCATAGTTCCTCGCGTGTCGATGGTCATCGACTTCGCCAAACCTGCCG<br>CCTCCTGTTCGAGACGACGCGAACGCTCCACGGCGGCCGATGGCGCGGGCAGGGCAGGGGGAGCCAGTTGCACGCTGTCGCGCTCGATCTTGGCCGTAGCTTGCTGGACCATCGAGCCGACGGACTGGAAGGTTTC<br>GCGGGGCGCACGCATGACGGTGCGGCTTGCGATGGTTTCGGCATCCTCGGCGGAAAACCCCGCGTCGATCAGTTCTTGCCTGTATGCCTTCCGGTCAAACGTCCGATTCATTCACCCTCCTTGCGGGATTGCCCCG<br>ACTCACGCCGGGGCAATGTGCCCTT]gTagctagcatagtacctaggactgagctagccgtaaa |
| 11 | aroA coding sequence<br>ATGGAATCCCTGACGTTACAACCCATCGCTCGTGTCGATGGCACTATTAATCTGCCCGGTTCCAAGAGCGTTTCTAACCGCGCTTTATTGCTGGCGGCATTAGCACACGGCAAAACAGTATTAACCAATCTGCTGG<br>ATAGCGATGACGTGCGCCATATGCTGAATGCATTAACAGCGTTAGGGGTAAGCTATACGCTTTCAGCCGATCGTACGCGTTGCGAAATTATCGGTAACGGCGGTCCATTACACGCAGAAGGTGCCCTGGAGTTGTT<br>CCTCGGTAACGCCGGAACGGCAATGCGTCCGCTGGCGGCAGCTCTTTGTCTGGGTAGCAATGATATTGTGCTGACCGGTGAGCCGCGTATGAAAGAACGCCCGATTGGTCATCTGGTGGATGCGCTGCGCCTGGGC<br>GGGGCGAAGATCACTTACCTGGAACAAGAAAATTATCCGCCGTTGCGTTTACAGGGCGGCTTTACTGGCGGCAACGTTGACGTTGATGGCTCCGTTTCCAGCCAATTCCTCACCGCACTGTTAATGACTGCGCCTC<br>TTGCGCCGGAAGATACGGTGATTCGTATTAAAGGCGATCTGGTTTCTAAACCTTATATCGACATCACACTCAATCTGATGAAGACGTTTGGTGTTGAAATTGAAAATCAGCACTATCAACAATTTGTCGTAAAAGG<br>CGGGCAGTCTTATCAGTCTCCGGGTACTTATTTGGTCGAAGGCGATGCATCTTCGGCTTCTTACTTTCTGGCAGCAGCAGCAATCAAAGGCGGCACTGTAAAAGTGACCGGTATTGGACGTAACAGTATGCAGGGT<br>GATATTCGCTTTGCTGATGTGCTGGAAAAAATGGGCGCGACCATTTGCTGGGGCGATGATTATATTTCCTGCACGCGTGGTGAACTGAACGCTATTGATATGGATATGAACCATATTCCTGATGCGGCGATGACCA |

TABLE 6-continued

| SEQ ID NO: | Sequences: |
|---|---|
| | TTGCCACGGCGGCGTTATTTGCAAAAGGCACCACCACGCTGCGCAATATCTATAACTGGCGTGTTAAAGAGACCGATCGCCTGTTTGCGATGGCAACAGAACTGCGTAAAGTCGGCGCGGAAGTGGAAGAGGGGCA<br>CGATTACATTCGTATCACTCCTCCGGAAAAACTGAACTTTGCCGAGATCGCGACATACAATGATCACCGGATGGCGATGTGTTTCTCGCTGGTGGCGTTGTCAGATACACCAGTGACGATTCTTGATCCCAAATGC<br>ACGGCCAAAACATTTCCGGATTATTTCGAGCAGCTGGCGCGGATTAGCCAGGCAGCCTGA |
| 12 | oriV RK2<br>Tgacacttgaggggcgtttagagcgagccaggaaagccgacccccctccttggagtaaaaacccttgcggcgttgcagccggcacggatcttccgatcgggcgcggtggtggccgcgtctgtgacctaaaaaggg<br>gggagtccagaggggcgcagcccctttgggcatagcgcagcgtaatcggagacgtaattgagcatttccaggcgcttgcgcctggtcaacgaaagagtcagcgccgtaggcgctgccattttttggggtgaggccg<br>ttcgcggccgaggggcgcagcccctgggggggatgggaggcccgcgttagcgggccgggagggttcgagaagggggggcacccccccttcggcgtgcgcggtcacgcgccagggcgcagccctggttaaaaa<br>caaggtttataaatattggtttaaaagcaggttaaaagacaggttagcggtggccgaaaaacgggcggaaacccttgcaaatgctggattttctgcctgtggacagcccctcaaatgtcaataggtgcgcccctcatctg<br>tcatcactctgcccctcaagtgtcaaggatcgcgcccctcatctgtcagtagtcgcgcccctcaagtgtcaataccgcagggcacttatccccaggcttgtccacatcatctgtgggaaactcgcgtaaaatcaggcgtt<br>ttcgccgatttgcgaggctggccagctccacgtcgccggccgaaatcgagcctgcccctcatctgtcaacgccgcgccgggtgagtcggcccctcaagtgtcaacgtccgcccctcatctgtcagtgagggccaag<br>ttttccgcgtggtatccacaacgccggcggccgcggtgtctcgcacacggcttcgacggcgtttctggcgcgtttgcagggccatagacggccgccagcccagcggcgagggcaaccagcccggtgagcgtcgg<br>aaaggcgctggaagccccgtagcgacgcggagaggggcgagacaagccaagggcgcaggctcgatgcgcagcacgacatagccggttctcgcaaggacgagaatttccctgcggtgcccctcaagtgtcaa |
| 13 | tra2 module trbB-L RK2<br>ttgcaggctaaacactttcggtatatcgtttgcctgtgcgataatgttgctaatgatttgttgcgtaggggttactgaaaagtgagcgggaaagaagagtttcagaccatcaaggagcgggccaagcgcaagctggaac<br>gcgacatgggtgcggacctgttggccgcgctcaacgacccgaaaaccgttgaagtcatgctcaacgcggacggcaaggtgtggcacgaacgccttggcgagccgatgcggtacatctgcgacatgcggcccag<br>ccagtcgcaggcgattatagaaacggtggccggattccacggcaaagaggtcacgcggcattcgcccatcctggaaggcgagttccccttggatggcagccgctttgccggccaattgccgccggtcgtggccgc<br>gccaacctttgcgatccgcaagcgcgcggtcgccatcttcacgctggaacagtacgtcgaggcgggcatcatgacccgcgagcaatacgaggtcattaaaagcgccgtcgcggcgcatcgaaacatcctcgtcatt<br>ggcggtactggctcgggcaagaccacgctcgtcaacgcgatcatcaatgaaatggtcgccttcaacccgtctgagcgcgtcgtcatcatcgaggacaccggcgaaatccagtgcgccgcagagaacgccgtccaa<br>taccacaccagcatcgacgtctcgatgacgctgctgctcaagacaacgctgcgtatgcgccccgaccgcatcctggtcggtgaggtacgtggccccgaagcccttgatctgttgatggcctggaacaccgggcatg<br>aaggaggtgccgccaccctgcacgcaaacaaccccaaagcgggcctgagccggctcgccatgcttatcagcatgcacccggattcaccgaaacccattgagccgctgattggcgaggcggttcatgtggtcgtcc<br>atatcgccaggacccctagcggccgtcgagtgcaagaaattctcgaagttcttggttacgagaacggccagtacatcaccaaaaccctgtaaggagtatttccaatgacaacggctgttccgttccgtctgaccatgaa<br>tcgcggcattttgttctaccttgccgtgttcttcgttctcgctctcgcgttatccgcgcatccggcgatggcctcggaaggcaccggcggcagcttgccatatgagagctggctgacgaacctgcgcaactccgtaaccg<br>gcccggtggccttcgcgctgtccatcatcggcatcgtcgtcgccggcggcgtgctgatcttcggcggcgaactcaacgccttcttccgaaccctgatcttcctggttctggtgatggcgctgctggtcggcgcgcaga<br>acgtgatgagcaccttcttcggtcgtggtgccgaaatcgcggccctcggcaacggggcgctgcaccaggtgcaagtcgcggcggcggatgccgtgcgtgcggtagcggctggacggctcgcctaatcatggctc<br>tgcgcacgatccccatccgtcgcgcaggcaaccgagaaaacctgttcatgggtggtgatcgtgaactggtgatgttctcgggcctgatggcgtttgcgctgattttcagcgcccaagagctgcgggccaccgtggtc<br>ggtctgatcctgtggttcggggcgctctatgcgttccgaatcatggcgaaggccgatccgaagatgcggttcgtgtacctgcgtcaccgccggtacaagccgtattacccggcccgctcgaccccgttccgcgagaa<br>caccaatagccaagggaagcaataccgatgatccaagcaattgcgattgcaatcgcgggcctcggcgcgcttctgttgttcatcctctttgcccgcatccgcgcggtcgatgccgaactgaaactgaaaaagcatcgt<br>tccaaggacgccggcctggccgatctgctcaactacgccgctgtcgtcgatgacggcgtaatcgtgggcaagaacggcagctttatggctgcctggctgtacaagggcgatgacaacgcaagcagcaccgacca<br>gcagcgcgaagtagtgtccgcccgcatcaaccaggccctcgcgggcctgggaagtgggtggatgatccatgtggacgccgtgcggcgtcctgctccgaactacgcggagcggggcctgtcggcgttccctgac<br>cgtctgacggcagcgattgaagaagagcgccggcggcatttcgagagcctgggaacgatgtacgagggctatttcgtcctcaccttgacctggttcccgccgctgctcgcccagcgcaagttcgtcgagctgatgttt<br>gacgacgacgcgaccgcaccggatcgcaaggcgcgcacgcggggcctcatcgaccaattcaagcgtgacgtgcgcagcatcgagtcgcgcctgtcgtcggccgtgtcgctcactcgcttgaaggggcacaaga<br>tcgtcaacgaggacggcacgaccgtcacgcatgacgacttcctgcgctggctgcaattctgcgtgacgggcctgcaccatccggtgcagctccccagcaacccgatgtacctggacgccctggtcggcggacagg<br>aaatgtggggcggggtagtgcccaaggtcggccgcaagttcgtccaggtggtcgctctcgaaggcttccccttggagtcctatcccggcatcctgacggcgctcggcgagctgccctgcgagtatcggtggtcgag<br>ccggttcatcttcatggaccagcacgaagccgtgaagcacctcgacaagttccgcaagaagtggcggcagaagattcgcggcttcttcgaccaggtgttcaacacgaacaccggcccggtcgatcaggacgcgctt<br>tcgatggtggccgatgctgaggcggccattgccgaagtcaacagcggcatcgtggccgtgggctactacaccagcgtcgtcgtgctgatggatgaggaccgcacgcgcctggaagctgcggcccgcgatgttga<br>aaaggccgtcaaccggttgggctttgccgcgcgcatcgagtccatcaacaccctggacgccttccttggtagtttgccgggccacggcgtggaaaacgtccgccggccgctcatcaacacgatgaacctggccgac<br>ctgctgccgaccagcaccatctggaccggcaacgcgaacgcgccatgcccgatgtacccgccgctgtcgccggcgctcatgcactgcgtcacgcaaggatcaacgccgttccggctgaacctgcacgtgcgcga<br>cctcggccacacctttatgttcgggccgaccggcgcaggtaaatcgacgcacctggcgatcctcgccgcgcagctccgtcgctatgccggcatgtcgatcttcgcctttgacaagggcatgtcgatgtacccgctgg<br>ccgccggcatccgtgcggccacgaagggcaccagcggcctgcacttcaccgtggcggccgacgacgaacgcctggcgttctgcccgttgcagttcctgagcaccaagggcgaccgtgcttgggcgatggagtg<br>gatcgacaccatcctggcgttgaacggcgtcgaaacgaccccggcccagcgcaacgaaatcggcaacgcgatcatgagcatgcacgccagcggcgcgcgcacgctctccgagttcagcgtgacgattcaggat<br>gaggcgatccgcgaggcgatccgccagtacaccgtcgatggcgcaatgggccatctgctcgacgccgaagaggacggcttggcgctgtccgactttacagtgttcgagatcgaagagctgatgaacctcggcga<br>gaaattcgccctgcctgtgttgctctacctgttccgccgtatcgagcgcgccctgacgggccagccggccgtcatcatcctggacgaagcctggttgatgctcggccacccggcattccgcgcgaagatcagggaat<br>ggctcaaggtgctgcgtaaggccaactgccttgtgctgatggcaacgcagagcctgtccgacgccgccaacagcggcatcctggacgtgatcgtggaatcgaccgcgaccaagattttcctgccgaatatttacgcc<br>agggatgaggacacggcggccctgtaccgccgcatgggcctgaacgctcgccagatcgagattctggcccaggccgttcccaagcgtcagtactactacgtgtcggaaaacggccgccgtctctacgacctggca<br>cttggcccgctcgcgctcgcgttcgtcggcgcatccgacaaggaatccgtcgccatcatcaagaacctggaagccaagttcggcgaccagtgggtggatgaatggctgcgtggccggggcctcgcccttgatgaat |

TABLE 6-continued

| SEQ ID NO: | Sequences: |
|---|---|
| | acctggaggcagcatgagttttgcagacacgatcaagggcttgatcttcaagaagaagcccgcaacggccgcagcagcggcgacgccggccgcgaccggcccgcaaaccgacaacccgtacctgacggcgcg<br>gcgcacctggaacgaccacgttggttccgttgtgtcgcaaaagcagacctggcaggttgtcggcatcctttcgctgatgatcgtcctcgcggcggtcggcggcatcatccacatcggcagccagtcgaagttcgtgc<br>cctatgtctacgaggtagacaagctcgggcagacggccgccgtggggccgatgaccagggcgtcgaaagccgatccgcgtgtcattcacgcctcggtggctgagttcgtcggcgatgctcgcctggtgacgccg<br>gacgtagctttgcagcgcaaggccgtctaccgcctctatgccaagctcgggccgaatgacccggccaccgccaagatgaacgaatggctcaacggcaccgccgacgccagcccgttcgctcgcgcggccgtcg<br>aaacggtcagcaccgaaatcacttccgtaatcccgcagacgcccgacacctggcaggtcgattgggtcgagacgacgcgcgacaggcaaggcgtggtgaaaggccagcccgtgcgcatgcgggccttggtgac<br>ggtctacgtcgtcgagccgacggcggacaccaaggaagaacaactgcgaaacaacccggccgggatctacgtccgggacttctcctggtcgagacttctgtgaggcactgaattatgaaaaaggaactgtttgcttt<br>ggtcctggccgcgtccgttagcgtgcctgcatttgccgccgatcccggcgcggacctgactgacctctatttttccggcaagaacccggagctgaccgcgcaagagcgggcggccatcgccatcgccaagaagtg<br>ggaggcgggtaccgccggcatgcggccggtggccggccccggtggttcggtgcgcttcctgttcggcgcgcagcagccgagcatcgtatgcgccgtgctgcaagtgtgcgacgtggccctgcaacccggcga<br>gcaagtcaactcgatcaacctgggcgacaccgcccgttggacggtcgagccggccattaccggcagcggcgcgaacgaaacccagcacctcatcatcaagccgatggatgtgggcctggaaaccagcctggtc<br>gtgaccacggaccgccgcagctaccacatgcgcctgcgctcgcatcgcacgcagtacatgccgcaggtgtcgttcacctacccggaagatgcccttgcgaagtgggacgccatcaagaaccgcgaacagcggg<br>atcgcgtcgagaaaaccattccgcagaccggcgagtacctgggcaacctgagcttcaactactccgtcagcgggtccacgtcgtggaagccggtgcgcgtctacaacgacggcaagaaaaccatcatccagatgc<br>cgcactcgatggaacagaccgaagcgccgacgctcctggtcgttcgcagggagggcggcctgttctccgacgatgaaacggtgatggtcaactaccgggtccagggcgaccgctacatcgtcgatacgattttcg<br>acaaggccatcctcatcgcgggcgtgggcagcagccaggaccgcgtgaccatttcaaggggggaactaaaccatgcgtaagattctgaccgtcatcgcactcgcggccacgttggccggctgcgcgacctccaagt<br>acggcagcttcgtccaggacgcgccggccgcctacaaccagaccattgcgaccgacgcggtgaagcagctcgtcaagctctacccgccggcgcaaaccaagctggaattgcagcaggctacgcccgatccgttc<br>ggcattgccctggtcactgaccttcgcgcccagggctatgctgtcatggagtacaagcccgacggcaacgcggccgcagctccggctgctgcgtcctcggccgctgcgaagccggcaacgccgcaagcccagg<br>gcggctatccgctgcgctacgtgctggaccaattcagcgacagcaacctgtatcgcctgaccgtcatggtcggctctcaatcgctcacgcgcgcctacctcgcccaaaacaacacgatggtcccggccggcgcatg<br>ggttcggaaggagtaagccaatgagcgaagatcaaatggcaccggacgcatcgccagatgcggtcaagccgaaaagcggggttcgccgcgtcaacaacatgccgatgtacctcatcggcggtgtgctcggcatc<br>ttcctgctggtgatggccctggttgctgcggatcgcgctgcgcagcagaaccagccgggagctgcgaaggctgagaaggccggcagcaccagcatgtttgccgacgaaattgccggcaaacagcaggacggca<br>tcatcaaggccaagccgctggagattccgccggaacaaaccgcccagcaaccgacgacggagctgacgccagccccggcgcagggaacgactatcacggtcgcacggcccgagaacctggaccagccccc<br>gacgccgccgcagggtgcgcgcaacgaggacctggaccgcatccgcatggcgaagttgcagatgctggaagaggcgatcaaggccaagacgacggtgcgcatcgacgcgccgcgcagccagggcagcgc<br>cggcggcggtgctccgcagggccgcgaggaaacccttgcgcgcatccaggagctgcgtcggcaggctgagaacgcccgcgccaccgatccgaccgccgcctatcaggccgcgcttgcgcaggctcgcacga<br>tgggcggcgcggcaggggggtggcggtatgggcggctcgggtgcgccgaccctcgtgcagacctcgaaccgcagtggtggcggcgctggctatgggtcgttcgacaaccgcagcgagggcgaccgttggcgg<br>ctcgactcccagccggaagcacctgcaacgccctatgtgctgcgcgctggcttcgtcgttccggctacgcttatctcgggcatcaactccgatctgccaggccaaatcatggcccaggtatcgcagtcggtgtacgac<br>acggcgaccggcaagcacatgctcatcccccaaggctcgcgcctggtgggcagctactcgaacgatgtggcctacgggcagaagcgcgttctggtggcatggcagcgcatcatcttccccgacggcaaggcaat<br>ggacattggggccatgccgggcggcgatagcgctgggtatgcaggcttcaacgacaaggtcaacaaccactacttccgcaccttcgcatcggcattcctcatgtcgggcgtcgttgcgggcatcagcttgagtcag<br>gaccgtggcaacagcaacagcggttacggacgacaagacgcgggttccgcgatgagtgaagcgttgggtcaacagctcggccaagtaacggcgcagatgatcgccaaaaacttgaatatcgcgccgacgctgg<br>aaatccgtccgggctatcgcttcaacgtcattgtcacgaaagacatgacgttttctaagccctaccaggcgtttgactattaactccaaggagtaacttatgaagaagctcgctaagaatgttttagccgctaaagtag<br>ctctggtgctggccctctcggtcggcaccttggcggtcacgcctgcgcaagcgggcattccggtcatcgacggcaccaacctgtcacaaaccactgtcaccgcgattcagcaggttgcgcaggtccagaagcaaatcga<br>ggaataccggacgcagttgcagcagtacgaaaacatgctgcaaaacacggtggccccggccgcctacgtgtgggaccaggcgcagtccaccatcaacggcctgatgagcgccgttgataccctgaactactaca<br>agaaccaggcgggcagcatcgacgcttacctgggcaagttcaaggacgtgtcctactacaaggggtcgccgtgcttctccctgtcgggctgctcggaaagcgagcgcaaggcgatggaagagaaccgccgcctg<br>gcgtccgaatcgcagaaaaaggccaacgatgcgctgttccgtggcctcgatcagcagcagagcaacctcaagtccgacgccgccacgctggagcaattgaagggcaaggcgacgacggcgcagggccagttg<br>gaagccctcggctacgccaaccagttcgccagccagcaggccaaccagctcatgcaaatccgtggccttctgcttgcgcagcagaacgccatcgccacgcagatgcaggcccagcaggaccggcaggcccagc<br>aggacgctgcgggcgcgaagctgcgcgagggttcgtaccgcgcaagcccgtctaagacctggtgaggggaggcgcgatgaagaaatccaacttcatcgcagttgccgcgctggccgccgtcatggcggccag<br>cctggcaggctgcgacaacaagcccgacaccgacaagctgacctgcgccgatctgccgaaggtcacggatgccgctcaacgcgcggagctgttgaagaagtgcccgcgcggagaaccgggaggcttcaagcc<br>cagcgaaaagaaagagtggtgatgacgtatgaaaatccagactagagctgccgcgctcgcggtcctgatgctggccttgatgccggtagcggcatacgcccaaatcgacaattcgggcatcctcgacaacgtattg<br>cagcgctaccagaacgccgcgagcggctgggccactgtcgtccagaacgccgcaacctggctgttctggaccttgaccgtgattagcatggtctggaccttcggcatgatggcactgcgcaaggccgacattggc<br>gagttcttcgccgagttcgtgcggttcaccatcttcaccggcttcttctggtggctgctgaccaacggcccgaatttcgcgtcgtccatctatgcgtccctgcggcagattgcaggccaggcaacggggttggggcagg<br>ggctttcgccgtccggcatcgtcgatgttggcttcgagattttcttcaaggtgatggacgaaacctcgtactggtcgccggtcgatagcttcgtcggtgcctcgttggcggccgccatcctctgcatcctggccctggtcg<br>gcgtgaatatgcttctgctcctggcgtccggatggattcttgcctacggcggtgtgttcttcctgggcttcggcggctcgcgctggacctcggacatggcgatcaactactacaagaccgtcctcggggtcgccgcgca<br>gctcttcgcaatggtgctgctcgtaggcatcggcaagaccttcctcgatgactactacagccgcatgagcgaaggcatcaacttcaaggaacttggagtgatgctgatcgtcggcctgatcctgctcgttctggtcaaca<br>aggtgccgcagctcatcgccggcatcatcaccggcgcgagcgtcggcggtgctggtatcggccagttcggcgctggcacgctcgtcggtgcggccgcgacggccggcgcggcaatcgcaactggcggcgcat<br>ctatcgcggccggcgctgcggcggcggccggtggcgcgcaggccatcatggcggccgcgtcgaaggccagcgataacgtctctgccggcactgacattctgtcgagcatgatgggcggcggcggtggcggcg<br>gcggtggtagcgccggcaccagcggcggcgacggcggcggctcgggtggcggcggtggctcgggcggcggtgaaaccccgatggcctcggccgccggcgacaacagcagcggcgcacgcggcggcagt<br>tcgggcggcggctcgggtggtggccgttcgtctggcggtatcggtgccacggcggccaagggcggccggatcgcggccgataccgtcgccaacctggcgaaaggtgccggctcgattgccaaggccaaggcc<br>ggcgaaatgcgcgcatcggcccaggaacgcatcggcgataccgtaggcggcaagatcgcgcaggcaattcgcggcgcgggtgcggcggcgcagaccgctgcaaccgtcgccgatagcaacagccaggcgc<br>aggaacaacctgcaccggcacccgcaccgtcgttcgacgacaacagcctttccgcaagcaacaacagggaagcggccgccgacgcggattccgaagtggcgagcttcgtcaacaagcccgcccaatcctga |

TABLE 6-continued

| SEQ ID NO: | Sequences: |
| --- | --- |
| 14 | tra1 module traFG-traJXIH-traKLM RK2<br>tcaccaggtcagaaccggcctgatgacggtgatgatttgcgaacgattgacaggcccgaagtagcggccgtcgaaagacgtgtcgcttacgtcggacataagcagaacctcggcggtccccagggtgtagctgtc<br>ggactgataacgaggcagcggccgtcctgatggatcggccttgatgagcgcgctgtgaggcagcagcccgccattcacgcgcacgccggcgtcggtgatggcaacctcgtcgcctttagcggctaaaactcgctt<br>catcatgtagccgtagtcgccggggcagaaaccgccggcgatgtagccccgctccttggcgtccgaaaacacgccgacttgcggcgggcagaacatgacgtaagccccccttctccaccggcgcattcgatttcca<br>gtacaggccgaccggaatgcttttggtggtgttgaccttcgcgccggcgagataggccgcgccggcgagcaacaaggccgcgccgcctccgatggcgacgtacttggtgaggcgctggaagcggctcatatcgt<br>gatcccctccccttcctcgacggtggccgtctggatcagcttgtcgctgaccttcggagccggtacggccgcgcgggcctggaatatcgggtctttgaagtagagcggctgcttgccgtagatcgcgggatagccgg<br>cgacgtacacaaccatgtcgcccgcctcttcaatgctgccgtcggcgctcttcttcggccccggcatgcgcaggcattcatcggggggtcagcaatggccgctgcacttcctggaaggtccgcgagacgttgcccaac<br>agcgccgacgtgcggcggccgctcgtcgtgatctgctccttcacgatggtcgtggtgcctgtcagttttgacaggtgctcggccgtctccacgcggttcggcgggtaggcgttctgcacgtggcagttcgacgtgatg<br>ctttcgtcgtggccgtagccggtttcgcggctcttgagctggttaatgtcctggcagatgaggtagcacttgatgccgtagccggcgacgaaggcaagggactcttgcaggatttcgagcttgcccaggctggggaac<br>tcgtcgagcatcatcagcagacgatgcttgtagtgcgcgacaggacggccgttctcgaagtccatcttgtcggccagcagccggacgatcatgttgaccatgacgcgcaccagaggccgcagacgggccttgtcgt<br>tgggctgcgtcacgatgaacaggcttaccgggtcgtcgtggtgcatcagttgcttgatgcggaagtcggacttgctgacgttgcgggccacaaccgggtcgcggtacagggccaggtaggacttggcggtggaca<br>gcacggaaccggattcttcctccgggcggtccatcatgtcgcgggccgcagagccgaccgcagggtggttctgcccgtcaacgtggccgtaggtggtcatttccatccaaagctcgcccacgtcgcggttcgggtc<br>ggcaagcatgccgtccaccgacggcagggtggccggcgtaccctcgttcttagccttgtagagcgcgtgcaggatgacgccgacaagcagcgcctggctggttttctgccagtgcgattccaggcccttgccgtcc<br>ggatcgacgatcagggtggcaaggttctgcacgtcgccaacctcgtactcggtccccaagcggatttcatcgagcgggttccagcacgcgctaccctgcgcggatgccggctcaaagcgcacgaccttgttgcgg<br>gcatgcttcttccgccagccggcggtcagcgcccacaactcgcctttcaggtcggtgatgacggcgctgtgcgcccaggaaagcagcgtcggaacgaccaggccgacgcccttgccggagcgcgtcggcgcgt<br>aggtcaagacgtgctcggggccgttgtgccgcaggtagtggaacttgccgtccttgtcctgccagccgcccacatagacgccgctggaagtgggcgggtgtttgcctgacaccagctcgacgacggtgcgcggcc<br>ggggcagcaggccggcggcctgtatgtccttcttgtcggcccagcgggccgaaccgtgcagatagtcgttcgccttgccggtgttcgccttgaccatctgcgtgacggccgtgcccagcaggcccacggtcgaaa<br>cgaccatacccatgctggccgcgcgcatgaaatcgtcgggatattggccgtaccacttgccggcccattgaaggatcgaccagggcgtgtagacgtggttgatattccagccaagtccggcctgatactggaagga<br>atgggcgaaatattgcgtcgcggtctgcaagcctgccccaagggacaggccggcgaggatgggaacggtcttgctggccttcggtttttttcgcccgtatctgtggccccacggcgttgtttcggttcttcatctactcct<br>acctcgggtagttttaagggagcctcgcggggtcacggtgacgggatcaccgatggcgaggcgcttcatgcgttgcaccgtggccttatcgacgggcagcaccagaatctcgtcgttttctttcctcaacagggcca<br>gcgcctggtcctcgacgttccgggtgcctgcataggacagcgcaccaacataatcagtatatcgtgcatgcttcggtatatcgaagccgtttagccgcttttgctcgcgctcggcaacatatttctcggccgccgcgatc<br>tgttcgggctttagccctcttcctggcccagaaactccccgtcgcagtgcgtgagctggttcggctccttgctgctccacgtgaccaggaacatcacgcggcaatagcatttcagctccgccggcgatgcgaaccaca<br>ccgagttgggacagcgctcgcaaacggttttggctttggggcggcggctttcgtccaatgcgtccaacgttgggcttgcggagtgcgacggttccgccggcgctgacggcgcgagcgtcccgtcggtcgccgtcg<br>ccgcctgtggcgttgagggtggttctggctgcggcaggtcgaatgcctccatcgccgccgcgatctcttcgtccgtcatttcgttcgggttgctcatgtgcttgctccttcgtcagtagttcttgacggcggcgctcaagg<br>gcggcgtcgtcaaaggtgattgccagacggccagcggcggccgcctgcgcgatccgctccttgaactctgctgtgccgttgacggtgatccggtcgccgaagcgctccattgccaggcgcagggcggcgtccag<br>gccgtccgtggtggcctcgcgcgagacttgcaggcggtcgccgtcgtcgcggacggcgctgctgccgacgcgatagatgatggttcccttcttcgtgatgttgtccgtcacggccgcatggcccggcttggcctcg<br>ccgctgccctggatggtgttgcccttgaggtcgctgcggccctcgcgtgcgcgcagcgcggccagggccttgtcgtcgcccttcatcgcctcggccttgagccagtcggcccacgcgcggcgctgcgtgcgctcct<br>ggaccgcctgacggccctgccggtactcgcggttgatcttgtccaggtcggcgcgcagagccttgtgcgcctgcgcgtacatcagtcgctttgcaatgcgcccctcgcccagcagcttgatagcggcgcggcgca<br>gccggttgctgcgcatcgcggcttcaatcaggcggtcacgacgccggcgcagcgtgtccagctcgcccttgcgcacggcccccatttcctggcgttcagactgataccgggcgtatagctcggtggtgtcgatgcg<br>ggtcttgagcggcttcgctcgatactcccgccgccggggggcttcgccgccctcggctggcgtgaatgccccgaatcgggcttcgagcttcggcttggacaggtcgcgcgaaacggtgctggccttgaccgtcgtg<br>ccgtcgccggcctcgaagatgaagccgtttccgcgctcgcgcagcttaagcccgttttcccgcaggacgcggtgcaggtcctcccaggattgcgccgcttgcagctccggcaggcattcgcgcttgatccagccga<br>ccaggctttccacgcccgcgtgccgctccatgtcgttcgcgcggttctcggaaacgcgctgccgcgtttcgtgattgtcacgctcaagcccgtagtcccgttcgagcgtcgcgcagaggtcagcgagggcgcggta<br>ggcccgatacggctcatggatggtgtttcgggtcgggtgaatcttgttgatggcgatatggatgtgcaggttgtcggtgtcgtgatgcacggcactgacgcgctgatgctcggcgaagccaagcccagcgcagatgc<br>ggtcctcaatcgcgcgcaacgtctccgcgtcgggcttctctcccgcgcggaagctaaccagcaggtgataggtcttgtcggcctcggaacgggtgttgccgtgctgggtcgccatcacctcggccatgacagcggg<br>cagggtgtttgcctcgcagttcgtgacgcgcacgtgacccaggcgctcggtcttgccttgctcgtcggtgatgtacttcaccagctccgcgaagtcgctcttcttgatggagcgcatggggacgtgcttggcaatcacg<br>cgcacccccggccgttttagcggctaaaaaagtcatggctctgccctcgggcggaccacgcccatcatgaccttgccaagctcgtcctgcttctcttcgatcttcgccagcagggcgaggatcgtggcatcaccgaa<br>ccgcgccgtgcgcgggtcgtcggtgagccagagtttcagcaggccgcccaggcggcccaggtcgccattgatgcgggccagctcgcggacgtgctcatagtccacgacgcccgtgattttgtagccctggccga<br>cggccagcaggtaggccgacaggctcatgccggccgccgccgccttttcctcaatcgctcttcgttcgtctggaaggcagtacaccttgataggtgggctgcccttcctggttggcttggtttcatcagccatccgcttg<br>ccctcatctgttacgccggcggtagccggccagcctcgcagagcaggattcccgttgagcaccgccaggtgcgaataagggacagtgaagaaggaacacccgctcgcgggtgggcctacttcacctatcctgccc<br>ggctgacgccgttggatacaccaaggaaagtctacacgaaccctttggcaaaatcctgtatatcgtgcgaaaaaggatggatataccgaaaaaatcgctataatgaccccgaagcagggttatgcagcggaaaagc<br>gctgcttccctgctgttttgtggaatatctaccgactggaaacaggcaaatgcaggaaattactgaactgaggggacaggcgagagacgatgccaaagagctacaccgacgagctggccgagtgggttgaatcccg<br>cgcggccaagaagcgccggcgtgatgaggctgcggttgcgttcctggcggtgagggcggatgtcgaggcggcgttagcgtccggctatgcgctcgtcaccatttgggagcacatgcgggaaacggggaaggtc<br>aagttctcctacgagacgttccgctcgcacgccaggcggcacatcaaggccaagcccgccgatgtgcccgcaccgcaggccaaggctgcggaacccgcgccggcacccaagacgccggagccacggcggcc<br>gaagcaggggggcaaggctgaaaagccggcccccgctgcggccccgaccggcttcaccttcaacccaacaccggacaaaaaggatctactgtaatggcgaaaattcacatggttttgcagggcaagggcgggg<br>tcggcaagtcggccatcgccgcgatcattgcgcagtacaagatggacaaggggcagacacccttgtgcatcgacaccgacccggtgaacgcgacgttcgagggctacaaggccctgaacgtccgccggctgaa<br>catcatggccggcgacgaaattaactcgcgcaacttcgacaccctggtcgagctgattgcgccgaccaaggatgacgtggtgatcgacaacggtgccagctcgttcgtgcctctgtcgcattacctcatcagcaacca<br>ggtgccggctctgctgcaagaaatggggcatgagctggtcatccataccgtcgtcaccggcggccaggctctcctggacacggtgagcggcttcgcccagctcgccagccagttcccggccgaagcgcttttcgtg |

TABLE 6-continued

| SEQ ID NO: | Sequences: |
|---|---|
| | gtctggctgaacccgtattgggggcctatcgagcatgagggcaagagctttgagcagatgaaggcgtacacggccaacaaggcccgcgtgtcgtccatcatccagattccggccctcaaggaagaaacctacggc<br>cgcgatttcagcgacatgctgcaagagcggctgacgttcgaccaggcgctggccgatgaatcgctcacgatcatgacgcggcaacgcctcaagatcgtgcggcgcggcctgtttgaacagctcgacgcggcggc<br>cgtgctatgagcgaccagattgaagagctgatccgggagattgcggccaagcacggcatcgccgtcggccgcgacgacccggtgctgatcctgcataccatcaacgcccggctcatggccgacagtgcggccaa<br>gcaagaggaaatccttgccgcgttcaaggaagagctggaagggatcgcccatcgttggggcgaggacgccaaggccaaagcggagcggatgctgaacgcggccctggcggccagcaaggacgcaatggcg<br>aaggtaatgaaggacagcgccgcgcaggcggccgaagcgatccgcagggaaatcgacgacggccttggccgccagctcgcggccaaggtcgcggacgcgcggcgcgtggcgatgatgaacatgatcgccg<br>gcggcatggtgttgttcgcggccgccctggtggtgtgggcctcgttatgaatcgcagaggcgcagatgaaaaagcccggcgttgccgggcttgttttt |
| 15 | Sal-crRNA Array 1 (522bp)<br>TTTGAAAACAAAGAATTAGCTGATCTTTAATAATAAGGAAA*TGTTACATT*AAGGTTGGTGGGTTGTTTTTATGGGAAAAAATGCTTTAAGAACAAATGTATACTTTTAGAGAGTTCCCCGCGCCAGCGGGGATAAACCG<br>**GCTTTAAGCGTTAGCTCCCCATTCTGCTCCCC**GAGTTCCCCGCGCCAGCGGGGATAAACCG**GTACGTTAGCGTATATTGATGCCGCAGAGACG**GAGTTCCCCGCGCCAGCGGGGATAAACCG**GCGATAACTGGACAG**<br>**TTTTATCCGCCGAGCAT**GAGTTCCCCGCGCCAGCGGGGATAAACCGGGCGCACTGGATGCGATGATGGATATCACTTGGAGTTCCCCCGCCTCTGCGGTAGAACTCCCAGCTCCCATTTTCAAACCCATCAAGACGCC<br>TTCGCCAACTCCTTCACCAGAGGTAGCATTATCCGCATAACGTCACGGCAGCGACGTTCTATTCTTCCAGGAAGAGCCTTATCAATATGTTGGTGATTATCCAGTCTT |
| 16 | Repeat Sequence<br>GAGTTCCCCGCGCCAGCGGGGATAAACCG |
| 17 | Spacer Sequence for targeting the *Salmonella* invB gene<br>GCTTTAAGCGTTAGCTCCCCATTCTGCTCCCC |
| 18 | Spacer Sequence for targeting the *Salmonella* sicP gene<br>GTACGTTAGCGTATATTGATGCCGCAGAGACG |
| 19 | Spacer Sequence for targeting the *Salmonella* seeE gene<br>GCGATAACTGGACAGTTTTATCCGCCGAGCAT |
| 20 | invB from *Salmonella enterica* subsp. *enterica* serovar Typhimurium str. LT2; spacer sequence in bold<br>atgcaacatttggatatcgctgaattagttcgttccgcactggaagtaagtggttgcgatccttcattaattggaggaatagatagccattcaacaattgttctggatttatttgcattgccaagtatctgtat<br>cagcgtcaaggacgatgatgtatggatctgggcgcaattgggtgctgacagcatggtggtattacaacagcgggcttatgaaatcttaatgaccataatggaaggatgccattttgcccgcggcggg<br>caattactactg**ggggagcagaatggggagctaacgcttaaagc***ctt*agtgcatccggatttttttatctgacggtgaaaagttctctactgccttgaatgggttttacaactatctggaagtttttagtc<br>ggtcgctaatgagatga |
| 21 | sicP from *Salmonella enterica* subsp. *enterica* serovar Typhimurium str. LT2; spacer sequence in bold<br>ttgcaagcacaccaggatattatcgctaatattggtgagaaattgggtttaccgctcacttttgacgacaacaatcagtgcttattattactcgatagcgatatttttacgtctattgaagctaaagatgatat<br>ctggttattgaacggtatgattataccgttatcgcctgtttgtggcgattctatctggcggcagattatggtgattaatggtgaactggctgcgaataatgaaggtacgttagcgtatattgatgccgca<br>**gagacg**ttgttgatatacatgcaattaccgatagacaaatacttaccatattatatcgcagcttgagtcatttgtgaatcagcaggaagcgctcaaaaacatactgcaggaatatgctaaagtatga |
| 22 | seeE from *Salmonella enterica* subsp. *enterica* serovar Typhimurium str. LT2; spacer sequence in bold<br>atggtgcaagaaatagagcaatggttacgtcggcatcaggtgtttactgagcctgcatatttaggggagaccgccatattacttgggcagcagtttatattatcgccttacctggtgatctatcgtattga<br>ggcaaaagaaatgattatttgtgagttcaggcgcctgacgcccgggcaacctcgaccacagcaattgtttcacttactgggacttttacgcgggatatttgtgcatcacccgcagttaacatgtttaaag<br>atgttgataatcaccgacgttctggatgaaaaaaaagccatgctacgcaggaaattattgcgcatcctgacagtaatgggagcgacctttacacagcttg*atg***gcgataactggacagttttatccg**<br>**ccgagcat**cttatccagcgacgtttttaa |

TABLE 7

Function and origin of each genetic element of the pFS-Sal-09-proAB-rm plasmid containing a Type I CRISPR/Cas system.

| Component | Location | Size (bp) | Origin | Function |
|---|---|---|---|---|
| J23114 promoter | 1-29 | 29 | Synthetic promoter | Initiates transcription of Cas3 and Cas3 cascade |
| Cas3 cascade (casABCDE) | 105-4455 | 4351 | *E. coli* K12 | Recruits Cas3 and recognition of PAM |
| Cas3 | 4472-7138 | 2667 | *E. coli* K12 | Nuclease activity; cleavage of DNA |
| Promoter-crRNA array | 7182-7210 | 29 | *E. coli* K12 | Initiates transcription of pre-crRNA array to mature crRNA array |
| invB-cr4 | 7278-7309 | 32 | Synthetic sequence | Spacer sequence of guide RNA. Binds to the complementary target DNA sequence of invB gene in *Salmonella enterica* |
| sicP-cr1 | 7339-7370 | 32 | Synthetic sequence | Spacer sequence of guide RNA. Binds to the complementary target DNA sequence of sicP gene in *Salmonella enterica* |
| sseE-cr2 | 7400-7431 | 32 | Synthetic sequence | Spacer sequence of guide RNA. Binds to the complementary target DNA sequence of sseE gene in *Salmonella enterica* |
| oriT | 7661-7781 | 121 | RP4 plasmid | Origin of transfer. Transfer of CRISPR/CAS3 system to recipient |
| rrnB T1 terminator | 7809-7895 | 87 | *E. coli* rrnB gene | Transcription termination |
| p15A ori | 8064-8609 | 546 | pZA31MCS vector | Plasmid replication |
| Lambda T0 terminator | 8723-8817 | 95 | Phage lambda | Transcription termination |
| proA | 8837-10090 | 1254 | *E. coli* K12 | Proline biosynthesis |
| proB | 10102-11205 | 1104 | *E. coli* K12 | Proline biosynthesis |
| proAB promoter | 11250-11278 | 29 | *E. coli* K12 | Initiates transcription of proAB |

TABLE 8

Conjugation results in JM109. Conjugation from S17-1::pFS-EcoCas3-01-rm, S17-1::pFS-Sal-09-rm, S17-1::pFS-EcoCas3-03-rm and S17-1::pFS-Sal-08-rm, in *E. coli* JM109 strain showed a comparable efficiency between the two constructs and the respective control plasmids. Conjugation efficiency is calculated dividing the number (CFU/mL) of transconjugants by the number of recipients.

| Donor | Recipient | CFU/mL | Conjugation Efficiency |
|---|---|---|---|
| S17-1::pFS-EcoCas3-01-rm | JM109 | 1.2 × 107 | 1.4 × 10−2 |
| S17-1::pFS-Sal-09-rm | JM109 | 7.0 × 106 | 7.4 × 10−3 |

TABLE 8-continued

Conjugation results in JM109. Conjugation from S17-1::pFS-EcoCas3-01-rm, S17-1::pFS-Sal-09-rm, S17-1::pFS-EcoCas3-03-rm and S17-1::pFS-Sal-08-rm, in *E. coli* JM109 strain showed a comparable efficiency between the two constructs and the respective control plasmids. Conjugation efficiency is calculated dividing the number (CFU/mL) of transconjugants by the number of recipients.

| Donor | Recipient | CFU/mL | Conjugation Efficiency |
|---|---|---|---|
| S17-1::pFS-EcoCas3-03-rm | JM109 | 8.1 × 106 | 3.4 × 10−2 |
| S17-1::pFS-Sal-08-rm | JM109 | 1.5 × 107 | 2.9 × 10−2 |

TABLE 9

Conjugation results in FS26. Conjugation from S17-1::pFS-EcoCas3-01-rm, S17-1::pFS-Sal-09-rm, S17-1::pFS-EcoCas3-03-rm and S17-1::pFS-Sal-08-rm in *S. Enteritidis* strain FS26 were carried out in two biological replicates. Results showed significant reduction in *S. Enteritidis* strain FS26 by conjugation with the active constructs, when compared to the respective control plasmids. Conjugation efficiency is calculated dividing the number (CFU/mL) of transconjugants by the number of recipients.

| Replicate | Donor | Recipient | Transconjugants (CFU/mL) | Conjugation Efficiency |
|---|---|---|---|---|
| 1st | S17-1::pFS-EcoCas3-01-rm | FS26 | 7.6 × 106 | 1.2 × 10−2 |
| | S17-1::pFS-Sal-09-rm | FS26 | 7.0 × 102 | 2.7 × 10−6 |

TABLE 9-continued

Conjugation results in FS26. Conjugation from S17-1::pFS-EcoCas3-01-rm, S17-1::pFS-Sal-09-rm, S17-1::pFS-EcoCas3-03-rm and S17-1::pFS-Sal-08-rm in *S. Enteritidis* strain FS26 were carried out in two biological replicates. Results showed significant reduction in *S. Enteritidis* strain FS26 by conjugation with the active constructs, when compared to the respective control plasmids. Conjugation efficiency is calculated dividing the number (CFU/mL) of transconjugants by the number of recipients.

| Replicate | Donor | Recipient | Transconjugants (CFU/mL) | Conjugation Efficiency |
|---|---|---|---|---|
| 2nd | S17-1::pFS-EcoCas3-01-rm | FS26 | 1.3 × 107 | 1.0 × 10−2 |
| | S17-1::pFS-Sal-09-rm | FS26 | 1.0 × 103 | 1.2 × 10−6 |
| 1st | S17-1::pFS-EcoCas3-03-rm | FS26 | 3.0 × 106 | 1.0 × 10−2 |
| | S17-1::pFS-Sal-08-rm | FS26 | 3.7 × 102 | 2.7 × 10−6 |
| 2nd | S17-1::pFS-EcoCas3-03-rm | FS26 | 1.0 × 107 | 2.9 × 10−2 |
| | S17-1::pFS-Sal-08-rm | FS26 | 2.0 × 103 | 5.6 × 10−6 |

TABLE 10

Selected spacer conservation in *Salmonella*

| Spacer | PAM | # hits in *S. enterica* | conservation level in *Salmonella* 100 | ≥95 | ≥90 | <90 | non-*Salmonella* hits |
|---|---|---|---|---|---|---|---|
| invB | AAG | 10613 | 96 | 2 | 2 | | 23 |
| sicP | AAG | 10610 | 74.5 | 20.7 | 4.7 | <1 | 46 |
| sseE | ATG | 10604 | 68.1 | 30 | 1.9 | | 52 |

TABLE 11

| Age (days) | Under lamp (° C.) | Ambient temperature in room (° C.) | Relative humidity (%) |
|---|---|---|---|
| Up to 1 | 35 | 25-30 | 60-80 |
| 1-7 | 32 | 22-27 | 60-80 |
| 7-14 | 29 | 19-25 | 40-80 |

TABLE 11-continued

| Age (days) | Under lamp (° C.) | Ambient temperature in room (° C.) | Relative humidity (%) |
|---|---|---|---|
| 14-21 | 26 | 18-25 | 40-80 |
| 21-28 | 24 | 18-25 | 40-80 |
| 28-35 | — | 18-25 | 40-80 |
| Over 35 | — | 15-25 | 40-80 |

TABLE 12

Plating protocol

| Plating for *Salmonella* | Enrichment for *Salmonella* |
|---|---|
| XLD + Nalidixic acid (25 µg/mL) | Selenite broth, Plate onto XLD + Nalidixic acid (25 µg/mL) |
| Direct counts - *Salmonella* | Enriched counts - *Salmonella* |

The invention claimed is:

1. A method for enhancing feed conversion rate in a chicken, wherein the method comprises:

(a) orally administering to the chicken a plurality of carrier cells, wherein the carrier cells are *E. coli* S17, wherein the chicken comprises target bacterial cells, wherein the target bacterial cells comprise *Salmonella enterica* cells, wherein each carrier cell is a bacterial cell comprising a first episomal DNA encoding an antibacterial agent, wherein the antibacterial agent comprises a guide RNA or crRNA and a Cas nuclease of a CRISPR/Cas system, and wherein the first DNA is transferred from the carrier cells into the target cells by conjugative transfer of the first DNA into the target cell for expression therein of the agent; and (b) performing husbandry of the chicken, thereby killing target cells in the chicken and enhancing feed conversion rate of the chicken as compared to a chicken not administered with the plurality of bacterial carrier cells and having the target bacterial cells.

2. The method of claim 1, wherein the target bacterial cells comprise a plurality of different *S. enterica* subspecies *enterica* serovars.

3. The method of claim 1, wherein the target bacterial cells are located in the gastrointestinal tract of the chicken.

4. The method of claim 1, wherein the first episomal DNA is comprised by a plasmid, and wherein the plasmid comprises a RP4 origin of transfer (oriT) and/or a p15A origin of replication.

5. The method of claim 1, wherein the CRISPR/Cas system is operable to cut at least 3 different protospacer sequences comprised by the genome of the target bacterial cells.

6. The method of claim 5, wherein each or some of said at least 3 different protospacer sequences is comprised by a pathogenicity island that is comprised by the target bacterial cell.

7. The method of claim 1, wherein the first episomal DNA is comprised by a plasmid, and wherein the plasmid is selected from the group consisting of an IncFI, IncFII, IncFIII, IncFIV, IncFV, IncM, Inc9, IncIO, Incl, IncA, IncB, IncC, IncH, IncIa, IncIIc, IncI2, IncIy, IncJ, IncL, IncN, Inc2e, IncO, IncP, IncS, IncT and IncW plasmid.

8. The method of claim 1, wherein:

(a) the protospacer sequence comprises one or more pathogenic island nucleotide sequences of the genome of the target bacterial cells;

(b) the protospacer sequence comprises one or more invasion gene sequences of the genome of the target bacterial cells;

(c) the protospacer sequence comprises one or more secretion system gene sequences of the genome of the target bacterial cells; and/or (d) the protospacer sequence comprises one or more nucleotide sequences of a gene selected from the group consisting of avrA, sptP, sicP, sipA, sipD, sipC, sipB, sicA, invB, ssaE, sseA, sseB, sscA, sseC, sseD, sseE, sscB, sseF, sseG, mgtC, cigR, pipA, pipB, pipC, sopB and pipD.

9. The method of claim 8, wherein the first episomal DNA is comprised by a plasmid which comprises an origin of transfer (oriT) and an origin of replication that is operable for replication of the first episomal DNA in the target bacterial cells.

10. The method of claim 8, wherein the first episomal DNA comprises SEQ ID NO: 15.

11. The method of claim 8, wherein the first episomal DNA comprises CRISPR repeat and spacer sequences, wherein (a) the repeat sequences each comprise SEQ ID NO: 16; and/or (b) the spacer sequences comprise one, two, or three sequences selected from the group consisting of SEQ ID NOs: 17-19 and complement sequences thereof.

12. The method of claim 11, wherein the first episomal DNA comprises SEQ ID NO: 17, SEQ ID NO: 18, and SEQ ID NO: 19.

* * * * *

SEQUENCE LISTING

<160> NUMBER OF SEQ ID NOS: 22

<210> SEQ ID NO 1
<211> LENGTH: 870
<212> TYPE: DNA
<213> ORGANISM: Artificial Sequence
<220> FEATURE:
<223> OTHER INFORMATION: Synthetic Construct

<400> SEQUENCE: 1
tgaaacacgc attgatttga gtcagctagg aggtgactga agtatatttt agatgaagat 60
tatttcttaa taactaaaaa tatggtataa tactcttaat aaatgcagta atacaggggc 120
ttttcaagac tgaagtctag ctgagacaaa tagtgcgatt acgaaatttt ttagacaaaa 180
atagtctacg aggttttaga gctatgctgt tttgaatggt cccaaaaccg ctttgggtat 240
acgcattttg aagtacgggt tttagagcta tgctgttttg aatggtccca aaactgtcaa 300
cgggtgtact atatgtctgt catggtttta gagctatgct gttttgaatg gtcccaaaac 360
gcaaaccagt accgaagaag aggcgctcac gttttagagc tatgctgttt tgaatggtcc 420
caaaactgcc gttctggtca tcctgctcga agccgcgttt tagagctatg ctgttttgaa 480
tggtcccaaa acccagaaat gaatcgcctg gcttcattat cggttttaga gctatgctgt 540
tttgaatggt cccaaaacat cagcaggaag cgctcaaaaa catactgcgt tttagagcta 600

-continued tgctgttttg aatggtccca aaacaagtgc gcctggtagt cttccggata gcgggtttta 660
gagctatgct gttttgaatg gactccattc ttcagcacac tgagacttgt tgagttccat 720
gttttagagc tatgctgttt tgaatggact ccattcaaca ttgccgatga taacttgaga 780
aagagggtta ataccagcag tcggatacct tcctattctt tctgttaaag cgttttcatg 840
ttataatagg caaaagaaga gtagtgtgat 870

<210> SEQ ID NO 2
<211> LENGTH: 870
<212> TYPE: DNA
<213> ORGANISM: Artificial Sequence
<220> FEATURE:
<223> OTHER INFORMATION: Synthetic Construct

<400> SEQUENCE: 2
tgaaacacgc attgatttga gtcagctagg aggtgactga agtatatttt agatgaagat 60
tatttcttaa taactaaaaa tatggtataa tactcttaat aaatgcagta atacaggggc 120
ttttcaagac tgaagtctag ctgagacaaa tagtgcgatt acgaaatttt ttagacaaaa 180
atagtctacg aggttttaga gctatgctgt tttgaatggt cccaaaactc tttttcatat 240
gcgtaattca tcagtctggt tttagagcta tgctgttttg aatggtccca aaactataac 300
cgaggatggt tttctgaacc tgcggtttta gagctatgct gttttgaatg gtcccaaaac 360
tattaaatcg tttatatgac gcgttaggcc gttttagagc tatgctgttt tgaatggtcc 420
caaaaccaca ataatccaca agctttagga ttactggttt tagagctatg ctgttttgaa 480
tggtcccaaa actctatttc ccttccagca gtcgcacccc aggttttaga gctatgctgt 540
tttgaatggt cccaaaactt atcgcctgtt tgtggcgatt ctatctgggt tttagagcta 600
tgctgttttg aatggtccca aaactactca ccgcgtcgaa tattttcggc aaaggtttta 660
gagctatgct gttttgaatg gactccattc ttcagcacac tgagacttgt tgagttccat 720
gttttagagc tatgctgttt tgaatggact ccattcaaca ttgccgatga taacttgaga 780
aagagggtta ataccagcag tcggatacct tcctattctt tctgttaaag cgttttcatg 840
ttataatagg caaaagaaga gtagtgtgat 870

<210> SEQ ID NO 3
<211> LENGTH: 870
<212> TYPE: DNA
<213> ORGANISM: Artificial Sequence
<220> FEATURE:
<223> OTHER INFORMATION: Synthetic Construct

<400> SEQUENCE: 3
tgaaacacgc attgatttga gtcagctagg aggtgactga agtatatttt agatgaagat 60
tatttcttaa taactaaaaa tatggtataa tactcttaat aaatgcagta atacaggggc 120
ttttcaagac tgaagtctag ctgagacaaa tagtgcgatt acgaaatttt ttagacaaaa 180
atagtctacg aggttttaga gctatgctgt tttgaatggt cccaaaacct atttattgaa 240
gatgtagacc attctggggt tttagagcta tgctgttttg aatggtccca aaacagaagc 300
aatgaaaagt gcaacttcac cacggtttta gagctatgct gttttgaatg gtcccaaaac 360
atcgcttgcc gcaaaccagt accgaagaag gttttagagc tatgctgttt tgaatggtcc 420
caaaacttcg attgacagta ctatggttta cttacggttt tagagctatg ctgttttgaa 480
tggtcccaaa acattgattt gtcagcaacc ttataaaacg cggttttaga gctatgctgt 540

-continued

```
tttgaatggt cccaaaacga agcaatctta taaaagatat aattcaaggt tttagagcta    600

tgctgttttg aatggtccca aaactaacct ggagattcag aaacaaaata cggggtttta    660

gagctatgct gttttgaatg gactccattc ttcagcacac tgagacttgt tgagttccat    720

gttttagagc tatgctgttt tgaatggact ccattcaaca ttgccgatga taacttgaga    780

aagagggtta ataccagcag tcggatacct tcctattctt tctgttaaag cgttttcatg    840

ttataatagg caaaagaaga gtagtgtgat                                     870
```

<210> SEQ ID NO 4
<211> LENGTH: 4647
<212> TYPE: DNA
<213> ORGANISM: Artificial Sequence
<220> FEATURE:
<223> OTHER INFORMATION: Synthetic Construct

<400> SEQUENCE: 4

```
cgaaatcatc ctgtggagct tagtaggttt agcaagatgg cagcgcctaa atgtagaatg     60

ataaaaggat taagagatta atttccctaa aaatgataaa acaagcgttt tgaaagcgct    120

tgtttttttg gtttgcagtc agagtagaat agaagtatca aaaaaagcac cgactcggtg    180

ccactttttc aagttgataa cggactagcc ttattttaac ttgctatgct gttttgaatg    240

gttccaacaa gattatttta taacttttat aacaaataat caaggagaaa ttcaaagaaa    300

tttatcagcc ataaaacaat acttaatact atagaatgat aacaaaataa actacttttt    360

aaaagaattt tgtgttataa tctatttatt attaagtatt gggtaatatt ttttgaagag    420

atattttgaa aaagaaaaat taaagcatat taaactaatt tcggaggtca ttaaaactat    480

tattgaaatc atcaaactca ttatggattt aatttaaact ttttatttta ggaggcaaaa    540

atggataaga aatactcaat aggcttagat atcggcacaa atagcgtcgg atgggcggtg    600

atcactgatg aatataaggt tccgtctaaa aagttcaagg ttctgggaaa tacagaccgc    660

cacagtatca aaaaaaatct tataggggct cttttatttg acagtggaga gacagcggaa    720

gcgactcgtc tcaaacggac agctcgtaga aggtatacac gtcggaagaa tcgtatttgt    780

tatctacagg agatttttc aaatgagatg gcgaaagtag atgatagttt ctttcatcga     840

cttgaagagt ctttttggt ggaagaagac aagaagcatg aacgtcatcc tatttttgga     900

aatatagtag atgaagttgc ttatcatgag aaatatccaa ctatctatca tctgcgaaaa    960

aaattggtag attctactga taaagcggat ttgcgcttaa tctatttggc cttagcgcat   1020

atgattaagt ttcgtggtca tttttgatt gagggagatt taaatcctga taatagtgat    1080

gtggacaaac tatttatcca gttggtacaa acctacaatc aattatttga agaaaaccct   1140

attaacgcaa gtggagtaga tgctaaagcg attctttctg cacgattgag taaatcaaga   1200

cgattagaaa atctcattgc tcagctcccc ggtgagaaga aaaatggctt atttgggaat   1260

ctcattgctt tgtcattggg tttgacccct aattttaaat caaattttga tttggcagaa   1320

gatgctaaat tacagctttc aaaagatact tacgatgatg atttagataa tttattggcg   1380

caaattggag atcaatatgc tgatttgttt ttggcagcta agaatttatc agatgctatt   1440

ttactttcag atatcctaag agtaaatact gaaataacta aggctcccct atcagcttca   1500

atgattaaac gctacgatga acatcatcaa gacttgactc ttttaaaagc tttagttcga   1560

caacaacttc cagaaaagta taaagaaatc tttttgatc aatcaaaaaa cggatatgca     1620

ggttatattg atgggggagc tagccaagaa gaattttata aatttatcaa accaatttta   1680

gaaaaaatgg atggtactga ggaattattg gtgaaactaa atcgtgaaga tttgctgcgc   1740
```

```
aagcaacgga cctttgacaa cggctctatt ccccatcaaa ttcacttggg tgagctgcat   1800
gctattttga gaagacaaga agacttttat ccatttttaa aagacaatcg tgagaagatt   1860
gaaaaaatct tgacttttcg aattccttat tatgttggtc cattggcgcg tggcaatagt   1920
cgttttgcat ggatgactcg gaagtctgaa gaaacaatta ccccatggaa ttttgaagaa   1980
gttgtcgata aaggtgcttc agctcaatca tttattgaac gcatgacaaa ctttgataaa   2040
aatcttccaa atgaaaaagt actaccaaaa catagtttgc tttatgagta ttttacggtt   2100
tataacgaat tgacaaaggt caaatatgtt actgaaggaa tgcgaaaacc agcatttctt   2160
tcaggtgaac agaagaaagc cattgttgat ttactcttca aaacaaatcg aaaagtaacc   2220
gttaagcaat taaaagaaga ttatttcaaa aaaatagaat gttttgatag tgttgaaatt   2280
tcaggagttg aagatagatt taatgcttca ttaggtacct accatgattt gctaaaaatt   2340
attaaagata aagatttttt ggataatgaa gaaaatgaag atatcttaga ggatattgtt   2400
ttaacattga ccttatttga agatagggag atgattgagg aaagacttaa aacatatgct   2460
cacctctttg atgataaggt gatgaaacag cttaaacgtc gccgttatac tggttgggga   2520
cgtttgtctc gaaaattgat taatggtatt agggataagc aatctggcaa aacaatatta   2580
gatttttga aatcagatgg ttttgccaat cgcaatttta tgcagctgat ccatgatgat   2640
agtttgacat ttaaagaaga cattcaaaaa gcacaagtgt ctggacaagg cgatagttta   2700
catgaacata ttgcaaattt agctggtagc cctgctatta aaaaaggtat tttacagact   2760
gtaaaagttg ttgatgaatt ggtcaaagta atggggcggc ataagccaga aaatatcgtt   2820
attgaaatgg cacgtgaaaa tcagacaact caaaagggcc agaaaaattc gcgagagcgt   2880
atgaaacgaa tcgaagaagg tatcaaagaa ttaggaagtc agattcttaa agagcatcct   2940
gttgaaaata ctcaattgca aaatgaaaag ctctatctct attatctcca aaatggaaga   3000
gacatgtatg tggaccaaga attagatatt aatcgtttaa gtgattatga tgtcgatcac   3060
attgttccac aaagtttcct taaagacgat tcaatagaca ataaggtctt aacgcgttct   3120
gataaaaatc gtggtaaatc ggataacgtt ccaagtgaag aagtagtcaa aaagatgaaa   3180
aactattgga gacaacttct aaacgccaag ttaatcactc aacgtaagtt tgataattta   3240
acgaaagctg aacgtggagg tttgagtgaa cttgataaag ctggttttat caaacgccaa   3300
ttggttgaaa ctcgccaaat cactaagcat gtggcacaaa ttttggatag tcgcatgaat   3360
actaaatacg atgaaaatga taaacttatt cgagaggtta aagtgattac cttaaaatct   3420
aaattagttt ctgacttccg aaaagatttc caattctata aagtacgtga gattaacaat   3480
taccatcatg cccatgatgc gtatctaaat gccgtcgttg gaactgcttt gattaagaaa   3540
tatccaaaac ttgaatcgga gtttgtctat ggtgattata aagtttatga tgttcgtaaa   3600
atgattgcta agtctgagca agaaataggc aaagcaaccg caaaatattt cttttactct   3660
aatatcatga acttcttcaa aacagaaatt acacttgcaa atggagagat tcgcaaacgc   3720
cctctaatcg aaactaatgg ggaaactgga gaaattgtct gggataaagg gcgagatttt   3780
gccacagtgc gcaaagtatt gtccatgccc caagtcaata ttgtcaagaa aacagaagta   3840
cagacaggcg gattctccaa ggagtcaatt ttaccaaaaa gaaattcgga caagcttatt   3900
gctcgtaaaa aagactggga tccaaaaaaa tatggtggtt ttgatagtcc aacggtagct   3960
tattcagtcc tagtggttgc taaggtggaa aaagggaaat cgaagaagtt aaaatccgtt   4020
aaagagttac tagggatcac aattatggaa agaagttcct ttgaaaaaaa tccgattgac   4080
```

-continued

```
tttttagaag ctaaaggata taaggaagtt aaaaaagact taatcattaa actacctaaa   4140

tatagtcttt ttgagttaga aaacggtcgt aaacggatgc tggctagtgc cggagaatta   4200

caaaaaggaa atgagctggc tctgccaagc aaatatgtga attttttata tttagctagt   4260

cattatgaaa agttgaaggg tagtccagaa gataacgaac aaaaacaatt gtttgtggag   4320

cagcataagc attatttaga tgagattatt gagcaaatca gtgaattttc taagcgtgtt   4380

attttagcag atgccaattt agataaagtt cttagtgcat ataacaaaca tagagacaaa   4440

ccaatacgtg aacaagcaga aaatattatt catttattta cgttgacgaa tcttggagct   4500

cccgctgctt ttaaatattt tgatacaaca attgatcgta aacgatatac gtctacaaaa   4560

gaagttttag atgccactct tatccatcaa tccatcactg gtctttatga aacacgcatt   4620

gatttgagtc agctaggagg tgactga                                       4647
```

<210> SEQ ID NO 5
<211> LENGTH: 573
<212> TYPE: DNA
<213> ORGANISM: Artificial Sequence
<220> FEATURE:
<223> OTHER INFORMATION: Synthetic Construct

<400> SEQUENCE: 5

```
tgtcgacggt atattttaga tgaagattat ttcttaataa ctaaaaatat ggtataatac     60

tcttaataaa tgcagtaata caggggcttt tcaagactga agtctagctg agacaaatag    120

tgcgattacg aaatttttta gacaaaaata gtctacgagg ttttagagct atgctgtttt    180

gaatggtccc aaaacatcgc ttgccgcaaa ccagtaccga agaaggtttt agagctatgc    240

tgttttgaat ggtcccaaaa cttcgattga cagtactatg gtttacttac ggttttagag    300

ctatgctgtt ttgaatggtc ccaaaacatt gatttgtcag caaccttata aaacgcggtt    360

ttagagctat gctgttttga atggtcccaa aacttcagca cactgagact tgttgagttc    420

catgttttag agctatgctg ttttgaatgg tctccattca acattgccga tgataacttg    480

agaaagaggg ttaataccag cagtcggata ccttcctatt ctttctgtta aagcgttttc    540

atgttataat aggcaaaaga agagtagtgt gat                                 573
```

<210> SEQ ID NO 6
<211> LENGTH: 121
<212> TYPE: DNA
<213> ORGANISM: Artificial Sequence
<220> FEATURE:
<223> OTHER INFORMATION: Synthetic Construct

<400> SEQUENCE: 6

```
ttgagcaccg ccaggtgcga ataagggaca gtgaagaagg aacacccgct cgcgggtggg     60

cctacttcac ctatcctgcc cggctgacgc cgttggatac accaaggaaa gtctacacga    120

a                                                                    121
```

<210> SEQ ID NO 7
<211> LENGTH: 1917
<212> TYPE: DNA
<213> ORGANISM: Artificial Sequence
<220> FEATURE:
<223> OTHER INFORMATION: Synthetic Construct

<400> SEQUENCE: 7

```
atcccatggt acgcgtgcta gaggcatcaa ataaaacgaa aggctcagtc gaaagactgg     60

gcctttcgtt ttatctgttg tttgtcggtg aacgctctcc tgagtaggac aaatccgccg    120
```

ccctagacct agggatatat tccgcttcct cgctcactga ctcgctacgc tcggtcgttc 180
gactgcggcg agcggaaatg gcttacgaac ggggcggaga tttcctggaa gatgccagga 240
agatacttaa cagggaagtg agagggccgc ggcaaagccg tttttccata ggctccgccc 300
ccctgacaag catcacgaaa tctgacgctc aaatcagtgg tggcgaaacc cgacaggact 360
ataaagatac caggcgtttc cccctggcgg ctccctcgtg cgctctcctg ttcctgcctt 420
tcggtttacc ggtgtcattc cgctgttatg gccgcgtttg tctcattcca cgcctgacac 480
tcagttccgg gtaggcagtt cgctccaagc tggactgtat gcacgaaccc cccgttcagt 540
ccgaccgctg cgccttatcc ggtaactatc gtcttgagtc caacccggaa agacatgcaa 600
aagcaccact ggcagcagcc actggtaatt gatttagagg agttagtctt gaagtcatgc 660
gccggttaag gctaaactga aaggacaagt tttggtgact gcgctcctcc aagccagtta 720
cctcggttca aagagttggt agctcagaga accttcgaaa aaccgccctg caaggcggtt 780
ttttcgtttt cagagcaaga gattacgcgc agaccaaaac gatctcaaga agatcatctt 840
attaatcaga taaaatatta ctagatttca gtgcaattta tctcttcaaa tgtagcacct 900
gaagtcagcc ccatacgata taagttgtta ctagtgcttg gattctcacc aataaaaaac 960
gcccggcggc aaccgagcgt tctgaacaaa tccagatgga gttctgaggt cattactgga 1020
tctatcaaca ggagtccaag cgagctcgat atcaaattac gccccgccct gccactcatc 1080
gcagtactgt tgtaattcat taagcattct gccgacatgg aagccatcac agacggcatg 1140
atgaacctga atcgccagcg gcatcagcac cttgtcgcct tgcgtataat atttgcccat 1200
ggtgaaaacg ggggcgaaga agttgtccat attggccacg tttaaatcaa aactggtgaa 1260
actcacccag ggattggctg agacgaaaaa catattctca ataaaccctt tagggaaata 1320
ggccaggttt tcaccgtaac acgccacatc ttgcgaatat atgtgtagaa actgccggaa 1380
atcgtcgtgg tattcactcc agagcgatga aaacgtttca gtttgctcat ggaaaacggt 1440
gtaacaaggg tgaacactat cccatatcac cagctcaccg tctttcattg ccatacgaaa 1500
ttccggatga gcattcatca ggcgggcaag aatgtgaata aaggccggat aaaacttgtg 1560
cttatttttc tttacggtct ttaaaaaggc cgtaatatcc agctgaacgg tctggttata 1620
ggtacattga gcaactgact gaaatgcctc aaaatgttct ttacgatgcc attgggatat 1680
atcaacggtg gtatatccag tgattttttt ctccatttta gcttccttag ctcctgaaaa 1740
tctcgataac tcaaaaaata cgcccggtag tgatcttatt tcattatggt gaaagttgga 1800
acctcttacg tgccgatcaa cgtctcattt tcgccagata tcgacgtcta agaaaccatt 1860
attatcatga cattaaccta taaaaatagg cgtatcacga ggccctttcg tcttcac 1917

<210> SEQ ID NO 8
<211> LENGTH: 23
<212> TYPE: DNA
<213> ORGANISM: Artificial Sequence
<220> FEATURE:
<223> OTHER INFORMATION: Synthetic Construct

<400> SEQUENCE: 8
attgtttgtg gagcagcata agc 23

<210> SEQ ID NO 9
<211> LENGTH: 25
<212> TYPE: DNA
<213> ORGANISM: Artificial Sequence
<220> FEATURE:

<223> OTHER INFORMATION: Synthetic Construct

<400> SEQUENCE: 9
gcctctagca cgcgtaccat gggat 25

<210> SEQ ID NO 10
<211> LENGTH: 1286
<212> TYPE: DNA
<213> ORGANISM: Artificial Sequence
<220> FEATURE:
<223> OTHER INFORMATION: Synthetic Construct

<400> SEQUENCE: 10
cttaataaaa acccgcttgg gcaagcgggt tttattgtgc aattaggccc tagcgtttgc 60
aatgcaccag gtcatcattg acccaggcgt gttccaccag gccgctgcct cgcaactctt 120
cgcaggcttc gccgacctgc tcgcgccact tcttcacgcg ggtggaatcc gatccgcaca 180
tgaggcggaa ggtttccagc ttgagcgggt acggctcccg gtgcgagctg aaatagtcga 240
acatccgtcg ggccgtcggc gacagcttgc ggtacttctc ccatatgaat ttcgtgtagt 300
ggtcgccagc aaacagcacg acgatttcct cgtcgatcag gacctggcaa cgggacgttt 360
tcttgccacg gtccaggacg cggaagcggt gcagcagcga caccgattcc aggtgcccaa 420
cgcggtcgga cgtgaagtcc atcgccgtcg cctgtaggcg cgacaggcat tcctcggcct 480
tcgtgtaata ccggccattg atcgaccagc ccaggtcctg gcaaagctcg tagaacgtga 540
aggtgatcgg ctcgccgata ggggtgcgct tcgcgtactc caacacctgc tgccacacca 600
gttcgtcatc gtcggcccgc agctcgacgc cggtgtaggt gatcttcacg tccttgttga 660
cgtggaaaat gaccttgttt tgcagcgcct cgcgcgggat tttcttgttg cgcgtggtga 720
acagggcaga gcgggccgtg tcgtttggca tcgctcgcat cgtgtccggc cacggcgcaa 780
tatcgaacaa ggaaagctgc atttccttga tctgctgctt cgtgtgtttc agcaacgcgg 840
cctgcttggc ctcgctgacc tgttttgcca ggtcctcgcc ggcggttttt cgcttcttgg 900
tcgtcatagt tcctcgcgtg tcgatggtca tcgacttcgc caaacctgcc gcctcctgtt 960
cgagacgacg cgaacgctcc acggcggccg atggcgcggg cagggcaggg ggagccagtt 1020
gcacgctgtc gcgctcgatc ttggccgtag cttgctggac catcgagccg acggactgga 1080
aggtttcgcg gggcgcacgc atgacggtgc ggcttgcgat ggtttcggca tcctcggcgg 1140
aaaaccccgc gtcgatcagt tcttgcctgt atgccttccg gtcaaacgtc cgattcattc 1200
accctccttg cgggattgcc ccgactcacg ccggggcaat gtgcccttgt agctagcata 1260
gtacctagga ctgagctagc cgtaaa 1286

<210> SEQ ID NO 11
<211> LENGTH: 1284
<212> TYPE: DNA
<213> ORGANISM: Artificial Sequence
<220> FEATURE:
<223> OTHER INFORMATION: Synthetic Construct

<400> SEQUENCE: 11
atggaatccc tgacgttaca acccatcgct cgtgtcgatg gcactattaa tctgcccggt 60
tccaagagcg tttctaaccg cgctttattg ctggcggcat tagcacacgg caaaacagta 120
ttaaccaatc tgctggatag cgatgacgtg cgccatatgc tgaatgcatt aacagcgtta 180
ggggtaagct atacgctttc agccgatcgt acgcgttgcg aaattatcgg taacggcggt 240
ccattacacg cagaaggtgc cctggagttg ttcctcggta acgccggaac ggcaatgcgt 300

```
ccgctggcgg cagctctttg tctgggtagc aatgatattg tgctgaccgg tgagccgcgt    360

atgaaagaac gcccgattgg tcatctggtg gatgcgctgc gcctgggcgg ggcgaagatc    420

acttacctgg aacaagaaaa ttatccgccg ttgcgtttac agggcggctt tactggcggc    480

aacgttgacg ttgatggctc cgtttccagc caattcctca ccgcactgtt aatgactgcg    540

cctcttgcgc cggaagatac ggtgattcgt attaaaggcg atctggtttc taaaccttat    600

atcgacatca cactcaatct gatgaagacg tttggtgttg aaattgaaaa tcagcactat    660

caacaatttg tcgtaaaagg cgggcagtct tatcagtctc cgggtactta tttggtcgaa    720

ggcgatgcat cttcggcttc ttactttctg gcagcagcag caatcaaagg cggcactgta    780

aaagtgaccg gtattggacg taacagtatg cagggtgata ttcgctttgc tgatgtgctg    840

gaaaaaatgg gcgcgaccat ttgctggggc gatgattata tttcctgcac gcgtggtgaa    900

ctgaacgcta ttgatatgga tatgaaccat attcctgatg cggcgatgac cattgccacg    960

gcggcgttat ttgcaaaagg caccaccacg ctgcgcaata tctataactg gcgtgttaaa   1020

gagaccgatc gcctgtttgc gatggcaaca gaactgcgta aagtcggcgc ggaagtggaa   1080

gaggggcacg attacattcg tatcactcct ccggaaaaac tgaactttgc cgagatcgcg   1140

acatacaatg atcaccggat ggcgatgtgt ttctcgctgg tggcgttgtc agatacacca   1200

gtgacgattc ttgatcccaa atgcacggcc aaaacatttc cggattattt cgagcagctg   1260

gcgcggatta gccaggcagc ctga                                          1284


<210> SEQ ID NO 12
<211> LENGTH: 1080
<212> TYPE: DNA
<213> ORGANISM: Artificial Sequence
<220> FEATURE:
<223> OTHER INFORMATION: Synthetic Construct

<400> SEQUENCE: 12

tgacacttga ggggcgttta gagcgagcca ggaaagccga ccccctcctt ggagtaaaaa     60

cccttgcggc gttgcagccg gcacggatct tccgatcggg cgcggtggtg gccgcgtctg    120

tgacctaaaa aggggggagt ccagaggggc gcagcccctt tgggcatagc gcagcgtaat    180

cggagacgta attgagcatt tccaggcgct tgcgcctggt caacgaaaga gtcagcgccg    240

taggcgctgc catttttggg gtgaggccgt tcgcggccga ggggcgcagc ccctgggggg    300

atgggaggcc cgcgttagcg ggccgggagg gttcgagaag ggggggcacc cccccttcggc   360

gtgcgcggtc acgcgccagg gcgcagccct ggttaaaaac aaggtttata aatattggtt    420

taaaagcagg ttaaaagaca ggttagcggt ggccgaaaaa cgggcggaaa cccttgcaaa    480

tgctggattt tctgcctgtg gacagcccct caaatgtcaa taggtgcgcc cctcatctgt    540

catcactctg cccctcaagt gtcaaggatc gcgcccctca tctgtcagta gtcgcgcccc    600

tcaagtgtca ataccgcagg gcacttatcc ccaggcttgt ccacatcatc tgtgggaaac    660

tcgcgtaaaa tcaggcgttt tcgccgattt gcgaggctgg ccagctccac gtcgccggcc    720

gaaatcgagc ctgcccctca tctgtcaacg ccgcgccggg tgagtcggcc cctcaagtgt    780

caacgtccgc ccctcatctg tcagtgaggg ccaagttttc cgcgtggtat ccacaacgcc    840

ggcggccgcg gtgtctcgca cacggcttcg acggcgtttc tggcgcgttt gcagggccat    900

agacggccgc cagcccagcg gcgagggcaa ccagcccggt gagcgtcgga aaggcgctgg    960

aagccccgta gcgacgcgga gaggggcgag acaagccaag ggcgcaggct cgatgcgcag   1020
```

-continued cacgacatag ccggttctcg caaggacgag aatttccctg cggtgcccct caagtgtcaa 1080

<210> SEQ ID NO 13
<211> LENGTH: 10509
<212> TYPE: DNA
<213> ORGANISM: Artificial Sequence
<220> FEATURE:
<223> OTHER INFORMATION: Synthetic Construct

<400> SEQUENCE: 13
ttgcaggcta aacactttcg gtatatcgtt tgcctgtgcg ataatgttgc taatgatttg 60
ttgcgtaggg gttactgaaa agtgagcggg aaagaagagt ttcagaccat caaggagcgg 120
gccaagcgca agctggaacg cgacatgggt gcggacctgt tggccgcgct caacgacccg 180
aaaaccgttg aagtcatgct caacgcggac ggcaaggtgt ggcacgaacg ccttggcgag 240
ccgatgcggt acatctgcga catgcggccc agccagtcgc aggcgattat agaaacggtg 300
gccggattcc acggcaaaga ggtcacgcgg cattcgccca tcctggaagg cgagttcccc 360
ttggatggca gccgctttgc cggccaattg ccgccggtcg tggccgcgcc aacctttgcg 420
atccgcaagc gcgcggtcgc catcttcacg ctggaacagt acgtcgaggc gggcatcatg 480
acccgcgagc aatacgaggt cattaaaagc gccgtcgcgg cgcatcgaaa catcctcgtc 540
attggcggta ctggctcggg caagaccacg ctcgtcaacg cgatcatcaa tgaaatggtc 600
gccttcaacc cgtctgagcg cgtcgtcatc atcgaggaca ccggcgaaat ccagtgcgcc 660
gcagagaacg ccgtccaata ccacaccagc atcgacgtct cgatgacgct gctgctcaag 720
acaacgctgc gtatgcgccc cgaccgcatc ctggtcggtg aggtacgtgg ccccgaagcc 780
cttgatctgt tgatggcctg gaacaccggg catgaaggag gtgccgccac cctgcacgca 840
aacaacccca aagcgggcct gagccggctc gccatgctta tcagcatgca cccggattca 900
ccgaaaccca ttgagccgct gattggcgag gcggttcatg tggtcgtcca tatcgccagg 960
acccctagcg gccgtcgagt gcaagaaatt ctcgaagttc ttggttacga gaacggccag 1020
tacatcacca aaaccctgta aggagtattt ccaatgacaa cggctgttcc gttccgtctg 1080
accatgaatc gcggcatttt gttctacctt gccgtgttct tcgttctcgc tctcgcgtta 1140
tccgcgcatc cggcgatggc ctcggaaggc accggcggca gcttgccata tgagagctgg 1200
ctgacgaacc tgcgcaactc cgtaaccggc ccggtggcct tcgcgctgtc catcatcggc 1260
atcgtcgtcg ccggcggcgt gctgatcttc ggcggcgaac tcaacgcctt cttccgaacc 1320
ctgatcttcc tggttctggt gatggcgctg ctggtcggcg cgcagaacgt gatgagcacc 1380
ttcttcggtc gtggtgccga aatcgcggcc ctcggcaacg gggcgctgca ccaggtgcaa 1440
gtcgcggcgg cggatgccgt gcgtgcggta gcggctggac ggctcgccta atcatggctc 1500
tgcgcacgat ccccatccgt cgcgcaggca accgagaaaa cctgttcatg ggtggtgatc 1560
gtgaactggt gatgttctcg ggcctgatgg cgtttgcgct gattttcagc gcccaagagc 1620
tgcgggccac cgtggtcggt ctgatcctgt ggttcggggc gctctatgcg ttccgaatca 1680
tggcgaaggc cgatccgaag atgcggttcg tgtacctgcg tcaccgccgg tacaagccgt 1740
attacccggc ccgctcgacc ccgttccgcg agaacaccaa tagccaaggg aagcaatacc 1800
gatgatccaa gcaattgcga ttgcaatcgc gggcctcggc gcgcttctgt tgttcatcct 1860
ctttgcccgc atccgcgcgg tcgatgccga actgaaactg aaaaagcatc gttccaagga 1920
cgccggcctg gccgatctgc tcaactacgc cgctgtcgtc gatgacggcg taatcgtggg 1980
caagaacggc agctttatgg ctgcctggct gtacaagggc gatgacaacg caagcagcac 2040

-continued

```
cgaccagcag cgcgaagtag tgtccgcccg catcaaccag gccctcgcgg gcctgggaag   2100
tgggtggatg atccatgtgg acgccgtgcg gcgtcctgct ccgaactacg cggagcgggg   2160
cctgtcggcg ttccctgacc gtctgacggc agcgattgaa gaagagcgcc ggcggcattt   2220
cgagagcctg ggaacgatgt acgagggcta tttcgtcctc accttgacct ggttcccgcc   2280
gctgctcgcc cagcgcaagt tcgtcgagct gatgtttgac gacgacgcga ccgcaccgga   2340
tcgcaaggcg cgcacgcggg gcctcatcga ccaattcaag cgtgacgtgc gcagcatcga   2400
gtcgcgcctg tcgtcggccg tgtcgctcac tcgcttgaag gggcacaaga tcgtcaacga   2460
ggacggcacg accgtcacgc atgacgactt cctgcgctgg ctgcaattct gcgtgacggg   2520
cctgcaccat ccggtgcagc tccccagcaa cccgatgtac ctggacgccc tggtcggcgg   2580
acaggaaatg tggggcgggg tagtgcccaa ggtcggccgc aagttcgtcc aggtggtcgc   2640
tctcgaaggc ttccccttgg agtcctatcc cggcatcctg acggcgctcg gcgagctgcc   2700
ctgcgagtat cggtggtcga gccggttcat cttcatggac cagcacgaag ccgtgaagca   2760
cctcgacaag ttccgcaaga agtggcggca gaagattcgc ggcttcttcg accaggtgtt   2820
caacacgaac accggcccgg tcgatcagga cgcgctttcg atggtggccg atgctgaggc   2880
ggccattgcc gaagtcaaca gcggcatcgt ggccgtgggc tactacacca gcgtcgtcgt   2940
gctgatggat gaggaccgca cgcgcctgga agctgcggcc cgcgatgttg aaaaggccgt   3000
caaccggttg ggctttgccg cgcgcatcga gtccatcaac accctggacg ccttccttgg   3060
tagtttgccg ggccacggcg tggaaaacgt ccgccggccg ctcatcaaca cgatgaacct   3120
ggccgacctg ctgccgacca gcaccatctg gaccggcaac gcgaacgcgc catgcccgat   3180
gtacccgccg ctgtcgccgg cgctcatgca ctgcgtcacg caaggatcaa cgccgttccg   3240
gctgaacctg cacgtgcgcg acctcggcca cacctttatg ttcgggccga ccggcgcagg   3300
taaatcgacg cacctggcga tcctcgccgc gcagctccgt cgctatgccg gcatgtcgat   3360
cttcgccttt gacaagggca tgtcgatgta cccgctggcc gccggcatcc gtgcggccac   3420
gaagggcacc agcggcctgc acttcaccgt ggcggccgac gacgaacgcc tggcgttctg   3480
cccgttgcag ttcctgagca ccaagggcga ccgtgcttgg gcgatggagt ggatcgacac   3540
catcctggcg ttgaacggcg tcgaaacgac cccggcccag cgcaacgaaa tcggcaacgc   3600
gatcatgagc atgcacgcca gcggcgcgcg cacgctctcc gagttcagcg tgacgattca   3660
ggatgaggcg atccgcgagg cgatccgcca gtacaccgtc gatggcgcaa tgggccatct   3720
gctcgacgcc gaagaggacg gcttggcgct gtccgacttt acagtgttcg agatcgaaga   3780
gctgatgaac ctcggcgaga aattcgccct gcctgtgttg ctctacctgt tccgccgtat   3840
cgagcgcgcc ctgacgggcc agccggccgt catcatcctg gacgaagcct ggttgatgct   3900
cggccacccg gcattccgcg cgaagatcag ggaatggctc aaggtgctgc gtaaggccaa   3960
ctgccttgtg ctgatggcaa cgcagagcct gtccgacgcc gccaacagcg gcatcctgga   4020
cgtgatcgtg gaatcgaccg cgaccaagat tttcctgccg aatatttacg ccagggatga   4080
ggacacggcg gccctgtacc gccgcatggg cctgaacgct cgccagatcg agattctggc   4140
ccaggccgtt cccaagcgtc agtactacta cgtgtcggaa aacggccgcc gtctctacga   4200
cctggcactt ggcccgctcg cgctcgcgtt cgtcggcgca tccgacaagg aatccgtcgc   4260
catcatcaag aacctggaag ccaagttcgg cgaccagtgg gtggatgaat ggctgcgtgg   4320
ccggggcctc gcccttgatg aatacctgga ggcagcatga gttttgcaga cacgatcaag   4380
```

-continued

```
ggcttgatct tcaagaagaa gcccgcaacg gccgcagcag cggcgacgcc ggccgcgacc   4440
ggcccgcaaa ccgacaaccc gtacctgacg gcgcggcgca cctggaacga ccacgttggt   4500
tccgttgtgt cgcaaaagca gacctggcag gttgtcggca tcctttcgct gatgatcgtc   4560
ctcgcggcgg tcggcggcat catccacatc ggcagccagt cgaagttcgt gccctatgtc   4620
tacgaggtag acaagctcgg gcagacggcc gccgtggggc cgatgaccag ggcgtcgaaa   4680
gccgatccgc gtgtcattca cgcctcggtg gctgagttcg tcggcgatgc tcgcctggtg   4740
acgccggacg tagctttgca gcgcaaggcc gtctaccgcc tctatgccaa gctcgggccg   4800
aatgacccgg ccaccgccaa gatgaacgaa tggctcaacg gcaccgccga cgccagcccg   4860
ttcgctcgcg cggccgtcga aacggtcagc accgaaatca cttccgtaat cccgcagacg   4920
cccgacacct ggcaggtcga ttgggtcgag acgacgcgcg acaggcaagg cgtggtgaaa   4980
ggccagcccg tgcgcatgcg ggccttggtg acggtctacg tcgtcgagcc gacggcggac   5040
accaaggaag aacaactgcg aaacaacccg gccgggatct acgtccggga cttctcctgg   5100
tcgagacttc tgtgaggcac tgaattatga aaaaggaact gtttgctttg gtcctggccg   5160
cgtccgttag cgtgcctgca tttgccgccg atcccggcgc ggacctgact gacctctatt   5220
tttccggcaa gaacccggag ctgaccgcgc aagagcgggc ggccatcgcc atcgccaaga   5280
agtgggaggc gggtaccgcc ggcatgcggc cggtggccgg ccccggtggt tcggtgcgct   5340
tcctgttcgg cgcgcagcag ccgagcatcg tatgcgccgt gctgcaagtg tgcgacgtgg   5400
ccctgcaacc cggcgagcaa gtcaactcga tcaacctggg cgacaccgcc cgttggacgg   5460
tcgagccggc cattaccggc agcggcgcga acgaaaccca gcacctcatc atcaagccga   5520
tggatgtggg cctggaaacc agcctggtcg tgaccacgga ccgccgcagc taccacatgc   5580
gcctgcgctc gcatcgcacg cagtacatgc cgcaggtgtc gttcacctac ccggaagatg   5640
cccttgcgaa gtgggacgcc atcaagaacc gcgaacagcg ggatcgcgtc gagaaaacca   5700
ttccgcagac cggcgagtac ctgggcaacc tgagcttcaa ctactccgtc agcgggtcca   5760
cgtcgtggaa gccggtgcgc gtctacaacg acggcaagaa aaccatcatc cagatgccgc   5820
actcgatgga acagaccgaa gcgccgacgc tcctggtcgt tcgcagggag ggcggcctgt   5880
tctccgacga tgaaacggtg atggtcaact accgggtcca gggcgaccgc tacatcgtcg   5940
atacgatttt cgacaaggcc atcctcatcg cgggcgtggg cagcagccag gaccgcgtga   6000
ccatttcaag gggaactaa accatgcgta agattctgac cgtcatcgca ctcgcggcca   6060
cgttggccgg ctgcgcgacc tccaagtacg gcagcttcgt ccaggacgcg ccggccgcct   6120
acaaccagac cattgcgacc gacgcggtga agcagctcgt caagctctac ccgccggcgc   6180
aaaccaagct ggaattgcag caggctacgc ccgatccgtt cggcattgcc ctggtcactg   6240
accttcgcgc ccagggctat gctgtcatgg agtacaagcc cgacggcaac gcggccgcag   6300
ctccggctgc tgcgtcctcg gccgctgcga agccggcaac gccgcaagcc cagggcggct   6360
atccgctgcg ctacgtgctg gaccaattca gcgacagcaa cctgtatcgc ctgaccgtca   6420
tggtcggctc tcaatcgctc acgcgcgcct acctcgccca aaacaacacg atggtcccgg   6480
ccggcgcatg ggttcggaag gagtaagcca atgagcgaag atcaaatggc accggacgca   6540
tcgccagatg cggtcaagcc gaaaagcggg gttcgccgcg tcaacaacat gccgatgtac   6600
ctcatcggcg gtgtgctcgg catcttcctg ctggtgatgg ccctggttgc tgcggatcgc   6660
gctgcgcagc agaaccagcc gggagctgcg aaggctgaga aggccggcag caccagcatg   6720
tttgccgacg aaattgccgg caaacagcag gacggcatca tcaaggccaa gccgctggag   6780
```

attccgccgg aacaaaccgc ccagcaaccg acgacggagc tgacgccagc cccggcgcag 6840
ggaacgacta tcacggtcgc acggcccgag aacctggacc agcccccgac gccgccgcag 6900
ggtgcgcgca acgaggacct ggaccgcatc cgcatggcga agttgcagat gctggaagag 6960
gcgatcaagg ccaagacgac ggtgcgcatc gacgcgccgc gcagccaggg cagcgccggc 7020
ggcggtgctc cgcagggccg cgaggaaacc cttgcgcgca tccaggagct gcgtcggcag 7080
gctgagaacg cccgcgccac cgatccgacc gccgcctatc aggccgcgct tgcgcaggct 7140
cgcacgatgg gcggcgcggc agggggtggc ggtatgggcg gctcgggtgc gccgaccctc 7200
gtgcagacct cgaaccgcag tggtggcggc gctggctatg ggtcgttcga caaccgcagc 7260
gagggcgacc gttggcggct cgactcccag ccggaagcac ctgcaacgcc ctatgtgctg 7320
cgcgctggct tcgtcgttcc ggctacgctt atctcgggca tcaactccga tctgccaggc 7380
caaatcatgg cccaggtatc gcagtcggtg tacgacacgg cgaccggcaa gcacatgctc 7440
atcccccaag gctcgcgcct ggtgggcagc tactcgaacg atgtggccta cgggcagaag 7500
cgcgttctgg tggcatggca gcgcatcatc ttccccgacg gcaaggcaat ggacattggg 7560
gccatgccgg gcggcgatag cgctgggtat gcaggcttca acgacaaggt caacaaccac 7620
tacttccgca ccttcgcatc ggcattcctc atgtcgggcg tcgttgcggg catcagcttg 7680
agtcaggacc gtggcaacag caacagcggt tacggacgac aagacgcggg ttccgcgatg 7740
agtgaagcgt tgggtcaaca gctcggccaa gtaacggcgc agatgatcgc caaaaacttg 7800
aatatcgcgc cgacgctgga aatccgtccg ggctatcgct tcaacgtcat tgtcacgaaa 7860
gacatgacgt tttctaagcc ctaccaggcg tttgactatt aactccaagg agtaacttat 7920
gaagaagctc gctaagaatg ttttagccgc taaagtagct ctggtgctgg ccctctcggt 7980
cggcaccttg gcggtcacgc ctgcgcaagc gggcattccg gtcatcgacg gcaccaacct 8040
gtcacaaacc actgtcaccg cgattcagca ggttgcgcag gtccagaagc aaatcgagga 8100
ataccggacg cagttgcagc agtacgaaaa catgctgcaa aacacggtgg ccccggccgc 8160
ctacgtgtgg gaccaggcgc agtccaccat caacggcctg atgagcgccg ttgataccct 8220
gaactactac aagaaccagg cgggcagcat cgacgcttac ctgggcaagt tcaaggacgt 8280
gtcctactac aaggggtcgc cgtgcttctc cctgtcgggc tgctcggaaa gcgagcgcaa 8340
ggcgatggaa gagaaccgcc gcctggcgtc cgaatcgcag aaaaaggcca acgatgcgct 8400
gttccgtggc ctcgatcagc agcagagcaa cctcaagtcc gacgccgcca cgctggagca 8460
attgaagggc aaggcgacga cggcgcaggg ccagttggaa gccctcggct acgccaacca 8520
gttcgccagc cagcaggcca accagctcat gcaaatccgt ggccttctgc ttgcgcagca 8580
gaacgccatc gccacgcaga tgcaggccca gcaggaccgg caggcccagc aggacgctgc 8640
gggcgcgaag ctgcgcgagg gttcgtaccg cgcaagcccg tctaagacct ggtgagggga 8700
ggcgcgatga agaaatccaa cttcatcgca gttgccgcgc tggccgccgt catggcggcc 8760
agcctggcag gctgcgacaa caagcccgac accgacaagc tgacctgcgc cgatctgccg 8820
aaggtcacgg atgccgctca acgcgcggag ctgttgaaga agtgcccgcg cggagaaccg 8880
ggaggcttca agcccagcga aaagaaagag tggtgatgac gtatgaaaat ccagactaga 8940
gctgccgcgc tcgcggtcct gatgctggcc ttgatgccgg tagcggcata cgcccaaatc 9000
gacaattcgg gcatcctcga caacgtattg cagcgctacc agaacgccgc gagcggctgg 9060
gccactgtcg tccagaacgc cgcaacctgg ctgttctgga ccttgaccgt gattagcatg 9120

```
gtctggacct tcggcatgat ggcactgcgc aaggccgaca ttggcgagtt cttcgccgag   9180
ttcgtgcggt tcaccatctt caccggcttc ttctggtggc tgctgaccaa cggcccgaat   9240
ttcgcgtcgt ccatctatgc gtccctgcgg cagattgcag gccaggcaac ggggttgggg   9300
caggggcttt cgccgtccgg catcgtcgat gttggcttcg agattttctt caaggtgatg   9360
gacgaaacct cgtactggtc gccggtcgat agcttcgtcg gtgcctcgtt ggcggccgcc   9420
atcctctgca tcctggccct ggtcggcgtg aatatgcttc tgctcctggc gtccggatgg   9480
attcttgcct acggcggtgt gttcttcctg ggcttcggcg gctcgcgctg gacctcggac   9540
atggcgatca actactacaa gaccgtcctc ggggtcgccg cgcagctctt cgcaatggtg   9600
ctgctcgtag gcatcggcaa gaccttcctc gatgactact acagccgcat gagcgaaggc   9660
atcaacttca aggaacttgg agtgatgctg atcgtcggcc tgatcctgct cgttctggtc   9720
aacaaggtgc cgcagctcat cgccggcatc atcaccggcg cgagcgtcgg cggtgctggt   9780
atcggccagt tcggcgctgg cacgctcgtc ggtgcggccg cgacggccgg cgcggcaatc   9840
gcaactggcg gcgcatctat cgcggccggc gctgcggcgg cggccggtgg cgcgcaggcc   9900
atcatggcgg ccgcgtcgaa ggccagcgat aacgtctctg ccggcactga cattctgtcg   9960
agcatgatgg gcggcggcgg tggcggcggc ggtggtagcg ccggcaccag cggcggcgac  10020
ggcggcggct cgggtggcgg cggtggctcg ggcggcggtg aaaccccgat ggcctcggcc  10080
gccggcgaca acagcagcgg cgcacgcggc ggcagttcgg gcggcggctc gggtggtggc  10140
cgttcgtctg gcggtatcgg tgccacggcg gccaagggcg gccggatcgc ggccgatacc  10200
gtcgccaacc tggcgaaagg tgccggctcg attgccaagg ccaaggccgg cgaaatgcgc  10260
gcatcggccc aggaacgcat cggcgatacc gtaggcggca agatcgcgca ggcaattcgc  10320
ggcgcgggtg cggcggcgca gaccgctgca accgtcgccg atagcaacag ccaggcgcag  10380
gaacaacctg caccggcacc cgcaccgtcg ttcgacgaca acagcctttc cgcaagcaac  10440
aacagggaag cggccgccga cgcggattcc gaagtggcga gcttcgtcaa caagcccgcc  10500
caatcctga                                                          10509
```

<210> SEQ ID NO 14
<211> LENGTH: 7018
<212> TYPE: DNA
<213> ORGANISM: Artificial Sequence
<220> FEATURE:
<223> OTHER INFORMATION: Synthetic Construct

<400> SEQUENCE: 14

```
tcaccaggtc agaaccggcc tgatgacggt gatgatttgc gaacgattga caggcccgaa     60
gtagcggccg tcgaaagacg tgtcgcttac gtcggacata agcagaacct cggcggtccc    120
cagggtgtag ctgtcggact gataacgagg cagcggccgt cctgatggat cggccttgat    180
gagcgcgctg tgaggcagca gcccgccatt cacgcgcacg ccggcgtcgg tgatggcaac    240
ctcgtcgcct ttagcggcta aaactcgctt catcatgtag ccgtagtcgc cggggcagaa    300
accgccggcg atgtagcccc gctccttggc gtccgaaaac acgccgactt gcggcgggca    360
gaacatgacg taagccccct tctccaccgg cgcattcgat ttccagtaca ggccgaccgg    420
aatgcttttg gtggtgttga ccttcgcgcc ggcgagatag gccgcgccgg cgagcaacaa    480
ggccgcgccg cctccgatgg cgacgtactt ggtgaggcgc tggaagcggc tcatatcgtg    540
atcccctccc cttcctcgac ggtggccgtc tggatcagct tgtcgctgac cttcggagcc    600
ggtacggccg cgcgggcctg gaatatcggg tctttgaagt agagcggctg cttgccgtag    660
```

```
atcgcgggat agccggcgac gtacacaacc atgtcgcccg cctcttcaat gctgccgtcg    720
gcgctcttct tcggccccgg catgcgcagg cattcatcgg gggtcagcaa tggccgctgc    780
acttcctgga aggtccgcga gacgttgccc aacagcgccg acgtgcggcg gccgctcgtc    840
gtgatctgct ccttcacgat ggtcgtggtg cctgtcagtt ttgacaggtg ctcggccgtc    900
tccacgcggt tcggcgggta ggcgttctgc acgtggcagt tcgacgtgat gctttcgtcg    960
tggccgtagc cggtttcgcg gctcttgagc tggttaatgt cctggcagat gaggtagcac   1020
ttgatgccgt agccggcgac gaaggcaagg gactcttgca ggatttcgag cttgcccagg   1080
ctggggaact cgtcgagcat catcagcaga cgatgcttgt agtgcgcgac aggacggccg   1140
ttctcgaagt ccatcttgtc ggccagcagc cggacgatca tgttgaccat gacgcgcacc   1200
agaggccgca gacgggcctt gtcgttgggc tgcgtcacga tgaacaggct taccgggtcg   1260
tcgtggtgca tcagttgctt gatgcggaag tcggacttgc tgacgttgcg ggccacaacc   1320
gggtcgcggt acagggccag gtaggacttg gcggtggaca gcacggaacc ggattcttcc   1380
tccgggcggt ccatcatgtc gcgggccgca gagccgaccg cagggtggtt ctgcccgtca   1440
acgtggccgt aggtggtcat ttccatccaa agctcgccca cgtcgcggtt cgggtcggca   1500
agcatgccgt ccaccgacgg cagggtggcc ggcgtaccct cgttcttagc cttgtagagc   1560
gcgtgcagga tgacgccgac aagcagcgcc tggctggttt tctgccagtg cgattccagg   1620
cccttgccgt ccggatcgac gatcagggtg gcaaggttct gcacgtcgcc aacctcgtac   1680
tcggtcccca agcggatttc atcgagcggg ttccagcacg cgctaccctg cgcggatgcc   1740
ggctcaaagc gcacgacctt gttgcgggca tgcttcttcc gccagccggc ggtcagcgcc   1800
cacaactcgc ctttcaggtc ggtgatgacg gcgctgtgcg cccaggaaag cagcgtcgga   1860
acgaccaggc cgacgccctt gccggagcgc gtcggcgcgt aggtcaagac gtgctcgggg   1920
ccgttgtgcc gcaggtagtg gaacttgccg tccttgtcct gccagccgcc cacatagacg   1980
ccgctggaag tgggcgggtg tttgcctgac accagctcga cgacggtgcg cggccggggc   2040
agcaggccgg cggcctgtat gtccttcttg tcggcccagc gggccgaacc gtgcagatag   2100
tcgttcgcct tgccggtgtt cgccttgacc atctgcgtga cggccgtgcc cagcaggccc   2160
acggtcgaaa cgaccatacc catgctggcc gcgcgcatga aatcgtcggg atattggccg   2220
taccacttgc cggcccattg aaggatcgac cagggcgtgt agacgtggtt gatattccag   2280
ccaagtccgg cctgatactg gaaggaatgg gcgaaatatt gcgtcgcggt ctgcaagcct   2340
gccccaaggg acaggccggc gaggatggga acggtcttgc tggccttcgg ttttttcgcc   2400
cgtatctgtg gccccacggc gttgtttcgg ttcttcatct actcctacct cgggtagttt   2460
taagggagcc tcgcggggtc acggtgacgg gatcaccgat ggcgaggcgc ttcatgcgtt   2520
gcaccgtggc cttatcgacg ggcagcacca gaatctcgtc gttttctttc ctcaacaggg   2580
ccagcgcctg gtcctcgacg ttccgggtgc ctgcatagga cagcgcacca acataatcag   2640
tatatcgtgc atgcttcggt atatcgaagc cgtttagccg cttttgctcg cgctcggcaa   2700
catatttctc ggccgccgcg atctgttcgg gctttagccc tcttcctggc ccagaaactc   2760
cccgtcgcag tgcgtgagct ggttcggctc cttgctgctc cacgtgacca ggaacatcac   2820
gcggcaatag catttcagct ccgccggcga tgcgaaccac accgagttgg gacagcgctc   2880
gcaaacggtt ttggctttgg ggcggcggct ttcgtccaat gcgtccaacg ttgggcttgc   2940
ggagtgcgac ggttccgccg gcgctgacgg cgcgagcgtc ccgtcggtcg ccgtcgccgc   3000
```

-continued

```
ctgtggcgtt gagggtggtt ctggctgcgg caggtcgaat gcctccatcg ccgccgcgat   3060

ctcttcgtcc gtcatttcgt tcgggttgct catgtgcttg ctccttcgtc agtagttctt   3120

gacggcggcg ctcaagggcg gcgtcgtcaa aggtgattgc cagacggcca gcggcggccg   3180

cctgcgcgat ccgctccttg aactctgctg tgccgttgac ggtgatccgg tcgccgaagc   3240

gctccattgc caggcgcagg gcggcgtcca ggccgtccgt ggtggcctcg cgcgagactt   3300

gcaggcggtc gccgtcgtcg cggacggcgc tgctgccgac gcgatagatg atggttccct   3360

tcttcgtgat gttgtccgtc acggccgcat ggcccggctt ggcctcgccg ctgccctgga   3420

tggtgttgcc cttgaggtcg ctgcggccct cgcgtgcgcg cagcgcggcc agggccttgt   3480

cgtcgccctt catcgcctcg gccttgagcc agtcggccca cgcgcggcgc tgcgtgcgct   3540

cctggaccgc ctgacggccc tgccggtact cgcggttgat cttgtccagg tcggcgcgca   3600

gagccttgtg cgcctgcgcg tacatcagtc gctttgcaat gcgcccctcg cccagcagct   3660

tgatagcggc gcggcgcagc cggttgctgc gcatcgcggc ttcaatcagg cggtcacgac   3720

gccggcgcag cgtgtccagc tcgcccttgc gcacggcccc catttcctgg cgttcagact   3780

gataccgggc gtatagctcg gtggtgtcga tgcgggtctt gagcggcttc gctcgatact   3840

cccgccgccg gggggcttcg ccgccctcgg ctggcgtgaa tgccccgaat cgggcttcga   3900

gcttcggctt ggacaggtcg cgcgaaacgg tgctggcctt gaccgtcgtg ccgtcgccgg   3960

cctcgaagat gaagccgttt ccgcgctcgc gcagcttaag cccgttttcc cgcaggacgc   4020

ggtgcaggtc ctcccaggat tgcgccgctt gcagctccgg caggcattcg cgcttgatcc   4080

agccgaccag gctttccacg cccgcgtgcc gctccatgtc gttcgcgcgg ttctcggaaa   4140

cgcgctgccg cgtttcgtga ttgtcacgct caagcccgta gtcccgttcg agcgtcgcgc   4200

agaggtcagc gagggcgcgg taggcccgat acggctcatg gatggtgttt cgggtcgggt   4260

gaatcttgtt gatggcgata tggatgtgca ggttgtcggt gtcgtgatgc acggcactga   4320

cgcgctgatg ctcggcgaag ccaagcccag cgcagatgcg gtcctcaatc gcgcgcaacg   4380

tctccgcgtc gggcttctct cccgcgcgga agctaaccag caggtgatag gtcttgtcgg   4440

cctcggaacg ggtgttgccg tgctgggtcg ccatcacctc ggccatgaca gcgggcaggg   4500

tgtttgcctc gcagttcgtg acgcgcacgt gacccaggcg ctcggtcttg ccttgctcgt   4560

cggtgatgta cttcaccagc tccgcgaagt cgctcttctt gatggagcgc atggggacgt   4620

gcttggcaat cacgcgcacc ccccggccgt tttagcggct aaaaaagtca tggctctgcc   4680

ctcgggcgga ccacgcccat catgaccttg ccaagctcgt cctgcttctc ttcgatcttc   4740

gccagcaggg cgaggatcgt ggcatcaccg aaccgcgccg tgcgcgggtc gtcggtgagc   4800

cagagtttca gcaggccgcc caggcggccc aggtcgccat tgatgcgggc cagctcgcgg   4860

acgtgctcat agtccacgac gcccgtgatt ttgtagccct ggccgacggc cagcaggtag   4920

gccgacaggc tcatgccggc cgccgccgcc ttttcctcaa tcgctcttcg ttcgtctgga   4980

aggcagtaca ccttgatagg tgggctgccc ttcctggttg gcttggtttc atcagccatc   5040

cgcttgccct catctgttac gccggcggta gccggccagc ctcgcagagc aggattcccg   5100

ttgagcaccg ccaggtgcga ataagggaca gtgaagaagg aacacccgct cgcgggtggg   5160

cctacttcac ctatcctgcc cggctgacgc cgttggatac accaaggaaa gtctacacga   5220

accctttggc aaaatcctgt atatcgtgcg aaaaaggatg gatataccga aaaaatcgct   5280

ataatgaccc cgaagcaggg ttatgcagcg gaaaagcgct gcttccctgc tgttttgtgg   5340

aatatctacc gactggaaac aggcaaatgc aggaaattac tgaactgagg ggacaggcga   5400
```

-continued gagacgatgc caaagagcta caccgacgag ctggccgagt gggttgaatc ccgcgcggcc 5460
aagaagcgcc ggcgtgatga ggctgcggtt gcgttcctgg cggtgagggc ggatgtcgag 5520
gcggcgttag cgtccggcta tgcgctcgtc accatttggg agcacatgcg ggaaacgggg 5580
aaggtcaagt tctcctacga gacgttccgc tcgcacgcca ggcggcacat caaggccaag 5640
cccgccgatg tgcccgcacc gcaggccaag gctgcggaac ccgcgccggc acccaagacg 5700
ccggagccac ggcggccgaa gcaggggggc aaggctgaaa agccggcccc cgctgcggcc 5760
ccgaccggct tcaccttcaa cccaacaccg gacaaaaagg atctactgta atggcgaaaa 5820
ttcacatggt tttgcagggc aagggcgggg tcggcaagtc ggccatcgcc gcgatcattg 5880
cgcagtacaa gatggacaag gggcagacac ccttgtgcat cgacaccgac ccggtgaacg 5940
cgacgttcga gggctacaag gccctgaacg tccgccggct gaacatcatg gccggcgacg 6000
aaattaactc gcgcaacttc gacaccctgg tcgagctgat tgcgccgacc aaggatgacg 6060
tggtgatcga caacggtgcc agctcgttcg tgcctctgtc gcattacctc atcagcaacc 6120
aggtgccggc tctgctgcaa gaaatggggc atgagctggt catccatacc gtcgtcaccg 6180
gcggccaggc tctcctggac acggtgagcg gcttcgccca gctcgccagc cagttcccgg 6240
ccgaagcgct tttcgtggtc tggctgaacc cgtattgggg gcctatcgag catgagggca 6300
agagctttga gcagatgaag gcgtacacgg ccaacaaggc ccgcgtgtcg tccatcatcc 6360
agattccggc cctcaaggaa gaaacctacg gccgcgattt cagcgacatg ctgcaagagc 6420
ggctgacgtt cgaccaggcg ctggccgatg aatcgctcac gatcatgacg cggcaacgcc 6480
tcaagatcgt gcggcgcggc ctgtttgaac agctcgacgc ggcggccgtg ctatgagcga 6540
ccagattgaa gagctgatcc gggagattgc ggccaagcac ggcatcgccg tcggccgcga 6600
cgacccggtg ctgatcctgc ataccatcaa cgcccggctc atggccgaca gtgcggccaa 6660
gcaagaggaa atccttgccg cgttcaagga agagctggaa gggatcgccc atcgttgggg 6720
cgaggacgcc aaggccaaag cggagcggat gctgaacgcg gccctggcgg ccagcaagga 6780
cgcaatggcg aaggtaatga aggacagcgc cgcgcaggcg gccgaagcga tccgcaggga 6840
aatcgacgac ggccttggcc gccagctcgc ggccaaggtc gcggacgcgc ggcgcgtggc 6900
gatgatgaac atgatcgccg gcggcatggt gttgttcgcg gccgccctgg tggtgtgggc 6960
ctcgttatga atcgcagagg cgcagatgaa aaagcccggc gttgccgggc ttgttttt 7018

<210> SEQ ID NO 15
<211> LENGTH: 522
<212> TYPE: DNA
<213> ORGANISM: Artificial Sequence
<220> FEATURE:
<223> OTHER INFORMATION: Synthetic Construct

<400> SEQUENCE: 15
tttgaaaaca aagaattagc tgatctttaa taataaggaa atgttacatt aaggttggtg 60
ggttgttttt atgggaaaaa atgctttaag aacaaatgta tacttttaga gagttccccg 120
cgccagcggg gataaaccgg ctttaagcgt tagctcccca ttctgctccc cgagttcccc 180
gcgccagcgg ggataaaccg gtacgttagc gtatattgat gccgcagaga cggagttccc 240
cgcgccagcg gggataaacc ggcgataact ggacagtttt atccgccgag catgagttcc 300
ccgcgccagc ggggataaac cgggcgcact ggatgcgatg atggatatca cttggagttc 360
ccccgcctct gcggtagaac tcccagctcc cattttcaaa cccatcaaga cgccttcgcc 420
aactccttca ccagaggtag cattatccgc ataacgtcac ggcagcgacg ttctattctt 480
ccaggaagag ccttatcaat atgttggtga ttatccagtc tt 522

<210> SEQ ID NO 16
<211> LENGTH: 29
<212> TYPE: DNA
<213> ORGANISM: Artificial Sequence
<220> FEATURE:
<223> OTHER INFORMATION: Synthetic Construct

<400> SEQUENCE: 16
gagttccccg cgccagcggg gataaaccg 29

<210> SEQ ID NO 17
<211> LENGTH: 32
<212> TYPE: DNA
<213> ORGANISM: Artificial Sequence
<220> FEATURE:
<223> OTHER INFORMATION: Synthetic Construct

<400> SEQUENCE: 17
gctttaagcg ttagctcccc attctgctcc cc 32

<210> SEQ ID NO 18
<211> LENGTH: 32
<212> TYPE: DNA
<213> ORGANISM: Artificial Sequence
<220> FEATURE:
<223> OTHER INFORMATION: Synthetic Construct

<400> SEQUENCE: 18
gtacgttagc gtatattgat gccgcagaga cg 32

<210> SEQ ID NO 19
<211> LENGTH: 32
<212> TYPE: DNA
<213> ORGANISM: Artificial Sequence
<220> FEATURE:
<223> OTHER INFORMATION: Synthetic Construct

<400> SEQUENCE: 19
gcgataactg gacagtttta tccgccgagc at 32

<210> SEQ ID NO 20
<211> LENGTH: 408
<212> TYPE: DNA
<213> ORGANISM: Artificial Sequence
<220> FEATURE:
<223> OTHER INFORMATION: Synthetic Construct

<400> SEQUENCE: 20
atgcaacatt tggatatcgc tgaattagtt cgttccgcac tggaagtaag tggttgcgat 60
ccttcattaa ttggaggaat agatagccat tcaacaattg ttctggattt atttgcattg 120
ccaagtatct gtatcagcgt caaggacgat gatgtatgga tctgggcgca attgggtgct 180
gacagcatgg tggtattaca acagcgggct tatgaaatct taatgaccat aatggaagga 240
tgccattttg cccgcggcgg gcaattacta ctgggggagc agaatgggga gctaacgctt 300
aaagccttag tgcatccgga tttttatct gacggtgaaa agttctctac tgccttgaat 360
gggttttaca actatctgga agtttttagt cggtcgctaa tgagatga 408

<210> SEQ ID NO 21
<211> LENGTH: 393

-continued

```
<212> TYPE: DNA
<213> ORGANISM: Artificial Sequence
<220> FEATURE:
<223> OTHER INFORMATION: Synthetic Construct

<400> SEQUENCE: 21

ttgcaagcac accaggatat tatcgctaat attggtgaga aattgggttt accgctcact     60

tttgacgaca acaatcagtg cttattatta ctcgatagcg atatttttac gtctattgaa    120

gctaaagatg atatctggtt attgaacggt atgattatac cgttatcgcc tgtttgtggc    180

gattctatct ggcggcagat tatggtgatt aatggtgaac tggctgcgaa taatgaaggt    240

acgttagcgt atattgatgc cgcagagacg ttgttgctta tacatgcaat taccgatctg    300

acaaatactt accatattat atcgcagctt gagtcatttg tgaatcagca ggaagcgctc    360

aaaaacatac tgcaggaata tgctaaagta tga                                 393


<210> SEQ ID NO 22
<211> LENGTH: 417
<212> TYPE: DNA
<213> ORGANISM: Artificial Sequence
<220> FEATURE:
<223> OTHER INFORMATION: Synthetic Construct

<400> SEQUENCE: 22

atggtgcaag aaatagagca atggttacgt cggcatcagg tgtttactga gcctgcatat     60

ttaggggaga ccgccatatt acttgggcag cagtttatat tatcgcctta cctggtgatc    120

tatcgtattg aggcaaaaga aatgattatt tgtgagttca ggcgcctgac gcccgggcaa    180

cctcgaccac agcaattgtt tcacttactg ggacttttac gcgggatatt tgtgcatcac    240

ccgcagttaa catgtttaaa gatgttgata atcaccgacg ttctggatga aaaaaaagcc    300

atgctacgca ggaaattatt gcgcatcctg acagtaatgg gagcgacctt tacacagctt    360

gatggcgata actggacagt tttatccgcc gagcatctta tccagcgacg tttttaa       417
```